US005656745A

United States Patent [19]
Bischofberger et al.

[11] Patent Number: 5,656,745
[45] Date of Patent: Aug. 12, 1997

[54] NUCLEOTIDE ANALOGS

[75] Inventors: Norbert Bischofberger, San Carlos; Robert J. Jones, Millbrae; Murty Arimilli; Kuei-Ying Lin, both of Fremont; Michael Louie, Burlingame; Lawrence R. McGee, Pacifica; Ernest J. Prisbe, Los Altos, all of Calif.

[73] Assignee: Gilead Sciences, Inc., Foster City, Calif.

[21] Appl. No.: 123,483

[22] Filed: Sep. 17, 1993

[51] Int. Cl.$^6$ .......................... C07H 19/06; C07H 19/16; C07D 239/00; C07D 473/00

[52] U.S. Cl. ................... 536/25.34; 536/27.14; 536/27.21; 536/27.6; 536/27.7; 536/27.8; 536/27.81; 536/28.2; 536/28.5; 536/28.51; 536/28.52; 536/28.53; 536/28.54; 536/28.55; 544/242; 544/243; 544/244; 544/264; 544/265; 544/267; 544/303; 544/304; 544/310

[58] Field of Search ................. 530/330; 536/25.34, 536/27.14, 27.21, 27.6, 27.7, 27.8, 27.81, 28.2, 28.5, 28.51, 28.52, 28.53, 28.54, 28.55; 544/242, 243, 244, 264, 265, 267, 303, 304, 310

[56] References Cited

U.S. PATENT DOCUMENTS

| | | | |
|---|---|---|---|
| 3,524,846 | 8/1970 | Moffatt et al. | |
| 5,043,339 | 8/1991 | Beauchamp. | |
| 5,047,533 | 9/1991 | Reist et al. | |
| 5,391,723 | 2/1995 | Priest | 536/23.1 |
| 5,495,006 | 2/1996 | Climie et al. | 536/24.1 |

FOREIGN PATENT DOCUMENTS

| | | |
|---|---|---|
| 0 253 412 A2 | 1/1988 | European Pat. Off. |
| 0 269 947 A1 | 6/1988 | European Pat. Off. |
| 0 343 133 A1 | 11/1989 | European Pat. Off. |
| 0 369 409 A1 | 5/1990 | European Pat. Off. |
| 0 398 231 A2 | 11/1990 | European Pat. Off. |
| 0 404 296 A1 | 12/1990 | European Pat. Off. |
| 0 465 297 A1 | 1/1992 | European Pat. Off. |
| 0 468 119 A1 | 1/1992 | European Pat. Off. |
| 0 468 866 A1 | 1/1992 | European Pat. Off. |
| 0 479 640 A2 | 4/1992 | European Pat. Off. |
| 0 481 214 A1 | 4/1992 | European Pat. Off. |
| 0 206 459 B1 | 7/1992 | European Pat. Off. |
| 0 494 370 A1 | 7/1992 | European Pat. Off. |
| 0 531 597 A1 | 3/1993 | European Pat. Off. |
| 0 632 048 A1 | 6/1994 | European Pat. Off. |
| 41 38 584 | 5/1993 | Germany. |
| 1 243 214 | 8/1971 | United Kingdom. |
| WO 91/19721 | 12/1991 | WIPO. |
| WO 92/01698 | 2/1992 | WIPO. |
| WO 92/09611 | 6/1992 | WIPO. |
| WO 92/13869 | 8/1992 | WIPO. |

OTHER PUBLICATIONS

Jahne et al., "Preparation of Carbocyclic Phosphonate Nucleosides," TET LETT 33(37):5335–5338 (1992).

Kraus, "New Phosphonate Analogues of 3'–thia-2', 3'–dideoxycytidine (BCH-189). Synthesis and Anti-HIV Evaluation.," NUCLS & NUCLT 12(2):157–162 (1993).

Wolff-Kugel et al., "Studies Towards the Synthesis of the Saturated and Unsaturated Carbocyclic Methylene Phosphonate Analogs of Dideoxyadenosine," NUCLS & NUCLT 12(3&4):279–294 (1993).

Bai et al, "Structural Specificity of Mucosal–Cell Transport and Metabolism of Peptide Drugs: Implication for Oral Peptide Drug Delivery", Pharmaceutical Research, vol. 9, No. 8, (1992), pp. 969–978.

Bronson et al, "Synthesis and Biological Activity of Carbocyclic Derivatives of the Potent Antiviral Agent 9–[2–(Phosphonomethoxy)Ethyl]Guanine (PMEG)", Bioorganic & Medicinal Chemistry Letters, vol. 2, No. 7, (1992), pp. 685–690.

Colla et al, "Synthesis and Antiviral Activity of Water–Soluble Esters of Acyclovir [9–[(2–Hydroxyethoxy)methyl] guanine]", J. Med. Chem., vol. 26, (1983), pp. 602–604.

Curley et al, "Synthesis and anti–HIV evaluation of some phosphoramidate derivatives of AZT: studies on the effect of chain elongation on biological activity", Antiviral Research, vol. 14, (1990), pp. 345–356.

Farquhar et al, "Biological Reversible Phosphate–Protective Groups", Journal of Pharmaceutical Sciences, vol. 72, No. 3, (Mar. 1983), pp. 324–325.

Farrow et al, "Synthesis and Biological Properties of Novel Phosphotriesters: A New Approach to the Introduction of Biologically Active Nucleotides into Cells", J. Med. Chem., vol. 33, (1990), pp. 1400–1406.

Freed et al, "Evidence for Acyloxymethyl Esters of Pyrimidine 5'–Deoxyribonucleotides as Extracellular Sources of Active 5'–Deoxyribonucleotides in Cultured Cells", Biochemical Pharmacology, vol. 38, No. 19, (1989), pp. 3193–3198.

Freeman et al, "3'–Azido–3', 5'–dideoxythymidine–5'–methylphosphonic Acid Diphosphate: Synthesis and HIV–1 Reverse Transcriptase Inhibition", J. Med. Chem., vol. 35, (1992), pp. 3192–3196.

Gabrielsen et al, "Synthesis and In Vivo Anti–RNA–Viral Evaluation of a Phosphoramidate Derivative of 6–Azauridine; Orotidylic Acid Decarboxylase Inhibitors, Pyrazofurin and 6–Azauridine; and 2–Thio–6–azauridine and its Triacetate", Antiviral Research, vol. 17, Supp. I, (1992), p. 149, Abstract No. 199.

Gumport et al, "Structure of the DNA Ligase–Adenylate Intermediate: Lysine (ε–amino)–Linked Adenosine Monophosphoramidate", Proc. Nat. Acad. Sci., vol. 68, No. 10, (Oct. 1971), pp. 2559–2563.

(List continued on next page.)

Primary Examiner—James O. Wilson
Attorney, Agent, or Firm—Daryl D. Muenchau

[57] ABSTRACT

Nucleotide analogs characterized by the presence of an amidate linked amino acid or an ester linked group which is bonded to the phosphorus atom of phosphonate nucleotide analogs are disclosed. The analogs comprise a phosphoamidate or ester bond that is hydrolyzed in vivo to yield a corresponding phosphonate nucleotide analog. Methods and intermediates for their synthesis and use are described.

29 Claims, 7 Drawing Sheets

OTHER PUBLICATIONS

Juodka et al, "Synthesis of Diribonucleoside Phospho–(P→N)–Amino Acid Derivatives", *Collection Czechoslov. Chem. Commun.*, vol. 39, (1974), pp. 963–968.

Kim et al, "Synthesis and HIV Activity of Phosphonate Isosteres of D4T Monophosphate", *Organic & Medicinal Chemistry Letters*, vol. 2, No. 5, (1992), pp. 367–370.

Kim et al, "A Novel Synthesis of 1–OXA–HPMPA: A Potent Antiviral Agent Against Herpesviruses", *Tetrahedron Letters*, vol. 33, No. 1, (1992), pp. 25–28.

Kim et al, "Acyclic Purine Phosphonate Analogues as Antiviral Agents. Synthesis and Structure—Activity Relationships", *J. Med. Chem.*, vol. 33, (1990), PP. 1207–1213.

Kumar et al, "Synthesis and Biological Evaluation of Some Cyclic Phosphoramidate Nucleoside Derivatives", *J. Med. Chem.*, vol. 33, (1990), pp. 2368–2375.

McGuigan et al, "Phosphoramidate derivatives of AZT as inhibitors of HIV: studies on the carboxyl terminus", *Antiviral Chemistry & Chemotherapy*, vol. 4, No. 2, (1993), pp. 97–101.

McGuigan et al, "Synthesis and anti–HIV activity of some haloalkyl phosphoramidate derivatives of 3'–azido–3'–deoxythymidine (AZT): potent activity of the trichloroethyl methoxyalaninyl compound", *Antiviral Research*, vol. 15 (1991), pp. 255–263.

Mukaiyama et al, "Synthesis of Oligothymidylates and Nucleoside Cyclic Phosphates by Oxidation—Reduction Condensation", *Journal of the American Chemical Society*, vol. 94, No. 24, (Nov. 29, 1972), pp. 8528–8532.

Palú et al, "Cellular uptake of phosphonylmethoxyalkylpurine derivatives", *Antiviral Research*, vol. 16, (1991), pp. 115–119.

Rosenberg et al, "Phosphonylmethoxyalkyl and Phosphonylalkyl Derivatives of Adenine", *Collection Czechoslovak Chem. Commun.*, vol. 53, (1988), pp. 2753–2777.

Rosenberg et al, "Synthesis of Potential Prodrugs and Metabolites of 9–(S)–(3–Hydroxy–2–Phosphonylmethoxypropyl)Adenines", *Collection Czechoslovak Chem. Commun.*, vol. 52, (1987), pp. 2792–2800.

Sastry et al, "Membrane–Permeable Dideoxyuridine 5'–Monophosphate Analogue Inhibits Human Immunodeficiency Virus Infection", *Molecular Pharmacology*, vol. 41 (1992), pp. 441–445.

Srivastva et al, "Bioreversible Phosphate Protective Groups: Synthesis and Stability of Model Acyloxymethyl Phosphates", *Bioorganic Chemistry*, vol. 12 (1984), pp. 118–129.

Starrett et al, "Synthesis and in vitro evaluation of a phosphonate prodrug: bis(pivaloyloxymethyl) 9–(2–phosphonylmethoxyethyl)adenine", *Antiviral Research*, vol. 19, (1992), pp. 267–273.

Wolff–Kugel et al, "Synthesis of New Carbocyclic Phosphonate Analogs of Dideoxypurine Nucleotides", *Tetrahedron Letters*, vol. 32, No. 44, (1991), pp. 6341–6344.

Yu et al, "Synthesis and Antiviral Activity of Methyl Derivatives of 9–[2–(Phosphonomethoxy)ethyl]guanine", *J. Med. Chem.*, vol. 35, (1992), pp. 2958–2969.

Midoux, "Drug Targeting: Anti–HSV–1 Activity of Mannosylated Polymer–Bound 9–(2–Phosphonylmethoxyethyl Adenine," Biochem Biophys Res Comm 167(3):1044–1049 (1990).

Beres, "Synthesis and Antitumor and Antiviral Properties of 5–Halo–and 5–(Trifluoromethyl)–2'–deoxyuridine 3',5'–Cyclic Monophosphates and Neutral Triesters," J Med Chem 29:1243–1249 (1986).

Engel, R., "Phosphonates as Analogues of Natural Phosphates," Chem Rev 77:349–367 (1977).

$X^2 = O, S, NH$

NUCLEOTIDE ANALOGS

BACKGROUND OF THE INVENTION

The present invention relates to novel nucleotide analog amidates and esters, their pharmaceutically acceptable acid addition salts, a process for their production, and to their use. The nucleotides of the present invention exhibit antitumor/antineoplastic activity, a broad spectrum of antimicrobial activity and certain other desirable activities.

Compounds related to the nucleotide analogs of the present invention may be found in: U.S. Pat. Nos. 5,043,339, 5,108,994 and 5,166,198; EP 206 459; EP 253 412; EP 269 947; EP 270 885; EP 319 228; EP 343 133; EP 398 231; EP 404 296; EP 465 297; EP 468 119; EP 468 866; EP 479 640; EP 481 214; EP 494 370; EP 531 597; PCT/GB91/01171; PCT/US92/01020; PCT/US92/05208; Bronson et al, *Bioorg Medicinal Chem Lett* (1992) 2:685–690; Bronson et al, *J Med Chem*, (1989) 32:1457–1463; Bronson et al, *Nucleotide Analogs as Antiviral Agents*, ACS Symposium Series 401, J. C. Martin, Ed., p. 72–87, American Chemical Society, Washington, D.C. (1989); Colla, et al, *J Med Chem* (1983) 26:602–604; Curley, et al, *Antiviral Res* (1990) 14:345–356; De Clercq, et al, *Nature*, (1986) 323:464–467; Farrow, et al, *J Med Chem* (1990) 33:1400–1406; Farquhar, et al, *J Pharm Sci* (1983) 72:324–325; Freed, et al, *Biochem Pharmacol* (1989) 19:3193–3198; Freeman, et al, *J Med Chem* (1992) 35:3192–3196; Gabrielsen, B., et al, *Antiviral Res Suppl I* (1992) 17:149; Gumport, et al, *Proc Natl Acad Sci* (1971) 2559–2563; Juodka, et al, *Coll Czech Chem Commun* (1974) 39:963–968; Kim, et al, *Bioorg Medicinal Chem Lett* (1992) 2:367–370; Kim, et al, *Tet Lett* (1992) 33:25–28; Kim, et al, *J Med Chem* (1990) 33:1207–1213; Kumar, et al, *J Med Chem* (1990) 33:2368–2375; McGuigan, et al, *Antiviral Chem Chemother* (1993) 4:97–101; McGuigan, et al, *Antiviral Res* (1991) 15:255–263; Rosenberg, et al, *Coll Czech Chem Commun* (1988) 53:2753–2777; Rosenberg, et al, *Coll Czech Chem Commun* (1988) 52:2792–2800; Rosenberg, et al, *Coll Czech Chem Commun* (1988) 52:2801–2808; Starrett, et al, *Antiviral Res* (1992) 19:267–273; Yu, et al, *J Med Chem* (1992) 35:2958–2969; Wolff-Kugel, et al, *Tet Lett* (1991) 32:6341–6344.

A characteristic of nucleotide analogs or nucleotides having a phosphonate or a phosphate group is the presence of one or two negative charges associated with the phosphorus group at physiologic pH. The charge associated with moieties such as phosphate or phosphonate groups is believed to generally limit bioavailability by limiting cell membrane permeation via passive diffusion (Liebman, et al, *J. Biol. Chem.*, (1955) 216:823–830; Roll, et al, *J Biol Chem*, (1956) 220:439–444; Srivastava, et al, *Bioorg Chem* (1984) 12:118–129; Palu, et al, *Antiviral Res* (1991) 16:115–119; Sastry, et al, *Mol Pharmacol* (1992) 41:441–445). These compounds are often, therefore, given parenterally in order to enhance bioavailability by increasing serum or intracellular levels.

Other characteristics of nucleotide analogs that can limit their efficacy include unfavorable pharmacokinetic or pharmacodynamic properties, insufficient potency and/or unfavorable toxicity characteristics.

Studies were conducted to ameliorate one or more of the above-mentioned problems associated with nucleotide analog drugs. The present invention discloses novel nucleotide analogs that are hydrolyzable in vivo, such nucleotide analogs having improved bioavailability, improved pharmacokinetic or pharmacodynamic properties, enhanced potency and/or improved toxicity characteristics. Methods to synthesize and use the compounds and methods to obtain and use antibodies that recognize the compounds are also disclosed.

SUMMARY OF THE INVENTION

In a principal embodiment, the objects of this invention are accomplished by a nucleotide analog amidate comprising a phosphonate radical wherein the improvement comprises an amino acid residue or polypeptide radical in which an amino group of the amino acid or polypeptide is bonded to the phosphorus atom of the nucleotide analog by an amidate bond, a carboxyl group of the amino acid residue or polypeptide radical is positioned such that it is capable as the free acid of hydrolyzing the phosphoroamidate bond, and the carboxyl group is blocked (such as by moieties including esters or amides). The nucleotide analog amidates of this invention are hydrolyzed in vivo to the corresponding nucleotide analog and are thus precursors of the corresponding nucleotide analog.

In accordance with this invention the nucleotide analog amidates or a physiologically acceptable salt thereof, have the structure of formula I

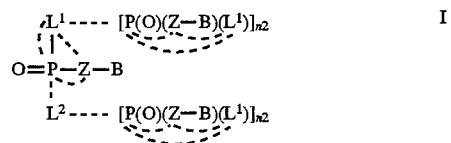

wherein $L^1$ and $L^2$ are independently an amino acid or polypeptide residue bonded to the phosphorus atom of the nucleotide analog by an amidate bond, or $L^1$ or $L^2$ are an oxyester, thioester, a substituted or unsubstituted amine, or hydroxy, provided that one or both of $L^1$ and $L^2$ is an amino acid or polypeptide residue and any carboxyl group that is linked by less than about 5 atoms to the amidate N is esterified or amidated, the dotted lines represent facultative bonds and wherein, (i) $L^1$ and P are linked to form a compound of the formula Ia

or (ii) P and Z are linked to form a compound of the formula Ib

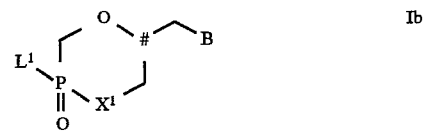

or (iii) $L^1$ and Z are linked to form a compound of the formula Ic

wherein atoms designated # are carbon in the R, S or RS configuration;

$X^1$ is O or S;

Z is —$CHR^7$—$R^{11}$—$(CH_2)_{m1}$—$C\#(R^8)((CH_2)_{m2}(R^9))$—$(CH_2)_{m3}$—$R^{10}$—$(CH_2)_{m4}$—, —Q—$C_6H_4$—$CH_2$—,

—CHR$^7$—O—CHR$^7$—O—CHR$^7$—, —CHR$^7$—(CHR$^{13}$)$_{m1}$—CHR$^{14}$—R$^{10}$—,

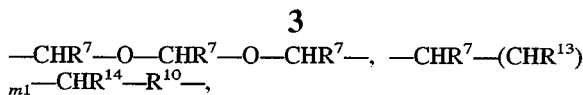

IV      V

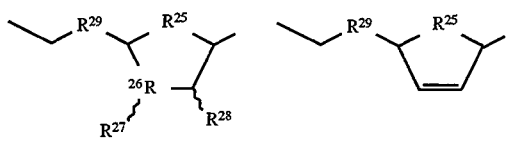

VI      VII

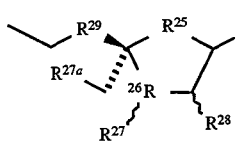

or VIII wherein

R$^7$ is H or C$_1$–C$_4$ alkyl;

R$^8$ is H or C$_1$–C$_4$ alkyl, C$_2$–C$_4$ alkenyl, azidomethyl or azidoethyl;

R$^9$ is halogen (F, Cl, Br or I), H or OH;

R$^{10}$ is O, CH$_2$ or a chemical bond;

R$^{11}$ is O, S, CH$_2$, CHF or CF$_2$;

Q is —C(R$^{12}$)$_2$—CH$_2$—, —C(R$^{12}$)$_2$—O—, —CR$^{12}$=CR$^{12}$—, or —C≡C—, wherein each R$^{12}$ is independently H, or halogen;

R$^{13}$ is H, halogen, OH, CH$_3$, CH$_2$OH, or C$_3$–C$_6$ acyloxymethyl;

R$^{14}$ is H, halogen, OH, CH$_3$, CH$_2$OH, C$_3$–C$_6$ acyloxymethyl, or C$_2$–C$_6$ acyloxy;

R$^{25}$ is CH$_2$, CHF or O;

R$^{26}$ is CH or S, provided that when R$^{25}$ is CH, R$^{26}$ is not S;

R$^{27}$ is H, OH, halogen, N$_3$, C$_1$–C$_4$ alkyl, C$_1$–C$_4$ alkoxy or, when R$^{26}$ is S, R$^{27}$ is absent;

R$^{27a}$ is H, OH, halogen, N$_3$, C$_1$–C$_4$ alkyl, C$_1$–C$_4$ alkoxy;

R$^{28}$ is H, OH, halogen, N$_3$, C$_1$–C$_4$ alkyl or C$_1$–C$_4$ alkoxy;

R$^{29}$ is O, S, CH$_2$, CHF, CF$_2$;

R$^{32}$ is O;

n2 is an integer having a value from 0 to 6;

m1 is an integer having a value from 0 to 4;

m2 is an integer having a value from 0 to 4;

m3 is an integer having a value from 0 to 4;

m4 is an integer having a value from 0 to 4;

B is a base; and the carbon atom designated C# is in the R, S or RS configuration.

In a further embodiment the objects are accomplished by compounds of the formula II, IIa, IIb and IIc

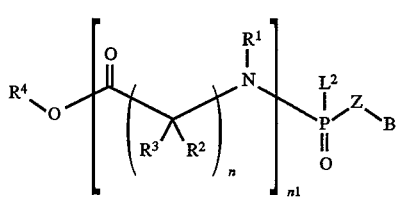

II

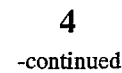

-continued

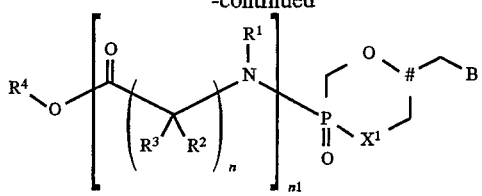

IIa

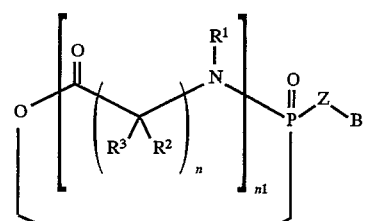

IIb

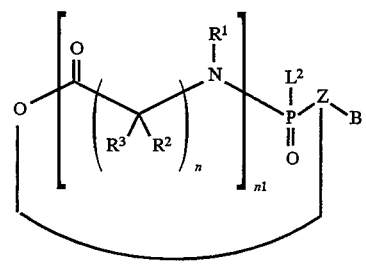

IIc wherein L$^2$ is OR, SR or

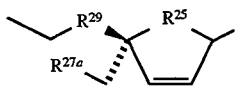

III n is an integer having a value from 1 to 5 and if n>1, each —C(R$^3$)(R$^2$)— may be the same or different;

n1 is an integer;

# is the R, S or RS configuration of the indicated carbon atom;

R is H, C$_1$–C$_{20}$ alkyl which is unsubstituted or substituted by substituents inependently selected from the group consisting of OH, O, N and halogen (F, Cl, Br, I), C$_3$–C$_{20}$ aryl which is unsubstituted or substituted by substituents independently selected from the group consisting of C$_1$–C$_6$ alkyl, C$_1$–C$_6$ alkoxy, C$_1$–C$_6$ haloalkyl (1 to 3 halogen atoms), cyano, nitro, OH, O, N and halogen or R is C$_4$–C$_{20}$ aryl-alkyl which is unsubstituted or substituted in the aryl moiety by substituents independently selected from the group consisting of C$_1$–C$_6$ alkyl, C$_1$–C$_6$ alkoxy, C$_1$–C$_6$ haloalkyl (1 to 3 halogen atoms), cyano, nitro, OH, O, N and halogen, or R is C$_3$–C$_{24}$ 1-acyloxy-1-alkyl (C$_1$–C$_8$ alkyl), or R is C$_6$–C$_{24}$ 1-acyloxy-1-aryl-1-alkyl (C$_1$–C$_6$ aryl, C$_1$–C$_4$ alkyl), or R is C$_3$–C$_{24}$ 1-acyloxy-2-alkoxy-1-alkyl (C$_1$–C$_8$ alkyl), or R is C$_3$–C$_{24}$ 1-acyloxy-2-haloalkyl (C$_1$–C$_8$ haloalkyl, 1 to 3 halogen atoms);

R$^1$ is H or C$_1$–C$_9$ alkyl which is unsubstituted or substituted by substituents independently selected from the group consisting of OH, O, N, COOR$^4$ and halogen, C$_3$–C$_6$ aryl which is unsubstituted or substituted by substituents independently selected from the group consisting of OH, O, N, COOR$^4$ and halogen or C$_3$–C$_9$ aryl-alkyl which is unsubstituted or substituted by substituents independently selected from the group consisting of OH, O, N, COOR$^4$ and halogen;

$R^2$ is H or $C_1$–$C_9$ alkyl which is unsubstituted or substituted by substituents independently selected from the group consisting of OH, O, N, COOR$^4$ and halogen, $C_3$–$C_6$ aryl which is unsubstituted or substituted by substituents independently selected from the group consisting of OH, O, N, COOR$^4$ and halogen or $C_3$–$C_9$ aryl-alkyl which is unsubstituted or substituted by substituents independently selected from the group consisting of OH, O, N, COOR$^4$ and halogen;

$R^3$ is C(O)—OR$^4$, amino, $C_1$–$C_3$ alkylamino, $C_1$–$C_3$ alkyldiamino, $C_1$–$C_6$ alkenylamino, hydroxy, thiol, $C_1$–$C_3$ alkoxy, $C_1$–$C_3$ alkthiol, $(CH_2)_n$COOR$^4$, $C_1$–$C_6$ alkyl which is unsubstituted or substituted with OH, halogen, SH, NH$_2$, phenyl, hydroxyphenyl or $C_7$–$C_{10}$ alkoxyphenyl; $C_2$–$C_6$ alkenyl which is unsubstituted or substituted with OH, halogen, SH, NH$_2$, phenyl, hydroxyphenyl or $C_7$–$C_{10}$ alkoxyphenyl; $C_6$–$C_{12}$ aryl which is unsubstituted or substituted with OH, halogen, SH, NH$_2$, phenyl, hydroxyphenyl or $C_7$–$C_{10}$ alkoxyphenyl; and $R^4$ is H provided that n1 greater than 1, or is $C_3$–$C_9$ alkyl which is substituted by substituents independently selected from the group consisting of OH, O, N and halogen, $C_3$–$C_6$ aryl which is substituted by substituents independently selected from the group consisting of OH, O, N and halogen or $C_3$–$C_9$ aryl-alkyl which is substituted by substituents independently selected from the group consisting of OH, O, N and halogen.

The structural formula I is meant to define compounds where the phosphorus (P) atom is tetravalent (PV oxidation state) and optionally linked via the facultative bonds shown as dotted lines to either $L^1$ or Z to form a heterocyclic ring containing at least the P atom itself and a nitrogen atom of $L^1$ or an atom present, usually oxygen (O), in Z. Such heterocyclic rings will preferably be 5-, 6- or 7-membered, but are also 4-, 8-, 9-, 10-, 11- or 12-membered. Alternatively the P atom is covalently linked to $L^2$ with $L^1$ and Z optionally linked to each other to form a heterocyclic ring. The structure is not intended to include compounds where heterocyclic rings are formed between both $L^1$ and P and Z and P in the same molecule which would exceed the valency of P. Thus, an exemplary class of compounds is represented by the structure of formula I includes $(L^1)(L^2)P(O)$—Z—B (formula Id) where no heterocyclic rings are formed between any $L^1$, $L^2$, P, Z or B moiety. Another exemplary class of compounds include a moiety of the formula —[P(O)(Z—B)($L^1$)]$_{n2}$ is linked, for example through a carboxyl or amine group in $L^1$, to the $L^1$ moiety in structures of formula Ia, Ib or Ic. The —[P(O)(Z—B)($L^1$)]$_{n2}$ moiety itself is optionally linked in a similar manner with, for example, Z and either $L^1$ or P optionally forming a heterocyclic ring. Compounds containing the —[P(O)(Z—B)($L^1$)]$_{n2}$ moiety include polymeric nucleotide analogs (such as dimers, trimers, etc) linked through $L^1$ or linked through alternating $L^1$ and P.

$R^2$ includes methyl, ethyl, propyl, isopropyl and benzyl.

In another embodiment, the objects of this invention are accomplished by a nucleotide analog ester comprising a phosphonate radical and an ester moiety bonded to the phosphorus atom of the nucleotide analog. The nucleotide analog esters of this invention are hydrolyzed in vivo to the corresponding nucleotide analog and are thus precursors of the corresponding nucleotide analog, or can be used as intermediates in the synthesis of the nucleotide analog amidates.

The substructure Z can have a range of atoms between the base, B, and the phosphorus atom. For example, four atoms separate the base and phosphorus moieties when Z is of the formula —CH$_2$—O—CH$_2$—CH$_2$—. In general, there will be from 2 to 16 atoms, preferably from 3 to 9 atoms, more preferably from 4 to 6 atoms that separate the base and the phosphorus atom. Thus, Z substructures of the formula —CHR$^7$—R$^{11}$—(CH$_2$)$_{m1}$—C(R$^8$)((CH$_2$)$_{m2}$(R$^9$))—(CH$_2$)$_{m3}$—R$^{10}$—(CH$_2$)$_{m4}$— may be characterized where the sum of m1, m3 and m4 is in a range between 0 and 12 or preferably in a range between 1 and 6, more preferably in a range between 1 and 4.

The nucleotide analog amidate and ester compounds of the instant invention include the corresponding salts, which may be base salts of the phosphonic acid moiety or an acid addition salt of the base in addition to the zwitterionic forms and/or solvates of compounds of formula I.

Some of the compounds of the present invention can exist as optical isomers and both racemic and diastereomeric mixtures of these isomers which may exist for certain compounds as well as the individual optical isomers which are all within the scope of the present invention. Compounds of formula IIa in the R, S or RS configuration at the chiral carbon, designated # herein, are examples of compounds having optical isomers. While the racemic mixtures can be separated into their individual isomers through well-known techniques such as, for example, the separation of diastereomeric salts formed with optically active adjuncts, e.g. acids or bases followed by conversion back to the optically active substrates; in most instances, for compounds of the present invention, the preferred optical isomer can be synthesized by means of stereospecific reactions, beginning with the appropriate stereoisomer of the desired starting material.

As indicated, the present invention also pertains to the pharmaceutically acceptable non-toxic salts of these compounds. Such salts may include those derived by combination of appropriate cations such as alkali and alkaline earth metal ions or ammonium and quaternary amino ions with the acid anion moiety of the phosphonic acid group. In addition salts may be formed from acid addition of certain organic and inorganic acids with basic centers of the purine, specifically guanine, or pyrimidine base. Finally it is to be understood that compounds of the present invention in their un-ionized as well as zwitterionic form and/or in the form of solvates are also considered part of the present invention.

In other embodiments, the foregoing nucleotide analog amidates and esters or their dihydroxy phosphonate hydrolysis products are labeled with a detectable tag such as a radioisotope (including $^{32}$P, $^{35}$S, $^{14}$C, $^{3}$H, $^{125}$I), a fluorescent moiety, an enzyme (including peroxidase, phosphatase) or the like.

Also included are immunogens for raising antibodies which are capable of binding to the nucleotide analog amidates and esters of this invention and/or their dihydroxy phosphonate hydrolysis products, as well as antibodies capable of binding to the amidate and ester compounds of this invention or to their dihydroxy phosphonate hydrolysis products.

Chemical Structures

Structural formulas and substructures are represented as ROMAN numerals (I, II, III, IV, V, etc) or as letters (B, Z, $L^1$, $L^2$, $R^1$, $R^2$, etc). The substructures Z and $Z^1$ represent linking groups between the base (B) and the phosphorus atom (P) of the phosphonate group in the nucleotide analogs described herein. Linking groups Z, such as —CHR$^7$—R$^{11}$—(CH$_2$)$_{m1}$—C(R$^8$)((CH$_2$)$_{m2}$(R$^9$))—(CH$_2$)$_{m3}$—R$^{10}$—(CH$_2$)$_{m4}$—, in the structure $(L^1)(L^2)P(O)$—Z—B have the structure $(L^1)(L^2)P(O)$—CHR$^7$—R$^{11}$—(CH$_2$)$_{m1}$—C(R$^8$)((CH$_2$)$_{m2}$(R$^9$))—(CH$_2$)$_{m3}$—R$^{10}$—(CH$_2$)$_{m4}$—B (i.e. the base (B) is covalently linked to the unfilled valence on the right side of the structure and the phosphorus atom is linked to the unfilled valence on the left side).

DETAILED DESCRIPTION OF THE INVENTION

Figure 1:
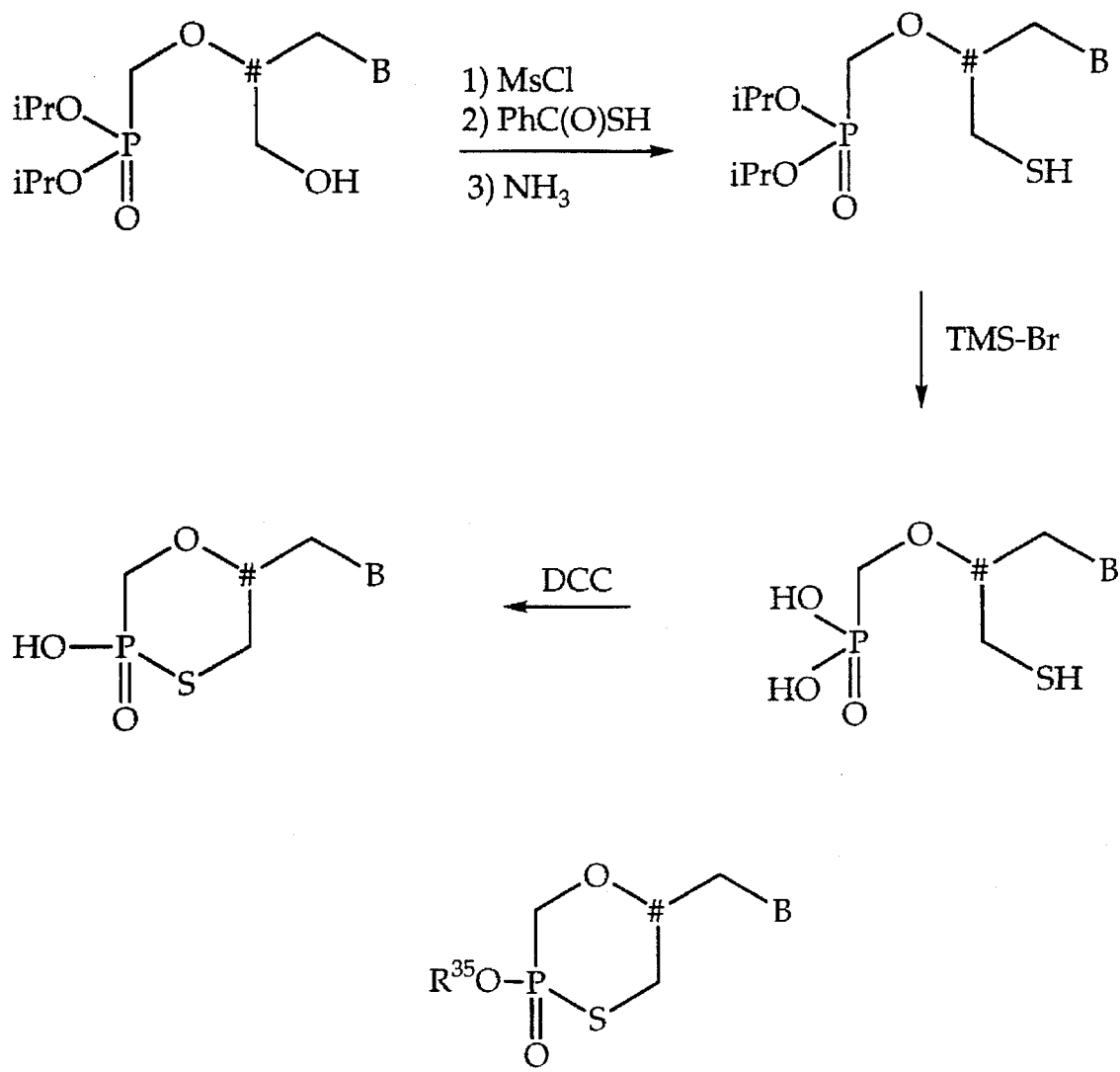
FIG. 1. Synthesis of formula Ib compounds where $X^1$ is S.
Figure 2:
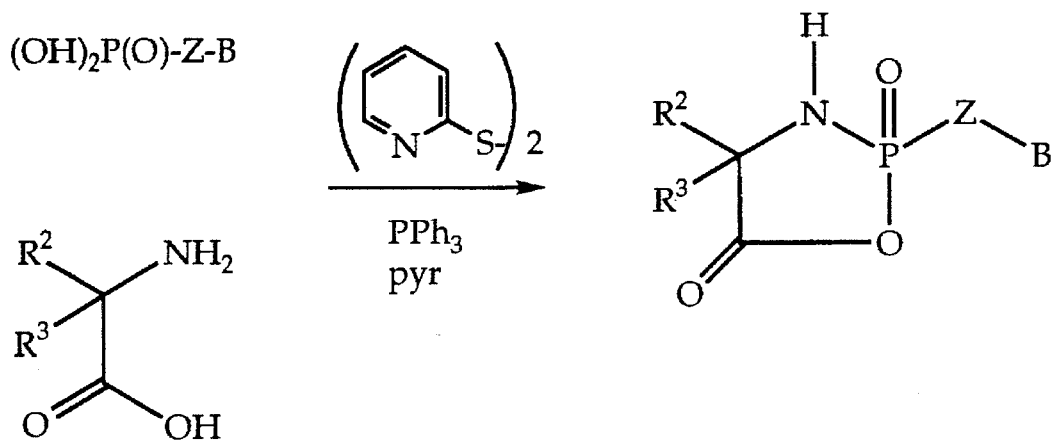
FIG. 2. Synthesis of formula Ia compounds.
Figure 2:
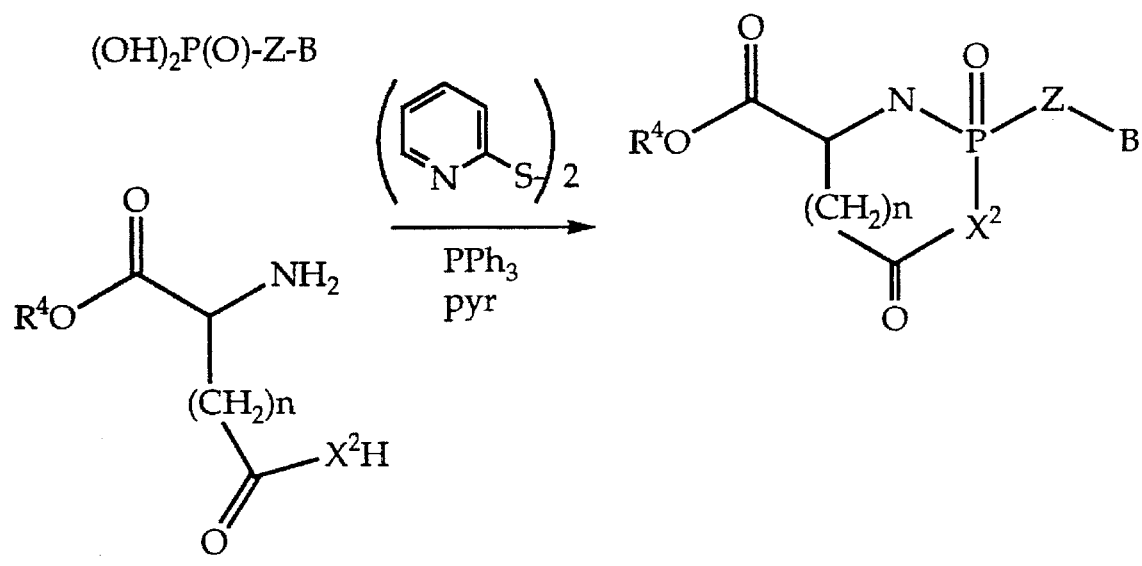

Amino Acid Residues.

When groups $L^1$ or $L^2$ comprise an amino acid residue they comprise any naturally-occurring or synthetic amino acid residue. i.e., any moiety comprising at least one carboxyl and at least one amino residue linked by at least one carbon atom, typically a single ($\alpha$) carbon atom. The nature and identity of the intervening structure located between the carboxyl and amino (amidate) groups can have a variety of structures including those described herein. All that is necessary is that the group have sufficient conformation and length to be capable of acid catalysis of the phosphoroamidate bond and release of the phosphonate when the free carboxyl is generated in vivo, e.g. by deesterification, deamidation or peptidolytic cleavage of the precursor. In general, the intervening structure may be as simple as methylene (when the residue is glycyl) or substituted methylene (other $\alpha$ amino acids). The structure ordinarily contains up to about 5 carbon or hetero atoms in the direct linkage between the carboxyl carbon and the amidate nitrogen, as for example in the case of intervening ethylene, propylene, butylene, or pentylene groups or their substituted analogs, such as for example oxyesters in which O replaces carbon and, as appropriate, hydrogen. An example of such an intervening structure would be —CH—O—CH($R^3$)($R^2$)—. In general, fewer intervening atoms are employed when more rapid hydrolysis is desired, although it will be understood that larger structures are suitable if they possess sufficient flexibility or are capable of conformationally positioning the carboxyl group adjacent to the amidate bond.

In general, the amino acid residue has the structure shown in formula III. Ordinarily, n is 1 or 2, $R^2$ is H and $R^3$ is a moiety containing one or more of the following groups: amino, carboxyl, amide, carboxyl ester, hydroxyl, $C_6$–$C_7$ aryl, ether, n-, s- or t-alkyl ($C_1$–$C_6$), guanidinyl, imidazolyl, indolyl, sulfhydryl, sulfoxide, and phosphoryl. The $R^2$ and $R^3$ substituents can have a wide variety of structures including those disclosed herein.

Ordinarily $R^2$ is H and $R^3$ is a side chain or group of a naturally occurring amino acid. With respect to the carboxyl-containing side chains it will be understood that if the C atom of the subject carboxyl is linked by 5 or less atoms to the phosphoamide N then the carboxyl will be blocked, e.g. by esterification or amidation wherein the ester or amide bonds are hydrolyzable in vivo. Thus, $R^3$ includes naturally occurring amino acid side groups such as H, —CH₃, —CH(CH₃)₂, —CH₂—CH(CH₃)₂, —CHCH₃—CH₂—CH₃, —CH₂—C₆H₅, —CH₂CH₂—S—CH₃, —CH₂OH, —CH(OH)—CH₃, —CH₂—SH, —CH₂—C₆H₄OH, —CH₂—CO—NH₂, —CH₂—CH₂—CO—NH₂, —CH₂—COOH, —CH₂—CH₂—COOH, —(CH₂)₄—NH₂ and —(CH₂)₃—NH—C(NH₂)—NH₂. $R^3$ also includes 1-guanidinoprop-3-yl, benzyl, 4-hydroxybenzyl, imidazol-4-yl, indol-3-yl, methoxyphenyl and ethoxyphenyl. The optimal $R^3$ group is readily selected using routine assays.

When the amino acid residues contain one or more chiral centers, any of the D, L, meso, threo or erythro (as appropriate) racemates, or mixtures thereof, fall within the scope of this invention. In general, if it is desired to rely on non-enzymatic means of hydrolysis, D isomers should be used. On the other hand, L isomers may be more versatile since they can be susceptible to both non-enzymatic as well as potential targeted enzymatic hydrolysis, and are more efficiently transported by amino acid or dipeptidyl transport systems in the gastrointestinal tract.

Examples of suitable amino acid residues include the following:

Glycyl;

Aminopolycarboxylic adds, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic add, 2-aminosuberic acid and 2-aminosebacic acid residues;

Amino acid amides such as glutaminyl and asparaginyl;

Polyamino- or polybasic-monocarboxylic acids such as arginine, lysine, β-aminoalanine, γ-aminobutyrine, ornithine, citruline, homoarginine, homocitrulline, 5-hydroxy-2,6-diaminohexanoic acid (commonly, hydroxylysine, including allohydroxylysine) and diaminobutyric add residues;

Other basic amino acid residues such as histidinyl;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid residues;

Imino acids such as proline, 4- or 3-hydroxy-2-pyrrolidinecarboxylic acid (commonly, hydroxyproline, including allohydroxyproline), γ-methylproline, pipecolic acid, 5-hydroxypipecolic acid, —N([CH₂]ₙCOOR⁴₂, wherein n and $R^4$ are as defined above, and azetidine-2-carboxylic acid residues;

A mono- or di-alkyl (typically $C_1$–$C_8$ branched or normal) amino acids such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid; isoleucine, alloisoleucine, tert-leucine, β-methyltryptophan and α-amino-β-ethyl-β-phenylpropionic acid residues; β-phenylserinyl;

Aliphatic α-amino-β-hydroxy acids such as serine, β-hydroxyleucine, β-hydroxynorleucine, β-hydroxynorvaline, and α-amino-β-hydroxystearic acid residues;

α-Amino, α-, γ-, δ- or ε-hydroxy acids such as homoserine, γ-hydroxynorvaline, δ-hydroxynorvaline and epsilon-hydroxynorleucine residues; canavinyl and canalinyl; γ-hydroxyornithinyl;

2-hexosaminic adds such as D-glucosaminic acid or D-galactosaminic acid residues;

α-Amino-β-thiols such as penicillamine, β-thiolnorvaline or β-thiolbutyrine residues;

Other sulfur containing amino acid residues including cysteine; homocystine; β-phenylmethionine; methionine; S-allyl-L-cysteine sulfoxide; 2-thiolhistidine; cystathionine; and thiol ethers of cysteine or homocysteine;

Phenylalanine, tryptophan and ring-substituted α amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dicloro, o-, m- or p-methyl-, 2,4, 6-trimethyl-, 2-ethoxy-5-nitro, 2-hydroxy-5-nitro and p-nitro-phenylalanine); furyl-, thienyl-, pyridyl-, pyrimidinyl-, purine or naphthylalanines; and tryptophan analogues and derivatives including kynurenine, 3-hydroxykynurenine, 2-hydroxytryptophan and 4-carboxytryptophan residues;

α-Amino substituted amino acid residues including sarcosine (N-methylglycine), N-benzylglycine, N-methylalanine, N-benzylalanine, N-methyphenylalanine, N-benzylphenylalanine, N-methylvaline and N-benzylvaline; and α-Hydroxy and substituted α-hydroxy amino acid residues including serine, threonine, allothreonine, phosphoserine and phosphothreonine residues.

Any one of the foregoing or other known amino acids are suitably employed in this invention provided that they are capable of autocatalytically hydrolyzing the amidate bond. Thus, they must contain, or must, upon being converted (hydrolyzed) in vivo, a free carboxyl group. In general, the amino acids corresponding to the residues employed in the compounds of this invention are naturally occurring and have no pharmacological activity. However, optimal pharmacokinetic activity may be achieved by the use of non-naturally occurring amino acid residues.

Of particular interest are hydrophobic residues such as mono-or di-alkyl or aryl amino adds, cycloalkylamino acids and the like. These residues, together with $R^4$, contribute to cell permeability by increasing the partition coefficient of the nucleotide analog amidate. Typically, the residue does not contain a sulfhydryl or guanidino substituent.

Polypeptide Radicals.

If n1 is greater than 1, then the group shown in formula II, IIa, IIb or III is greater than 1, then the moiety comprises a polypeptide radical. This comprises dipeptides, short polypeptides of 3, 5 or 10 residues, or proteins having up to 100 or more residues. For the most part, dipeptides not containing aspartic or glutamic acid in the residue adjacent to the P atom, will not autocatalytically hydrolyze the amidate bond and therefore the carboxyl groups (generally 1 or 2) in the distal residue do not need to be esterified or amidated, i.e., $R^4$ can be H in these circumstances. However, if such compounds are intended to be used as precursors for the free phosphonate nucleotide analog in vivo, rather than as immunogens for example, the polypeptides ordinarily will contain a peptidolytic enzyme cleavage site at the peptide bond linking the first residue and the next residue distal to the phosphorus atom. Such cleavage sites are flanked by enzymatic recognition structures, e.g. particular residues recognized by a hydrolytic enzyme.

Peptidolytic enzymes are well known, and in particular include carboxypeptidases. Carboxypeptidases digest polypeptides by removing C-terminal residues, and are specific in many instances for particular C-terminal sequences. Such enzymes and their substrate requirements in general are well known.

Examples of suitable dipeptidyl groups (designated by their single letter code) include AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Exemplary dipeptidyl compounds have the structure of formula IX wherein $R^2$ is H, $R^3$ is the side chain of a naturally occurring amino acid, $L^1$, $R^4$, B and Z are as defined above.

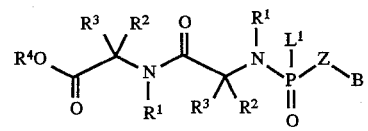

Bases.

The compounds of this invention comprise any naturally-occurring heterocyde found in nucleic acids, nucleotides or nucleosides, or analogs thereof. The radicals of such bases, designated herein as B, are generally the purine, pyrimidine or related heterocycles shown in formulas X–XIII.

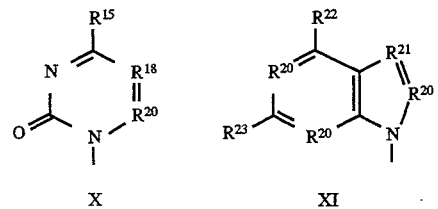

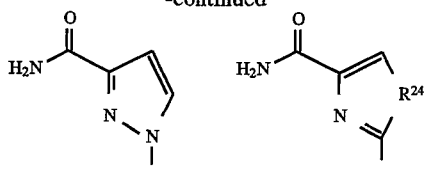

wherein R[15] is H, OH, F, Cl, Br, I, OR[16], SH, SR[16], NH$_2$, or NHR[17];

R[16] is $C_1$–$C_6$ alkyl including $CH_3$, $CH_2CH_3$, $CH_2CCH$ (2-propynyl), $CH_2CHCH_2$ (2-allyl), $C_3H_7$;

R[17] is $C_1$–$C_6$ alkyl including $CH_3$, $CH_2CH_3$, $CH_2CCH$, $CH_2CHCH_2$, $C_3H_7$;

R[18] is N, CF, CCl, CBr, CI, CR[19] or CSR[19], COR[19];

R[19] is H, $C_1$–$C_9$ alkyl, $C_2$–$C_9$ alkenyl, $C_2$–$C_9$ alkynyl or $C_7$–$C_9$ aryl-alkyl unsubstituted or substituted by OH, O, N, F, Cl, Br or I including $CH_3$, $CH_2CH_3$, $CHCH_2$, $CHCHBr$, $CH_2CH_2Cl$, $CH_2CH_2F$, $CH_2CCH$, $CH_2CHCH_2$, $C_3H_7$, $CH_2OH$, $CH_2OCH_3$, $CH_2OC_2H_5$, $CH_2OCCH$, $CH_2OCH_2CHCH_2$, $CH_2C_3H_7$, $CH_2CH_2OH$, $CH_2CH_2OCH_3$, $CH_2CH_2OC_2H_5$, $CH_2CH_2OCCH$, $CH_2CH_2OCH_2CHCH_2$, $CH_2CH_2OC_3H_7$;

R[20] is N or CH;

R[21] is N, CH, CCN, $CCF_3$, CC≡CH or CC(O)$NH_2$;

R[22] is H, OH, $NH_2$, SH, $SCH_3$, $SCH_2CH_3$, $SCH_2CCH$, $SCH_2CHCH_2$, $SC_3H_7$, $NH(CH_3)$, $N(CH_3)_2$, $NH(CH_2CH_3)$, $N(CH_2CH_3)_2$, $NH(CH_2CCH)$, $NH(CH_2CHCH_2)$, $NH(C_3H_7)$ or halogen (F, Cl, Br or I);

R[23] is H, OH, F, Cl, Br, I, $SCH_3$, $SCH_2CH_3$, $SCH_2CCH$, $SCH_2CHCH_2$, $SC_3H_7$, OR[16], $NH_2$, or NHR[17]; and R[24] is O, S or Se.

B includes both protected and unprotected forms of the bases. Protecting groups for exocyclic amines and other groups are known and include N-benzyl, isobutyryl, 4,4-dimethoxytrityl (DMT) and the like.

Exemplary bases include adenine, cytosine, guanine, hypoxanthine, inosine, thymine, uracil, xanthine, 2-aminopurine, 2,6-diaminopurine, 8-aza derivatives of adenine, guanine, 2-aminopurine, 2,6-diaminopurine, hypoxanthine, inosine and xanthine; 7-deaza-8-aza derivatives of adenine, guanine, 2-aminopurine, 2,6-diaminopurine, hypoxanthine, inosine and xanthine; 1-deaza derivatives of adenine, guanine, 2-aminopurine, 2,6-diaminopurine, hypoxanthine, inosine and xanthine; 7-deaza derivatives of adenine, guanine, 2-aminopurine, 2,6-diaminopurine, hypoxanthine, inosine and xanthine; 3-deaza derivatives of adenine, guanine, 2-aminopurine, 2,6-diaminopurine, hypoxanthine, inosine and xanthine; 6-azacytosine, 5-fluorocytosine, 5-chlorocytosine, 5-iodocytosine, 5-bromocytosine, 5-methylcytosine, 5-bromovinyluracil, 5-fluorouracil, 5-chlorouracil, 5-iodouracil, 5-bromouracil, 5-trifluoromethyluracil, 5-methoxymethyluracil, 5-ethynyluracil, 5-propynyluracil and the like. Bases also include protected species such as N[4]-benzoylcytosine, N[6]-benzoyladenine, N[2]-isobutyrylguanine and the like.

Typical bases include adenine, 1-deazaadenine, 3-deazaadenine, 7-deaza-8-azaadenine, 8-azaadenine, guanine, 2, 6-diaminopurine, 2-aminopurine, cytosine, 6-azacytosine, 5-fluorocytosine, 5-methylcytosine, 5-bromovinyluracil, 5-fluorouracil and 5-trifluoromethyluracil.

If the amino acid residue has 2 or more amine groups, e.g., a lysinyl or arginyl, or ornithinyl residue, then R[3] represents the group —[C(R[6])$_2$]$_{n2}$N(R[2])— where n2 is 0 to 6, R[6] is H, $C_1$–$C_{20}$ alkyl, $C_6$–$C_{20}$ aryl, $C_7$–$C_{20}$ alkylaryl, $C_7$–$C_{20}$ arylalkyl, $C_1$–$C_{20}$ alkoxy, $C_6$–$C_{20}$ aryloxy or hydroxyl, and R[2] is defined above. Such compounds will contain a plurality of phosphonate moieties. For example when both the epsilon (ε)/delta (δ) and alpha (α) amino groups of lysine or ornithine are substituted with nucleotide phosphonate moieties the amidate is believed to be capable of releasing two molecules of active drug, each expected to emerge under different pharmacokinetics and therefore further sustaining the drug release.

The number of amino acid residues, n1, in the nucleotide analog amidates of this invention can vary extensively. Where n1=1, a single amino acid is found at the designated site, and where n1>1 then a polypeptide radical is present. Typically, n1 is 1 or 2, but may range up to 3, 5, 10 or 100 or more residues.

If the residue is immediately adjacent to the phosphonate atom and its side chain contains a carboxyl group, e.g. in the case of glutamic acid or aspartic acid, then this carboxylate is substituted with R[4].

The amidate group optionally is taken together with Z to form a cyclic amidate precursor. Such compounds have structure XIV.

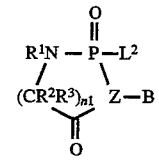

wherein L[2], R[1], R[2], R[3], Z, n1 and B are as defined above. Typically, in this embodiment R[3] is not carboxyl, R[2] is H, and n1 is 1.

Hydrolysis of the cyclic amidates of formulas IIa–c and IV leaves a hydroxyl-substituted substructure Z and the free carboxyl, which in turn will autolyze the amidate. Substructures Z in which the methylene backbone is substituted with hydroxymethyl are advantageous in this embodiment, particularly linkers in compounds of the formula —$CH_2OCH$($CH_2O$—)$CH_2$—B.

The invention compounds, such as those of the formulas (L[1])(RO)P(O)—Z—B, are optionally esterified at the phosphorus atom by the group R defined above. Exemplary R groups include phenyl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 2-, 3- and 4-pyridinyl, 2-, 4- and 5-pyrimidinyl, 2-, 3- and 4-alkoxyphenyl ($C_1$–$C_{12}$ alkyl including 2-, 3-and 4-methoxyphenyl and 2-, 3- and 4-ethoxyphenyl), 2-, 3- and 4-halophenyl (including 2-, 3- and 4-fluorophenyl), 2,3-, 2,4-, 2,5-, 2,6-, 3,4- and 3,5-dihalophenyl (including 2,4-difluorophenyl and 2,4-dichlorophenyl), 2-, 3-and 4-haloalkylphenyl (1 to 5 halogen atoms, $C_1$–$C_{12}$ alkyl including 2-, 3- and 4-trifluoromethylphenyl and 2-, 3- and 4-trichloromethylphenyl), 2-, 3- and 4-cyanophenyl, carboalkoxyphenyl ($C_1$–$C_4$ alkyl including 2-, 3- and 4-carboethoxyphenyl (—$C_6H_4$—C(O)—$OC_2H_5$) and 2,3-, 2,4-, 2,5-, 2,6-, 3,4- and 3,5-dicarboethoxyphenyl), 1-, 2-, 3-, and 4-pyridinyl (—$C_5H_4N$), 2-, 3- and 4-nitrophenyl, 2-, 3- and 4-haloalkylbenzyl (1 to 5 halogen atoms, $C_1$–$C_{12}$ alkyl including 4-trifluoromethylbenzyl), alkylsalicylphenyl ($C_1$–$C_4$ alkyl including 2-, 3- and 4-ethylsalicylphenyl), 2-,3- and 4-acetylphenyl, 1,8-dihydroxy-naphthyl (—O—$C_{10}H_6$—OH or —O—$C_{10}H_6$—O—), 2,2'-dihydroxybiphenyl (—O—$C_6H_4$—$C_6H_4$—O—; both oxygen atoms are linked to the phosphorus atom), alkoxy ethyl

[C$_1$-C$_6$ alkyl including —CH$_2$—CH$_2$—O—CH$_3$ (methoxy ethyl) and phenoxymethyl], aryloxy ethyl [C$_6$-C$_9$ aryl (including phenoxy ethyl) or C$_6$-C$_9$ aryl substituted by OH, NH$_2$, halo, C$_1$-C$_4$ alkyl or C$_1$-C$_4$ alkyl substituted by OH or by 1 to 3 halo atoms], —C$_6$H$_4$—CH$_2$—N(CH$_3$)$_2$, N-ethylmorpholino

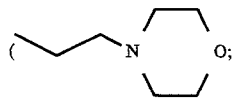

(CH$_2$)$_2$—N[(CH$_2$)$_2$(CH$_2$)$_2$]O), adamantoyl oxymethyl, pivaloyloxy(methoxyethyl)methyl (—CH(CH$_2$CH$_2$OCH$_3$)—O—C(O)—C(CH$_3$)$_3$),

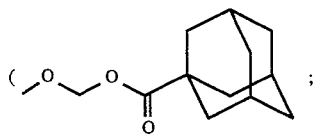

—O —CH$_2$—O—C(O)—C$_{10}$H$_{15}$), pivaloyloxymethyl (—CH$_2$—O—C(O)—C(CH$_3$)$_3$), pivaloyloxy (methoxymethyl)-methyl (—CH(CH$_2$OCH$_3$)—O—C(O)—C(CH$_3$)$_3$), pivaloyloxyisobutyl (—CH(CH(CH$_3$)$_2$)—O—C(O)—C(CH$_3$)$_3$) isobutyryloxymethyl (—CH$_2$—O—C(O)—CH$_2$—CH(CH$_3$)$_2$), cyclohexanoyl oxymethyl (—CH$_2$—O—C(O)—C$_6$H$_{11}$), phenyl (—C$_6$H$_5$), benzyl (—CH$_2$-C$_6$H$_5$), isopropyl (—CH(CH$_3$)$_2$), t-butyl (—C(CH$_3$)$_3$), —CH$_2$—CH$_3$, —(CH$_2$)$_2$—CH$_3$, —(CH$_2$)$_3$—CH$_3$, —(CH$_2$)$_4$—CH$_3$, —(CH$_2$)$_5$—CH$_3$, —CH$_2$—CH$_2$F, —CH$_2$—CH$_2$Cl, —CH$_2$—CF$_3$, —CH$_2$—CCl$_3$, R$^5$, NHR$^6$ or N(R$^6$)$_2$ wherein R$^5$ is CH$_2$C(O)N(R$^6$)$_2$, CH$_2$C(O)OR$^6$, CH$_2$OC(O)R$^6$, CH(R$^6$)OC(O)R$^6$, CH$_2$C(R$^6$)$_2$CH$_2$OH, or CH$_2$OR$^6$, and wherein R$^6$ is C$_1$-C$_{20}$ alkyl which is unsubstituted or substituted by substituents independently selected from the group consisting of OH, O, N and halogen (1 to 5 halogen atoms), C$_6$-C$_{20}$ aryl which is unsubstituted or substituted by substituents independently selected from the group consisting of OH, O, N and halogen (1 to 5 halogen atoms) or C$_7$-C$_{20}$ aryl-alkyl which is unsubstituted or substituted by substituents independently selected from the group consisting of OH, O, N and halogen (1 to 5 halogen atoms), provided that for compounds of formulas N(R$^6$)$_2$, CH$_2$C(O)N(R$^6$)$_2$, CH$_2$C(O)OR$^6$, CH$_2$OC(O)R$^6$, CH(R$^6$)OC(O)R$^6$ and CH$_2$C(R$^6$)$_2$CH$_2$OH, the total number of carbon atoms present is less than 25 (preferably the number of carbon atoms present is about 4 to about 14).

The invention compounds are optionally alkylated at the α-nitrogen atom of the amino acid by the R$^1$ group defined above. Exemplary R$^1$ groups include H, CH$_3$, CH$_2$CH$_3$, benzyl, 4—O—N-methylpiperidinyl

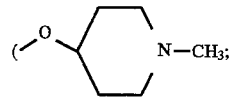

—O—CH[(CH$_2$)$_2$(CH$_2$)$_2$]N(CH$_3$)), 3—O—N-methylpiperidinyl and the like.

The invention compounds are optionally esterified at the amino acid carboxyl moiety by the R$^4$ group defined above. Exemplary R$^4$ groups include H, methyl, ethyl, propyl, isopropyl, butyl, t-butyl (C(CH$_3$)$_3$), phenyl (—C$_6$H$_5$), benzyl (—CH$_2$—C$_6$H$_5$), 1-pyridyl, 3-pyridyl, 1-pyrimidinyl, N-ethylmorpholino (—CH$_2$—CH$_2$—N[(CH$_2$)$_2$(CH$_2$)$_2$]O), N-2-propylmorpholino (—CH(CH$_3$)—CH$_2$—N[(CH$_2$)$_2$(CH$_2$)$_2$]O), methoxyethyl (—CH$_2$—CH$_2$—O—CH$_3$), 4-N-methylpiperidyl (—CH[(CH$_2$)$_2$(CH$_2$)$_2$]N(CH$_3$)), 3-N-methylpiperidyl, phenol which is 2-, 3-, or 4-substituted by N(R$^{30}$)$_2$ where R$^{30}$ is independently H or C$_1$-C$_6$ alkyl unsubstituted or substituted by substituents independently selected from the group consisting of OH, O, N, COOR$^4$ and halogen or C$_6$-C$_{12}$ aryl unsubstituted or substituted by substituents independently selected from the group consisting of OH, O, N, COOR$^4$, NR$^7$ and halogen (including 2-, 3-, and 4-N,N-dimethylaminophenol and 2-, 3-, and 4-N,N-diethylaminophenol), 1-ethylpiperazinyl

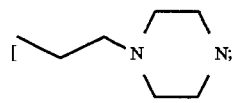

—CH$_2$—CH$_2$—NC$_4$H$_8$NH], and N$^4$-substituted 1-ethylpiperazinyl (—(CH$_2$)$_2$—N[(CH$_2$)$_2$(CH$_2$)$_2$]NR$^2$, where R$^2$ is as defined above).

Additional compounds that are included in the invention are nucleotide analog dimers that are linked via an amino or carboxyl group. As used herein, dimers (or trimers) refer to the presence of two (or three) nucleoside residues that comprise a compound. Thus, a —L$^1$—P(O)(L$^1$)—Z—B or —P(O)(L$^1$)—Z—B radical covalently linked to a —L$^1$—P(O)(L$^1$)—Z—B or —P(O)(L$^1$)—Z—B radical gives B—Z—P(O)(L$^1$)—P(O)(L$^1$)—Z—B, B—Z—P(O)(L$^1$)—L$^1$—P(O)(L$^1$)—Z—B or B—Z—P(O)(L$^1$)—L$^1$—L$^1$—P(O)L$^1$)—Z—S.

Dimer nucleotide analogs are conveniently linked via amino acids, diamino acids, dicarboxylic amino acids, diamines or dicarboxylic acids such as β-aminoalanine, diaminobutyric acid, citrulline, homoarginine, homocitrulline, ornithine, γ-aminobutyric acid, arginine, histidine, asparagine, glutamine, β-hydroxyaspartic acid, β-hydroxyglutamic acid, β-methylaspartic acid, β-methylglutamic acid, β-aminoadipic acid, 2-aminopimelic acid, 2-aminosuberic acid, β-amino acid analogs of lysine (NH$_2$—(CH$_2$)$_3$—CH(NH$_2$)—CH$_2$—CH—C(O)OH), arginine, histidine, asparagine, glutamine and the like. Exemplary compounds include dimers linked via lysine or β-lysine having the formulas B—Z—P(O)(L)—NH—(CH$_2$)$_4$—CH(C(O)OR$^4$)—NR$^1$— P(O)(L)—Z—B and B—Z—P(O)(L)—NH—(CH$_2$)$_3$—CH(CH$_2$C(O)OR$^4$)—NR$^1$—P(O)(L)—Z—B and dimers linked via aspartic or glutamic acid having the formula B—Z—P(O)(L)—O—C(O)—(CH$_2$)$_{1-2}$—CH(C(O)OR$^4$)—NR$^1$—P(O)(L)—Z—B. L, Z and B are independently selected.

Nucleotide analogs comprising dipeptidyl or tripeptidyl L groups are also included in the compounds of the invention. Nucleotide radicals are linked through side chain groups (usually amino or carboxyl) or through amino and carboxyl groups of the amino acids. Exemplary dipeptidyl and tripeptidyl dimers and trimers include compounds of the formulas B—Z—P(O)(L$^1$)—O—C(O)—(CR$^2$R$^3$)$_n$—NR$^1$—C(O)—(CR$^2$R$^3$)$_n$—NR$^1$—P(O)(L$^1$)—Z—B, B—Z—P(O)(L$^1$)—O—C(O )—(CR$_2$R$^3$)$_n$—NR$^1$—C(O )—(CR$^2$R$^3$)$_n$—NR$^1$—O—C(O)—(CR$^2$R$^3$)$_n$—NR$^1$—P(O)(L$^1$)—Z—B, B—Z—P(O)(L$^1$)—O—C(O)—CR$^2$(R$^3$—P(O)(L$^1$)—Z—B)—NR$^1$—C(O)—(CR$^2$R$^3$)$_n$—NR$^1$—P(O)(L$^1$)—Z—B and B—Z—P(O)(L$^1$)—O—C(O)—(CR$^2$R$^3$)$_n$—NR$^1$—C(O)—CR$^2$(R$^3$—P(O)(L$^1$)—Z—B)—NR$^1$—P(O)(L$^1$)—Z—B. In order to provide a compound with a desired molar ratio of one Z—B compared to a second Z—B, tetramer, pentamer and higher polymer forms can also be prepared where Z and/or B are independently chosen.

As used herein, the term alkyl, alkenyl and alkynyl refer to straight chain, branched and cyclic residues. Thus, $C_1$-$C_4$ alkyl includes methyl, ethyl, propyl, cydopropyl, isopropyl, n-, sec-, iso- and tert-butyl, cyclobutyl and the like while alkenyl includes ethenyl, propenyl, isopropenyl, 1-, 2- and 3-butenyl, 1- and 2-isobutenyl and the like. The term aryl includes phenyl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 2-, 3- and 4-pyridinyl, 2-, 4- and 5-pyrimidinyl.

Nucleoside Phosphonates.

Table 1 lists a group of exemplary nucleotide analogs of formula I having the structure $(L^1)(L^2)P(O)$—Z—B. These compounds generally have $L^1$ and $L^2$ groups that, when amino acids, are identical, although one of the amino acid groups can be different or replaced by another hydrolyzable group such as —O—$CH_2$—O—C(O)—$C(CH_3)_3$ or —O—$C_6H_5$ as listed below.

TABLE 1

| $L^1, L^{2*}$ | Z-B** |
|---|---|
| 1 —NH—$CH_2$—C(O)—$OR^4$ | 1 —$CH_2$—O—$CH_2$—$CH_2$—B |
| 2 —NH—$CH(CH_3)$—C(O)—$OR^4$ | 2 —$CH_2$—O—$C^\#H(CH_2$—$OR^4)$—$CH_2$—B |
| 3 —NH—$CH(CH)_2$—C(O)—$OR^4$ | 3 —$CH_2$—O—$C^\#H(CH_3)$—$CH_2$—B |
| 4 —NH—$CH(CH(CH_3)_2)$—C(O)—$OR^4$ | 4 —$CH_2$—O—$C^\#H(CH_2F)$—$CH_2$—B |
| 5 —NH—$CH(CH_3)(CH_3)_2$—C(O)—$OR^4$ | 5 —$CH_2$—O—$C^\#H(CH$=$CH_2)$—$CH_2$—B |
| 6 —NH—$CH_2$—$CH_2$—$CH_2$—CH—C(O)—$OR^4$ | 6 —$CH_2$—O—$C\# H(CH_2N_3)$—$CH_2$—B |
| 7 —NH—$CH(CH_2$—$C_6H_5)$—C(O)—$OR^4$ | 7 *** |
| 8 —NH—$CH(CH_2$—$C_3NH_6)$—C(O)—$OR^4$ | 8 **** |
| 9 —NH—$CH(CH_2$—$CH_2$—S—$CH_3)$—C(O)—$OR^4$ | |
| 10 —NH—$CH(CH_2OH)$—C(O)—$OR^4$ | |
| 11 —NH—$CH(CH(OH)(CH_3)$—C(O)—$OR^4$ | |
| 12 —NH—CH(—$CH_2SH)$—C(O)—$OR^4$ | |
| 13 —NH—$CH(CH_2$—$C_6H_5OH)$—C(O)—$OR^4$ | |
| 14 —NH—$CH(CH_2$—C(O)—$NH_2)$—C(O)—$OR^4$ | |
| 15 —NH—$CH(CH_2$—$CH_2$—C(O)—$NH_2)$—C(O)—$OR^4$ | |
| 16 —NH—$CH(CH_2C(O)OR^4)$—C(O)—$OR^4$ | |
| 17 —NH—$CH(CH_2CH_2C(O)OR^4)$—C(O)—$OR^4$ | |
| 18 —NH—$CH(CH_2CH_2CH_2CH_2NH_2)$—C(O)—$OR^4$ | |
| 19 —NH—$CH(CH_2CH_2CH_2NHC(NH)(NH_2))$—C(O)—$OR^4$ | |
| 20 —NH—$CH(CH_2C_3N_2H_3)$—C(O)—$OR^4$ | |
| 21 —NH—$CH(CH_3)2$—$CH_2$—C(O)—$OR^4$ | |
| 22 —NH—$CH_2$—$CH_2$—C(O)—$OR^4$ | |
| 23 —NH—$CH(CH_2$—$C_6H_5)$—$CH_2$—C(O)—$OR^4$ | |
| 24 —NH—$CH(CH_2CH_2CH_2NH_2)$—$CH_2$—C(O)—$OR^4$ | |
| 25 —NH—$CH(CH_2CH_2CH_2CH_2NH_2)$—$CH_2$—C(O)—$OR^4$ | |
| 26 —NH—$CH(CH_2CH_2NHC(NH)(NH_2))$—$CH_2$—C(O)—$OR^4$ | |
| 27 —NH—$CH(C(O)OR^4)$—$CH_2$—C(O)—$OR^4$ | |
| 28 —NH—$CH(CH_2C(O)OR^4)$—$CH_2$—C(O)—$OR^4$ | |
| 29 —NH—$CH(CH_2CH_2C(O)OR^4)$—$CH_2$—C(O)—$OR^4$ | |
| 30 —$N(CH_3)$—$CH_2$—C(O)—$OR^4$ | |
| 31 —$NHR^6$ | |
| 32 —O—$CH_2$—$CH_2$—$N[CH_2)_2(CH_2)_2]O$ | |
| 33 —O—$CH_2$—O—C(O)—$C(CH_3)_3$ | |
| 34 —O—$CH_2$—O—C(O)—$CH(CH_3)_2$ | |
| 35 —O—$CH_2$—O—C(O)—$CH_2C_6H_4$—O—$CH_2CH_3$ | |
| 36 —O—$CH_2$—O—C(O)—$C_{10}H_{15}$ | |
| 37 —O—$CH_2$—$C_6H_5$ | |
| 38 —O—$C_6H_5$ | |
| 39 —O—$CH_2$—$C_6H_4N(CH_3)_2$ | |
| 40 —OH | |

| B |
|---|
| 1 adenin-9-yl |
| 2 guanin-9-yl |
| 3 cytosin-1-yl |
| 4 2,6-diaminopurin-9-yl |
| 5 2-aminopurin-9-yl |
| 6 6-azacytosin-1-yl |
| 7 1-deazaadertin-9-yl |
| 8 3-deazaadenin-9-yl |
| 9 8-azaadenin-9-yl |
| 10 7-deaza-8-azaadenin-9-yl |

*$R^4$ includes H, propyl, isopropyl, t-butyl, phenyl, benzyl, 1-pyridinyl, 1-pyrimidinyl, N-ethylmorpholino, methoxyethyl, 4-hydroxy-N-methylpiperidinyl, 3-hydroxy-N-methylpiperidinyl, 1-ethylpiperazinyl; atoms with unfilled valences are linked to each other.
**The carbon atom on the left of each structure is attached to the phosphorus atom; #carbon atom in the R, S or RS configuration.
***Z—B substructure 7 is of formula V where $R^{25}$ and $R^{29}$ are O and B is thymin-1-yl (base 11) or one of the bases listed (1–10).
****Z—B substructure 8 is of formula IV where $R^{25}$ and $R^{29}$ are O, $R^{26}$ is S, $R^{27}$ is absent, $R^{28}$ is H and B is thymin-1-yl (base 11) or one of the bases listed (1–10) and includes the (+) and (−) enantiomers.

Compounds listed in Table 1 are designated herein by numbers assigned to $L^1$, $L^2$, Z and B according to the following convention, $L^1.L^2.Z.B$.

Thus, compound 1.2.1.1, where $R^4$ is benzyl, represents $L^1$ structure 1 (—NH—$CH_2$—C(O)—O—$CH_2$—$C_6H_5$), $L^2$ structure 2 (—NH—CH($CH_3$)—C(O)—O—$CH_2$—$C_6H_5$), Z structure 1 (—$CH_2$—O—$CH_2$—$CH_2$—) and B structure 1 (adenin-9-yl). This compound would have the structure

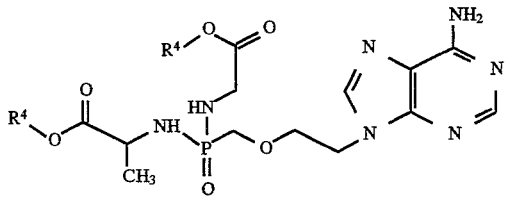

which corresponds to the compound designated herein bis (alanyl benzyl ester)PMEA. Similarly, for the compound 7.7.1.1, $L^1$ structure 7 (NH—CH($CH_2$—$C_6H_5$)—C(O)—$OR^4$), $L^2$ structure 7 (NH—CH($CH_2$—$C_6H_5$)—C(O)—$OR^4$), Z structure 2 (—$CH_2$—O—$CH_2$—$CH_2$—) and B structure 1 (adenin-9-yl) would have, when $R^4$ is methyl, the structure

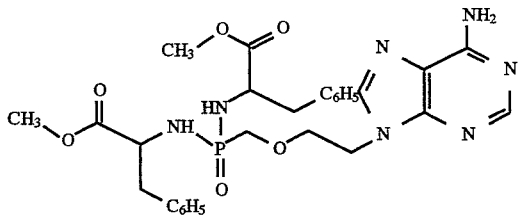

and would represent the compound designated herein bis (phenylalanyl methyl ester)PMEA. Exemplary compounds include 1.1.1.1, 2.1.1.1, 3.1.1.1, 4.1.1.1, 5.1.1.1, 6.1.1.1, 7.1.1.1, 8.1.1.1, 9.1.1.1, 10.1.1.1, 11.1.1.1, 12.1.1.1, 13.1.1.1, 14.1.1.1, 15.1.1.1, 16.1.1.1, 17.1.1.1, 18.1.1.1, 19.1.1.1, 20.1.1.1, 21.1.1.1, 22.1.1.1, 23.1.1.1, 24.1.1.1, 25.1.1.1, 26.1.1.1, 27.1.1.1, 28.1.1.1, 29.1.1.1, 30.1.1.1, 31.1.1.1, 32.1.1.1, 33.1.1.1, 34.1.1.1, 35.1.1.1, 36.1.1.1, 37.1.1.1, 38.1.1.1, 39.1.1.1, 40.1.1.1, 1.2.1.1, 2.2.1.1, 3.2.1.1, 4.2.1.1, 5.2.1.1, 6.2.1.1, 7.2.1.1, 8.2.1.1, 9.2.1.1, 10.2.1.1, 11.2.1.1, 12.2.1.1, 13.2.1.1, 14.2.1.1, 15.2.1.1, 16.2.1.1, 17.2.1.1, 18.2.1.1, 19.2.1.1, 20.2.1.1, 21.2.1.1, 22.2.1.1, 23.2.1.1, 24.2.1.1, 25.2.1.1, 26.2.1.1, 27.2.1.1, 28.2.1.1, 29.2.1.1, 30.2.1.1, 31.2.1.1, 32.2.1.1, 33.2.1.1, 34.2.1.1, 35.2.1.1, 36.2.1.1, 37.2.1.1, 38.2.1.1, 39.2.1.1, 40.2.1.1, 1.3.1.1, 2.3.1.1, 3.3.1.1, 4.3.1.1, 5.3.1.1, 6.3.1.1, 7.3.1.1, 8.3.1.1, 9.3.1.1, 10.3.1.1, 11.3.1.1, 12.3.1.1, 13.3.1.1, 14.3.1.1, 15.3.1.1, 16.3.1.1, 17.3.1.1, 18.3.1.1, 19.3.1.1, 20.3.1.1, 21.3.1.1, 22.3.1.1, 23.3.1.1, 24.3.1.1, 25.3.1.1, 26.3.1.1, 27.3.1.1, 28.3.1.1, 29.3.1.1, 30.3.1.1, 31.3.1.1, 32.3.1.1, 33.3.1.1, 34.3.1.1, 35.3.1.1, 36.3.1.1, 37.3.1.1, 38.3.1.1, 39.3.1.1, 40.3.1.1, 1.4.1.1, 2.4.1.1, 3.4.1.1, 4.4.1.1, 5.4.1.1, 6.4.1.1, 7.4.1.1, 8.4.1.1, 9.4.1.1, 10.4.1.1, 11.4.1.1, 12.4.1.1, 13.4.1.1, 14.4.1.1, 15.4.1.1, 16.4.1.1, 17.4.1.1, 18.4.1.1, 19.4.1.1, 20.4.1.1, 21.4.1.1, 22.4.1.1, 23.4.1.1, 24.4.1.1, 25.4.1.1, 26.4.1.1, 27.4.1.1, 28.4.1.1, 29.4.1.1, 30.4.1.1, 31.4.1.1, 32.4.1.1, 33.4.1.1, 34.4.1.1, 35.4.1.1, 36.4.1.1, 37.4.1.1, 38.4.1.1, 39.4.1.1, 40.4.1.1, 1.5.1.1, 2.5.1.1, 3.5.1.1, 4.5.1.1, 5.5.1.1, 6.5.1.1, 7.5.1.1, 8.5.1.1, 9.5.1.1, 10.5.1.1, 11.5.1.1, 12.5.1.1, 13.5.1.1, 14.5.1.1, 15.5.1.1, 16.5.1.1, 17.5.1.1, 18.5.1.1, 19.5.1.1, 20.5.1.1, 21.5.1.1, 22.5.1.1, 23.5.1.1, 24.5.1.1, 25.5.1.1, 26.5.1.1, 27.5.1.1, 28.5.1.1, 29.5.1.1, 30.5.1.1, 31.5.1.1, 32.5.1.1, 33.5.1.1, 34.5.1.1, 35.5.1.1, 36.5.1.1, 37.5.1.1, 38.5.1.1, 39.5.1.1, 40.5.1.1, 1.6.1.1, 2.6.1.1, 3.6.1.1, 4.6.1.1, 5.6.1.1, 6.6.1.1, 7.6.1.1, 8.6.1.1, 9.6.1.1, 10.6.1.1, 11.6.1.1, 12.6.1.1, 13.6.1.1, 14.6.1.1, 15.6.1.1, 16.6.1.1, 17.6.1.1, 18.6.1.1, 19.6.1.1, 20.6.1.1, 21.6.1.1, 22.6.1.1, 23.6.1.1, 24.6.1.1, 25.6.1.1, 26.6.1.1, 27.6.1.1, 28.6.1.1, 29.6.1.1, 30.6.1.1, 31.6.1.1, 32.6.1.1, 33.6.1.1, 34.6.1.1, 35.6.1.1, 36.6.1.1, 37.6.1.1, 38.6.1.1, 39.6.1.1, 40.6.1.1, 1.7.1.1, 2.7.1.1, 3.7.1.1, 4.7.1.1, 5.7.1.1, 6.7.1.1, 7.7.1.1, 8.7.1.1, 9.7.1.1, 10.7.1.1, 11.7.1.1, 12.7.1.1, 13.7.1.1, 14.7.1.1, 15.7.1.1, 16.7.1.1, 17.7.1.1, 18.7.1.1, 19.7.1.1, 20.7.1.1, 21.7.1.1, 22.7.1.1, 23.7.1.1, 24.7.1.1, 25.7.1.1, 26.7.1.1, 27.7.1.1, 28.7.1.1, 29.7.1.1, 30.7.1.1, 31.7.1.1, 32.7.1.1, 33.7.1.1, 34.7.1.1, 35.7.1.1, 36.7.1.1, 37.7.1.1, 38.7.1.1, 39.7.1.1, 40.7.1.1, 1.8.1.1, 2.8.1.1, 3.8.1.1, 4.8.1.1, 5.8.1.1, 6.8.1.1, 7.8.1.1, 8.8.1.1, 9.8.1.1, 10.8.1.1, 11.8.1.1, 12.8.1.1, 13.8.1.1, 14.8.1.1, 15.8.1.1, 16.8.1.1, 17.8.1.1, 18.8.1.1, 19.8.1.1, 20.8.1.1, 21.8.1.1, 22.8.1.1, 23.8.1.1, 24.8.1.1, 25.8.1.1, 26.8.1.1, 27.8.1.1, 28.8.1.1, 29.8.1.1, 30.8.1.1, 31.8.1.1, 32.8.1.1, 33.8.1.1, 34.8.1.1, 35.8.1.1, 36.8.1.1, 37.8.1.1, 38.8.1.1, 39.8.1.1, 40.8.1.1, 1.9.1.1, 2.9.1.1, 3.9.1.1, 4.9.1.1, 5.9.1.1, 6.9.1.1, 7.9.1.1, 8.9.1.1, 9.9.1.1, 10.9.1.1, 11.9.1.1, 12.9.1.1, 13.9.1.1, 14.9.1.1, 15.9.1.1, 16.9.1.1, 17.9.1.1, 18.9.1.1, 19.9.1.1, 20.9.1.1, 21.9.1.1, 22.9.1.1, 23.9.1.1, 24.9.1.1, 25.9.1.1, 26.9.1.1, 27.9.1.1, 28.9.1.1, 29.9.1.1, 30.9.1.1, 31.9.1.1, 32.9.1.1, 33.9.1.1, 34.9.1.1, 35.9.1.1, 36.9.1.1, 37.9.1.1, 38.9.1.1, 39.9.1.1, 40.9.1.1, 1.10.1.1, 2.10.1.1, 3.10.1.1, 4.10.1.1, 5.10.1.1, 6.10.1.1, 7.10.1.1, 8.10.1.1, 9.10.1.1, 10.10.1.1, 11.10.1.1, 12.10.1.1, 13.10.1.1, 14.10.1.1, 15.10.1.1, 16.10.1.1, 17.10.1.1, 18.10.1.1, 19.10.1.1, 20.10.1.1, 21.10.1.1, 22.10.1.1, 23.10.1.1, 24.10.1.1, 25.10.1.1, 26.10.1.1, 27.10.1.1, 28.10.1.1, 29.10.1.1, 30.10.1.1, 31.10.1.1, 32.10.1.1, 33.10.1.1, 34.10.1.1, 35.10.1.1, 36.10.1.1, 37.10.1.1, 38.10.1.1, 39.10.1.1, 40.10.1.1, 1.11.1.1, 2.11.1.1, 3.11.1.1, 4.11.1.1, 5.11.1.1, 6.11.1.1, 7.11.1.1, 8.11.1.1, 9.11.1.1, 10.11.1.1, 11.11.1.1, 12.11.1.1, 13.11.1.1, 14.11.1.1, 15.11.1.1, 16.11.1.1, 17.11.1.1, 18.11.1.1, 19.11.1.1, 20.11.1.1, 21.11.1.1, 22.11.1.1, 23.11.1.1, 24.11.1.1, 25.11.1.1, 26.11.1.1, 27.11.1.1, 28.11.1.1, 29.11.1.1, 30.11.1.1, 31.11.1.1, 32.11.1.1, 33.11.1.1, 34.11.1.1, 35.11.1.1, 36.11.1.1, 37.11.1.1, 38.11.1.1, 39.11.1.1, 40.11.1.1, 1.12.1.1, 2.12.1.1, 3.12.1.1, 4.12.1.1, 5.12.1.1, 6.12.1.1, 7.12.1.1, 8.12.1.1, 9.12.1.1, 10.12.1.1, 11.12.1.1, 12.12.1.1, 13.12.1.1, 14.12.1.1, 15.12.1.1, 16.12.1.1, 17.12.1.1, 18.12.1.1, 19.12.1.1, 20.12.1.1, 21.12.1.1, 22.12.1.1, 23.12.1.1, 24.12.1.1, 25.12.1.1, 26.12.1.1, 27.12.1.1, 28.12.1.1, 29.12.1.1, 30.12.1.1, 31.12.1.1, 32.12.1.1, 33.12.1.1, 34.12.1.1, 35.12.1.1, 36.12.1.1, 37.12.1.1, 38.12.1.1, 39.12.1.1, 40.12.1.1, 1.13.1.1, 2.13.1.1, 3.13.1.1, 4.13.1.1, 5.13.1.1, 6.13.1.1, 7.13.1.1, 8.13.1.1, 9.13.1.1, 10.13.1.1, 11.13.1.1, 12.13.1.1, 13.13.1.1, 14.13.1.1, 15.13.1.1, 16.13.1.1, 17.13.1.1, 18.13.1.1, 19.13.1.1, 20.13.1.1, 21.13.1.1, 22.13.1.1, 23.13.1.1, 24.13.1.1, 25.13.1.1, 26.13.1.1, 27.13.1.1, 28.13.1.1, 29.13.1.1, 30.13.1.1, 31.13.1.1, 32.13.1.1, 33.13.1.1, 34.13.1.1, 35.13.1.1, 36.13.1.1, 37.13.1.1, 38.13.1.1, 39.13.1.1, 40.13.1.1, 1.14.1.1, 2.14.1.1, 3.14.1.1, 4.14.1.1, 5.14.1.1, 6.14.1.1, 7.14.1.1, 8.14.1.1, 9.14.1.1, 10.14.1.1, 11.14.1.1, 12.14.1.1, 13.14.1.1, 14.14.1.1, 15.14.1.1, 16.14.1.1, 17.14.1.1, 18.14.1.1, 19.14.1.1, 20.14.1.1, 21.14.1.1, 22.14.1.1, 23.14.1.1, 24.14.1.1, 25.14.1.1, 26.14.1.1, 27.14.1.1, 28.14.1.1, 29.14.1.1, 30.14.1.1, 31.14.1.1, 32.14.1.1, 33.14.1.1, 34.14.1.1, 35.14.1.1, 36.14.1.1, 37.14.1.1, 38.14.1.1, 39.14.1.1, 40.14.1.1, 1.15.1.1, 2.15.1.1, 3.15.1.1, 4.15.1.1, 5.15.1.1, 6.15.1.1, 7.15.1.1, 8.15.1.1, 9.15.1.1, 10.15.1.1, 11.15.1.1, 12.15.1.1, 13.15.1.1, 14.15.1.1, 15.15.1.1, 16.15.1.1, 17.15.1.1, 18.15.1.1, 19.15.1.1, 20.15.1.1, 21.15.1.1, 22.15.1.1, 23.15.1.1, 24.15.1.1, 25.15.1.1, 26.15.1.1, 27.15.1.1, 28.15.1.1, 29.15.1.1, 30.15.1.1, 31.15.1.1, 32.15.1.1, 33.15.1.1, 34.15.1.1, 35.15.1.1, 36.15.1.1, 37.15.1.1, 38.15.1.1, 39.15.1.1, 40.15.1.1, 1.16.1.1, 2.16.1.1, 3.16.1.1, 4.16.1.1, 5.16.1.1, 6.16.1.1, 7.16.1.1, 8.16.1.1, 9.16.1.1, 10.16.1.1, 11.16.1.1, 12.16.1.1, 13.16.1.1, 14.16.1.1, 15.16.1.1, 16.16.1.1, 17.16.1.1, 18.16.1.1, 19.16.1.1, 20.16.1.1, 21.16.1.1, 22.16.1.1, 23.16.1.1, 24.16.1.1, 25.16.1.1, 26.16.1.1, 27.16.1.1, 28.16.1.1, 29.16.1.1, 30.16.1.1, 31.16.1.1, 32.16.1.1, 33.16.1.1, 34.16.1.1, 35.16.1.1, 36.16.1.1, 37.16.1.1, 38.16.1.1, 39.16.1.1, 40.16.1.1, 1.17.1.1, 2.17.1.1, 3.17.1.1, 4.17.1.1, 5.17.1.1, 6.17.1.1, 7.17.1.1, 8.17.1.1, 9.17.1.1, 10.17.1.1, 11.17.1.1, 12.17.1.1, 13.17.1.1, 14.17.1.1, 15.17.1.1, 16.17.1.1, 17.17.1.1, 18.17.1.1, 19.17.1.1, 20.17.1.1, 21.17.1.1, 22.17.1.1, 23.17.1.1, 24.17.1.1, 25.17.1.1, 26.17.1.1, 27.17.1.1, 28.17.1.1, 29.17.1.1, 30.17.1.1, 31.17.1.1, 32.17.1.1, 33.17.1.1, 34.17.1.1, 35.17.1.1, 36.17.1.1, 37.17.1.1, 38.17.1.1, 39.17.1.1, 40.17.1.1, 1.18.1.1, 2.18.1.1, 3.18.1.1, 4.18.1.1, 5.18.1.1, 6.18.1.1, 7.18.1.1, 8.18.1.1, 9.18.1.1, 10.18.1.1, 11.18.1.1, 12.18.1.1, 13.18.1.1, 14.18.1.1, 15.18.1.1, 16.18.1.1, 17.18.1.1, 18.18.1.1, 19.18.1.1, 20.18.1.1, 21.18.1.1, 22.18.1.1, 23.18.1.1, 24.18.1.1, 25.18.1.1, 26.18.1.1, 27.18.1.1, 28.18.1.1, 29.18.1.1, 30.18.1.1, 31.18.1.1, 32.18.1.1, 33.18.1.1, 34.18.1.1, 35.18.1.1, 36.18.1.1, 37.18.1.1, 38.18.1.1, 39.18.1.1, 40.18.1.1, 1.19.1.1, 2.19.1.1, 3.19.1.1, 4.19.1.1, 5.19.1.1, 6.19.1.1, 7.19.1.1, 8.19.1.1, 9.19.1.1, 10.19.1.1, 11.19.1.1, 12.19.1.1, 13.19.1.1, 14.19.1.1, 15.19.1.1, 16.19.1.1, 17.19.1.1, 18.19.1.1, 19.19.1.1, 20.19.1.1, 21.19.1.1, 22.19.1.1, 23.19.1.1, 24.19.1.1, 25.19.1.1, 26.19.1.1, 27.19.1.1, 28.19.1.1, 29.19.1.1, 30.19.1.1, 31.19.1.1, 32.19.1.1, 33.19.1.1, 34.19.1.1, 35.19.1.1, 36.19.1.1, 37.19.1.1, 38.19.1.1, 39.19.1.1, 40.19.1.1, 1.20.1.1, 2.20.1.1, 3.20.1.1, 4.20.1.1, 5.20.1.1, 6.20.1.1, 7.20.1.1, 8.20.1.1, 9.20.1.1, 10.20.1.1, 11.20.1.1, 12.20.1.1, 13.20.1.1, 14.20.1.1, 15.20.1.1, 16.20.1.1, 17.20.1.1, 18.20.1.1, 19.20.1.1, 20.20.1.1, 21.20.1.1, 22.20.1.1, 23.20.1.1, 24.20.1.1, 25.20.1.1, 26.20.1.1, 27.20.1.1, 28.20.1.1, 29.20.1.1, 30.20.1.1, 31.20.1.1, 32.20.1.1, 33.20.1.1, 34.20.1.1, 35.20.1.1, 36.20.1.1, 37.20.1.1, 38.20.1.1, 39.20.1.1, 40.20.1.1, 1.21.1.1, 2.21.1.1, 3.21.1.1, 4.21.1.1, 5.21.1.1, 6.21.1.1, 7.21.1.1, 8.21.1.1, 9.21.1.1, 10.21.1.1, 11.21.1.1, 12.21.1.1, 13.21.1.1, 14.21.1.1, 15.21.1.1, 16.21.1.1, 17.21.1.1, 18.21.1.1, 19.21.1.1, 20.21.1.1, 21.21.1.1, 22.21.1.1, 23.21.1.1, 24.21.1.1, 25.21.1.1, 26.21.1.1, 27.21.1.1, 28.21.1.1, 29.21.1.1, 30.21.1.1, 31.21.1.1, 32.21.1.1, 33.21.1.1, 34.21.1.1, 35.21.1.1, 36.21.1.1, 37.21.1.1, 38.21.1.1, 39.21.1.1, 40.21.1.1, 1.22.1.1, 2.22.1.1, 3.22.1.1, 4.22.1.1, 5.22.1.1, 6.22.1.1, 7.22.1.1, 8.22.1.1, 9.22.1.1, 10.22.1.1, 11.22.1.1, 12.22.1.1, 13.22.1.1, 14.22.1.1, 15.22.1.1, 16.22.1.1, 17.22.1.1, 18.22.1.1, 19.22.1.1, 20.22.1.1, 21.22.1.1, 22.22.1.1, 23.22.1.1, 24.22.1.1, 25.22.1.1, 26.22.1.1, 27.22.1.1, 28.22.1.1, 29.22.1.1, 30.22.1.1, 31.22.1.1, 32.22.1.1, 33.22.1.1, 34.22.1.1, 35.22.1.1, 36.22.1.1, 37.22.1.1, 38.22.1.1, 39.22.1.1, 40.22.1.1, 1.23.1.1, 2.23.1.1, 3.23.1.1, 4.23.1.1, 5.23.1.1, 6.23.1.1, 7.23.1.1, 8.23.1.1, 9.23.1.1, 10.23.1.1, 11.23.1.1, 12.23.1.1, 13.23.1.1, 14.23.1.1, 15.23.1.1, 16.23.1.1, 17.23.1.1, 18.23.1.1, 19.23.1.1, 20.23.1.1, 21.23.1.1, 22.23.1.1, 23.23.1.1, 24.23.1.1, 25.23.1.1, 26.23.1.1, 27.23.1.1, 28.23.1.1, 29.23.1.1, 30.23.1.1, 31.23.1.1, 32.23.1.1, 33.23.1.1, 34.23.1.1, 35.23.1.1, 36.23.1.1, 37.23.1.1, 38.23.1.1, 39.23.1.1, 40.23.1.1, 1.24.1.1, 2.24.1.1, 3.24.1.1, 4.24.1.1, 5.24.1.1, 6.24.1.1, 7.24.1.1, 8.24.1.1, 9.24.1.1, 10.24.1.1, 11.24.1.1, 12.24.1.1, 13.24.1.1, 14.24.1.1, 15.24.1.1, 16.24.1.1, 17.24.1.1, 18.24.1.1, 19.24.1.1, 20.24.1.1, 21.24.1.1, 22.24.1.1, 23.24.1.1, 24.24.1.1, 25.24.1.1, 26.24.1.1, 27.24.1.1, 28.24.1.1, 29.24.1.1, 30.24.1.1, 31.24.1.1, 32.24.1.1, 33.24.1.1, 34.24.1.1, 35.24.1.1, 36.24.1.1, 37.24.1.1, 38.24.1.1, 39.24.1.1, 40.24.1.1, 1.25.1.1, 2.25.1.1, 3.25.1.1, 4.25.1.1, 5.25.1.1, 6.25.1.1, 7.25.1.1, 8.25.1.1, 9.25.1.1, 10.25.1.1, 11.25.1.1, 12.25.1.1, 13.25.1.1, 14.25.1.1, 15.25.1.1, 16.25.1.1, 17.25.1.1, 18.25.1.1, 19.25.1.1, 20.25.1.1, 21.25.1.1, 22.25.1.1, 23.25.1.1, 24.25.1.1, 25.25.1.1, 26.25.1.1, 27.25.1.1, 28.25.1.1, 29.25.1.1, 30.25.1.1, 31.25.1.1, 32.25.1.1, 33.25.1.1, 34.25.1.1, 35.25.1.1, 36.25.1.1, 37.25.1.1, 38.25.1.1, 39.25.1.1, 40.25.1.1, 1.26.1.1, 2.26.1.1, 3.26.1.1, 4.26.1.1, 5.26.1.1, 6.26.1.1, 7.26.1.1, 8.26.1.1, 9.26.1.1, 10.26.1.1, 11.26.1.1, 12.26.1.1, 13.26.1.1, 14.26.1.1, 15.26.1.1, 16.26.1.1, 17.26.1.1, 18.26.1.1, 19.26.1.1, 20.26.1.1, 21.26.1.1, 22.26.1.1, 23.26.1.1, 24.26.1.1, 25.26.1.1, 26.26.1.1, 27.26.1.1, 28.26.1.1, 29.26.1.1, 30.26.1.1, 31.26.1.1, 32.26.1.1, 33.26.1.1, 34.26.1.1, 35.26.1.1, 36.26.1.1, 37.26.1.1, 38.26.1.1, 39.26.1.1, 40.26.1.1, 1.27.1.1, 2.27.1.1, 3.27.1.1, 4.27.1.1, 5.27.1.1, 6.27.1.1, 7.27.1.1, 8.27.1.1, 9.27.1.1, 10.27.1.1, 11.27.1.1, 12.27.1.1, 13.27.1.1, 14.27.1.1, 15.27.1.1, 16.27.1.1, 17.27.1.1, 18.27.1.1, 19.27.1.1, 20.27.1.1, 21.27.1.1, 22.27.1.1, 23.27.1.1, 24.27.1.1, 25.27.1.1, 26.27.1.1, 27.27.1.1, 28.27.1.1, 29.27.1.1, 30.27.1.1, 31.27.1.1, 32.27.1.1, 33.27.1.1, 34.27.1.1, 35.27.1.1, 36.27.1.1, 37.27.1.1, 38.27.1.1, 39.27.1.1, 40.27.1.1, 1.28.1.1, 2.28.1.1, 3.28.1.1, 4.28.1.1, 5.28.1.1, 6.28.1.1, 7.28.1.1, 8.28.1.1, 9.28.1.1, 10.28.1.1, 11.28.1.1, 12.28.1.1, 13.28.1.1, 14.28.1.1, 15.28.1.1, 16.28.1.1, 17.28.1.1, 18.28.1.1, 19.28.1.1, 20.28.1.1, 21.28.1.1, 22.28.1.1, 23.28.1.1, 24.28.1.1, 25.28.1.1, 26.28.1.1, 27.28.1.1, 28.28.1.1, 29.28.1.1, 30.28.1.1, 31.28.1.1, 32.28.1.1, 33.28.1.1, 34.28.1.1, 35.28.1.1, 36.28.1.1, 37.28.1.1, 38.28.1.1, 39.28.1.1, 40.28.1.1, 1.29.1.1, 2.29.1.1, 3.29.1.1, 4.29.1.1, 5.29.1.1, 6.29.1.1, 7.29.1.1, 8.29.1.1, 9.29.1.1, 10.29.1.1, 11.29.1.1, 12.29.1.1, 13.29.1.1, 14.29.1.1, 15.29.1.1, 16.29.1.1, 17.29.1.1, 18.29.1.1, 19.29.1.1, 20.29.1.1, 21.29.1.1, 22.29.1.1, 23.29.1.1, 24.29.1.1, 25.29.1.1, 26.29.1.1, 27.29.1.1, 28.29.1.1, 29.29.1.1, 30.29.1.1, 31.29.1.1, 32.29.1.1, 33.29.1.1, 34.29.1.1, 35.29.1.1, 36.29.1.1, 37.29.1.1, 38.29.1.1, 39.29.1.1, 40.29.1.1, 1.1.1.2, 2.1.1.2, 3.1.1.2, 4.1.1.2, 5.1.1.2, 6.1.1.2, 7.1.1.2, 8.1.1.2, 9.1.1.2, 10.1.1.2, 11.1.1.2, 12.1.1.2, 13.1.1.2, 14.1.1.2, 15.1.1.2, 16.1.1.2, 17.1.1.2, 18.1.1.2, 19.1.1.2, 20.1.1.2, 21.1.1.2, 22.1.1.2, 23.1.1.2, 24.1.1.2, 25.1.1.2, 26.1.1.2, 27.1.1.2, 28.1.1.2, 29.1.1.2, 30.1.1.2, 31.1.1.2, 32.1.1.2, 33.1.1.2, 34.1.1.2, 35.1.1.2, 36.1.1.2, 37.1.1.2, 38.1.1.2, 39.1.1.2, 40.1.1.2, 1.2.1.2, 2.2.1.2, 3.2.1.2, 4.2.1.2, 5.2.1.2, 6.2.1.2, 7.2.1.2, 8.2.1.2, 9.2.1.2, 10.2.1.2, 11.2.1.2, 12.2.1.2, 13.2.1.2, 14.2.1.2, 15.2.1.2, 16.2.1.2, 17.2.1.2, 18.2.1.2, 19.2.1.2, 20.2.1.2, 21.2.1.2, 22.2.1.2, 23.2.1.2, 24.2.1.2, 25.2.1.2, 26.2.1.2, 27.2.1.2, 28.2.1.2, 29.2.1.2, 30.2.1.2, 31.2.1.2, 32.2.1.2, 33.2.1.2, 34.2.1.2, 35.2.1.2, 36.2.1.2, 37.2.1.2, 38.2.1.2, 39.2.1.2, 40.2.1.2, 1.3.1.2, 2.3.1.2, 3.3.1.2, 4.3.1.2, 5.3.1.2, 6.3.1.2, 7.3.1.2, 8.3.1.2, 9.3.1.2, 10.3.1.2, 11.3.1.2, 12.3.1.2, 13.3.1.2, 14.3.1.2, 15.3.1.2, 16.3.1.2, 17.3.1.2, 18.3.1.2, 19.3.1.2, 20.3.1.2, 21.3.1.2, 22.3.1.2, 23.3.1.2, 24.3.1.2, 25.3.1.2, 26.3.1.2, 27.3.1.2, 28.3.1.2, 29.3.1.2, 30.3.1.2, 31.3.1.2, 32.3.1.2, 33.3.1.2, 34.3.1.2, 35.3.1.2, 36.3.1.2, 37.3.1.2, 38.3.1.2, 39.3.1.2, 40.3.1.2, 1.4.1.2, 2.4.1.2, 3.4.1.2, 4.4.1.2, 5.4.1.2, 6.4.1.2, 7.4.1.2, 8.4.1.2, 9.4.1.2, 10.4.1.2, 11.4.1.2, 12.4.1.2, 13.4.1.2, 14.4.1.2, 15.4.1.2, 16.4.1.2, 17.4.1.2, 18.4.1.2, 19.4.1.2, 20.4.1.2, 21.4.1.2, 22.4.1.2, 23.4.1.2, 24.4.1.2, 25.4.1.2, 26.4.1.2, 27.4.1.2, 28.4.1.2, 29.4.1.2, 30.4.1.2, 31.4.1.2, 32.4.1.2, 33.4.1.2, 34.4.1.2, 35.4.1.2, 36.4.1.2, 37.4.1.2, 38.4.1.2, 39.4.1.2, 40.4.1.2, 1.5.1.2, 2.5.1.2, 3.5.1.2, 4.5.1.2, 5.5.1.2, 6.5.1.2, 7.5.1.2, 8.5.1.2, 9.5.1.2, 10.5.1.2, 11.5.1.2, 12.5.1.2, 13.5.1.2, 14.5.1.2, 15.5.1.2, 16.5.1.2, 17.5.1.2, 18.5.1.2, 19.5.1.2, 20.5.1.2, 21.5.1.2, 22.5.1.2, 23.5.1.2, 24.5.1.2, 25.5.1.2, 26.5.1.2, 27.5.1.2, 28.5.1.2, 29.5.1.2, 30.5.1.2, 31.5.1.2, 32.5.1.2, 33.5.1.2, 34.5.1.2, 35.5.1.2, 36.5.1.2, 37.5.1.2, 38.5.1.2, 39.5.1.2, 40.5.1.2, 1.6.1.2, 2.6.1.2, 3.6.1.2, 4.6.1.2, 5.6.1.2, 6.6.1.2, 7.6.1.2, 8.6.1.2, 9.6.1.2, 10.6.1.2, 11.6.1.2, 12.6.1.2, 13.6.1.2, 14.6.1.2, 15.6.1.2, 16.6.1.2, 17.6.1.2, 18.6.1.2, 19.6.1.2, 20.6.1.2, 21.6.1.2, 22.6.1.2, 23.6.1.2, 24.6.1.2, 25.6.1.2, 26.6.1.2, 27.6.1.2, 28.6.1.2, 29.6.1.2, 30.6.1.2, 31.6.1.2, 32.6.1.2, 33.6.1.2, 34.6.1.2, 35.6.1.2, 36.6.1.2, 37.6.1.2, 38.6.1.2, 39.6.1.2, 40.6.1.2, 1.7.1.2, 2.7.1.2, 3.7.1.2, 4.7.1.2, 5.7.1.2, 6.7.1.2, 7.7.1.2, 8.7.1.2, 9.7.1.2, 10.7.1.2, 11.7.1.2, 12.7.1.2, 13.7.1.2, 14.7.1.2, 15.7.1.2, 16.7.1.2, 17.7.1.2, 18.7.1.2, 19.7.1.2, 20.7.1.2, 21.7.1.2, 22.7.1.2, 23.7.1.2, 24.7.1.2, 25.7.1.2, 26.7.1.2, 27.7.1.2, 28.7.1.2, 29.7.1.2, 30.7.1.2, 31.7.1.2, 32.7.1.2, 33.7.1.2, 34.7.1.2, 35.7.1.2, 36.7.1.2, 37.7.1.2, 38.7.1.2, 39.7.1.2, 40.7.1.2, 1.8.1.2, 2.8.1.2, 3.8.1.2, 4.8.1.2, 5.8.1.2, 6.8.1.2, 7.8.1.2, 8.8.1.2, 9.8.1.2, 10.8.1.2, 11.8.1.2, 12.8.1.2, 13.8.1.2, 14.8.1.2, 15.8.1.2, 16.8.1.2, 17.8.1.2, 18.8.1.2, 19.8.1.2, 20.8.1.2, 21.8.1.2, 22.8.1.2, 23.8.1.2, 24.8.1.2, 25.8.1.2, 26.8.1.2, 27.8.1.2, 28.8.1.2, 29.8.1.2, 30.8.1.2, 31.8.1.2, 32.8.1.2, 33.8.1.2, 34.8.1.2, 35.8.1.2, 36.8.1.2, 37.8.1.2, 38.8.1.2, 39.8.1.2, 40.8.1.2, 1.9.1.2, 2.9.1.2, 3.9.1.2, 4.9.1.2, 5.9.1.2, 6.9.1.2, 7.9.1.2, 8.9.1.2, 9.9.1.2, 10.9.1.2, 11.9.1.2, 12.9.1.2, 13.9.1.2, 14.9.1.2, 15.9.1.2, 16.9.1.2, 17.9.1.2, 18.9.1.2, 19.9.1.2, 20.9.1.2, 21.9.1.2, 22.9.1.2, 23.9.1.2, 24.9.1.2, 25.9.1.2, 26.9.1.2, 27.9.1.2, 28.9.1.2, 29.9.1.2, 30.9.1.2, 31.9.1.2, 32.9.1.2, 33.9.1.2, 34.9.1.2, 35.9.1.2, 36.9.1.2, 37.9.1.2, 38.9.1.2, 39.9.1.2, 40.9.1.2, 1.10.1.2, 2.10.1.2, 3.10.1.2, 4.10.1.2, 5.10.1.2, 6.10.1.2, 7.10.1.2, 8.10.1.2, 9.10.1.2, 10.10.1.2, 11.10.1.2, 12.10.1.2, 13.10.1.2, 14.10.1.2, 15.10.1.2, 16.10.1.2, 17.10.1.2, 18.10.1.2, 19.10.1.2, 20.10.1.2, 21.10.1.2, 22.10.1.2, 23.10.1.2, 24.10.1.2, 25.10.1.2, 26.10.1.2, 27.10.1.2, 28.10.1.2, 29.10.1.2, 30.10.1.2, 31.10.1.2, 32.10.1.2, 33.10.1.2, 34.10.1.2, 35.10.1.2, 36.10.1.2, 37.10.1.2, 38.10.1.2, 39.10.1.2, 40.10.1.2, 1.11.1.2, 2.11.1.2, 3.11.1.2, 4.11.1.2, 5.11.1.2, 6.11.1.2, 7.11.1.2, 8.11.1.2, 9.11.1.2, 10.11.1.2, 11.11.1.2, 12.11.1.2, 13.11.1.2, 14.11.1.2, 15.11.1.2, 16.11.1.2, 17.11.1.2, 18.11.1.2, 19.11.1.2, 20.11.1.2, 21.11.1.2, 22.11.1.2, 23.11.1.2, 24.11.1.2, 25.11.1.2, 26.11.1.2, 27.11.1.2, 28.11.1.2, 29.11.1.2, 30.11.1.2, 31.11.1.2, 32.11.1.2, 33.11.1.2, 34.11.1.2, 35.11.1.2, 36.11.1.2, 37.11.1.2, 38.11.1.2, 39.11.1.2, 40.11.1.2, 1.12.1.2, 2.12.1.2, 3.12.1.2, 4.12.1.2, 5.12.1.2, 6.12.1.2, 7.12.1.2, 8.12.1.2, 9.12.1.2, 10.12.1.2, 11.12.1.2, 12.12.1.2, 13.12.1.2, 14.12.1.2, 15.12.1.2, 16.12.1.2, 17.12.1.2, 18.12.1.2, 19.12.1.2, 20.12.1.2, 21.12.1.2, 22.12.1.2, 23.12.1.2, 24.12.1.2, 25.12.1.2, 26.12.1.2, 27.12.1.2, 28.12.1.2, 29.12.1.2, 30.12.1.2, 31.12.1.2, 32.12.1.2, 33.12.1.2, 34.12.1.2, 35.12.1.2, 36.12.1.2, 37.12.1.2, 38.12.1.2, 39.12.1.2, 40.12.1.2, 1.13.1.2, 2.13.1.2, 3.13.1.2, 4.13.1.2, 5.13.1.2, 6.13.1.2, 7.13.1.2, 8.13.1.2, 9.13.1.2, 10.13.1.2, 11.13.1.2, 12.13.1.2, 13.13.1.2, 14.13.1.2, 15.13.1.2, 16.13.1.2, 17.13.1.2, 18.13.1.2, 19.13.1.2, 20.13.1.2, 21.13.1.2, 22.13.1.2, 23.13.1.2, 24.13.1.2, 25.13.1.2, 26.13.1.2, 27.13.1.2, 28.13.1.2, 29.13.1.2, 30.13.1.2, 31.13.1.2, 32.13.1.2, 33.13.1.2, 34.13.1.2, 35.13.1.2, 36.13.1.2, 37.13.1.2, 38.13.1.2, 39.13.1.2, 40.13.1.2, 1.14.1.2, 2.14.1.2, 3.14.1.2, 4.14.1.2, 5.14.1.2, 6.14.1.2, 7.14.1.2, 8.14.1.2, 9.14.1.2, 10.14.1.2, 11.14.1.2, 12.14.1.2, 13.14.1.2, 14.14.1.2, 15.14.1.2, 16.14.1.2, 17.14.1.2, 18.14.1.2, 19.14.1.2, 20.14.1.2, 21.14.1.2, 22.14.1.2, 23.14.1.2, 24.14.1.2, 25.14.1.2, 26.14.1.2, 27.14.1.2, 28.14.1.2, 29.14.1.2, 30.14.1.2, 31.14.1.2, 32.14.1.2, 33.14.1.2, 34.14.1.2, 35.14.1.2, 36.14.1.2, 37.14.1.2, 38.14.1.2, 39.14.1.2, 40.14.1.2, 1.15.1.2, 2.15.1.2, 3.15.1.2, 4.15.1.2, 5.15.1.2, 6.15.1.2, 7.15.1.2, 8.15.1.2, 9.15.1.2, 10.15.1.2, 11.15.1.2, 12.15.1.2, 13.15.1.2, 14.15.1.2, 15.15.1.2, 16.15.1.2, 17.15.1.2, 18.15.1.2, 19.15.1.2, 20.15.1.2, 21.15.1.2, 22.15.1.2, 23.15.1.2, 24.15.1.2, 25.15.1.2, 26.15.1.2, 27.15.1.2, 28.15.1.2, 29.15.1.2, 30.15.1.2, 31.15.1.2, 32.15.1.2, 33.15.1.2, 34.15.1.2, 35.15.1.2, 36.15.1.2, 37.15.1.2, 38.15.1.2, 39.15.1.2, 40.15.1.2, 1.16.1.2, 2.16.1.2, 3.16.1.2, 4.16.1.2, 5.16.1.2, 6.16.1.2, 7.16.1.2, 8.16.1.2, 9.16.1.2, 10.16.1.2, 11.16.1.2, 12.16.1.2, 13.16.1.2, 14.16.1.2, 15.16.1.2, 16.16.1.2, 17.16.1.2, 18.16.1.2, 19.16.1.2, 20.16.1.2, 21.16.1.2, 22.16.1.2, 23.16.1.2, 24.16.1.2, 25.16.1.2, 26.16.1.2, 27.16.1.2, 28.16.1.2, 29.16.1.2, 30.16.1.2, 31.16.1.2, 32.16.1.2, 33.16.1.2, 34.16.1.2, 35.16.1.2, 36.16.1.2, 37.16.1.2, 38.16.1.2, 39.16.1.2, 40.16.1.2, 1.17.1.2, 2.17.1.2, 3.17.1.2, 4.17.1.2, 5.17.1.2, 6.17.1.2, 7.17.1.2, 8.17.1.2, 9.17.1.2, 10.17.1.2, 11.17.1.2, 12.17.1.2, 13.17.1.2, 14.17.1.2, 15.17.1.2, 16.17.1.2, 17.17.1.2, 18.17.1.2, 19.17.1.2, 20.17.1.2, 21.17.1.2, 22.17.1.2, 23.17.1.2, 24.17.1.2, 25.17.1.2, 26.17.1.2, 27.17.1.2, 28.17.1.2, 29.17.1.2, 30.17.1.2, 31.17.1.2, 32.17.1.2, 33.17.1.2, 34.17.1.2, 35.17.1.2, 36.17.1.2, 37.17.1.2, 38.17.1.2, 39.17.1.2, 40.17.1.2, 1.18.1.2, 2.18.1.2, 3.18.1.2, 4.18.1.2, 5.18.1.2, 6.18.1.2, 7.18.1.2, 8.18.1.2, 9.18.1.2, 10.18.1.2, 11.18.1.2, 12.18.1.2, 13.18.1.2, 14.18.1.2, 15.18.1.2, 16.18.1.2, 17.18.1.2, 18.18.1.2, 19.18.1.2, 20.18.1.2, 21.18.1.2, 22.18.1.2, 23.18.1.2, 24.18.1.2, 25.18.1.2, 26.18.1.2, 27.18.1.2, 28.18.1.2, 29.18.1.2, 30.18.1.2, 31.18.1.2, 32.18.1.2, 33.18.1.2, 34.18.1.2, 35.18.1.2, 36.18.1.2, 37.18.1.2, 38.18.1.2, 39.18.1.2, 40.18.1.2, 1.19.1.2, 2.19.1.2, 3.19.1.2, 4.19.1.2, 5.19.1.2, 6.19.1.2, 7.19.1.2, 8.19.1.2, 9.19.1.2, 10.19.1.2, 11.19.1.2, 12.19.1.2, 13.19.1.2, 14.19.1.2, 15.19.1.2, 16.19.1.2, 17.19.1.2, 18.19.1.2, 19.19.1.2, 20.19.1.2, 21.19.1.2, 22.19.1.2, 23.19.1.2, 24.19.1.2, 25.19.1.2, 26.19.1.2, 27.19.1.2, 28.19.1.2, 29.19.1.2, 30.19.1.2, 31.19.1.2, 32.19.1.2, 33.19.1.2, 34.19.1.2, 35.19.1.2, 36.19.1.2, 37.19.1.2, 38.19.1.2, 39.19.1.2, 40.19.1.2, 1.20.1.2, 2.20.1.2, 3.20.1.2, 4.20.1.2, 5.20.1.2, 6.20.1.2, 7.20.1.2, 8.20.1.2, 9.20.1.2, 10.20.1.2, 11.20.1.2, 12.20.1.2, 13.20.1.2, 14.20.1.2, 15.20.1.2, 16.20.1.2, 17.20.1.2, 18.20.1.2, 19.20.1.2, 20.20.1.2, 21.20.1.2, 22.20.1.2, 23.20.1.2, 24.20.1.2, 25.20.1.2, 26.20.1.2, 27.20.1.2, 28.20.1.2, 29.20.1.2, 30.20.1.2, 31.20.1.2, 32.20.1.2, 33.20.1.2, 34.20.1.2, 35.20.1.2, 36.20.1.2, 37.20.1.2, 38.20.1.2, 39.20.1.2, 40.20.1.2, 1.21.1.2, 2.21.1.2, 3.21.1.2, 4.21.1.2, 5.21.1.2, 6.21.1.2, 7.21.1.2, 8.21.1.2, 9.21.1.2, 10.21.1.2, 11.21.1.2, 12.21.1.2, 13.21.1.2, 14.21.1.2, 15.21.1.2, 16.21.1.2, 17.21.1.2, 18.21.1.2, 19.21.1.2, 20.21.1.2, 21.21.1.2, 22.21.1.2, 23.21.1.2, 24.21.1.2, 25.21.1.2, 26.21.1.2, 27.21.1.2, 28.21.1.2, 29.21.1.2, 30.21.1.2, 31.21.1.2, 32.21.1.2, 33.21.1.2, 34.21.1.2, 35.21.1.2, 36.21.1.2, 37.21.1.2, 38.21.1.2, 39.21.1.2, 40.21.1.2, 1.22.1.2, 2.22.1.2, 3.22.1.2, 4.22.1.2, 5.22.1.2, 6.22.1.2, 7.22.1.2, 8.22.1.2, 9.22.1.2, 10.22.1.2, 11.22.1.2, 12.22.1.2, 13.22.1.2, 14.22.1.2, 15.22.1.2, 16.22.1.2, 17.22.1.2, 18.22.1.2, 19.22.1.2, 20.22.1.2, 21.22.1.2, 22.22.1.2, 23.22.1.2, 24.22.1.2, 25.22.1.2, 26.22.1.2, 27.22.1.2, 28.22.1.2, 29.22.1.2, 30.22.1.2, 31.22.1.2, 32.22.1.2, 33.22.1.2, 34.22.1.2, 35.22.1.2, 36.22.1.2, 37.22.1.2, 38.22.1.2, 39.22.1.2, 40.22.1.2, 1.23.1.2, 2.23.1.2, 3.23.1.2, 4.23.1.2, 5.23.1.2, 6.23.1.2, 7.23.1.2, 8.23.1.2, 9.23.1.2, 10.23.1.2, 11.23.1.2, 12.23.1.2, 13.23.1.2, 14.23.1.2, 15.23.1.2, 16.23.1.2, 17.23.1.2, 18.23.1.2, 19.23.1.2, 20.23.1.2, 21.23.1.2, 22.23.1.2, 23.23.1.2, 24.23.1.2, 25.23.1.2, 26.23.1.2, 27.23.1.2, 28.23.1.2, 29.23.1.2, 30.23.1.2, 31.23.1.2, 32.23.1.2, 33.23.1.2, 34.23.1.2, 35.23.1.2, 36.23.1.2, 37.23.1.2, 38.23.1.2, 39.23.1.2, 40.23.1.2, 1.24.1.2, 2.24.1.2, 3.24.1.2, 4.24.1.2, 5.24.1.2, 6.24.1.2, 7.24.1.2, 8.24.1.2, 9.24.1.2, 10.24.1.2, 11.24.1.2, 12.24.1.2, 13.24.1.2, 14.24.1.2, 15.24.1.2, 16.24.1.2, 17.24.1.2, 18.24.1.2, 19.24.1.2, 20.24.1.2, 21.24.1.2, 22.24.1.2, 23.24.1.2, 24.24.1.2, 25.24.1.2, 26.24.1.2, 27.24.1.2, 28.24.1.2, 29.24.1.2, 30.24.1.2, 31.24.1.2, 32.24.1.2, 33.24.1.2, 34.24.1.2, 35.24.1.2, 36.24.1.2, 37.24.1.2, 38.24.1.2, 39.24.1.2, 40.24.1.2, 1.25.1.2, 2.25.1.2, 3.25.1.2, 4.25.1.2, 5.25.1.2, 6.25.1.2, 7.25.1.2, 8.25.1.2, 9.25.1.2, 10.25.1.2, 11.25.1.2, 12.25.1.2, 13.25.1.2, 14.25.1.2, 15.25.1.2, 16.25.1.2, 17.25.1.2, 18.25.1.2, 19.25.1.2, 20.25.1.2, 21.25.1.2, 22.25.1.2, 23.25.1.2, 24.25.1.2, 25.25.1.2, 26.25.1.2, 27.25.1.2, 28.25.1.2, 29.25.1.2, 30.25.1.2, 31.25.1.2, 32.25.1.2, 33.25.1.2, 34.25.1.2, 35.25.1.2, 36.25.1.2, 37.25.1.2, 38.25.1.2, 39.25.1.2, 40.25.1.2, 1.26.1.2, 2.26.1.2, 3.26.1.2, 4.26.1.2, 5.26.1.2, 6.26.1.2, 7.26.1.2, 8.26.1.2, 9.26.1.2, 10.26.1.2, 11.26.1.2, 12.26.1.2, 13.26.1:2, 14.26.1.2, 15.26.1.2, 16.26.1.2, 17.26.1.2, 18.26.1.2, 19.26.1.2, 20.26.1.2, 21.26.1.2, 22.26.1.2, 23.26.1.2, 24.26.1.2, 25.26.1.2, 26.26.1.2, 27.26.1.2, 28.26.1.2, 29.26.1.2, 30.26.1.2, 31.26.1.2, 32.26.1.2, 33.26.1.2, 34.26.1.2, 35.26.1.2, 36.26.1.2, 37.26.1.2, 38.26.1.2, 39.26.1.2, 40.26.1.2, 1.27.1.2, 2.27.1.2, 3.27.1.2, 4.27.1.2, 5.27.1.2, 6.27.1.2, 7.27.1.2, 8.27.1.2, 9.27.1.2, 10.27.1.2, 11.27.1.2, 12.27.1.2, 13.27.1.2, 14.27.1.2, 15.27.1.2, 16.27.1.2, 17.27.1.2, 18.27.1.2, 19.27.1.2, 20.27.1.2, 21.27.1.2, 22.27.1.2, 23.27.1.2, 24.27.1.2, 25.27.1.2, 26.27.1.2, 27.27.1.2, 28.27.1.2, 29.27.1.2, 30.27.1.2, 31.27.1.2, 32.27.1.2, 33.27.1.2, 34.27.1.2, 35.27.1.2, 36.27.1.2, 37.27.1.2, 38.27.1.2, 39.27.1.2, 40.27.1.2, 1.28.1.2, 2.28.1.2, 3.28.1.2, 4.28.1.2, 5.28.1.2, 6.28.1.2, 7.28.1.2, 8.28.1.2, 9.28.1.2, 10.28.1.2, 11.28.1.2, 12.28.1.2, 13.28.1.2, 14.28.1.2, 15.28.1.2, 16.28.1.2, 17.28.1.2, 18.28.1.2, 19.28.1.2, 20.28.1.2, 21.28.1.2, 22.28.1.2, 23.28.1.2, 24.28.1.2, 25.28.1.2, 26.28.1.2, 27.28.1.2, 28.28.1.2, 29.28.1.2, 30.28.1.2, 31.28.1.2, 32.28.1.2, 33.28.1.2, 34.28.1.2, 35.28.1.2, 36.28.1.2, 37.28.1.2, 38.28.1.2, 39.28.1.2, 40.28.1.2, 1.29.1.2, 2.29.1.2, 3.29.1.2, 4.29.1.2, 5.29.1.2, 6.29.1.2, 7.29.1.2, 8.29.1.2, 9.29.1.2, 10.29.1.2, 11.29.1.2, 12.29.1.2, 13.29.1.2, 14.29.1.2, 15.29.1.2, 16.29.1.2, 17.29.1.2, 18.29.1.2, 19.29.1.2, 20.29.1.2, 21.29.1.2, 22.29.1.2, 23.29.1.2, 24.29.1.2, 25.29.1.2, 26.29.1.2, 27.29.1.2, 28.29.1.2, 29.29.1.2, 30.29.1.2, 31.29.1.2, 32.29.1.2, 33.29.1.2, 34.29.1.2, 35.29.1.2, 36.29.1.2, 37.29.1.2, 38.29.1.2, 39.29.1.2, 40.29.1.2, 1.1.3.1, 2.1.3.1, 3.1.3.1, 4.1.3.1, 5.1.3.1, 6.1.3.1, 7.1.3.1, 8.1.3.1, 9.1.3.1, 10.1.3.1, 11.1.3.1, 12.1.3.1, 13.1.3.1, 14.1.3.1, 15.1.3.1, 16.1.3.1, 17.1.3.1, 18.1.3.1, 19.1.3.1, 20.1.3.1, 21.1.3.1, 22.1.3.1, 23.1.3.1, 24.1.3.1, 25.1.3.1, 26.1.3.1, 27.1.3.1, 28.1.3.1, 29.1.3.1, 30.1.3.1, 31.1.3.1, 32.1.3.1, 33.1.3.1, 34.1.3.1, 35.1.3.1, 36.1.3.1, 37.1.3.1, 38.1.3.1, 39.1.3.1, 40.1.3.1, 1.2.3.1, 2.2.3.1, 3.2.3.1, 4.2.3.1, 5.2.3.1, 6.2.3.1, 7.2.3.1, 8.2.3.1, 9.2.3.1, 10.2.3.1, 11.2.3.1, 12.2.3.1, 13.2.3.1, 14.2.3.1, 15.2.3.1, 16.2.3.1, 17.2.3.1, 18.2.3.1, 19.2.3.1, 20.2.3.1, 21.2.3.1, 22.2.3.1, 23.2.3.1, 24.2.3.1, 25.2.3.1, 26.2.3.1, 27.2.3.1, 28.2.3.1, 29.2.3.1, 30.2.3.1, 31.2.3.1, 32.2.3.1, 33.2.3.1, 34.2.3.1, 35.2.3.1, 36.2.3.1, 37.2.3.1, 38.2.3.1, 39.2.3.1, 40.2.3.1, 1.3.3.1, 2.3.3.1, 3.3.3.1, 4.3.3.1, 5.3.3.1, 6.3.3.1, 7.3.3.1, 8.3.3.1, 9.3.3.1, 10.3.3.1, 11.3.3.1, 12.3.3.1, 13.3.3.1, 14.3.3.1, 15.3.3.1, 16.3.3.1, 17.3.3.1, 18.3.3.1, 19.3.3.1, 20.3.3.1, 21.3.3.1, 22.3.3.1, 23.3.3.1, 24.3.3.1, 25.3.3.1, 26.3.3.1, 27.3.3.1, 28.3.3.1, 29.3.3.1, 30.3.3.1, 31.3.3.1, 32.3.3.1, 33.3.3.1, 34.3.3.1, 35.3.3.1, 36.3.3.1, 37.3.3.1, 38.3.3.1, 39.3.3.1, 40.3.3.1, 1.4.3.1, 2.4.3.1, 3.4.3.1, 4.4.3.1, 5.4.3.1, 6.4.3.1, 7.4.3.1, 8.4.3.1, 9.4.3.1, 10.4.3.1, 11.4.3.1, 12.4.3.1, 13.4.3.1, 14.4.3.1, 15.4.3.1, 16.4.3.1, 17.4.3.1, 18.4.3.1, 19.4.3.1, 20.4.3.1, 21.4.3.1, 22.4.3.1, 23.4.3.1, 24.4.3.1, 25.4.3.1, 26.4.3.1, 27.4.3.1, 28.4.3.1, 29.4.3.1, 30.4.3.1, 31.4.3.1, 32.4.3.1, 33.4.3.1, 34.4.3.1, 35.4.3.1, 36.4.3.1, 37.4.3.1, 38.4.3.1, 39.4.3.1, 40.4.3.1, 1.5.3.1, 2.5.3.1, 3.5.3.1, 4.5.3.1, 5.5.3.1, 6.5.3.1, 7.5.3.1, 8.5.3.1, 9.5.3.1, 10.5.3.1, 11.5.3.1, 12.5.3.1, 13.5.3.1, 14.5.3.1, 15.5.3.1, 16.5.3.1, 17.5.3.1, 18.5.3.1, 19.5.3.1, 20.5.3.1, 21.5.3.1, 22.5.3.1, 23.5.3.1, 24.5.3.1, 25.5.3.1, 26.5.3.1, 27.5.3.1, 28.5.3.1, 29.5.3.1, 30.5.3.1, 31.5.3.1, 32.5.3.1, 33.5.3.1, 34.5.3.1, 35.5.3.1, 36.5.3.1, 37.5.3.1, 38.5.3.1, 39.5.3.1, 40.5.3.1, 1.6.3.1, 2.6.3.1, 3.6.3.1, 4.6.3.1, 5.6.3.1, 6.6.3.1, 7.6.3.1, 8.6.3.1, 9.6.3.1, 10.6.3.1, 11.6.3.1, 12.6.3.1, 13.6.3.1, 14.6.3.1, 15.6.3.1, 16.6.3.1, 17.6.3.1, 18.6.3.1, 19.6.3.1, 20.6.3.1, 21.6.3.1, 22.6.3.1, 23.6.3.1, 24.6.3.1, 25.6.3.1, 26.6.3.1, 27.6.3.1, 28.6.3.1, 29.6.3.1, 30.6.3.1, 31.6.3.1, 32.6.3.1, 33.6.3.1, 34.6.3.1, 35.6.3.1, 36.6.3.1, 37.6.3.1, 38.6.3.1, 39.6.3.1, 40.6.3.1, 1.7.3.1, 2.7.3.1, 3.7.3.1, 4.7.3.1, 5.7.3.1, 6.7.3.1, 7.7.3.1, 8.7.3.1, 9.7.3.1, 10.7.3.1, 11.7.3.1, 12.7.3.1, 13.7.3.1, 14.7.3.1, 15.7.3.1, 16.7.3.1, 17.7.3.1, 18.7.3.1, 19.7.3.1, 20.7.3.1, 21.7.3.1, 22.7.3.1, 23.7.3.1, 24.7.3.1, 25.7.3.1, 26.7.3.1, 27.7.3.1, 28.7.3.1, 29.7.3.1, 30.7.3.1, 31.7.3.1, 32.7.3.1, 33.7.3.1, 34.7.3.1, 35.7.3.1, 36.7.3.1, 37.7.3.1, 38.7.3.1, 39.7.3.1, 40.7.3.1, 1.8.3.1, 2.8.3.1, 3.8.3.1, 4.8.3.1, 5.8.3.1, 6.8.3.1, 7.8.3.1, 8.8.3.1, 9.8.3.1, 10.8.3.1, 11.8.3.1, 12.8.3.1, 13.8.3.1, 14.8.3.1, 15.8.3.1, 16.8.3.1, 17.8.3.1, 18.8.3.1, 19.8.3.1, 20.8.3.1, 21.8.3.1, 22.8.3.1, 23.8.3.1, 24.8.3.1, 25.8.3.1, 26.8.3.1, 27.8.3.1, 28.8.3.1, 29.8.3.1, 30.8.3.1, 31.8.3.1, 32.8.3.1, 33.8.3.1, 34.8.3.1, 35.8.3.1, 36.8.3.1, 37.8.3.1, 38.8.3.1, 39.8.3.1, 40.8.3.1, 1.9.3.1, 2.9.3.1, 3.9.3.1, 4.9.3.1, 5.9.3.1, 6.9.3.1, 7.9.3.1, 8.9.3.1, 9.9.3.1, 10.9.3.1, 11.9.3.1, 12.9.3.1, 13.9.3.1, 14.9.3.1, 15.9.3.1, 16.9.3.1, 17.9.3.1, 18.9.3.1, 19.9.3.1, 20.9.3.1, 21.9.3.1, 22.9.3.1, 23.9.3.1, 24.9.3.1, 25.9.3.1, 26.9.3.1, 27.9.3.1, 28.9.3.1, 29.9.3.1, 30.9.3.1, 31.9.3.1, 32.9.3.1, 33.9.3.1, 34.9.3.1, 35.9.3.1, 36.9.3.1, 37.9.3.1, 38.9.3.1, 39.9.3.1, 40.9.3.1, 1.10.3.1, 2.10.3.1, 3.10.3.1, 4.10.3.1, 5.10.3.1, 6.10.3.1, 7.10.3.1, 8.10.3.1, 9.10.3.1, 10.10.3.1, 11.10.3.1, 12.10.3.1, 13.10.3.1, 14.10.3.1, 15.10.3.1, 16.10.3.1, 17.10.3.1, 18.10.3.1, 19.10.3.1, 20.10.3.1, 21.10.3.1, 22.10.3.1, 23.10.3.1, 24.10.3.1, 25.10.3.1, 26.10.3.1, 27.10.3.1, 28.10.3.1, 29.10.3.1, 30.10.3.1, 31.10.3.1, 32.10.3.1, 33.10.3.1, 34.10.3.1, 35.10.3.1, 36.10.3.1, 37.10.3.1; 38.10.3.1, 39.10.3.1, 40.10.3.1, 1.11.3.1, 2.11.3.1, 3.11.3.1, 4.11.3.1, 5.11.3.1, 6.11.3.1, 7.11.3.1, 8.11.3.1, 9.11.3.1, 10.11.3.1, 11.11.3.1, 12.11.3.1, 13.11.3.1, 14.11.3.1, 15.11.3.1, 16.11.3.1, 17.11.3.1, 18.11.3.1, 19.11.3.1, 20.11.3.1, 21.11.3.1, 22.11.3.1, 23.11.3.1, 24.11.3.1, 25.11.3.1, 26.11.3.1, 27.11.3.1, 28.11.3.1, 29.11.3.1, 30.11.3.1, 31.11.3.1, 32.11.3.1, 33.11.3.1, 34.11.3.1, 35.11.3.1, 36.11.3.1, 37.11.3.1, 38.11.3.1, 39.11.3.1, 40.11.3.1, 1.12.3.1, 2.12.3.1, 3.12.3.1, 4.12.3.1, 5.12.3.1, 6.12.3.1, 7.12.3.1, 8.12.3.1, 9.12.3.1, 10.12.3.1, 11.12.3.1, 12.12.3.1, 13.12.3.1, 14.12.3.1, 15.12.3.1, 16.12.3.1, 17.12.3.1, 18.12.3.1, 19.12.3.1, 20.12.3.1, 21.12.3.1, 22.12.3.1, 23.12.3.1, 24.12.3.1, 25.12.3.1, 26.12.3.1, 27.12.3.1, 28.12.3.1, 29.12.3.1, 30.12.3.1, 31.12.3.1, 32.12.3.1, 33.12.3.1, 34.12.3.1, 35.12.3.1, 35.12.3.1, 37.12.3.1, 38.12.3.1, 39.12.3.1, 40.12.3.1, 1.13.3.1, 2.13.3.1, 3.13.3.1, 4.13.3.1, 5.13.3.1, 6.13.3. 7.13.3.1, 8.13.3.1, 9.13.3.1, 10.13.3.1, 11.13.3.1, 12.13.3.1, 13.13.3.1, 14.13.3.1, 15.13.3.1, 16.13.3.1, 17.13.3.1, 18.13.3.1, 19.13.3.1, 20.13.3.1, 21.13.3.1, 22.13.3.1, 23.13.3.1, 24.13.3.1, 25.13.3.1, 26.13.3.1, 27.13.3.1, 28.13.3.1, 29.13.3.1, 30.13.3.1, 31.13.3.1, 32.13.3.1, 33.13.3.1, 34.13.3.1, 35.13.3.1, 36.13.3.1, 37.13.3.1, 38.13.3.1, 39.13.3.1, 40.13.3.1, 1.14.3.1, 2.14.3.1, 3.14.3.1, 4.14.3.1, 5.14.3.1, 6.14.3.1, 7.14.3.1, 8.14.3.1, 9.14.3.1, 10.14.3.1, 11.14.3.1, 12.14.3.1, 13.14.3.1, 14.14.3.1, 15.14.3.1, 16.14.3.1, 17.14.3.1, 18.14.3.1, 19.14.3.1, 20.14.3.1, 21.14.3.1, 22.14.3.1, 23.14.3.1 24.14.3.1, 25.14.3.1, 26.14.3.1, 27.14.3.1, 28.14.3.1, 29.14.3.1, 30.14.3.1, 31.14.3.1, 32.14.3.1, 33.14.3.1, 34.14.3.1, 35.14.3.1, 36.14.3.1, 37.14.3.1, 38.14.3.1, 39.14.3.1, 40.14.3.1, 1.15.3.1, 2.15.3.1, 3.15.3.1, 4.15.3.1, 5.15.3.1, 6.15.3.1, 7.15.3.1, 8.15.3.1, 9.15.3.1, 10.15.3.1, 11.15.3.1, 12.15.3.1, 13.15.3.1, 14.15.3.1, 15.15.3.1, 16.15.3.1, 17.15.3.1, 18.15.3.1, 19.15.3.1, 20.15.3.1, 21.15.3.1, 22.15.3.1, 23.15.3.1, 24.15.3.1, 25.15.3.1, 26.15.3.1, 27.15.3.1, 28.15.3.1, 29.15.3.1, 30.15.3.1, 31.15.3.1, 32.15.3.1, 33.15.3.1, 34.15.3.1, 35.15.3.1, 36.15.3.1, 37.15.3.1, 38.15.3.1, 39.15.3.1, 40.15.3.1, 1.16.3.1, 2.16.3.1, 3.16.3.1, 4.16.3.1, 5.16.3.1, 6.16.3.1, 7.16.3.1, 8.16.3.1, 9.16.3.1, 10.16.3.1, 11.16.3.1, 12.16.3.1, 13.16.3.1, 14.16.3.1, 15.15.3.1, 16.16.3.1, 17.16.3.1, 18.16.3.1, 19.16.3.1, 20.16.3.1, 21.16.3.1, 22.16.3.1, 23.16.3.1, 24.16.3.1, 25.16.3.1, 26.16.3.1, 27.16.3.1, 28.16.3.1, 29.16.3.1, 30.16.3.1, 31.16.3.1, 32.16.3.1, 33.16.3.1, 34.16.3.1, 35.16.3.1, 36.16.3.1, 37.16.3.1, 38.16.3.1, 39.16.3.1, 40.16.3.1, 1.17.3.1, 2.17.3.1, 3.17.3.1, 4.17.3.1, 5.17.3.1, 6.17.3.1, 7.17.3.1, 8.17.3.1, 9.17.3.1, 10.17.3.1, 11.17.3.1, 12.17.3.1, 13.17.3.1, 14.17.3.1, 15.17.3.1, 16.17.3.1, 17.17.3.1, 18.17.3.1, 19.17.3.1, 20.17.3.1, 21.17.3.1, 22.17.3.1, 23.17.3.1, 24.17.3.1, 25.17.3.1, 26.17.3.1, 27.17.3.1, 28.17.3.1, 29.17.3.1, 30.17.3.1, 31.17.3.1, 32.17.3.1, 33.17.3.1, 34.17.3.1, 35.17.3.1, 36.17.3.1, 37.17.3.1, 38.17.3.1, 39.17.3.1, 40.17.3.1, 1.18.3.1, 2.18.3.1, 3.18.3.1, 4.18.3.1, 5.18.3.1, 6.18.3.1, 7.18.3.1, 8.18.3.1, 9.18.3.1, 10.18.3.1, 11.18.3.1, 12.18.3.1, 13.18.3.1, 14.18.3.1, 15.18.3.1, 16.18.3.1, 17.18.3.1, 18.18.3.1, 19.18.3.1, 20.18.3.1, 21.18.3.1, 22.18.3.1, 23.18.3.1, 24.18.3.1, 25.18.3.1, 26.18.3.1, 27.18.3.1, 28.18.3.1, 29.18.3.1, 30.18.3.1, 31.18.3.1, 32.18.3.1, 33.18.3.1, 34.18.3.1, 35.18.3.1, 36.18.3.1, 37.18.3.1, 38.18.3.1, 39.18.3.1, 40.18.3.1, 1.19.3.1, 2.19.3.1, 3.19.3.1, 4.19.3.1, 5.19.3.1, 6.19.3.1, 7.19.3.1, 8.19.3.1, 9.19.3.1, 10.19.3.1, 11.19.3.1, 12.19.3.1, 13.19.3.1, 14.19.3.1, 15.19.3.1, 16.19.3.1, 17.19.3.1, 18.19.3.1, 19.19.3.1, 20.19.3.1, 21.19.3.1, 22.19.3.1, 23.19.3.1, 24.19.3.1, 25.19.3.1, 26.19.3.1, 27.19.3.1, 28.19.3.1, 29.19.3.1, 30.19.3.1, 31.19.3.1, 32.19.3.1, 33.19.3.1, 34.19.3.1, 35.19.3.1, 36.19.3.1, 37.19.3.1, 38.19.3.1, 39.19.3.1, 40.19.3.1, 1.20.3.1, 2.20.3.1, 3.20.3.1, 4.20.3.1, 5.20.3.1, 6.20.3.1, 7.20.3.1, 8.20.3.1, 9.20.3.1, 10.20.3.1, 11.20.3.1, 12.20.3.1, 13.20.3.1, 14.20.3.1, 15.20.3.1, 16.20.3.1, 17.20.3.1, 18.20.3.1, 19.20.3.1, 20.20.3.1, 21.20.3.1, 22.20.3.1, 23.20.3.1, 24.20.3.1, 25.20.3.1, 26.20.3.1, 27.20.3.1, 28.20.3.1, 29.20.3.1, 30.20.3.1, 31.20.3.1, 32.20.3.1, 33.20.3.1, 34.20.3.1, 35.20.3.1, 36.20.3.1, 37.20.3.1, 38.20.3.1, 39.20.3.1, 40.20.3.1, 1.21.3.1, 2.21.3.1, 3.21.3.1, 4.21.3.1, 5.21.3.1, 6.21.3.1, 7.21.3.1, 8.21.3.1, 9.21.3.1, 10.21.3.1, 11.21.3.1, 12.21.3.1, 13.21.3.1, 14.21.3.1, 15.21.3.1, 16.21.3.1, 17.21.3.1, 18.21.3.1, 19.21.3.1, 20.21.3.1, 21.21.3.1, 22.21.3.1, 23.21.3.1, 24.21.3.1, 25.21.3.1, 26.21.3.1, 27.21.3.1, 28.21.3.1, 29.21.3.1, 30.21.3.1, 31.21.3.1, 32.21.3.1, 33.21.3.1, 34.21.3.1, 35.21.3.1, 36.21.3.1, 37.21.3.1, 38.21.3.1, 39.21.3.1, 40.21.3.1, 1.22.3.1, 2.22.3.1, 3.22.3.1, 4.22.3.1, 5.22.3.1, 6.22.3.1, 7.22.3.1, 8.22.3.1, 9.22.3.1, 10.22.3.1, 11.22.3.1, 12.22.3.1, 13.22.3.1, 14.22.3.1, 15.22.3.1, 16.22.3.1, 17.22.3.1, 18.22.3.1, 19.22.3.1, 20.22.3.1, 21.22.3.1, 22.22.3.1, 23.22.3.1, 24.22.3.1, 25.22.3.1, 26.22.3.1, 27.22.3.1, 28.22.3.1, 29.22.3.1, 30.22.3.1, 31.22.3.1, 32.22.3.1, 33.22.3.1, 34.22.3.1, 35.22.3.1, 36.22.3.1, 37.22.3.1, 38.22.3.1, 39.22.3.1, 40.22.3.1, 1.23.3.1, 2.23.3.1, 3.23.3.1, 4.23.3.1, 5.23.3.1, 6.23.3.1, 7.23.3.1, 8.23.3.1, 9.23.3.1, 10.23.3.1, 11.23.3.1, 12.23.3.1, 13.23.3.1, 14.23.3.1, 15.23.3.1, 16.23.3.1, 17.23.3.1, 18.23.3.1, 19.23.3.1, 20.23.3.1, 21.23.3.1, 22.23.3.1, 23.23.3.1, 24.23.3.1, 25.23.3.1, 26.23.3.1, 27.23.3.1, 28.23.3.1, 29.23.3.1, 30.23.3.1, 31.23.3.1, 32.23.3.1, 33.23.3.1, 34.23.3.1, 35.23.3.1, 36.23.3.1, 37.23.3.1, 38.23.3.1, 39.23.3.1, 40.23.3.1, 1.24.3.1, 2.24.3.1, 3.24.3.1, 4.24.3.1, 5.24.3.1, 6.24.3.1, 7.24.3.1, 8.24.3.1, 9.24.3.1, 10.24.3.1, 11.24.3.1, 12.24.3.1, 13.24.3.1, 14.24.3.1, 15.24.3.1, 16.24.3.1, 17.24.3.1, 18.24.3.1, 19.24.3.1, 20.24.3.1, 21.24.3.1, 22.24.3.1, 23.24.3.1, 24.24.3.1, 25.24.3.1, 26.24.3.1, 27.24.3.1, 28.24.3.1, 29.24.3.1, 30.24.3.1, 31.24.3.1, 32.24.3.1, 33.24.3.1, 34.24.3.1, 35.24.3.1, 36.24.3.1, 37.24.3.1, 38.24.3.1, 39.24.3.1, 40.24.3.1, 1.25.3.1, 2.25.3.1, 3.25.3.1, 4.25.3.1, 5.25.3.1, 6.25.3.1, 7.25.3.1, 8.25.3.1, 9.25.3.1, 10.25.3.1, 11.25.3.1, 12.25.3.1, 13.25.3.1, 14.25.3.1, 15.25.3.1, 16.25.3.1, 17.25.3.1, 18.25.3.1, 19.25.3.1, 20.25.3.1, 21.25.3.1, 22.25.3.1, 23.25.3.1, 24.25.3.1, 25.25.3.1, 26.25.3.1, 27.25.3.1, 28.25.3.1, 29.25.3.1, 30.25.3.1, 31.25.3.1, 32.25.3.1, 33.25.3.1, 34.25.3.1, 35.25.3.1, 36.25.3.1, 37.25.3.1, 38.25.3.1, 39.25.3.1, 40.25.3.1, 1.26.3.1, 2.26.3.1, 3.26.3.1, 4.26.3.1, 5.26.3.1, 6.26.3.1, 7.26.3.1, 8.26.3.1, 9.26.3.1, 10.26.3.1, 11.26.3.1, 12.26.3.1, 13.26.3.1, 14.26.3.1, 15.26.3.1, 16.26.3.1, 17.26.3.1, 18.26.3.1, 19.26.3.1, 20.26.3.1, 21.26.3.1, 22.26.3.1, 23.26.3.1, 24.26.3.1, 25.26.3.1, 26.26.3.1, 27.26.3.1, 28.26.3.1, 29.26.3.1, 30.26.3.1, 31.26.3.1, 32.26.3.1, 33.26.3.1, 34.26.3.1, 35.26.3.1, 36.26.3.1, 37.26.3.1, 38.26.3.1, 39.26.3.1, 40.26.3.1, 1.27.3.1, 2.27.3.1, 3.27.3.1, 4.27.3.1, 5.27.3.1, 6.27.3.1, 7.27.3.1, 8.27.3.1, 9.27.3.1, 10.27.3.1, 11.27.3.1, 12.27.3.1, 13.27.3.1, 14.27.3.1, 15.27.3.1, 16.27.3.1, 17.27.3.1, 18.27.3.1, 19.27.3.1, 20.27.3.1, 21.27.3.1, 22.27.3.1, 23.27.3.1, 24.27.3.1, 25.27.3.1, 26.27.3.1, 27.27.3.1, 28.27.3.1, 29.27.3.1, 30.27.3.1, 31.27.3.1, 32.27.3.1, 33.27.3.1, 34.27.3.1, 35.27.3.1, 36.27.3.1, 37.27.3.1, 38.27.3.1, 39.27.3.1, 40.27.3.1, 1.28.3.1, 2.28.3.1, 3.28.3.1, 4.28.3.1, 5.28.3.1, 6.28.3.1, 7.28.3.1, 8.28.3.1, 9.28.3.1, 10.28.3.1, 11.28.3.1, 12.28.3.1, 13.28.3.1, 14.28.3.1, 15.28.3.1, 16.28.3.1, 17.28.3.1, 18.28.3.1, 19.28.3.1, 20.28.3.1, 21.28.3.1, 22.28.3.1, 23.28.3.1, 24.28.3.1, 25.28.3.1, 26.28.3.1, 27.28.3.1, 28.28.3.1, 29.28.3.1, 30.28.3.1, 31.28.3.1, 32.28.3.1, 33.28.3.1, 34.28.3.1, 35.28.3.1, 36.28.3.1, 37.28.3.1, 38.28.3.1, 39.28.3.1, 40.28.3.1, 1.29.3.1, 2.29.3.1, 3.29.3.1, 4.29.3.1, 5.29.3.1, 6.29.3.1, 7.29.3.1, 8.29.3.1, 9.29.3.1, 10.29.3.1, 11.29.3.1, 12.29.3.1, 13.29.3.1, 14.29.3.1, 15.29.3.1, 16.29.3.1, 17.29.3.1, 18.29.3.1, 19.29.3.1, 20.29.3.1, 21.29.3.1, 22.29.3.1, 23.29.3.1, 24.29.3.1, 25.29.3.1, 26.29.3.1, 27.29.3.1, 28.29.3.1, 29.29.3.1, 30.29.3.1, 31.29.3.1, 32.29.3.1, 33.29.3.1, 34.29.3.1, 35.29.3.1, 36.29.3.1, 37.29.3.1, 38.29.3.1, 39.29.3.1, 40.29.3.1, 1.1.3.2, 2.1.3.2, 3.1.3.2, 4.1.3.2, 5.1.3.2, 6.1.3.2, 7.1.3.2, 8.1.3.2, 9.1.3.2, 10.1.3.2, 11.1.3.2, 12.1.3.2, 13.1.3.2, 14.1.3.2, 15.1.3.2, 16.1.3.2, 17.1.3.2, 18.1.3.2, 19.1.3.2, 20.1.3.2, 21.1.3.2, 22.1.3.2, 23.1.3.2, 24.1.3.2, 25.1.3.2, 26.1.3.2, 27.1.3.2, 28.1.3.2, 29.1.3.2, 30.1.3.2, 31.1.3.2, 32.1.3.2, 33.1.3.2, 34.1.3.2, 35.1.3.2, 36.1.3.2, 37.1.3.2, 38.1.3.2, 39.1.3.2, 40.1.3.2, 1.2.3.2, 2.2.3.2, 3.2.3.2, 4.2.3.2, 5.2.3.2, 6.2.3.2, 7.2.3.2, 8.2.3.2, 9.2.3.2, 10.2.3.2, 11.2.3.2, 12.2.3.2, 13.2.3.2, 14.2.3.2, 15.2.3.2, 16.2.3.2, 17.2.3.2, 18.2.3.2, 19.2.3.2, 20.2.3.2, 21.2.3.2, 22.2.3.2, 23.2.3.2, 24.2.3.2, 25.2.3.2, 26.2.3.2, 27.2.3.2, 28.2.3.2, 29.2.3.2, 30.2.3.2, 31.2.3.2, 32.2.3.2, 33.2.3.2, 34.2.3.2, 35.2.3.2, 36.2.3.2, 37.2.3.2, 38.2.3.2, 39.2.3.2, 40.2.3.2, 1.3.3.2, 2.3.3.2, 3.3.3.2, 4.3.3.2, 5.3.3.2, 6.3.3.2, 7.3.3.2, 8.3.3.2, 9.3.3.2, 10.3.3.2, 11.3.3.2, 12.3.3.2, 13.3.3.2, 14.3.3.2, 15.3.3.2, 16.3.3.2, 17.3.3.2, 18.3.3.2, 19.3.3.2, 20.3.3.2, 21.3.3.2, 22.3.3.2, 23.3.3.2, 24.3.3.2, 25.3.3.2, 26.3.3.2, 27.3.3.2, 28.3.3.2, 29.3.3.2, 30.3.3.2, 31.3.3.2, 32.3.3.2, 33.3.3.2, 34.3.3.2, 35.3.3.2, 36.3.3.2, 37.3.3.2, 38.3.3.2, 39.3.3.2, 40.3.3.2, 1.4.3.2, 2.4.3.2, 3.4.3.2, 4.4.3.2, 5.4.3.2, 6.4.3.2, 7.4.3.2, 8.4.3.2, 9.4.3.2, 10.4.3.2, 11.4.3.2, 12.4.3.2, 13.4.3.2, 14.4.3.2, 15.4.3.2, 16.4.3.2, 17.4.3.2, 18.4.3.2, 19.4.3.2, 20.4.3.2, 21.4.3.2, 22.4.3.2, 23.4.3.2, 24.4.3.2, 25.4.3.2, 26.4.3.2, 27.4.3.2, 28.4.3.2, 29.4.3.2, 30.4.3.2, 31.4.3.2, 32.4.3.2, 33.4.3.2, 34.4.3.2, 35.4.3.2, 36.4.3.2, 37.4.3.2, 38.4.3.2, 39.4.3.2, 40.4.3.2, 1.5.3.2, 2.5.3.2, 3.5.3.2, 4.5.3.2, 5.5.3.2, 6.5.3.2, 7.5.3.2, 8.5.3.2, 9.5.3.2, 10.5.3.2, 11.5.3.2, 12.5.3.2, 13.5.3.2, 14.5.3.2, 15.5.3.2, 16.5.3.2, 17.5.3.2, 18.5.3.2, 19.5.3.2, 20.5.3.2, 21.5.3.2, 22.5.3.2, 23.5.3.2, 24.5.3.2, 25.5.3.2, 26.5.3.2, 27.5.3.2, 28.5.3.2, 29.5.3.2, 30.5.3.2, 31.5.3.2, 32.5.3.2, 33.5.3.2, 34.5.3.2, 35.5.3.2, 36.5.3.2, 37.5.3.2, 38.5.3.2, 39.5.3.2, 40.5.3.2, 1.6.3.2, 2.6.3.2, 3.6.3.2, 4.6.3.2, 5.6.3.2, 6.6.3.2, 7.6.3.2, 8.6.3.2, 9.6.3.2, 10.6.3.2, 11.6.3.2, 12.6.3.2, 13.6.3.2, 14.6.3.2, 15.6.3.2, 16.6.3.2, 17.6.3.2, 18.6.3.2, 19.6.3.2, 20.6.3.2, 21.6.3.2, 22.6.3.2, 23.6.3.2, 24.6.3.2, 25.6.3.2, 26.6.3.2, 27.6.3.2, 28.6.3.2, 29.6.3.2, 30.6.3.2, 31.6.3.2, 32.6.3.2, 33.6.3.2, 34.6.3.2, 35.6.3.2, 36.6.3.2, 37.6.3.2, 38.6.3.2, 39.6.3.2, 40.6.3.2, 1.7.3.2, 2.7.3.2, 3.7.3.2, 4.7.3.2, 5.7.3.2, 6.7.3.2, 7.7.3.2, 8.7.3.2, 9.7.3.2, 10.7.3.2, 11.7.3.2, 12.7.3.2, 13.7.3.2, 14.7.3.2, 15.7.3.2, 16.7.3.2, 17.7.3.2, 18.7.3.2, 19.7.3.2, 20.7.3.2, 21.7.3.2, 22.7.3.2, 23.7.3.2, 24.7.3.2, 25.7.3.2, 26.7.3.2, 27.7.3.2, 28.7.3.2, 29.7.3.2, 30.7.3.2, 31.7.3.2, 32.7.3.2, 33.7.3.2, 34.7.3.2, 35.7.3.2, 36.7.3.2, 37.7.3.2, 38.7.3.2, 39.7.3.2, 40.7.3.2, 1.8.3.2, 2.8.3.2, 3.8.3.2, 4.8.3.2, 5.8.3.2, 6.8.3.2, 7.8.3.2, 8.8.3.2, 9.8.3.2, 10.8.3.2, 11.8.3.2, 12.8.3.2, 13.8.3.2, 14.8.3.2, 15.8.3.2, 16.8.3.2, 17.8.3.2, 18.8.3.2, 19.8.3.2, 20.8.3.2, 21.8.3.2, 22.8.3.2, 23.8.3.2, 24.8.3.2, 25.8.3.2, 26.8.3.2, 27.8.3.2, 28.8.3.2, 29.8.3.2, 30.8.3.2, 31.8.3.2, 32.8.3.2, 33.8.3.2, 34.8.3.2, 35.8.3.2, 36.8.3.2, 37.8.3.2, 38.8.3.2, 39.8.3.2, 40.8.3.2, 1.9.3.2, 2.9.3.2, 3.9.3.2, 4.9.3.2, 5.9.3.2, 6.9.3.2, 7.9.3.2, 8.9.3.2, 9.9.3.2, 10.9.3.2, 11.9.3.2, 12.9.3.2, 13.9.3.2, 14.9.3.2, 15.9.3.2, 16.9.3.2, 17.9.3.2, 18.9.3.2, 19.9.3.2, 20.9.3.2, 21.9.3.2, 22.9.3.2, 23.9.3.2, 24.9.3.2, 25.9.3.2, 26.9.3.2, 27.9.3.2, 28.9.3.2, 29.9.3.2, 30.9.3.2, 31.9.3.2, 32.9.3.2, 33.9.3.2, 34.9.3.2, 35.9.3.2, 36.9.3.2, 37.9.3.2, 38.9.3.2, 39.9.3.2, 40.9.3.2, 1.10.3.2, 2.10.3.2, 3.10.3.2, 4.10.3.2, 5.10.3.2, 6.10.3.2, 7.10.3.2, 8.10.3.2, 9.10.3.2, 10.10.3.2, 11.10.3.2, 12.10.3.2, 13.10.3.2, 14.10.3.2, 15.10.3.2, 16.10.3.2, 17.10.3.2, 18.10.3.2, 19.10.3.2, 20.10.3.2, 21.10.3.2, 22.10.3.2, 23.10.3.2, 24.10.3.2, 25.10.3.2, 26.10.3.2, 27.10.3.2, 28.10.3.2, 29.10.3.2, 30.10.3.2, 31.10.3.2, 32.10.3.2, 33.10.3.2, 34.10.3.2, 35.10.3.2, 36.10.3.2, 37.10.3.2, 38.10.3.2, 39.10.3.2, 40.10.3.2, 1.11.3.2, 2.11.3.2, 3.11.3.2, 4.11.3.2, 5.11.3.2, 6.11.3.2, 7.11.3.2, 8.11.3.2, 9.11.3.2, 10.11.3.2, 11.11.3.2, 12.11.3.2, 13.11.3.2, 14.11.3.2, 15.11.3.2, 16.11.3.2, 17.11.3.2, 18.11.3.2, 19.11.3.2, 20.11.3.2, 21.11.3.2, 22.11.3.2, 23.11.3.2, 24.11.3.2, 25.11.3.2, 26.11.3.2, 27.11.3.2, 28.11.3.2, 29.11.3.2, 30.11.3.2, 31.11.3.2, 32.11.3.2, 33.11.3.2, 34.11.3.2, 35.11.3.2, 36.11.3.2, 37.11.3.2, 38.11.3.2, 39.11.3.2, 40.11.3.2, 1.12.3.2, 2.12.3.2, 3.12.3.2, 4.12.3.2, 5.12.3.2, 6.12.3.2, 7.12.3.2, 8.12.3.2, 9.12.3.2, 10.12.3.2, 11.12.3.2, 12.12.3.2, 13.12.3.2, 14.12.3.2, 15.12.3.2, 16.12.3.2, 17.12.3.2, 18.12.3.2, 19.12.3.2, 20.12.3.2, 21.12.3.2, 22.12.3.2, 23.12.3.2, 24.12.3.2, 25.12.3.2, 26.12.3.2, 27.12.3.2, 28.12.3.2, 29.12.3.2, 30.12.3.2, 31.12.3.2, 32.12.3.2, 33.12.3.2, 34.12.3.2, 35.12.3.2, 36.12.3.2, 37.12.3.2, 38.12.3.2, 39.12.3.2, 40.12.3.2, 1.13.3.2, 2.13.3.2, 3.13.3.2, 4.13.3.2, 5.13.3.2, 6.13.3.2, 7.13.3.2, 8.13.3.2, 9.13.3.2, 10.13.3.2, 11.13.3.2, 12.13.3.2, 13.13.3.2, 14.13.3.2, 15.13.3.2, 16.13.3.2, 17.13.3.2, 18.13.3.2, 19.13.3.2, 20.13.3.2, 21.13.3.2, 22.13.3.2, 23.13.3.2, 24.13.3.2, 25.13.3.2, 26.13.3.2, 27.13.3.2, 28.13.3.2, 29.13.3.2, 30.13.3.2, 31.13.3.2, 32.13.3.2, 33.13.3.2, 34.13.3.2, 35.13.3.2, 36.13.3.2, 37.13.3.2, 38.13.3.2, 39.13.3.2, 40.13.3.2, 1.14.3.2, 2.14.3.2, 3.14.3.2, 4.14.3.2, 5.14.3.2, 6.14.3.2, 7.14.3.2, 8.14.3.2, 9.14.3.2, 10.14.3.2, 11.14.3.2, 12.14.3.2, 13.14.3.2, 14.14.3.2, 15.14.3.2, 16.14.3.2, 17.14.3.2, 18.14.3.2, 19.14.3.2, 20.14.3.2, 21.14.3.2, 22.14.3.2, 23.14.3.2, 24.14.3.2, 25.14.3.2, 26.14.3.2, 27.14.3.2, 28.14.3.2, 29.14.3.2, 30.14.3.2, 31.14.3.2, 32.14.3.2, 33.14.3.2, 34.14.3.2, 35.14.3.2, 36.14.3.2, 37.14.3.2, 38.14.3.2, 39.14.3.2, 40.14.3.2, 1.15.3.2, 2.15.3.2, 3.15.3.2, 4.15.3.2, 5.15.3.2, 6.15.3.2, 7.15.3.2, 8.15.3.2, 9.15.3.2, 10.15.3.2, 11.15.3.2, 12.15.3.2, 13.15.3.2, 14.15.3.2, 15.15.3.2, 16.15.3.2, 17.15.3.2, 18.15.3.2, 19.15.3.2, 20.15.3.2, 21.15.3.2, 22.15.3.2, 23.15.3.2, 24.15.3.2, 25.15.3.2, 26.15.3.2, 27.15.3.2, 28.15.3.2, 29.15.3.2, 30.15.3.2, 31.15.3.2, 32.15.3.2, 33.15.3.2, 34.15.3.2, 35.15.3.2, 36.15.3.2, 37.15.3.2, 38.15.3.2, 39.15.3.2, 40.15.3.2, 1.16.3.2, 2.16.3.2, 3.16.3.2, 4.16.3.2, 5.16.3.2, 6.16.3.2, 7.16.3.2, 8.16.3.2, 9.16.3.2, 10.16.3.2, 11.16.3.2, 12.16.3.2, 13.16.3.2, 14.16.3.2, 15.16.3.2, 16.16.3.2, 17.16.3.2, 18.16.3.2, 19.16.3.2, 20.16.3.2, 21.16.3.2, 22.16.3.2, 23.16.3.2, 24.16.3.2, 25.16.3.2, 26.16.3.2, 27.16.3.2, 28.16.3.2, 29.16.3.2, 30.16.3.2, 31.16.3.2, 32.16.3.2, 33.16.3.2, 34.16.3.2, 35.16.3.2, 36.16.3.2, 37.16.3.2, 38.16.3.2, 39.16.3.2, 40.16.3.2, 1.17.3.2, 2.17.3.2, 3.17.3.2, 4.17.3.2, 5.17.3.2, 6.17.3.2, 7.17.3.2, 8.17.3.2, 9.17.3.2, 10.17.3.2, 11.17.3.2, 12.17.3.2, 13.17.3.2, 14.17.3.2, 15.17.3.2, 16.17.3.2, 17.17.3.2, 18.17.3.2, 19.17.3.2, 20.17.3.2, 21.17.3.2, 22.17.3.2, 23.17.3.2, 24.17.3.2, 25.17.3.2, 26.17.3.2, 27.17.3.2, 28.17.3.2, 29.17.3.2, 30.17.3.2, 31.17.3.2, 32.17.3.2, 33.17.3.2, 34.17.3.2, 35.17.3.2, 36.17.3.2, 37.17.3.2, 38.17.3.2, 39.17.3.2, 40.17.3.2, 1.18.3.2, 2.18.3.2, 3.18.3.2, 4.18.3.2, 5.18.3.2, 6.18.3.2, 7.18.3.2, 8.18.3.2, 9.18.3.2, 10.18.3.2, 11.18.3.2, 12.18.3.2, 13.18.3.2, 14.18.3.2, 15.18.3.2, 16.18.3.2, 17.18.3.2, 18.18.3.2, 19.18.3.2, 20.18.3.2, 21.18.3.2, 22.18.3.2, 23.18.3.2, 24.18.3.2, 25.18.3.2, 26.18.3.2, 27.18.3.2, 28.18.3.2, 29.18.3.2, 30.18.3.2, 31.18.3.2, 32.18.3.2, 33.18.3.2, 34.18.3.2, 35.18.3.2, 36.18.3.2, 37.18.3.2, 38.18.3.2, 39.18.3.2, 40.18.3.2, 1.19.3.2, 2.19.3.2, 3.19.3.2, 4.19.3.2, 5.19.3.2, 6.19.3.2, 7.19.3.2, 8.19.3.2, 9.19.3.2, 10.19.3.2, 11.19.3.2, 12.19.3.2, 13.19.3.2, 14.19.3.2, 15.19.3.2, 16.19.3.2, 17.19.3.2, 18.19.3.2, 19.19.3.2, 20.19.3.2, 21.19.3.2, 22.19.3.2, 23.19.3.2, 24.19.3.2, 25.19.3.2, 26.19.3.2, 27.19.3.2, 28.19.3.2, 29.19.3.2, 30.19.3.2, 31.19.3.2, 32.19.3.2, 33.19.3.2, 34.19.3.2, 35.19.3.2, 36.19.3.2, 37.19.3.2, 38.19.3.2, 39.19.3.2, 40.19.3.2, 1.20.3.2, 2.20.3.2, 3.20.3.2, 4.20.3.2, 5.20.3.2, 6.20.3.2, 7.20.3.2, 8.20.3.2, 9.20.3.2, 10.20.3.2, 11.20.3.2, 12.20.3.2, 13.20.3.2, 14.20.3.2, 15.20.3.2, 16.20.3.2, 17.20.3.2, 18.20.3.2, 19.20.3.2, 20.20.3.2, 21.20.3.2, 22.20.3.2, 23.20.3.2, 24.20.3.2, 25.20.3.2, 26.20.3.2, 27.20.3.2, 28.20.3.2, 29.20.3.2, 30.20.3.2, 31.20.3.2, 32.20.3.2, 33.20.3.2, 34.20.3.2, 35.20.3.2, 36.20.3.2, 37.20.3.2, 38.20.3.2, 39.20.3.2, 40.20.3.2, 1.21.3.2, 2.21.3.2, 3.21.3.2, 4.21.3.2, 5.21.3.2, 6.21.3.2, 7.21.3.2, 8.21.3.2, 9.21.3.2, 10.21.3.2, 11.21.3.2, 12.21.3.2, 13.21.3.2, 14.21.3.2, 15.21.3.2, 16.21.3.2, 17.21.3.2, 18.21.3.2, 19.21.3.2, 20.21.3.2, 21.21.3.2, 22.21.3.2, 23.21.3.2, 24.21.3.2, 25.21.3.2, 26.21.3.2, 27.21.3.2, 28.21.3.2, 29.21.3.2, 30.21.3.2, 31.21.3.2, 32.21.3.2, 33.21.3.2, 34.21.3.2, 35.21.3.2, 36.21.3.2, 37.21.3.2, 38.21.3.2, 39.21.3.2, 40.21.3.2, 1.22.3.2, 2.22.3.2, 3.22.3.2, 4.22.3.2, 5.22.3.2, 6.22.3.2, 7.22.3.2, 8.22.3.2, 9.22.3.2, 10.22.3.2, 11.22.3.2, 12.22.3.2, 13.22.3.2, 14.22.3.2, 15.22.3.2, 16.22.3.2, 17.22.3.2, 18.22.3.2, 19.22.3.2, 20.22.3.2, 21.22.3.2, 22.22.3.2, 23.22.3.2, 24.22.3.2, 25.22.3.2, 26.22.3.2, 27.22.3.2, 28.22.3.2, 29.22.3.2, 30.22.3.2, 31.22.3.2, 32.22.3.2, 33.22.3.2, 34.22.3.2, 35.22.3.2, 36.22.3.2, 37.22.3.2, 38.22.3.2, 39.22.3.2, 40.22.3.2, 1.23.3.2, 2.23.3.2, 3.23.3.2, 4.23.3.2, 5.23.3.2, 6.23.3.2, 7.23.3.2, 8.23.3.2, 9.23.3.2, 10.23.3.2, 11.23.3.2, 12.23.3.2, 13.23.3.2, 14.23.3.2, 15.23.3.2, 16.23.3.2, 17.23.3.2, 18.23.3.2, 19.23.3.2, 20.23.3.2, 21.23.3.2, 22.23.3.2, 23.23.3.2, 24.23.3.2, 25.23.3.2, 26.23.3.2, 27.23.3.2, 28.23.3.2, 29.23.3.2, 30.23.3.2, 31.23.3.2, 32.23.3.2, 33.23.3.2, 34.23.3.2, 35.23.3.2, 36.23.3.2, 37.23.3.2, 38.23.3.2, 39.23.3.2, 40.23.3.2, 1.24.3.2, 2.24.3.2, 3.24.3.2, 4.24.3.2, 5.24.3.2, 6.24.3.2, 7.24.3.2, 8.24.3.2, 9.24.3.2, 10.24.3.2, 11.24.3.2, 12.24.3.2, 13.24.3.2, 14.24.3.2, 15.24.3.2, 16.24.3.2, 17.24.3.2, 18.24.3.2, 19.24.3.2, 20.24.3.2, 21.24.3.2, 22.24.3.2, 23.24.3.2, 24.24.3.2, 25.24.3.2, 26.24.3.2, 27.24.3.2, 28.24.3.2, 29.24.3.2, 30.24.3.2, 31.24.3.2, 32.24.3.2, 33.24.3.2, 34.24.3.2, 35.24.3.2, 36.24.3.2, 37.24.3.2, 38.24.3.2, 39.24.3.2, 40.24.3.2, 1.25.3.2, 2.25.3.2, 3.25.3.2, 4.25.3.2, 5.25.3.2, 6.25.3.2, 7.25.3.2, 8.25.3.2, 9.25.3.2, 10.25.3.2, 11.25.3.2, 12.25.3.2, 13.25.3.2, 14.25.3.2, 15.25.3.2, 16.25.3.2, 17.25.3.2, 18.25.3.2, 19.25.3.2, 20.25.3.2, 21.25.3.2, 22.25.3.2, 23.25.3.2, 24.25.3.2, 25.25.3.2, 26.25.3.2, 27.25.3.2, 28.25.3.2, 29.25.3.2, 30.25.3.2, 31.25.3.2, 32.25.3.2, 33.25.3.2, 34.25.3.2, 35.25.3.2, 36.25.3.2, 37.25.3.2, 38.25.3.2, 39.25.3.2, 40.25.3.2, 1.26.3.2, 2.26.3.2, 3.26.3.2, 4.26.3.2, 5.26.3.2, 6.26.3.2, 7.26.3.2, 8.26.3.2, 9.26.3.2, 10.26.3.2, 11.26.3.2, 12.26.3.2, 13.26.3.2, 14.26.3.2, 15.26.3.2, 16.26.3.2, 17.26.3.2, 18.26.3.2, 19.26.3.2, 20.26.3.2, 21.26.3.2, 22.26.3.2, 23.26.3.2, 24.26.3.2, 25.26.3.2, 26.26.3.2, 27.26.3.2, 28.26.3.2, 29.26.3.2, 30.26.3.2, 31.26.3.2, 32.26.3.2, 33.26.3.2, 34.26.3.2, 35.26.3.2, 36.26.3.2, 37.26.3.2, 38.26.3.2, 39.26.3.2, 40.26.3.2, 1.27.3.2, 2.27.3.2, 3.27.3.2, 4.27.3.2, 5.27.3.2, 6.27.3.2, 7.27.3.2, 8.27.3.2, 9.27.3.2, 10.27.3.2, 11.27.3.2, 12.27.3.2, 13.27.3.2, 14.27.3.2, 15.27.3.2, 16.27.3.2, 17.27.3.2, 18.27.3.2, 19.27.3.2, 20.27.3.2, 21.27.3.2, 22.27.3.2, 23.27.3.2, 24.27.3.2, 25.27.3.2, 26.27.3.2, 27.27.3.2, 28.27.3.2, 29.27.3.2, 30.27.3.2, 31.27.3.2, 32.27.3.2, 33.27.3.2, 34.27.3.2, 35.27.3.2, 36.27.3.2, 37.27.3.2, 38.27.3.2, 39.27.3.2, 40.27.3.2, 1.28.3.2, 2.28.3.2, 3.28.3.2, 4.28.3.2, 5.28.3.2, 6.28.3.2, 7.28.3.2, 8.28.3.2, 9.28.3.2, 10.28.3.2, 11.28.3.2, 12.28.3.2, 13.28.3.2, 14.28.3.2, 15.28.3.2, 16.28.3.2, 17.28.3.2, 18.28.3.2, 19.28.3.2, 20.28.3.2, 21.28.3.2, 22.28.3.2, 23.28.3.2, 24.28.3.2, 25.28.3.2, 26.28.3.2, 27.28.3.2, 28.28.3.2, 29.28.3.2, 30.28.3.2, 31.28.3.2, 32.28.3.2, 33.28.3.2, 34.28.3.2, 35.28.3.2, 36.28.3.2, 37.28.3.2, 38.28.3.2, 39.28.3.2, 40.28.3.2, 1.29.3.2, 2.29.3.2, 3.29.3.2, 4.29.3.2, 5.29.3.2, 6.29.3.2, 7.29.3.2, 8.29.3.2, 9.29.3.2, 10.29.3.2, 11.29.3.2, 12.29.3.2, 13.29.3.2, 14.29.3.2, 15.29.3.2, 16.29.3.2, 17.29.3.2, 18.29.3.2, 19.29.3.2, 20.29.3.2, 21.29.3.2, 22.29.3.2, 23.29.3.2, 24.29.3.2, 25.29.3.2, 26.29.3.2, 27.29.3.2, 28.29.3.2, 29.29.3.2, 30.29.3.2, 31.29.3.2, 32.29.3.2, 33.29.3.2, 34.29.3.2, 35.29.3.2, 36.29.3.2, 37.29.3.2, 38.29.3.2, 39.29.3.2, 40.29.3.2, 1.1.3.4, 2.1.3.4, 3.1.3.4, 4.1.3.4, 5.1.3.4, 6.1.3.4, 7.1.3.4, 8.1.3.4, 9.1.3.4, 10.1.3.4, 11.1.3.4, 12.1.3.4, 13.1.3.4, 14.1.3.4, 15.1.3.4, 16.1.3.4, 17.1.3.4, 18.1.3.4, 19.1.3.4, 20.1.3.4, 21.1.3.4, 22.1.3.4, 23.1.3.4, 24.1.3.4, 25.1.3.4, 26.1.3.4, 27.1.3.4, 28.1.3.4, 29.1.3.4, 30.1.3.4, 31.1.3.4, 32.1.3.4, 33.1.3.4, 34.1.3.4, 35.1.3.4, 36.1.3.4, 37.1.3.4, 38.1.3.4, 39.1.3.4, 40.1.3.4, 1.2.3.4, 2.2.3.4, 3.2.3.4, 4.2.3.4, 5.2.3.4, 6.2.3.4, 7.2.3.4, 8.2.3.4, 9.2.3.4, 10.2.3.4, 11.2.3.4, 12.2.3.4, 13.2.3.4, 14.2.3.4, 15.2.3.4, 16.2.3.4, 17.2.3.4, 18.2.3.4, 19.2.3.4, 20.2.3.4, 21.2.3.4, 22.2.3.4, 23.2.3.4, 24.2.3.4, 25.2.3.4, 26.2.3.4, 27.2.3.4, 28.2.3.4, 29.2.3.4, 30.2.3.4, 31.2.3.4, 32.2.3.4, 33.2.3.4, 34.2.3.4, 35.2.3.4, 36.2.3.4, 37.2.3.4, 38.2.3.4, 39.2.3.4, 40.2.3.4, 1.3.3.4, 2.3.3.4, 3.3.3.4, 4.3.3.4, 5.3.3.4, 6.3.3.4, 7.3.3.4, 8.3.3.4, 9.3.3.4, 10.3.3.4, 11.3.3.4, 12.3.3.4, 13.3.3.4, 14.3.3.4, 15.3.3.4, 16.3.3.4, 17.3.3.4, 18.3.3.4, 19.3.3.4, 20.3.3.4, 21.3.3.4, 22.3.3.4, 23.3.3.4, 24.3.3.4, 25.3.3.4, 26.3.3.4, 27.3.3.4, 28.3.3.4, 29.3.3.4, 30.3.3.4, 31.3.3.4, 32.3.3.4, 33.3.3.4, 34.3.3.4, 35.3.3.4, 36.3.3.4, 37.3.3.4, 38.3.3.4, 39.3.3.4, 40.3.3.4, 1.4.3.4, 2.4.3.4, 3.4.3.4, 4.4.3.4, 5.4.3.4, 6.4.3.4, 7.4.3.4, 8.4.3.4, 9.4.3.4, 10.4.3.4, 11.4.3.4, 12.4.3.4, 13.4.3.4, 14.4.3.4, 15.4.3.4, 16.4.3.4, 17.4.3.4, 18.4.3.4, 19.4.3.4, 20.4.3.4, 21.4.3.4, 22.4.3.4, 23.4.3.4, 24.4.3.4, 25.4.3.4, 26.4.3.4, 27.4.3.4, 28.4.3.4, 29.4.3.4, 30.4.3.4, 31.4.3.4, 32.4.3.4, 33.4.3.4, 34.4.3.4, 35.4.3.4, 36.4.3.4, 37.4.3.4, 38.4.3.4, 39.4.3.4, 40.4.3.4, 1.5.3.4, 2.5.3.4, 3.5.3.4, 4.5.3.4, 5.5.3.4, 6.5.3.4, 7.5.3.4, 8.5.3.4, 9.5.3.4, 10.5.3.4, 11.5.3.4, 12.5.3.4, 13.5.3.4, 14.5.3.4, 15.5.3.4, 16.5.3.4, 17.5.3.4, 18.5.3.4, 19.5.3.4, 20.5.3.4, 21.5.3.4, 22.5.3.4, 23.5.3.4, 24.5.3.4, 25.5.3.4, 26.5.3.4, 27.5.3.4, 28.5.3.4, 29.5.3.4, 30.5.3.4, 31.5.3.4, 32.5.3.4, 33.5.3.4, 34.5.3.4, 35.5.3.4, 36.5.3.4, 37.5.3.4, 38.5.3.4, 39.5.3.4, 40.5.3.4, 1.6.3.4, 2.6.3.4, 3.6.3.4, 4.6.3.4, 5.6.3.4, 6.6.3.4, 7.6.3.4, 8.6.3.4, 9.6.3.4, 10.6.3.4, 11.6.3.4, 12.6.3.4, 13.6.3.4, 14.6.3.4, 15.6.3.4, 16.6.3.4, 17.6.3.4, 18.6.3.4, 19.6.3.4, 20.6.3.4, 21.6.3.4, 22.6.3.4, 23.6.3.4, 24.6.3.4, 25.6.3.4, 26.6.3.4, 27.6.3.4, 28.6.3.4, 29.6.3.4, 30.6.3.4, 31.6.3.4, 32.6.3.4, 33.6.3.4, 34.6.3.4, 35.6.3.4, 36.6.3.4, 37.6.3.4, 38.6.3.4, 39.6.3.4, 40.6.3.4, 1.7.3.4, 2.7.3.4, 3.7.3.4, 4.7.3.4, 5.7.3.4, 6.7.3.4, 7.7.3.4, 8.7.3.4, 9.7.3.4, 10.7.3.4, 11.7.3.4, 12.7.3.4, 13.7.3.4, 14.7.3.4, 15.7.3.4, 16.7.3.4, 17.7.3.4, 18.7.3.4, 19.7.3.4, 20.7.3.4, 21.7.3.4, 22.7.3.4, 23.7.3.4, 24.7.3.4, 25.7.3.4, 26.7.3.4, 27.7.3.4, 28.7.3.4, 29.7.3.4, 30.7.3.4, 31.7.3.4, 32.7.3.4, 33.7.3.4, 34.7.3.4, 35.7.3.4, 36.7.3.4, 37.7.3.4, 38.7.3.4, 39.7.3.4, 40.7.3.4, 1.8.3.4, 2.8.3.4, 3.8.3.4, 4.8.3.4, 5.8.3.4, 6.8.3.4, 7.8.3.4, 8.8.3.4, 9.8.3.4, 10.8.3.4, 11.8.3.4, 12.8.3.4, 13.8.3.4, 14.8.3.4, 15.8.3.4, 16.8.3.4, 17.8.3.4, 18.8.3.4, 19.8.3.4, 20.8.3.4, 21.8.3.4, 22.8.3.4, 23.8.3.4, 24.8.3.4, 25.8.3.4, 26.8.3.4, 27.8.3.4, 28.8.3.4, 29.8.3.4, 30.8.3.4, 31.8.3.4, 32.8.3.4, 33.8.3.4, 34.8.3.4, 35.8.3.4, 36.8.3.4, 37.8.3.4, 38.8.3.4, 39.8.3.4, 40.8.3.4, 1.9.3.4, 2.9.3.4, 3.9.3.4, 4.9.3.4, 5.9.3.4, 6.9.3.4, 7.9.3.4, 8.9.3.4, 9.9.3.4, 10.9.3.4, 11.9.3.4, 12.9.3.4, 13.9.3.4, 14.9.3.4, 15.9.3.4, 16.9.3.4, 17.9.3.4, 18.9.3.4, 19.9.3.4, 20.9.3.4, 21.9.3.4, 22.9.3.4, 23.9.3.4, 24.9.3.4, 25.9.3.4, 26.9.3.4, 27.9.3.4, 28.9.3.4, 29.9.3.4, 30.9.3.4, 31.9.3.4, 32.9.3.4, 33.9.3.4, 34.9.3.4, 35.9.3.4, 36.9.3.4, 37.9.3.4, 38.9.3.4, 39.9.3.4, 40.9.3.4, 1.10.3.4, 2.10.3.4, 3.10.3.4, 4.10.3.4, 5.10.3.4, 6.10.3.4, 7.10.3.4, 8.10.3.4, 9.10.3.4, 10.10.3.4, 11.10.3.4, 12.10.3.4, 13.10.3.4, 14.10.3.4, 15.10.3.4, 16.10.3.4, 17.10.3.4, 18.10.3.4, 19.10.3.4, 20.10.3.4, 21.10.3.4, 22.10.3.4, 23.10.3.4, 24.10.3.4, 25.10.3.4, 26.10.3.4, 27.10.3.4, 28.10.3.4, 29.10.3.4, 30.10.3.4, 31.10.3.4, 32.10.3.4, 33.10.3.4, 34.10.3.4, 35.10.3.4, 36.10.3.4, 37.10.3.4, 38.10.3.4, 39.10.3.4, 40.10.3.4, 1.11.3.4, 2.11.3.4, 3.11.3.4, 4.11.3.4, 5.11.3.4, 6.11.3.4, 7.11.3.4, 8.11.3.4, 9.11.3.4, 10.11.3.4, 11.11.3.4, 12.11.3.4, 13.11.3.4, 14.11.3.4, 15.11.3.4, 16.11.3.4, 17.11.3.4, 18.11.3.4, 19.11.3.4, 20.11.3.4, 21.11.3.4, 22.11.3.4, 23.11.3.4, 24.11.3.4, 25.11.3.4, 26.11.3.4, 27.11.3.4, 28.11.3.4, 29.11.3.4, 30.11.3.4, 31.11.3.4, 32.11.3.4, 33.11.3.4, 34.11.3.4, 35.11.3.4, 36.11.3.4, 37.11.3.4, 38.11.3.4, 39.11.3.4, 40.11.3.4, 1.12.3.4, 2.12.3.4, 3.12.3.4, 4.12.3.4, 5.12.3.4, 6.12.3.4, 7.12.3.4, 8.12.3.4, 9.12.3.4, 10.12.3.4, 11.12.3.4, 12.12.3.4, 13.12.3.4, 14.12.3.4, 15.12.3.4, 16.12.3.4, 17.12.3.4, 18.12.3.4, 19.12.3.4, 20.12.3.4, 21.12.3.4, 22.12.3.4, 23.12.3.4, 24.12.3.4, 25.12.3.4, 26.12.3.4, 27.12.3.4, 28.12.3.4, 29.12.3.4, 30.12.3.4, 31.12.3.4, 32.12.3.4, 33.12.3.4, 34.12.3.4, 35.12.3.4, 36.12.3.4, 37.12.3.4, 38.12.3.4, 39.12.3.4, 40.12.3.4, 1.13.3.4, 2.13.3.4, 3.13.3.4, 4.13.3.4, 5.13.3.4, 6.13.3.4, 7.13.3.4, 8.13.3.4, 9.13.3.4, 10.13.3.4, 11.13.3.4, 12.13.3.4, 13.13.3.4, 14.13.3.4, 15.13.3.4, 16.13.3.4, 17.13.3.4, 18.13.3.4, 19.13.3.4, 20.13.3.4, 21.13.3.4, 22.13.3.4, 23.13.3.4, 24.13.3.4, 25.13.3.4, 26.13.3.4, 27.13.3.4, 28.13.3.4, 29.13.3.4, 30.13.3.4, 31.13.3.4, 32.13.3.4, 33.13.3.4, 34.13.3.4, 35.13.3.4, 36.13.3.4, 37.13.3.4, 38.13.3.4, 39.13.3.4, 40.13.3.4, 1.14.3.4, 2.14.3.4, 3.14.3.4, 4.14.3.4, 5.14.3.4, 6.14.3.4, 7.14.3.4, 8.14.3.4, 9.14.3.4, 10.14.3.4, 11.14.3.4, 12.14.3.4, 13.14.3.4, 14.14.3.4, 15.14.3.4, 16.14.3.4, 17.14.3.4, 18.14.3.4, 19.14.3.4, 20.14.3.4, 21.14.3.4, 22.14.3.4, 23.14.3.4, 24.14.3.4, 25.14.3.4, 26.14.3.4, 27.14.3.4, 28.14.3.4, 29.14.3.4, 30.14.3.4, 31.14.3.4, 32.14.3.4, 33.14.3.4, 34.14.3.4, 35.14.3.4, 36.14.3.4, 37.14.3.4, 38.14.3.4, 39.14.3.4, 40.14.3.4, 1.15.3.4, 2.15.3.4, 3.15.3.4, 4.15.3.4, 5.15.3.4, 6.15.3.4, 7.15.3.4, 8.15.3.4, 9.15.3.4, 10.15.3.4, 11.15.3.4, 12.15.3.4, 13.15.3.4, 14.15.3.4, 15.15.3.4, 16.15.3.4, 17.15.3.4, 18.15.3.4, 19.15.3.4, 20.15.3.4, 21.15.3.4, 22.15.3.4, 23.15.3.4, 24.15.3.4, 25.15.3.4, 26.15.3.4, 27.15.3.4, 28.15.3.4, 29.15.3.4, 30.15.3.4, 31.15.3.4, 32.15.3.4, 33.15.3.4, 34.15.3.4, 35.15.3.4, 36.15.3.4, 37.15.3.4, 38.15.3.4, 39.15.3.4, 40.15.3.4, 1.16.3.4, 2.16.3.4, 3.16.3.4, 4.16.3.4, 5.16.3.4, 6.16.3.4, 7.16.3.4, 8.16.3.4, 9.16.3.4, 10.16.3.4, 11.16.3.4, 12.16.3.4, 13.16.3.4, 14.16.3.4, 15.16.3.4, 16.16.3.4, 17.16.3.4, 18.16.3.4, 19.16.3.4, 20.16.3.4, 21.16.3.4, 22.16.3.4, 23.16.3.4, 24.16.3.4, 25.16.3.4, 26.16.3.4, 27.16.3.4, 28.16.3.4, 29.16.3.4, 30.16.3.4, 31.16.3.4, 32.16.3.4, 33.16.3.4, 34.16.3.4, 35.16.3.4, 36.16.3.4, 37.16.3.4, 38.16.3.4, 39.16.3.4, 40.16.3.4, 1.17.3.4, 2.17.3.4, 3.17.3.4, 4.17.3.4, 5.17.3.4, 6.17.3.4, 7.17.3.4, 8.17.3.4, 9.17.3.4, 10.17.3.4, 11.17.3.4, 12.17.3.4, 13.17.3.4, 14.17.3.4, 15.17.3.4, 16.17.3.4, 17.17.3.4, 18.17.3.4, 19.17.3.4, 20.17.3.4, 21.17.3.4, 22.17.3.4, 23.17.3.4, 24.17.3.4, 25.17.3.4, 26.17.3.4, 27.17.3.4, 28.17.3.4, 29.17.3.4, 30.17.3.4, 31.17.3.4, 32.17.3.4, 33.17.3.4, 34.17.3.4, 35.17.3.4, 36.17.3.4, 37.17.3.4, 38.17.3.4, 39.17.3.4, 40.17.3.4, 1.18.3.4, 2.18.3.4, 3.18.3.4, 4.18.3.4, 5.18.3.4, 6.18.3.4, 7.18.3.4, 8.18.3.4, 9.18.3.4, 10.18.3.4, 11.18.3.4, 12.18.3.4, 13.18.3.4, 14.18.3.4, 15.18.3.4, 16.18.3.4, 17.18.3.4, 18.18.3.4, 19.18.3.4, 20.18.3.4, 21.18.3.4, 22.18.3.4, 23.18.3.4, 24.18.3.4, 25.18.3.4, 26.18.3.4, 27.18.3.4, 28.18.3.4, 29.18.3.4, 30.18.3.4, 31.18.3.4, 32.18.3.4, 33.18.3.4, 34.18.3.4, 35.18.3.4, 36.18.3.4, 37.18.3.4, 38.18.3.4, 39.18.3.4, 40.18.3.4, 1.19.3.4, 2.19.3.4, 3.19.3.4, 4.19.3.4, 5.19.3.4, 6.19.3.4, 7.19.3.4, 8.19.3.4, 9.19.3.4, 10.19.3.4, 11.19.3.4, 12.19.3.4, 13.19.3.4, 14.19.3.4, 15.19.3.4, 16.19.3.4, 17.19.3.4, 18.19.3.4, 19.19.3.4, 20.19.3.4, 21.19.3.4, 22.19.3.4, 23.19.3.4, 24.19.3.4, 25.19.3.4, 26.19.3.4, 27.19.3.4, 28.19.3.4, 29.19.3.4, 30.19.3.4, 31.19.3.4, 32.19.3.4, 33.19.3.4, 34.19.3.4, 35.19.3.4, 36.19.3.4, 37.19.3.4, 38.19.3.4, 39.19.3.4, 40.19.3.4, 1.20.3.4, 2.20.3.4, 3.20.3.4, 4.20.3.4, 5.20.3.4, 6.20.3.4, 7.20.3.4, 8.20.3.4, 9.20.3.4, 10.20.3.4, 11.20.3.4, 12.20.3.4, 13.20.3.4, 14.20.3.4, 15.20.3.4, 16.20.3.4, 17.20.3.4, 18.20.3.4, 19.20.3.4, 20.20.3.4, 21.20.3.4, 22.20.3.4, 23.20.3.4, 24.20.3.4, 25.20.3.4, 26.20.3.4, 27.20.3.4, 28.20.3.4, 29.20.3.4, 30.20.3.4, 31.20.3.4, 32.20.3.4, 33.20.3.4, 34.20.3.4, 35.20.3.4, 36.20.3.4, 37.20.3.4, 38.20.3.4, 39.20.3.4, 40.20.3.4, 1.21.3.4, 2.21.3.4, 3.21.3.4, 4.21.3.4, 5.21.3.4, 6.21.3.4, 7.21.3.4, 8.21.3.4, 9.21.3.4, 10.21.3.4, 11.21.3.4, 12.21.3.4, 13.21.3.4, 14.21.3.4, 15.21.3.4, 16.21.3.4, 17.21.3.4, 18.21.3.4, 19.21.3.4, 20.21.3.4, 21.21.3.4, 22.21.3.4, 23.21.3.4, 24.21.3.4, 25.21.3.4, 26.21.3.4, 27.21.3.4, 28.21.3.4, 29.21.3.4, 30.21.3.4, 31.21.3.4, 32.21.3.4, 33.21.3.4, 34.21.3.4, 35.21.3.4, 36.21.3.4, 37.21.3.4, 38.21.3.4, 39.21.3.4, 40.21.3.4, 1.22.3.4, 2.22.3.4, 3.22.3.4, 4.22.3.4, 5.22.3.4, 6.22.3.4, 7.22.3.4, 8.22.3.4, 9.22.3.4, 10.22.3.4, 11.22.3.4, 12.22.3.4, 13.22.3.4, 14.22.3.4, 15.22.3.4, 16.22.3.4, 17.22.3.4, 18.22.3.4, 19.22.3.4, 20.22.3.4, 21.22.3.4, 22.22.3.4, 23.22.3.4, 24.22.3.4, 25.22.3.4, 26.22.3.4, 27.22.3.4, 28.22.3.4, 29.22.3.4, 30.22.3.4, 31.22.3.4, 32.22.3.4, 33.22.3.4, 34.22.3.4, 35.22.3.4, 36.22.3.4, 37.22.3.4, 38.22.3.4, 39.22.3.4, 40.22.3.4, 1.23.3.4, 2.23.3.4, 3.23.3.4, 4.23.3.4, 5.23.3.4, 6.23.3.4, 7.23.3.4, 8.23.3.4, 9.23.3.4, 10.23.3.4, 11.23.3.4, 12.23.3.4, 13.23.3.4, 14.23.3.4, 15.23.3.4, 16.23.3.4, 17.23.3.4, 18.23.3.4, 19.23.3.4, 20.23.3.4, 21.23.3.4, 22.23.3.4, 23.23.3.4, 24.23.3.4, 25.23.3.4, 26.23.3.4, 27.23.3.4, 28.23.3.4, 29.23.3.4, 30.23.3.4, 31.23.3.4, 32.23.3.4, 33.23.3.4, 34.23.3.4, 35.23.3.4, 36.23.3.4, 37.23.3.4, 38.23.3.4, 39.23.3.4, 40.23.3.4, 1.24.3.4, 2.24.3.4, 3.24.3.4, 4.24.3.4, 5.24.3.4, 6.24.3.4, 7.24.3.4, 8.24.3.4, 9.24.3.4, 10.24.3.4, 11.24.3.4, 12.24.3.4, 13.24.3.4, 14.24.3.4, 15.24.3.4, 16.24.3.4, 17.24.3.4, 18.24.3.4, 19.24.3.4, 20.24.3.4, 21.24.3.4, 22.24.3.4, 23.24.3.4, 24.24.3.4, 25.24.3.4, 26.24.3.4, 27.24.3.4, 28.24.3.4, 29.24.3.4, 30.24.3.4, 31.24.3.4, 32.24.3.4, 33.24.3.4, 34.24.3.4, 35.24.3.4, 36.24.3.4, 37.24.3.4, 38.24.3.4, 39.24.3.4, 40.24.3.4, 1.25.3.4, 2.25.3.4, 3.25.3.4, 4.25.3.4, 5.25.3.4, 6.25.3.4, 7.25.3.4, 8.25.3.4, 9.25.3.4, 10.25.3.4, 11.25.3.4, 12.25.3.4, 13.25.3.4, 14.25.3.4, 15.25.3.4, 16.25.3.4, 17.25.3.4, 18.25.3.4, 19.25.3.4, 20.25.3.4, 21.25.3.4, 22.25.3.4, 23.25.3.4, 24.25.3.4, 25.25.3.4, 26.25.3.4, 27.25.3.4, 28.25.3.4, 29.25.3.4, 30.25.3.4, 31.25.3.4, 32.25.3.4, 33.25.3.4, 34.25.3.4, 35.25.3.4, 36.25.3.4, 37.25.3.4, 38.25.3.4, 39.25.3.4, 40.25.3.4, 1.26.3.4, 2.26.3.4, 3.26.3.4, 4.26.3.4, 5.26.3.4, 6.26.3.4, 7.26.3.4, 8.26.3.4, 9.26.3.4, 10.26.3.4, 11.26.3.4, 12.26.3.4, 13.26.3.4, 14.26.3.4, 15.26.3.4, 16.26.3.4, 17.26.3.4, 18.26.3.4, 19.26.3.4, 20.26.3.4, 21.26.3.4, 22.26.3.4, 23.26.3.4, 24.26.3.4, 25.26.3.4, 26.26.3.4, 27.26.3.4, 28.26.3.4, 29.26.3.4, 30.26.3.4, 31.26.3.4, 32.26.3.4, 33.26.3.4, 34.26.3.4, 35.26.3.4, 36.26.3.4, 37.26.3.4, 38.26.3.4, 39.26.3.4, 40.26.3.4, 1.27.3.4, 2.27.3.4, 3.27.3.4, 4.27.3.4, 5.27.3.4, 6.27.3.4, 7.27.3.4, 8.27.3.4, 9.27.3.4, 10.27.3.4, 11.27.3.4, 12.27.3.4, 13.27.3.4, 14.27.3.4, 15.27.3.4, 16.27.3.4, 17.27.3.4, 18.27.3.4, 19.27.3.4, 20.27.3.4, 21.27.3.4, 22.27.3.4, 23.27.3.4, 24.27.3.4, 25.27.3.4, 26.27.3.4, 27.27.3.4, 28.27.3.4, 29.27.3.4, 30.27.3.4, 31.27.3.4, 32.27.3.4, 33.27.3.4, 34.27.3.4, 35.27.3.4, 36.27.3.4, 37.27.3.4, 38.27.3.4, 39.27.3.4, 40.27.3.4, 1.28.3.4, 2.28.3.4, 3.28.3.4, 4.28.3.4, 5.28.3.4, 6.28.3.4, 7.28.3.4, 8.28.3.4, 9.28.3.4, 10.28.3.4, 11.28.3.4, 12.28.3.4, 13.28.3.4, 14.28.3.4, 15.28.3.4, 16.28.3.4, 17.28.3.4, 18.28.3.4, 19.28.3.4, 20.28.3.4, 21.28.3.4, 22.28.3.4, 23.28.3.4, 24.28.3.4, 25.28.3.4, 26.28.3.4, 27.28.3.4, 28.28.3.4, 29.28.3.4, 30.28.3.4, 31.28.3.4, 32.28.3.4, 33.28.3.4, 34.28.3.4, 35.28.3.4, 36.28.3.4, 37.28.3.4, 38.28.3.4, 39.28.3.4, 40.28.3.4, 1.29.3.4, 2.29.3.4, 3.29.3.4, 4.29.3.4, 5.29.3.4, 6.29.3.4, 7.29.3.4, 8.29.3.4, 9.29.3.4, 10.29.3.4, 11.29.3.4, 12.29.3.4, 13.29.3.4, 14.29.3.4, 15.29.3.4, 16.29.3.4, 17.29.3.4, 18.29.3.4, 19.29.3.4, 20.29.3.4, 21.29.3.4, 22.29.3.4, 23.29.3.4, 24.29.3.4, 25.29.3.4, 26.29.3.4, 27.29.3.4, 28.29.3.4, 29.29.3.4, 30.29.3.4, 31.29.3.4, 32.29.3.4, 33.29.3.4, 34.29.3.4, 35.29.3.4, 36.29.3.4, 37.29.3.4, 38.29.3.4, 39.29.3.4, 40.29.3.4, 1.1.3.5, 2.1.3.5, 3.1.3.5, 4.1.3.5, 5.1.3.5, 6.1.3.5, 7.1.3.5, 8.1.3.5, 9.1.3.5, 10.1.3.5, 11.1.3.5, 12.1.3.5, 13.1.3.5, 14.1.3.5, 15.1.3.5, 16.1.3.5, 17.1.3.5, 18.1.3.5, 19.1.3.5, 20.1.3.5, 21.1.3.5, 22.1.3.5, 23.1.3.5, 24.1.3.5, 25.1.3.5, 26.1.3.5, 27.1.3.5, 28.1.3.5, 29.1.3.5, 30.1.3.5, 31.1.3.5, 32.1.3.5, 33.1.3.5, 34.1.3.5, 35.1.3.5, 36.1.3.5, 37.1.3.5, 38.1.3.5, 39.1.3.5, 40.1.3.5, 1.2.3.5, 2.2.3.5, 3.2.3.5, 4.2.3.5, 5.2.3.5, 6.2.3.5, 7.2.3.5, 8.2.3.5, 9.2.3.5, 10.2.3.5, 11.2.3.5, 12.2.3.5, 13.2.3.5, 14.2.3.5, 15.2.3.5, 16.2.3.5, 17.2.3.5, 18.2.3.5, 19.2.3.5, 20.2.3.5, 21.2.3.5, 22.2.3.5, 23.2.3.5, 24.2.3.5, 25.2.3.5, 26.2.3.5, 27.2.3.5, 28.2.3.5, 29.2.3.5, 30.2.3.5, 31.2.3.5, 32.2.3.5, 33.2.3.5, 34.2.3.5, 35.2.3.5, 36.2.3.5, 37.2.3.5, 38.2.3.5, 39.2.3.5, 40.2.3.5, 1.3.3.5, 2.3.3.5, 3.3.3.5, 4.3.3.5, 5.3.3.5, 6.3.3.5, 7.3.3.5, 8.3.3.5, 9.3.3.5, 10.3.3.5, 11.3.3.5, 12.3.3.5, 13.3.3.5, 14.3.3.5, 15.3.3.5, 16.3.3.5, 17.3.3.5, 18.3.3.5, 19.3.3.5, 20.3.3.5, 21.3.3.5, 22.3.3.5, 23.3.3.5, 24.3.3.5, 25.3.3.5, 26.3.3.5, 27.3.3.5, 28.3.3.5, 29.3.3.5, 30.3.3.5, 31.3.3.5, 32.3.3.5, 33.3.3.5, 34.3.3.5, 35.3.3.5, 36.3.3.5, 37.3.3.5, 38.3.3.5, 39.3.3.5, 40.3.3.5, 1.4.3.5, 2.4.3.5, 3.4.3.5, 4.4.3.5, 5.4.3.5, 6.4.3.5, 7.4.3.5, 8.4.3.5, 9.4.3.5, 10.4.3.5, 11.4.3.5, 12.4.3.5, 13.4.3.5, 14.4.3.5, 15.4.3.5, 16.4.3.5, 17.4.3.5, 18.4.3.5, 19.4.3.5, 20.4.3.5, 21.4.3.5, 22.4.3.5, 23.4.3.5, 24.4.3.5, 25.4.3.5, 26.4.3.5, 27.4.3.5, 28.4.3.5, 29.4.3.5, 30.4.3.5, 31.4.3.5, 32.4.3.5, 33.4.3.5, 34.4.3.5, 35.4.3.5, 36.4.3.5, 37.4.3.5, 38.4.3.5, 39.4.3.5, 40.4.3.5, 1.5.3.5, 2.5.3.5, 3.5.3.5, 4.5.3.5, 5.5.3.5, 6.5.3.5, 7.5.3.5, 8.5.3.5, 9.5.3.5, 10.5.3.5, 11.5.3.5, 12.5.3.5, 13.5.3.5, 14.5.3.5, 15.5.3.5, 16.5.3.5, 17.5.3.5, 18.5.3.5, 19.5.3.5, 20.5.3.5, 21.5.3.5, 22.5.3.5, 23.5.3.5, 24.5.3.5, 25.5.3.5, 26.5.3.5, 27.5.3.5, 28.5.3.5, 29.5.3.5, 30.5.3.5, 31.5.3.5, 32.5.3.5, 33.5.3.5, 34.5.3.5, 35.5.3.5, 36.5.3.5, 37.5.3.5, 38.5.3.5, 39.5.3.5, 40.5.3.5, 1.6.3.5, 2.6.3.5, 3.6.3.5, 4.6.3.5, 5.6.3.5, 6.6.3.5, 7.6.3.5, 8.6.3.5, 9.6.3.5, 10.6.3.5, 11.6.3.5, 12.6.3.5, 13.6.3.5, 14.6.3.5, 15.6.3.5, 16.6.3.5, 17.6.3.5, 18.6.3.5, 19.6.3.5, 20.6.3.5, 21.6.3.5, 22.6.3.5, 23.6.3.5, 24.6.3.5, 25.6.3.5, 26.6.3.5, 27.6.3.5, 28.6.3.5, 29.6.3.5, 30.6.3.5, 31.6.3.5, 32.6.3.5, 33.6.3.5, 34.6.3.5, 35.6.3.5, 36.6.3.5, 37.6.3.5, 38.6.3.5, 39.6.3.5, 40.6.3.5, 1.7.3.5, 2.7.3.5, 3.7.3.5, 4.7.3.5, 5.7.3.5, 6.7.3.5, 7.7.3.5, 8.7.3.5, 9.7.3.5, 10.7.3.5, 11.7.3.5, 12.7.3.5, 13.7.3.5, 14.7.3.5, 15.7.3.5, 16.7.3.5, 17.7.3.5, 18.7.3.5, 19.7.3.5, 20.7.3.5, 21.7.3.5, 22.7.3.5, 23.7.3.5, 24.7.3.5, 25.7.3.5, 26.7.3.5, 27.7.3.5, 28.7.3.5, 29.7.3.5, 30.7.3.5, 31.7.3.5, 32.7.3.5, 33.7.3.5, 34.7.3.5, 35.7.3.5, 36.7.3.5, 37.7.3.5, 38.7.3.5, 39.7.3.5, 40.7.3.5, 1.8.3.5, 2.8.3.5, 3.8.3.5, 4.8.3.5, 5.8.3.5, 6.8.3.5, 7.8.3.5, 8.8.3.5, 9.8.3.5, 10.8.3.5, 11.8.3.5, 12.8.3.5, 13.8.3.5, 14.8.3.5, 15.8.3.5, 16.8.3.5, 17.8.3.5, 18.8.3.5, 19.8.3.5, 20.8.3.5, 21.8.3.5, 22.8.3.5, 23.8.3.5, 24.8.3.5, 25.8.3.5, 26.8.3.5, 27.8.3.5, 28.8.3.5, 29.8.3.5, 30.8.3.5, 31.8.3.5, 32.8.3.5, 33.8.3.5, 34.8.3.5, 35.8.3.5, 36.8.3.5, 37.8.3.5, 38.8.3.5, 39.8.3.5, 40.8.3.5, 1.9.3.5, 2.9.3.5, 3.9.3.5, 4.9.3.5, 5.9.3.5, 6.9.3.5, 7.9.3.5, 8.9.3.5, 9.9.3.5, 10.9.3.5, 11.9.3.5, 12.9.3.5, 13.9.3.5, 14.9.3.5, 15.9.3.5, 16.9.3.5, 17.9.3.5, 18.9.3.5, 19.9.3.5, 20.9.3.5, 21.9.3.5, 22.9.3.5, 23.9.3.5, 24.9.3.5, 25.9.3.5, 26.9.3.5, 27.9.3.5, 28.9.3.5, 29.9.3.5, 30.9.3.5, 31.9.3.5, 32.9.3.5, 33.9.3.5, 34.9.3.5, 35.9.3.5, 36.9.3.5, 37.9.3.5, 38.9.3.5, 39.9.3.5, 40.9.3.5, 1.10.3.5, 2.10.3.5, 3.10.3.5, 4.10.3.5, 5.10.3.5, 6.10.3.5, 7.10.3.5, 8.10.3.5, 9.10.3.5, 10.10.3.5, 11.10.3.5, 12.10.3.5, 13.10.3.5, 14.10.3.5, 15.10.3.5, 16.10.3.5, 17.10.3.5, 18.10.3.5, 19.10.3.5, 20.10.3.5, 21.10.3.5, 22.10.3.5, 23.10.3.5, 24.10.3.5, 25.10.3.5, 26.10.3.5, 27.10.3.5, 28.10.3.5, 29.10.3.5, 30.10.3.5, 31.10.3.5, 32.10.3.5, 33.10.3.5, 34.10.3.5, 35.10.3.5, 36.10.3.5, 37.10.3.5, 38.10.3.5, 39.10.3.5, 40.10.3.5, 1.11.3.5, 2.11.3.5, 3.11.3.5, 4.11.3.5, 5.11.3.5, 6.11.3.5, 7.11.3.5, 8.11.3.5, 9.11.3.5, 10.11.3.5, 11.11.3.5, 12.11.3.5, 13.11.3.5, 14.11.3.5, 15.11.3.5, 16.11.3.5, 17.11.3.5, 18.11.3.5, 19.11.3.5, 20.11.3.5, 21.11.3.5, 22.11.3.5, 23.11.3.5, 24.11.3.5, 25.11.3.5, 26.11.3.5, 27.11.3.5, 28.11.3.5, 29.11.3.5, 30.11.3.5, 31.11.3.5, 32.11.3.5, 33.11.3.5, 34.11.3.5, 35.11.3.5, 36.11.3.5, 37.11.3.5, 38.11.3.5, 39.11.3.5, 40.11.3.5, 1.12.3.5, 2.12.3.5, 3.12.3.5, 4.12.3.5, 5.12.3.5, 6.12.3.5, 7.12.3.5, 8.12.3.5, 9.12.3.5, 10.12.3.5, 11.12.3.5, 12.12.3.5, 13.12.3.5, 14.12.3.5, 15.12.3.5, 16.12.3.5, 17.12.3.5, 18.12.3.5, 19.12.3.5, 20.12.3.5, 21.12.3.5, 22.12.3.5, 23.12.3.5, 24.12.3.5, 25.12.3.5, 26.12.3.5, 27.12.3.5, 28.12.3.5, 29.12.3.5, 30.12.3.5, 31.12.3.5, 32.12.3.5, 33.12.3.5, 34.12.3.5, 35.12.3.5, 36.12.3.5, 37.12.3.5, 38.12.3.5, 39.12.3.5, 40.12.3.5, 1.13.3.5, 2.13.3.5, 3.13.3.5, 4.13.3.5, 5.13.3.5, 6.13.3.5, 7.13.3.5, 8.13.3.5, 9.13.3.5, 10.13.3.5, 11.13.3.5, 12.13.3.5, 13.13.3.5, 14.13.3.5, 15.13.3.5, 16.13.3.5, 17.13.3.5, 18.13.3.5, 19.13.3.5, 20.13.3.5, 21.13.3.5, 22.13.3.5, 23.13.3.5, 24.13.3.5, 25.13.3.5, 26.13.3.5, 27.13.3.5, 28.13.3.5, 29.13.3.5, 30.13.3.5, 31.13.3.5, 32.13.3.5, 33.13.3.5, 34.13.3.5, 35.13.3.5, 36.13.3.5, 37.13.3.5, 38.13.3.5, 39.13.3.5, 40.13.3.5, 1.14.3.5, 2.14.3.5, 3.14.3.5, 4.14.3.5, 5.14.3.5, 6.14.3.5, 7.14.3.5, 8.14.3.5, 9.14.3.5, 10.14.3.5, 11.14.3.5, 12.14.3.5, 13.14.3.5, 14.14.3.5, 15.14.3.5, 16.14.3.5, 17.14.3.5, 18.14.3.5, 19.14.3.5, 20.14.3.5, 21.14.3.5, 22.14.3.5, 23.14.3.5, 24.14.3.5, 25.14.3.5, 26.14.3.5, 27.14.3.5, 28.14.3.5, 29.14.3.5, 30.14.3.5, 31.14.3.5, 32.14.3.5, 33.14.3.5, 34.14.3.5, 35.14.3.5, 36.14.3.5, 37.14.3.5, 38.14.3.5, 39.14.3.5, 40.14.3.5, 1.15.3.5, 2.15.3.5, 3.15.3.5, 4.15.3.5, 5.15.3.5, 6.15.3.5, 7.15.3.5, 8.15.3.5, 9.15.3.5, 10.15.3.5, 11.15.3.5, 12.15.3.5, 13.15.3.5, 14.15.3.5, 15.15.3.5, 16.15.3.5, 17.15.3.5, 18.15.3.5, 19.15.3.5, 20.15.3.5, 21.15.3.5, 22.15.3.5, 23.15.3.5, 24.15.3.5, 25.15.3.5, 26.15.3.5, 27.15.3.5, 28.15.3.5, 29.15.3.5, 30.15.3.5, 31.15.3.5, 32.15.3.5, 33.15.3.5, 34.15.3.5, 35.15.3.5, 36.15.3.5, 37.15.3.5, 38.15.3.5, 39.15.3.5, 40.15.3.5, 1.16.3.5, 2.16.3.5, 3.16.3.5, 4.16.3.5, 5.16.3.5, 6.16.3.5, 7.16.3.5, 8.16.3.5, 9.16.3.5, 10.16.3.5, 11.16.3.5, 12.16.3.5, 13.16.3.5, 14.16.3.5, 15.16.3.5, 16.16.3.5, 17.16.3.5, 18.16.3.5, 19.16.3.5, 20.16.3.5, 21.16.3.5, 22.16.3.5, 23.16.3.5, 24.16.3.5, 25.16.3.5, 26.16.3.5, 27.16.3.5, 28.16.3.5, 29.16.3.5, 30.16.3.5, 31.16.3.5, 32.16.3.5, 33.16.3.5, 34.16.3.5, 35.16.3.5, 36.16.3.5, 37.16.3.5, 38.16.3.5, 39.16.3.5, 40.16.3.5, 1.17.3.5, 2.17.3.5, 3.17.3.5, 4.17.3.5, 5.17.3.5, 6.17.3.5, 7.17.3.5, 8.17.3.5, 9.17.3.5, 10.17.3.5, 11.17.3.5, 12.17.3.5, 13.17.3.5, 14.17.3.5, 15.17.3.5, 16.17.3.5, 17.17.3.5, 18.17.3.5, 19.17.3.5, 20.17.3.5, 21.17.3.5, 22.17.3.5, 23.17.3.5, 24.17.3.5, 25.17.3.5, 26.17.3.5, 27.17.3.5, 28.17.3.5, 29.17.3.5, 30.17.3.5, 31.17.3.5, 32.17.3.5, 33.17.3.5, 34.17.3.5, 35.17.3.5, 36.17.3.5, 37.17.3.5, 38.17.3.5, 39.17.3.5, 40.17.3.5, 1.18.3.5, 2.18.3.5, 3.18.3.5, 4.18.3.5, 5.18.3.5, 6.18.3.5, 7.18.3.5, 8.18.3.5, 9.18.3.5, 10.18.3.5, 11.18.3.5, 12.18.3.5, 13.18.3.5, 14.18.3.5, 15.18.3.5, 16.18.3.5, 17.18.3.5, 18.18.3.5, 19.18.3.5, 20.18.3.5, 21.18.3.5, 22.18.3.5, 23.18.3.5, 24.18.3.5, 25.18.3.5, 26.18.3.5, 27.18.3.5, 28.18.3.5, 29.18.3.5, 30.18.3.5, 31.18.3.5, 32.18.3.5, 33.18.3.5, 34.18.3.5, 35.18.3.5, 36.18.3.5, 37.18.3.5, 38.18.3.5, 39.18.3.5, 40.18.3.5, 1.19.3.5, 2.19.3.5, 3.19.3.5, 4.19.3.5, 5.19.3.5, 6.19.3.5, 7.19.3.5, 8.19.3.5, 9.19.3.5, 10.19.3.5, 11.19.3.5, 12.19.3.5, 13.19.3.5, 14.19.3.5, 15.19.3.5, 16.19.3.5, 17.19.3.5, 18.19.3.5, 19.19.3.5, 20.19.3.5, 21.19.3.5, 22.19.3.5, 23.19.3.5, 24.19.3.5, 25.19.3.5, 26.19.3.5, 27.19.3.5, 28.19.3.5, 29.19.3.5, 30.19.3.5, 31.19.3.5, 32.19.3.5, 33.19.3.5, 34.19.3.5, 35.19.3.5, 36.19.3.5, 37.19.3.5, 38.19.3.5, 39.19.3.5, 40.19.3.5, 1.20.3.5, 2.20.3.5, 3.20.3.5, 4.20.3.5, 5.20.3.5, 6.20.3.5, 7.20.3.5, 8.20.3.5, 9.20.3.5, 10.20.3.5, 11.20.3.5, 12.20.3.5, 13.20.3.5, 14.20.3.5, 15.20.3.5, 16.20.3.5, 17.20.3.5, 18.20.3.5, 19.20.3.5, 20.20.3.5, 21.20.3.5, 22.20.3.5, 23.20.3.5, 24.20.3.5, 25.20.3.5, 26.20.3.5, 27.20.3.5, 28.20.3.5, 29.20.3.5, 30.20.3.5, 31.20.3.5, 32.20.3.5, 33.20.3.5, 34.20.3.5, 35.20.3.5, 36.20.3.5, 37.20.3.5, 38.20.3.5, 39.20.3.5, 40.20.3.5, 1.21.3.5, 2.21.3.5, 3.21.3.5, 4.21.3.5, 5.21.3.5, 6.21.3.5, 7.21.3.5, 8.21.3.5, 9.21.3.5, 10.21.3.5, 11.21.3.5, 12.21.3.5, 13.21.3.5, 14.21.3.5, 15.21.3.5, 16.21.3.5, 17.21.3.5, 18.21.3.5, 19.21.3.5, 20.21.3.5, 21.21.3.5, 22.21.3.5, 23.21.3.5, 24.21.3.5, 25.21.3.5, 26.21.3.5, 27.21.3.5, 28.21.3.5, 29.21.3.5, 30.21.3.5, 31.21.3.5, 32.21.3.5, 33.21.3.5, 34.21.3.5, 35.21.3.5, 36.21.3.5, 37.21.3.5, 38.21.3.5, 39.21.3.5, 40.21.3.5, 1.22.3.5, 2.22.3.5, 3.22.3.5, 4.22.3.5, 5.22.3.5, 6.22.3.5, 7.22.3.5, 8.22.3.5, 9.22.3.5, 10.22.3.5, 11.22.3.5, 12.22.3.5, 13.22.3.5, 14.22.3.5, 15.22.3.5, 16.22.3.5, 17.22.3.5, 18.22.3.5, 19.22.3.5, 20.22.3.5, 21.22.3.5, 22.22.3.5, 23.22.3.5, 24.22.3.5, 25.22.3.5, 26.22.3.5, 27.22.3.5, 28.22.3.5, 29.22.3.5, 30.22.3.5, 31.22.3.5, 32.22.3.5, 33.22.3.5, 34.22.3.5, 35.22.3.5, 36.22.3.5, 37.22.3.5, 38.22.3.5, 39.22.3.5, 40.22.3.5, 1.23.3.5, 2.23.3.5, 3.23.3.5, 4.23.3.5, 5.23.3.5, 6.23.3.5, 7.23.3.5, 8.23.3.5, 9.23.3.5, 10.23.3.5, 11.23.3.5, 12.23.3.5, 13.23.3.5, 14.23.3.5, 15.23.3.5, 16.23.3.5, 17.23.3.5, 18.23.3.5, 19.23.3.5, 20.23.3.5, 21.23.3.5, 22.23.3.5, 23.23.3.5, 24.23.3.5, 25.23.3.5, 26.23.3.5, 27.23.3.5, 28.23.3.5, 29.23.3.5, 30.23.3.5, 31.23.3.5, 32.23.3.5, 33.23.3.5, 34.23.3.5, 35.23.3.5, 36.23.3.5, 37.23.3.5, 38.23.3.5, 39.23.3.5, 40.23.3.5, 1.24.3.5, 2.24.3.5, 3.24.3.5, 4.24.3.5, 5.24.3.5, 6.24.3.5, 7.24.3.5, 8.24.3.5, 9.24.3.5, 10.24.3.5, 11.24.3.5, 12.24.3.5, 13.24.3.5, 14.24.3.5, 15.24.3.5, 16.24.3.5, 17.24.3.5, 18.24.3.5, 19.24.3.5, 20.24.3.5, 21.24.3.5, 22.24.3.5, 23.24.3.5, 24.24.3.5, 25.24.3.5, 26.24.3.5, 27.24.3.5, 28.24.3.5, 29.24.3.5, 30.24.3.5, 31.24.3.5, 32.24.3.5, 33.24.3.5, 34.24.3.5, 35.24.3.5, 36.24.3.5, 37.24.3.5, 38.24.3.5, 39.24.3.5, 40.24.3.5, 1.25.3.5, 2.25.3.5, 3.25.3.5, 4.25.3.5, 5.25.3.5, 6.25.3.5, 7.25.3.5, 8.25.3.5, 9.25.3.5, 10.25.3.5, 11.25.3.5, 12.25.3.5, 13.25.3.5, 14.25.3.5, 15.25.3.5, 16.25.3.5, 17.25.3.5, 18.25.3.5, 19.25.3.5, 20.25.3.5, 21.25.3.5, 22.25.3.5, 23.25.3.5, 24.25.3.5, 25.25.3.5, 26.25.3.5, 27.25.3.5, 28.25.3.5, 29.25.3.5, 30.25.3.5, 31.25.3.5, 32.25.3.5, 33.25.3.5, 34.25.3.5, 35.25.3.5, 36.25.3.5, 37.25.3.5, 38.25.3.5, 39.25.3.5, 40.25.3.5, 1.26.3.5, 2.26.3.5, 3.26.3.5, 4.26.3.5, 5.26.3.5, 6.26.3.5, 7.26.3.5, 8.26.3.5, 9.26.3.5, 10.26.3.5, 11.26.3.5, 12.26.3.5, 13.26.3.5, 14.26.3.5, 15.26.3.5, 16.26.3.5, 17.26.3.5, 18.26.3.5, 19.26.3.5, 20.26.3.5, 21.26.3.5, 22.26.3.5, 23.26.3.5, 24.26.3.5, 25.26.3.5, 26.26.3.5, 27.26.3.5, 28.26.3.5, 29.26.3.5, 30.26.3.5, 31.26.3.5, 32.26.3.5, 33.26.3.5, 34.26.3.5, 35.26.3.5, 36.26.3.5, 37.26.3.5, 38.26.3.5, 39.26.3.5, 40.26.3.5, 1.27.3.5, 2.27.3.5, 3.27.3.5, 4.27.3.5, 5.27.3.5, 6.27.3.5, 7.27.3.5, 8.27.3.5, 9.27.3.5, 10.27.3.5, 11.27.3.5, 12.27.3.5, 13.27.3.5, 14.27.3.5, 15.27.3.5, 16.27.3.5, 17.27.3.5, 18.27.3.5, 19.27.3.5, 20.27.3.5, 21.27.3.5, 22.27.3.5, 23.27.3.5, 24.27.3.5, 25.27.3.5, 26.27.3.5, 27.27.3.5, 28.27.3.5, 29.27.3.5, 30.27.3.5, 31.27.3.5, 32.27.3.5, 33.27.3.5, 34.27.3.5, 35.27.3.5, 36.27.3.5, 37.27.3.5, 38.27.3.5, 39.27.3.5, 40.27.3.5, 1.28.3.5, 2.28.3.5, 3.28.3.5, 4.28.3.5, 5.28.3.5, 6.28.3.5, 7.28.3.5, 8.28.3.5, 9.28.3.5, 10.28.3.5, 11.28.3.5, 12.28.3.5, 13.28.3.5, 14.28.3.5, 15.28.3.5, 16.28.3.5, 17.28.3.5, 18.28.3.5, 19.28.3.5, 20.28.3.5, 21.28.3.5, 22.28.3.5, 23.28.3.5, 24.28.3.5, 25.28.3.5, 26.28.3.5, 27.28.3.5, 28.28.3.5, 29.28.3.5, 30.28.3.5, 31.28.3.5, 32.28.3.5, 33.28.3.5, 34.28.3.5, 35.28.3.5, 36.28.3.5, 37.28.3.5, 38.28.3.5, 39.28.3.5, 40.28.3.5, 1.29.3.5, 2.29.3.5, 3.29.3.5, 4.29.3.5, 5.29.3.5, 6.29.3.5, 7.29.3.5, 8.29.3.5, 9.29.3.5, 10.29.3.5, 11.29.3.5, 12.29.3.5, 13.29.3.5, 14.29.3.5, 15.29.3.5, 16.29.3.5, 17.29.3.5, 18.29.3.5, 19.29.3.5, 20.29.3.5, 21.29.3.5, 22.29.3.5, 23.29.3.5, 24.29.3.5, 25.29.3.5, 26.29.3.5, 27.29.3.5, 28.29.3.5, 29.29.3.5, 30.29.3.5, 31.29.3.5, 32.29.3.5, 33.29.3.5, 34.29.3.5, 35.29.3.5, 36.29.3.5, 37.29.3.5, 38.29.3.5, 39.29.3.5 and 40.29.3.5.

Table 2 lists a group of cyclic nucleotide analogs of structure I wherein Z forms a heterocyclic ring containing the phosphorus atom of the phosphonate group and two oxygen atoms as shown. Hydrolysis of the $L^1$ group linked to the phosphorus atom and subsequent ring hydrolysis results in formation of an HPMP nucleoside such as HPMPC (1-(2-phosphonomethoxy-3-hydroxypropyl)-cytosine).

TABLE 2

| | $L^{1*}$ |
|---|---|
| 1 | $-NH-CH_2-C(O)-OR^4$ |
| 2 | $-NH-CH(CH_3)-C(O)-OR^4$ |
| 3 | $-NH-CH(CH_3)_2-C(O)-OR^4$ |
| 4 | $-NH-CH(CH(CH_3)_2)-C(O)-OR^4$ |
| 5 | $-NH-CH(CH_3)(CH_3)_2-C(O)-OR^4$ |
| 6 | $-N-CH_2-CH_2-CH_2-CH-C(O)-OR^4$ |
| 7 | $-NH-CH(CH_2-C_6H_5)-C(O)-OR^4$ |
| 8 | $-NH-CH(CH_2-C_8NH_6)-C(O)-OR^4$ |
| 9 | $-NH-CH(CH_2-CH_2-S-CH_3)-C(O)-OR^4$ |
| 10 | $-NH-CH(CH_2OH)-C(O)-OR^4$ |
| 11 | $-NH-CH(CH(OH)(CH_3))-C(O)-OR^4$ |
| 12 | $-NH-CH(-CH_2SH)-C(O)-OR^4$ |
| 13 | $-NH-CH(CH_2-C_6H_5OH)-C(O)-OR^4$ |
| 14 | $-NH-CH(CH_2-C(O)-NH_2)-C(O)-OR^4$ |
| 15 | $-NH-CH(CH_2-CH_2-C(O)-NH_2)-C(O)-OR^4$ |
| 16 | $-NH-CH(CH_2C(O)OR^4)-C(O)-OR^4$ |
| 17 | $-NH-CH(CH_2CH_2C(OR^4)-C(O)-OR^4$ |
| 18 | $-NH-CH(CH_2CH_2CH_2CH_2NH_2)-C(O)-OR^4$ |
| 19 | $-NH-CH(CH_2CH_2CH_2NHC(NH)(NH_2))-C(O)-OR^4$ |
| 20 | $-NH-CH(CH_2C_3N_2H_3)-C(O)-OR^4$ |
| 21 | $-NH-CH(CH_2CH_2CH_2NH_2)-CH_2-C(O)-OR^4$ |
| 22 | $-NH-CH(CH_2CH_2CH_2CH_2NH_2)-CH_2-C(O)-OR^4$ |
| 23 | $-NH-CH(CH_2CH_2NHC(NH)(NH_2))-CH_2-C(O)-OR^4$ |
| 24 | $-NH-CH(C(O)OR^4)-CH_2-C(O)-OR^4$ |
| 25 | $-NH-CH(CH_2C(O)OR^4)-CH_2-C(O)-OR^4$ |
| 26 | $-NH-CH(CH_2CH_2C(O)OR^4)-CH_2-C(O)-OR^4$ |
| | Z-B** |
| 1 | 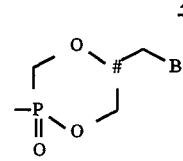 |

TABLE 2-continued

2

[Structure: cyclic phosphonate with P(=O)(O-)-O-CH2-#-CH2-B-S ring]

| | B |
|---|---|
| 1 | adenin-9-yl |
| 2 | guanin-9-yl |
| 3 | cytosin-1-yl |
| 4 | 2,6-diaminopurin-9-yl |
| 5 | 2-aminopurin-9-yl |
| 6 | 6-azacytosin-1-yl |
| 7 | 1-deazaadenin-9-yl |
| 8 | 3-deazaadenin-9-yl |
| 9 | 8-azaadenin-9-yl |
| 10 | 7-deaza-8-azaadenin-9-yl |

*See Table 1 footnote.
**See Table 1 footnote.
-See Table 1 footnote.

Compounds listed in Table 2 are designated herein by numbers assigned to $L^1$, Z and B according to the following convention, L.Z.B. Thus, compounds 1.1.3 and 1.2.3 represent, when R4 is H, glycinyl cyclic HPMPC and alanyl cyclic HPMPC. Exemplary compounds include 1.1.1, 1.1.2, 1.1.3, 1.1.4, 1.1.5, 1.1.6, 1.1.7, 1.1.8, 1.1.9, 1.1.10, 2.1.1, 2.1.2, 2.1.3, 2.1.4, 2.1.5, 2.1.6, 2.1.7, 2.1.8, 2.1.9, 2.1.10, 3.1.1, 3.1.2, 3.1.3, 3.1.4, 3.1.5, 3.1.6, 3.1.7, 3.1.8, 3.1.9, 3.1.10, 4.1.1, 4.1.2, 4.1.3, 4.1.4, 4.1.5, 4.1.6, 4.1.7, 4.1.8, 4.1.9, 4.1.10, 5.1.1, 5.1.2, 5.1.3, 5.1.4, 5.1.5, 5.1.6, 5.1.7, 5.1.8, 5.1.9, 5.1.10, 6.1.1, 6.1.2, 6.1.3, 6.1.4, 6.1.5, 6.1.6, 6.1.7, 6.1.8, 6.1.9, 6.1.10, 7.1.1, 7.1.2, 7.1.3, 7.1.4, 7.1.5, 7.1.6, 7.1.7, 7.1.8, 7.1.9, 7.1.10, 8.1.1, 8.1.2, 8.1.3, 8.1.4, 8.1.5, 8.1.6, 8.1.7, 8.1.8, 8.1.9, 8.1.10, 9.1.1, 9.1.2, 9.1.3, 9.1.4, 9.1.5, 9.1.6, 9.1.7, 9.1.8, 9.1.9, 9.1.10, 10.1.1, 10.1.2, 10.1.3, 10.1.4, 10.1.5, 10.1.6, 10.1.7, 10.1.8, 10.1.9, 10.1.10, 11.1.1, 11.1.2, 11.1.3, 11.1.4, 11.1.5, 11.1.6, 11.1.7, 11.1.8, 11.1.9, 11.1.10, 12.1.1, 12.1.2, 12.1.3, 12.1.4, 12.1.5, 12.1.6, 12.1.7, 12.1.8, 12.1.9, 12.1.10, 13.1.1, 13.1.2, 13.1.3, 13.1.4, 13.1.5, 13.1.6, 13.1.7, 13.1.8, 13.1.9, 13.1.10, 14.1.1, 14.1.2, 14.1.3, 14.1.4, 14.1.5, 14.1.6, 14.1.7, 14.1.8, 14.1.9, 14.1.10, 15.1.1, 15.1.2, 15.1.3, 15.1.4, 15.1.5, 15.1.6, 15.1.7, 15.1.8, 15.1.9, 15.1.10, 16.1.1, 16.1.2, 16.1.3, 16.1.4, 16.1.5, 16.1.6, 16.1.7, 16.1.8, 16.1.9, 16.1.10, 17.1.1, 17.1.2, 17.1.3, 17.1.4, 17.1.5, 17.1.6, 17.1.7, 17.1.8, 17.1.9, 17.1.10, 18.1.1, 18.1.2, 18.1.3, 18.1.4, 18.1.5, 18.1.6, 18.1.7, 18.1.8, 18.1.9, 18.1.10, 19.1.1, 19.1.2, 19.1.3, 19.1.4, 19.1.5, 19.1.6, 19.1.7, 19.1.8, 19.1.9, 19.1.10, 20.1.1, 20.1.2, 20.1.3, 20.1.4, 20.1.5, 20.1.6, 20.1.7, 20.1.8, 20.1.9, 20.1.10, 21.1.1, 21.1.2, 21.1.3, 21.1.4, 21.1.5, 21.1.6, 21.1.7, 21.1.8, 21.1.9, 21.1.10, 22.1.1, 22.1.2, 22.1.3, 22.1.4, 22.1.5, 22.1.6, 22.1.7, 22.1.8, 22.1.9, 22.1.10, 23.1.1, 23.1.2, 23.1.3, 23.1.4, 23.1.5, 23.1.6, 23.1.7, 23.1.8, 23.1.9, 23.1.10, 24.1.1, 24.1.2, 24.1.3, 24.1.4, 24.1.5, 24.1.6, 24.1.7, 24.1.8, 24.1.9, 24.1.10, 25.1.1, 25.1.2, 25.1.3, 25.1.4, 25.1.5, 25.1.6, 25.1.7, 25.1.8, 25.1.9, 25.1.10, 26.1.1, 26.1.2, 26.1.3, 26.1.4, 26.1.5, 26.1.6, 26.1.7, 26.1.8, 26.1.9, 26.1.10, 27.1.1, 27.1.2, 27.1.3, 27.1.4, 27.1.5, 27.1.6, 27.1.7, 27.1.8, 27.1.9, 27.1.10, 28.1.1, 28.1.2, 28.1.3, 28.1.4, 28.1.5, 28.1.6, 28.1.7, 28.1.8, 28.1.9, 28.1.10, 1.2.1, 1.2.2, 1.2.3, 1.2.4, 1.2.5, 1.2.6, 1.2.7, 1.2.8, 1.2.9, 1.2.10, 2.2.1, 2.2.2, 2.2.3, 2.2.4, 2.2.5, 2.2.6, 2.2.7, 2.2.8, 2.2.9, 2.2.10, 3.2.1, 3.2.2, 3.2.3, 3.2.4, 3.2.5, 3.2.6, 3.2.7, 3.2.8, 3.2.9, 3.2.10, 4.2.1, 4.2.2, 4.2.3, 4.2.4, 4.2.5, 4.2.6, 4.2.7, 4.2.8, 4.2.9, 4.2.10, 5.2.1, 5.2.2, 5.2.3, 5.2.4, 5.2.5, 5.2.6, 5.2.7, 5.2.8, 5.2.9, 5.2.10, 6.2.1, 6.2.2, 6.2.3, 6.2.4, 6.2.5, 6.2.6, 6.2.7, 6.2.8, 6.2.9, 6.2.10, 7.2.1, 7.2.2, 7.2.3, 7.2.4, 7.2.5, 7.2.6, 7.2.7, 7.2.8, 7.2.9, 7.2.10, 8.2.1, 8.2.2, 8.2.3, 8.2.4, 8.2.5, 8.2.6, 8.2.7, 8.2.8, 8.2.9, 8.2.10, 9.2.1, 9.2.2, 9.2.3, 9.2.4, 9.2.5, 9.2.6, 9.2.7, 9.2.8, 9.2.9, 9.2.10, 10.2.1, 10.2.2, 10.2.3, 10.2.4, 10.2.5, 10.2.6, 10.2.7, 10.2.8, 10.2.9, 10.2.10, 11.2.1, 11.2.2, 11.2.3, 11.2.4, 11.2.5, 11.2.6, 11.2.7, 11.2.8, 11.2.9, 11.2.10, 12.2.1, 12.2.2, 12.2.3, 12.2.4, 12.2.5, 12.2.6, 12.2.7, 12.2.8, 12.2.9, 12.2.10, 13.2.1, 13.2.2, 13.2.3, 13.2.4, 13.2.5, 13.2.6, 13.2.7, 13.2.8, 13.2.9, 13.2.10, 14.2.1, 14.2.2, 14.2.3, 14.2.4, 14.2.5, 14.2.6, 14.2.7, 14.2.8, 14.2.9, 14.2.10, 15.2.1, 15.2.2, 15.2.3, 15.2.4, 15.2.5, 15.2.6, 15.2.7, 15.2.8, 15.2.9, 15.2.10, 16.2.1, 16.2.2, 16.2.3, 16.2.4, 16.2.5, 16.2.6, 16.2.7, 16.2.8, 16.2.9, 16.2.10, 17.2.1, 17.2.2, 17.2.3, 17.2.4, 17.2.5, 17.2.6, 17.2.7, 17.2.8, 17.2.9, 17.2.10, 18.2.1, 18.2.2, 18.2.3, 18.2.4, 18.2.5, 18.2.6, 18.2.7, 18.2.8, 18.2.9, 18.2.10, 19.2.1, 19.2.2, 19.2.3, 19.2.4, 19.2.5, 19.2.6, 19.2.7, 19.2.8, 19.2.9, 19.2.10, 20.2.1, 20.2.2, 20.2.3, 20.2.4, 20.2.5, 20.2.6, 20.2.7, 20.2.8, 20.2.9, 20.2.10, 21.2.1, 21.2.2, 21.2.3, 21.2.4, 21.2.5, 21.2.6, 21.2.7, 21.2.8, 21.2.9, 21.2.10, 22.2.1, 22.2.2, 22.2.3, 22.2.4, 22.2.5, 22.2.6, 22.2.7, 22.2.8, 22.2.9, 22.2.10, 23.2.1, 23.2.2, 23.2.3, 23.2.4, 23.2.5, 23.2.6, 23.2.7, 23.2.8, 23.2.9, 23.2.10, 24.2.1, 24.2.2, 24.2.3, 24.2.4, 24.2.5, 24.2.6, 24.2.7, 24.2.8, 24.2.9, 24.2.10, 25.2.1, 25.2.2, 25.2.3, 25.2.4, 25.2.5, 25.2.6, 25.2.7, 25.2.8, 25.2.9, 25.2.10, 26.2.1, 26.2.2, 26.2.3, 26.2.4, 26.2.5, 26.2.6, 26.2.7, 26.2.8, 26.2.9 and 26.2.10.

Table 3 lists a group of cyclic nucleotide analog amidates of structure I wherein $L^1$ forms a heterocyclic ring containing the phosphorus atom of the phosphonate group. Hydrolysis of the heterocyclic ring linked through the phosphorus atom results in formation of a phosphonate nucleotide analog such as HPMPC, PMEA, PMEG or PMPDAP depending on the Z group that is present.

TABLE 3

| $L^1$ | Z-B** |
|---|---|
| 1 —NH—CH$_2$—C(O)—O—CH$_2$—O— | 1 —CH$_2$—O—CH$_2$—CH$_2$—B |
| 2 —NH—CH(CH$_3$)—C(O)—O—CH$_2$—O— | 2 —CH$_2$O—C*H(CH$_2$—OR⁴)—CH$_2$—B |
| 3 —NH—CH(CH$_3$)$_2$—C(O)—O—CH$_2$—O— | 3 —CH$_2$—O—C*H(CH$_3$)—CH$_2$—B |
| 4 —NH—CH(CH(CH$_3$)$_2$)—C(O)—O—CH$_2$—O— | 4 —CH$_2$—O—C*H(CH$_2$F)—CH$_2$—B |
| 5 —NH—CH(CH$_3$)(CH$_3$)$_2$—C(O)—O—CH$_2$—O— | 5 —CH$_2$—O—C*H(CH=CH$_2$)—CH$_2$—B |
| 6 —NH—CH$_2$—CH$_2$—CH$_2$—CH—C(O)—O—CH$_2$—O— | 6 —CH$_2$—O—C*H(CH$_2$N$_3$)—CH$_2$—B |
| 7 —NH—CH(CH$_2$—C$_6$H$_5$)—C(O)—O—CH$_2$—O— | |
| 8 —NH—CH(CH$_2$—C$_8$NH$_6$)—C(O)—O—CH$_2$—O— | |
| 9 —NH—CH(CH$_2$—CH$_2$—S—CH$_3$)—C(O)—O— | |
| 10 —NH—CH(CH$_2$OH)—C(O)—O—CH$_2$—O— | |
| 11 —NH—CH(CH(OH)(CH$_3$))—C(O)—O—CH$_2$—O— | |
| 12 —NH—CH(—CH$_2$SH)—C(O)—O—CH$_2$—O— | |
| 13 —NH—CH(CH$_2$—C$_6$HD$_5$OH)—C(O)—O—CH$_2$—O— | |
| 14 —NH—CH(CH$_2$—C(O)—NH$_2$)—C(O)—O—CH$_2$—O— | |

TABLE 3-continued

15 —NH—CH(CH$_2$—CH$_2$—C(O)—NH$_2$)—C(O)—O—CH$_2$O—
16 —NH—CH(CH$_2$C(O)OR$^4$)—C(O)—O—CH$_2$—O—
17 —NH—CH(CH$_2$CH$_2$C(O)OR$^4$)—C(O)—O—CH$_2$—O—
18 —NH—CH(CH$_2$CH$_2$CH$_2$CH$_2$NH$_2$)—C(O)—O—CH$_2$—O—
19 —NH—CH(CH$_2$CH$_2$CH$_2$NHC(NH)(NH$_2$)0—C(O)—O—CH$_2$—O—
20 —NH—CH(CH$_2$C$_3$N$_2$H$_3$)—C(O)—O—CH$_2$—O—
21 —NH—CH(CH$_2$CH$_2$NH$_2$)—CH$_2$—C(O)—O—CH$_2$—O—
22 —NH—CH(CH$_2$CH$_2$CH$_2$CH$_2$NH$_2$)—CH$_2$—C(O)—O—CH$_2$—O—
23 —NH—CH(CH$_2$CH$_2$NHC(NH)(NH$_2$))—CH$_2$—C(O)—O—CH$_2$—O—
24 —NH—CH(C(O)OR$^4$)—CH$_2$—C(O)—O—CH$_2$—O—
25 —NH—CH(CH$_2$C(O)OR$^4$)—CH$_2$—C(O)—O—
26 —NH—CH(CH$_2$CH$_2$C(O)OR$^4$)—CH$_2$—C(O)—O—CH$_2$—O—
27 —NH—CH2—C(O)—O—CH(C(O)OR$^4$)—N—
28 —NH—CH(CH$_3$)—C(O)—O—CH(C(O)OR$^4$)—N—

B 1 adenin-9-yl
2 guanin-9-yl
3 cytosin-1-yl
4 2,6-diaminopurin-9-yl
5 2-aminopurin-9-yl
6 6-azacytosin-1-yl
7 1-deazaadenin-9-yl
8 3-deazaadenin-9-yl
9 8-azaadenin-9-yl
10 7-deaza-8-azaadenin-9-yl

*See Table 1 footnote; the terminal nitrogen and oxygen or nitrogen atoms are both linked to the phosphorus atom of the phosphonate group.
**See Table 1 footnote.
See Table 1 footnote.

Compounds listed in Table 3 are designated herein by numbers assigned to L$^1$, Z and B according to the following convention, L$^1$.Z.B. Thus, compounds 1.1.1 and 2.3.4 represent compounds designated cyclic glycinylPMEA and cyclic alanylPMPDAP. Exemplary compounds include 1.1.1, 1.1.2, 1.1.3, 1.1.4, 1.1.5, 1.1.6, 1.1.7, 1.1.8, 1.1.9, 1.1.10, 2.1.1, 2.1.2, 2.1.3, 2.1.4, 2.1.5, 2.1.6, 2.1.7, 2.1.8, 2.1.9, 2.1.10, 3.1.1, 3.1.2, 3.1.3, 3.1.4, 3.1.5, 3.1.6, 3.1.7, 3.1.8, 3.1.9, 3.1.10, 4.1.1, 4.1.2, 4.1.3, 4.1.4, 4.1.5, 4.1.6, 4.1.7, 4.1.8, 4.1.9, 4.1.10, 5.1.1, 5.1.2, 5.1.3, 5.1.4, 5.1.5, 5.1.6, 5.1.7, 5.1.8, 5.1.9, 5.1.10, 6.1.1, 6.1.2, 6.1.3, 6.1.4, 6.1.5, 6.1.6, 6.1.7, 6.1.8, 6.1.9, 6.1.10, 7.1.1, 7.1.2, 7.1.3, 7.1.4, 7.1.5, 7.1.6, 7.1.7, 7.1.8, 7.1.9, 7.1.10, 8.1.1, 8.1.2, 8.1.3, 8.1.4, 8.1.5, 8.1.6, 8.1.7, 8.1.8, 8.1.9, 8.1.10, 9.1.1, 9.1.2, 9.1.3, 9.1.4, 9.1.5, 9.1.6, 9.1.7, 9.1.8, 9.1.9, 9.1.10, 10.1.1, 10.1.2, 10.1.3, 10.1.4, 10.1.5, 10.1.6, 10.1.7, 10.1.8, 10.1.9, 10.1.10, 11.1.1, 11.1.2, 11.1.3, 11.1.4, 11.1.5, 11.1.6, 11.1.7, 11.1.8, 11.1.9, 11.1.10, 12.1.1, 12.1.2, 12.1.3, 12.1.4, 12.1.5, 12.1.6, 12.1.7, 12.1.8, 12.1.9, 12.1.10, 13.1.1, 13.1.2, 13.1.3, 13.1.4, 13.1.5, 13.1.6, 13.1.7, 13.1.8, 13.1.9, 13.1.10, 14.1.1, 14.1.2, 14.1.3, 14.1.4, 14.1.5, 14.1.6, 14.1.7, 14.1.8, 14.1.9, 14.1.10, 15.1.1, 15.1.2, 15.1.3, 15.1.4, 15.1.5, 15.1.6, 15.1.7, 15.1.8, 15.1.9, 15.1.10, 16.1.1, 16.1.2, 16.1.3, 16.1.4, 16.1.5, 16.1.6, 16.1.7, 16.1.8, 16.1.9, 16.1.10, 17.1.1, 17.1.2, 17.1.3, 17.1.4, 17.1.5, 17.1.6, 17.1.7, 17.1.8, 17.1.9, 17.1.10, 18.1.1, 18.1.2, 18.1.3, 18.1.4, 18.1.5, 18.1.6, 18.1.7, 18.1.8, 18.1.9, 18.1.10, 19.1.1, 19.1.2, 19.1.3, 19.1.4, 19.1.5, 19.1.6, 19.1.7, 19.1.8, 19.1.9, 19.1.10, 20.1.1, 20.1.2, 20.1.3, 20.1.4, 20.1.5, 20.1.6, 20.1.7, 20.1.8, 20.1.9, 20.1.10, 21.1.1, 21.1.2, 21.1.3, 21.1.4, 21.1.5, 21.1.6, 21.1.7, 21.1.8, 21.1.9, 21.1.10, 22.1.1, 22.1.2, 22.1.3, 22.1.4, 22.1.5, 22.1.6, 22.1.7, 22.1.8, 22.1.9, 22.1.10, 23.1.1, 23.1.2, 23.1.3, 23.1.4, 23.1.5, 23.1.6, 23.1.7, 23.1.8, 23.1.9, 23.1.10, 24.1.1, 24.1.2, 24.1.3, 24.1.4, 24.1.5, 24.1.6, 24.1.7, 24.1.8, 24.1.9, 24.1.10, 25.1.1, 25.1.2, 25.1.3, 25.1.4, 25.1.5, 25.1.6, 25.1.7, 25.1.8, 25.1.9, 25.1.10, 26.1.1, 26.1.2, 26.1.3, 26.1.4, 26.1.5, 26.1.6, 26.1.7, 26.1.8, 26.1.9, 26.1.10, 27.1.1, 27.1.2, 27.1.3, 27.1.4, 27.1.5, 27.1.6, 27.1.7, 27.1.8, 27.1.9, 27.1.10, 28.1.1, 28.1.2, 28.1.3, 28.1.4, 28.1.5, 28.1.6, 28.1.7, 28.1.8, 28.1.9, 28.1.10, 1.2.1, 1.2.2, 1.2.3, 1.2.4, 1.2.5, 1.2.6, 1.2.7, 1.2.8, 1.2.9, 1.2.10, 2.2.1, 2.2.2, 2.2.3, 2.2.4, 2.2.5, 2.2.6, 2.2.7, 2.2.8, 2.2.9, 2.2.10, 3.2.1, 3.2.2, 3.2.3, 3.2.4, 3.2.5, 3.2.6, 3.2.7, 3.2.8, 3.2.9, 3.2.10, 4.2.1, 4.2.2, 4.2.3, 4.2.4, 4.2.5, 4.2.6, 4.2.7, 4.2.8, 4.2.9, 4.2.10, 5.2.1, 5.2.2, 5.2.3, 5.2.4, 5.2.5, 5.2.6, 5.2.7, 5.2.8, 5.2.9, 5.2.10, 6.2.1, 6.2.2, 6.2.3, 6.2.4, 6.2.5, 6.2.6, 6.2.7, 6.2.8, 6.2.9, 6.2.10, 7.2.1, 7.2.2, 7.2.3, 7.2.4, 7.2.5, 7.2.6, 7.2.7, 7.2.8, 7.2.9, 7.2.10, 8.2.1, 8.2.2, 8.2.3, 8.2.4, 8.2.5, 8.2.6, 8.2.7, 8.2.8, 8.2.9, 8.2.10, 9.2.1, 9.2.2, 9.2.3, 9.2.4, 9.2.5, 9.2.6, 9.2.7, 9.2.8, 9.2.9, 9.2.10, 10.2.1, 10.2.2, 10.2.3, 10.2.4, 10.2.5, 10.2.6, 10.2.7, 10.2.8, 10.2.9, 10.2.10, 11.2.1, 11.2.2, 11.2.3, 11.2.4, 11.2.5, 11.2.6, 11.2.7, 11.2.8, 11.2.9, 11.2.10, 12.2.1, 12.2.2, 12.2.3, 12.2.4, 12.2.5, 12.2.6, 12.2.7, 12.2.8, 12.2.9, 12.2.10, 13.2.1, 13.2.2, 13.2.3, 13.2.4, 13.2.5, 13.2.6, 13.2.7, 13.2.8, 13.2.9, 13.2.10, 14.2.1, 14.2.2, 14.2.3, 14.2.4, 14.2.5, 14.2.6, 14.2.7, 14.2.8, 14.2.9, 14.2.10, 15.2.1, 15.2.2, 15.2.3, 15.2.4, 15.2.5, 15.2.6, 15.2.7, 15.2.8, 15.2.9, 15.2.10, 16.2.1, 16.2.2, 16.2.3, 16.2.4, 16.2.5, 16.2.6, 16.2.7, 16.2.8, 16.2.9, 16.2.10, 17.2.1, 17.2.2, 17.2.3, 17.2.4, 17.2.5, 17.2.6, 17.2.7, 17.2.8, 17.2.9, 17.2.10, 18.2.1, 18.2.2, 18.2.3, 18.2.4, 18.2.5, 18.2.6, 18.2.7, 18.2.8, 18.2.9, 18.2.10, 19.2.1, 19.2.2, 19.2.3, 19.2.4, 19.2.5, 19.2.6, 19.2.7, 19.2.8, 19.2.9, 19.2.10, 20.2.1, 20.2.2, 20.2.3, 20.2.4, 20.2.5, 20.2.6, 20.2.7, 20.2.8, 20.2.9, 20.2.10, 21.2.1, 21.2.2, 21.2.3, 21.2.4, 21.2.5, 21.2.6, 21.2.7, 21.2.8, 21.2.9, 21.2.10, 22.2.1, 22.2.2, 22.2.3, 22.2.4, 22.2.5, 22.2.6, 22.2.7, 22.2.8, 22.2.9, 22.2.10, 23.2.1, 23.2.2, 23.2.3, 23.2.4, 23.2.5, 23.2.6, 23.2.7, 23.2.8, 23.2.9, 23.2.10, 24.2.1, 24.2.2, 24.2.3, 24.2.4, 24.2.5, 24.2.6, 24.2.7, 24.2.8, 24.2.9, 24.2.10, 25.2.1, 25.2.2, 25.2.3, 25.2.4, 25.2.5, 25.2.6, 25.2.7, 25.2.8, 25.2.9, 25.2.10, 26.2.1, 26.2.2, 26.2.3, 26.2.4, 26.2.5, 26.2.6, 26.2.7, 26.2.8, 26.2.9, 26.2.10, 27.2.1, 27.2.2, 27.2.3, 27.2.4, 27.2.5, 27.2.6, 27.2.7, 27.2.8, 27.2.9, 27.2.10, 28.2.1, 28.2.2, 28.2.3, 28.2.4, 28.2.5, 28.2.6, 28.2.7, 28.2.8, 28.2.9, 28.2.10, 1.3.1, 1.3.2, 1.3.3, 1.3.4, 1.3.5, 1.3.6, 1.3.7, 1.3.8, 1.3.9, 1.3.10, 2.3.1, 2.3.2, 2.3.3, 2.3.4, 2.3.5, 2.3.6, 2.3.7, 2.3.8, 2.3.9, 2.3.10, 3.3.1, 3.3.2, 3.3.3, 3.3.4, 3.3.5, 3.3.6, 3.3.7, 3.3.8, 3.3.9, 3.3.10, 4.3.1, 4.3.2, 4.3.3, 4.3.4, 4.3.5, 4.3.6, 4.3.7, 4.3.8, 4.3.9, 4.3.10, 5.3.1, 5.3.2, 5.3.3, 5.3.4, 5.3.5, 5.3.6, 5.3.7, 5.3.8, 5.3.9, 5.3.10, 6.3.1, 6.3.2, 6.3.3, 6.3.4, 6.3.5, 6.3.6, 6.3.7, 6.3.8, 6.3.9, 6.3.10, 7.3.1, 7.3.2, 7.3.3, 7.3.4, 7.3.5, 7.3.6, 7.3.7, 7.3.8, 7.3.9, 7.3.10, 8.3.1, 8.3.2, 8.3.3, 8.3.4, 8.3.5, 8.3.6, 8.3.7, 8.3.8, 8.3.9, 8.3.10, 9.3.1, 9.3.2, 9.3.3, 9.3.4, 9.3.5, 9.3.6, 9.3.7, 9.3.8, 9.3.9, 9.3.10, 10.3.1, 10.3.2, 10.3.3, 10.3.4, 10.3.5, 10.3.6, 10.3.7, 10.3.8, 10.3.9, 10.3.10, 11.3.1, 11.3.2, 11.3.3, 11.3.4, 11.3.5, 11.3.6, 11.3.7, 11.3.8, 11.3.9, 11.3.10, 12.3.1, 12.3.2, 12.3.3, 12.3.4, 12.3.5, 12.3.6, 12.3.7, 12.3.8, 12.3.9, 12.3.10, 13.3.1, 13.3.2, 13.3.3, 13.3.4, 13.3.5, 13.3.6, 13.3.7, 13.3.8, 13.3.9, 13.3.10, 14.3.1, 14.3.2, 14.3.3, 14.3.4, 14.3.5, 14.3.6, 14.3.7, 14.3.8, 14.3.9, 14.3.10, 15.3.1, 15.3.2, 15.3.3, 15.3.4, 15.3.5, 15.3.6, 15.3.7, 15.3.8, 15.3.9, 15.3.10, 16.3.1, 16.3.2, 16.3.3, 16.3.4, 16.3.5, 16.3.6, 16.3.7, 16.3.8, 16.3.9, 16.3.10, 17.3.1, 17.3.2, 17.3.3, 17.3.4, 17.3.5, 17.3.6, 17.3.7, 17.3.8, 17.3.9, 17.3.10, 18.3.1, 18.3.2, 18.3.3, 18.3.4, 18.3.5, 18.3.6, 18.3.7, 18.3.8, 18.3.9, 18.3.10, 19.3.1, 19.3.2, 19.3.3, 19.3.4, 19.3.5, 19.3.6, 19.3.7, 19.3.8, 19.3.9, 19.3.10, 20.3.1, 20.3.2, 20.3.3, 20.3.4, 20.3.5, 20.3.6, 20.3.7, 20.3.8, 20.3.9, 20.3.10, 21.3.1, 21.3.2, 21.3.3, 21.3.4, 21.3.5, 21.3.6, 21.3.7, 21.3.8, 21.3.9, 21.3.10, 22.3.1, 22.3.2, 22.3.3, 22.3.4, 22.3.5, 22.3.6, 22.3.7, 22.3.8, 22.3.9, 22.3.10, 23.3.1, 23.3.2, 23.3.3, 23.3.4, 23.3.5, 23.3.6, 23.3.7, 23.3.8, 23.3.9, 23.3.10, 24.3.1, 24.3.2, 24.3.3, 24.3.4, 24.3.5, 24.3.6, 24.3.7, 24.3.8, 24.3.9, 24.3.10, 25.3.1, 25.3.2, 25.3.3, 25.3.4, 25.3.5, 25.3.6, 25.3.7, 25.3.8, 25.3.9, 25.3.10, 26.3.1, 26.3.2, 26.3.3, 26.3.4, 26.3.5, 26.3.6, 26.3.7, 26.3.8, 26.3.9, 26.3.10, 27.3.1, 27.3.2, 27.3.3, 27.3.4, 27.3.5, 27.3.6, 27.3.7, 27.3.8, 27.3.9, 27.3.10, 28.3.1, 28.3.2, 28.3.3, 28.3.4, 28.3.5, 28.3.6, 28.3.7, 28.3.8, 28.3.9 and 28.3.10.

Table 4 lists a group of cyclic nucleotide analogs of structure I wherein a heterocyclic ring comprising $L^1$ and the phosphorus atom of the phosphonate group along with part of the Z—B substructure —O—$CH_2$—C#H($CH_2$—)—$CH_2$—B. The unbonded O atom in the Z substructure is linked to $L^1$ through the α carboxyl group of the amino acid while the $CH_2$ moiety on the right side is linked to the P atom and the $CH_2$ moiety linked to the chiral carbon is linked to B (i.e., —$L^1$—O—$CH_2$—C#H($CH_2$—B)—O—$CH_2$—P(O)($L^2$)— with —P(O)($L^2$)— and —$L^1$—linked together). Hydrolysis of the compound results in formation of an HPMP nucleoside phosphonate. A related group of compounds comprises a heterocyclic ring linked through a side chain or other carboxyl group instead of through the carboxyl group linked to the α carbon atom. Hydrolysis of these compounds also result in formation of an HPMP nucleoside phosphonate.

TABLE 4

$L^{1*}$-Z(B)—P(O)($L^2$)

1 —NH—$CH_2$—C(O)—O—$CH_2$—C#H($CH_2$—B)—O—$CH_2$—P(O)($L^2$)—
2 —NH—CH($CH_3$)—C(O)—O—$CH_2$—C#H($CH_2$—B)—O—$CH_2$—P(O)($L^2$)—
3 —NH—CH($CH_3$)$_2$—C(O)—O—$CH_2$—C#H($CH_2$—B)—O—$CH_2$—P(O)($L^2$)—
4 —NH—CH(CH($CH_3$)$_2$)—C(O)—O—$CH_2$—C#H($CH_2$—B)—O—$CH_2$—P(O)($L^2$)—
5 —NH—CH($CH_3$(CH$_3$)$_2$)—C(O)—O—$CH_2$—C#H($CH_2$—B)—O—$CH_2$—P(O)($L^2$)—
6 —NH—$CH_2$—$CH_2$—$CH_2$—CH—C(O)—O—$CH_2$—C#H($CH_2$—B)—O—$CH_2$—P(O)($L^2$)—
7 —NH—CH($CH_2$—$C_6H_5$)—C(O)—O—$CH_2$—C#H($CH_2$—B)—O—$CH_2$—P(O)($L^2$)—
8 —NH—CH($CH_2$—$C_8NH_6$)—C(O)—O—$CH_2$—C#H($CH_2$—B)—O—$CH_2$—P(O)($L^2$)—
9 —NH—CH($CH_2$—$CH_2$—S—$CH_3$)—C(O)—O—$CH_2$—C#H($CH_2$—B)—O—$CH_2$—P(O)($L^2$)—
10 —NH—CH($CH_2$OH)—C(O)—O—$CH_2$—O—$CH_2$—C#H($CH_2$—B)—O—$CH_2$P(O)($L^2$)—
11 —NH—CH(CH(OH)($CH_3$))—C(O)—O—$CH_2$—C#H($CH_2$—B)—O—$CH_2$—P(O)($L^2$)—
12 —NH—CH(—$CH_2$SH)—C(O)—O—$CH_2$—O—$CH_2$—C#H($CH_2$—B)—O—$CH_2$—P(O)($L^2$)—
13 —NH—CH(CH2—$C_6H_5$OH)—C(O)—O—$CH_2$—C#H($CH_2$—B)—O—$CH_2$—P(O)($L^2$)—
14 —NH—CH($CH_2$C(O)—$NH_2$)—C(O)—O—$CH_2$—C#H($CH_2$—B)—O—$CH_2$—P(O)($L^2$)—
15 —NH—CH($CH_2$—$CH_2$—C(O)—$NH_2$)—C(O)—O—$CH_2$—C#H($CH_2$—B)—O—$CH_2$—P(O)($L^2$)—
16 —NH—CH($CH_2$C(O)$OR^4$)—C(O)—O—$CH_2$—C#H($CH_2$—B)—O—$CH_2$—P(O)($L^2$)—
17 —NH—CH($CH_2$$CH_2$C(O)$OR^4$)—C(O)—O—$CH_2$—C#H($CH_2$—B)—O—$CH_2$—P(O)($L^2$)—
18 —NH—CH($CH_2$$CH_2$$CH_2$$CH_2$$NH_2$)—C(O)—O—$CH_2$—C#H($CH_2$—B)—O—$CH_2$—P(O)($L^2$)—
19 —NH—CH($CH_2$$CH_2$$CH_2$NHC(NH)($NH_2$))—C(O)—O—$CH_2$—C#H($CH_2$—B)—O—$CH_2$—P(O)($L^2$)—
20 —NH—CH($CH_2$$C_3N_2H_3$)—C(O)—O—$CH_2$—C#H($CH_2$—B)—O—$CH_2$—P(O)($L^2$)—
21 —NH—CH($CH_3$)—$CH_2$—C(O)—O—$CH_2$—C#H($CH_2$—B)—O—$CH_2$—P(O)($L^2$)—
22 —NH—CH($CH_2$$CH_2$$CH_2$$NH_2$)—$CH_2$—C(O)—O—$CH_2$—C#H($CH_2$—B)—O—$CH_2$—P(O)($L^2$)—

$L^2$

1 —NH—$CH_2$—C(O)—$OR^4$
2 —NH—CH($CH_3$)—C(O)—$OR^4$
3 —O—$CH_2$—O—C(O)—C($CH_3$)$_3$
4 —O—$CH_2C_6H_5$
5 —O—$C_6H_5$
6 —O—CH($CH_3$)$_2$
7 —NH—CH($CH_2C_6H_4$)—C(O)—$OR^4$
8 —OH

B 1 adenin-9-yl
2 guanin-9-yl
3 cytosin-1-yl
4 2,6-diaminopurin-9-yl
5 2-aminopurin-9-yl
6 6-azacytosin-1-yl
7 1-deazaadenin-9-yl
8 3-deazaadenin-9-yl
9 8-azaadenin-9-yl
10 7-deaza-8-azaadenin-9-yl

*See Table 1 footnote; the terminal nitrogen and phosphorus atoms are linked to each other.

Compounds listed in Table 4 are designated herein by numbers assigned to $L^1$, $L^2$, and B according to the following convention, $L^1.L^2.B$. All Z correspond to the esterified HPMP substructure moiety. Thus, compounds 1.1.3 and 2.4.3 represent compounds designated "glycyl cyclic glycinyl HPMPC" and "benzyl cyclic alanyl HPMPC" esters. Exemplary compounds include 1.1.1, 1.1.2, 1.1.3, 1.1.4, 1.1.5, 1.1.6, 1.1.7, 1.1.8, 1.1.9, 1.1.10, 2.1.1, 2.1.2, 2.1.3, 2.1.4, 2.1.5, 2.1.6, 2.1.7, 2.1.8, 2.1.9, 2.1.10, 3.1.1, 3.1.2, 3.1.3, 3.1.4, 3.1.5, 3.1.6, 3.1.7, 3.1.8, 3.1.9, 3.1.10, 4.1.1, 4.1.2, 4.1.3, 4.1.4, 4.1.5, 4.1.6, 4.1.7, 4.1.8, 4.1.9, 4.1.10, 5.1.1, 5.1.2, 5.1.3, 5.1.4, 5.1.5, 5.1.6, 5.1.7, 5.1.8, 5.1.9, 5.1.10, 6.1.1, 6.1.2, 6.1.3, 6.1.4, 6.1.5, 6.1.6, 6.1.7, 6.1.8, 6.1.9, 6.1.10, 7.1.1, 7.1.2, 7.1.3, 7.1.4, 7.1.5, 7.1.6, 7.1.7, 7.1.8, 7.1.9, 7.1.10, 8.1.1, 8.1.2, 8.1.3, 8.1.4, 8.1.5, 8.1.6, 8.1.7, 8.1.8, 8.1.9, 8.1.10, 9.1.1, 9.1.2, 9.1.3, 9.1.4, 9.1.5, 9.1.6, 9.1.7, 9.1.8, 9.1.9, 9.1.10, 10.1.1, 10.1.2, 10.1.3, 10.1.4, 10.1.5, 10.1.6, 10.1.7, 10.1.8, 10.1.9, 10.1.10, 11.1.1, 11.1.2, 11.1.3, 11.1.4, 11.1.5, 11.1.6, 11.1.7, 11.1.8, 11.1.9, 11.1.10, 12.1.1, 12.1.2, 12.1.3, 12.1.4, 12.1.5, 12.1.6, 12.1.7, 12.1.8, 12.1.9, 12.1.10, 13.1.1, 13.1.2, 13.1.3, 13.1.4, 13.1.5, 13.1.6, 13.1.7, 13.1.8, 13.1.9, 13.1.10, 14.1.1, 14.1.2, 14.1.3, 14.1.4, 14.1.5, 14.1.6, 14.1.7, 14.1.8, 14.1.9, 14.1.10, 15.1.1, 15.1.2, 15.1.3, 15.1.4, 15.1.5, 15.1.6, 15.1.7, 15.1.8, 15.1.9, 15.1.10, 16.1.1, 16.1.2, 16.1.3, 16.1.4, 16.1.5, 16.1.6, 16.1.7, 16.1.8, 16.1.9, 16.1.10, 17.1.1, 17.1.2, 17.1.3, 17.1.4, 17.1.5, 17.1.6, 17.1.7, 17.1.8, 17.1.9, 17.1.10, 18.1.1, 18.1.2, 18.1.3, 18.1.5, 18.1.6, 18.1.7, 18.1.8, 18.1.9, 18.1.10, 19.1.1, 19.1.2, 19.1.3, 19.1.4, 19.1.6, 19.1.7, 19.1.8, 19.1.9, 19.1.10, 20.1.1, 20.1.2, 20.1.3, 20.1.4, 20.1.5, 20.1.6, 20.1.7, 20.1.8, 20.1.9, 20.1.10, 21.1.1, 21.1.2, 21.1.3, 21.1.4, 21.1.5, 21.1.6, 21.1.7, 21.1.8, 21.1.9, 21.1.10, 22.1.1, 22.1.2, 22.1.3, 22.1.4, 22.1.5, 22.1.6, 22.1.7, 22.1.8, 22.1.9, 22.1.10, 1.2.1, 1.2.2, 1.2.3, 1.2.4, 1.2.5, 1.2.6, 1.2.7, 1.2.8, 1.2.9, 1.2.10, 2.1, 2.2.2, 2.2.3, 2.2.4, 2.2.5, 2.2.6, 2.2.7, 2.2.8, 2.2.9, 2.2.10, 3.2.1, 3.2.2, 3.2.3, 3.2.4, 3.2.5, 3.2.6, 3.2.7, 3.2.8, 3.2.9, 3.2.10, 4.2.1, 4.2.2, 4.2.3, 4.2.4, 4.2.5, 4.2.6, 4.2.7, 4.2.8, 4.2.9, 4.2.10, 5.2.1, 5.2.2, 5.2.3, 5.2.4, 5.2.5, 5.2.6, 5.2.7, 5.2.8, 5.2.9, 5.2.10, 6.2.1, 6.2.2, 6.2.3, 6.2.4, 6.2.5, 6.2.6, 6.2.7, 6.2.8, 6.2.9, 6.2.10, 7.2.1, 7.2.2, 7.2.3, 7.2.4, 7.2.5, 7.2.6, 7.2.7, 7.2.8, 7.2.9, 7.2.10, 8.2.1, 8.2.2, 8.2.3, 8.2.4, 8.2.5, 8.2.6, 8.2.7, 8.2.8, 8.2.9, 8.2.10, 9.2.1, 9.2.2, 9.2.3, 9.2.4, 9.2.5, 9.2.6, 9.2.7, 9.2.8, 9.2.9, 9.2.10, 10.2.1, 10.2.2, 10.2.3, 1o.2.4, 10.2.5, 10.2.6, 10.2.7, 10.2.8, 10.2.9, 10.2.10, 11.2.1, 11.2.2, 11.2.3, 11.2.4, 11.2.5, 11.2.6, 11.2.7, 11.2.8, 11.2.9, 11.2.10, 12.2.1, 12.2.2, 12.2.3, 12.2.4, 12.2.5, 12.2.6, 12.2.7, 12.2.8, 12.2.9, 12.2.10, 13.2.1, 13.2.2, 13.2.3, 13.2.4, 13.2.5, 13.2.6, 13.2.7, 13.2.8, 13.2.9, 13.2.10, 14.2.1, 14.2.2, 14.2.3, 14.2.4, 14.2.5, 14.2.6, 14.2.7, 14.2.8, 14.2.9, 14.2.10, 15.2.1, 15.2.2, 15.2.3, 15.2.4, 15.2.5, 15.2.6, 15.2.7,.15.2.8, 15.2.9, 15.2.10, 16.2.1, 16.2.2, 16.2.3, 16.2.4, 16.2.5, 16.2.6, 16.2.7, 16.2.8, 16.2.9, 16.2.10, 17.2.1, 17.2.2, 17.2.3, 17.2.4, 17.2.5, 17.2.6, 17.2.7, 17.2.8, 17.2.9, 17.2.10, 18.2.1, 18.2.2, 18.2.3, 18.2.4, 18.2.5, 18.2.6, 18.2.7, 18.2.8, 18.2.9, 18.2.10, 19.2.1, 19.2.2, 19.2.3, 19.2.4, 19.2.5, 19.2.6, 19.2.7, 19.2.8, 19.2.9, 19.2.10, 20.2.1, 20.2.2, 20.2.3, 20.2.4, 20.2.5, 20.2.6, 20.2.7, 20.2.8, 20.2.9, 20.2.10, 21.2.1, 21.2.2, 21.2.3, 21.2.4, 21.2.5, 21.2.6, 21.2.7, 21.2.8, 21.2.9, 21.2.10, 22.2.1, 22.2.2, 22.2.3, 22.2.4, 22.2.5, 22.2.6, 22.2.7, 22.2.8, 22.2.9, 22.2.10, 1.3.1, 1.3.2, 1.3.3, 1.3.4, 1.3.5, 1.3.6, 1.3.7, 1.3.8, 1.3.9, 1.3.10, 2.3.1, 2.3.2, 2.3.3, 2.3.4, 2.3.5, 2.3.6, 2.3.7, 2.3.8, 2.3.9, 2.3.10, 3.3.1, 3.3.2, 3.3.3, 3.3.4, 3.3.5, 3.3.6, 3.3.7, 3.3.8, 3.3.9, 3.3.10, 4.3.1, 4.3.2, 4.3.3, 4.3.4, 4.3.5, 4.3.6, 4.3.7, 4.3.8, 4.3.9, 4.3.10, 5.3.1, 5.3.2, 5.3.3, 5.3.4, 5.3.5, 5.3.6, 5.3.7, 5.3.8, 5.3.9, 5.3.10, 6.3.1, 6.3.2, 6.3.3, 6.3.4, 6.3.5, 6.3.6, 6.3.7, 6.3.8, 6.3.9, 6.3.10, 7.3.1, 7.3.2, 7.3.3, 7.3:4, 7.3.5, 7.3.6, 7.3.7, 7.3.8, 7.3.9, 7.3.10, 8.3.1, 8.3.2, 8.3.3, 8.3.4, 8.3.5, 8.3.6, 8.3.7, 8.3.8, 8.3.9, 8.3.10, 9.3.1, 9.3.2, 9.3.3, 9.3.4, 9.3.5, 9.3.6, 9.3.7, 9.3.8, 9.3.9, 9.3.10, 10.3.1, 10.3.2, 10.3.3, 10.3.4, 10.3.5, 10.3.6, 10.3.7, 10.3.8, 10.3.9, 10.3.10, 11.3.1, 11.3.2, 11.3.3, 11.3.4, 11.3.5, 11.3.6, 11.3.7, 11.3.8, 11.3.9, 11.3.10, 12.3.1, 12.3.2, 12.3.3, 12.3.4, 12.3.5, 12.3.6, 12.3.7, 12.3.8, 12.3.9, 12.3.10, 13.3.1, 13.3.2, 13.3.3, 13.3.4, 13.3.5, 13.3.6, 13.3.7, 13.3.8, 13.3.9, 13.3.10, 14.3.1, 14.3.2, 14.3.3, 14.3.4, 14.3.5, 14.3.6, 14.3.7, 14.3.8, 14.3.9, 14.3.10, 15.3.1, 15.3.2, 15.3.3, 15.3.4, 15.3.5, 15.3.6, 15.3.7, 15.3.8, 15.3.9, 15.3.10, 16.3.1, 16.3.2, 16.3.3, 16.3.4, 16.3.5, 16.3.6, 16.3.7, 16.3.8, 16.3.9, 16.3.10, 17.3.1, 17.3.2, 17.3.3, 17.3.4, 17.3.5, 17.3.6, 17.3.7, 17.3.8, 17.3.9, 17.3.10, 18.3.1, 18.3.2, 18.3.3, 18.3.4, 18.3.5, 18.3.6, 18.3.7, 18.3.8, 18.3.9, 18.3.10, 19.3.1, 19.3.2, 19.3.3, 19.3.4, 19.3.5, 19.3.6, 19.3.7, 19.3.8, 19.3.9, 19.3.10, 20.3.1, 20.3.2, 20.3.3, 20.3.4, 20.3.5, 20.3.6, 20.3.7, 20.3.8, 20.3.9, 20.3.10, 21.3.1, 21.3.2, 21.3.3, 21.3.4, 21.3.5, 21.3.6, 21.3.7, 21.3.8, 21.3.9, 21.3.10, 22.3.1, 22.3.2, 22.3.3, 22.3.4, 22.3.5, 22.3.6, 22.3.7, 22.3.8, 22.3.9, 22.3.10, 1.4.1, 1.4.2, 1.4.3, 1.4.4, 1.4.5, 1.4.6, 1.4.7, 1.4.8, 1.4.9, 1.4.10, 2.4.1, 2.4.2, 2.4.3, 2.4.4, 2.4.5, 2.4.6, 2.4.7, 2.4.8, 2.4.9, 2.4.10, 3.4.1, 3.4.2, 3.4.3, 3.4.4, 3.4.5, 3.4.6, 3.4.7, 3.4.8, 3.4.9, 3.4.10, 4.4.1, 4.4.2, 4.4.3, 4.4.4, 4.4.5, 4.4.6, 4.4.7, 4.4.8, 4.4.9, 4.4.10, 5.4.1, 5.4.2, 5.4.3, 5.4.4, 5.4.5, 5.4.6, 5.4.7, 5.4.8, 5.4.9, 5.4.10, 6.4.1, 6.4.2, 6.4.3, 6.4.4, 6.4.5, 6.4.6, 6.4.7, 6.4.8, 6.4.9, 6.4.10, 7.4.1, 7.4.2, 7.4.3, 7.4.4, 7.4.5, 7.4.6, 7.4.7, 7.4.8, 7.4.9, 7.4.10, 8.4.1, 8.4.2, 8.4.3, 8.4.4, 8.4.5, 8.4.6, 8.4.7, 8.4.8, 8.4.9, 8.4.10, 9.4.1, 9.4.2, 9.4.3, 9.4.4, 9.4.5, 9.4.6, 9.4.7, 9.4.8, 9.4.9, 9.4.10, 10.4.1, 10.4.2, 10.4.3, 10.4.4, 10.4.5, 10.4.6, 10.4.7, 10.4.8, 10.4.9, 10.4.10, 11.4.1, 11.4.2, 11.4.3, 11.4.4, 11.4.5, 11.4.6, 11.4.7, 11.4.8, 11.4.9, 11.4.10, 12.4.1, 12.4.2, 12.4.3, 12.4.4, 12.4.5, 12.4.6, 12.4.7, 12.4.8, 12.4.9, 12.4.10, 13.4.2, 13.4.3, 13.4.4, 13.4.5, 13.4.6, 13.4.7, 13.4.8, 13.4.9, 13.4.10, 14.4.1, 14.4.2, 14.4.3, 14.4.4, 14.4.5, 14.4.6, 14.4.7, 14.4.8, 14.4.9, 14.4.10, 15.4.1, 15.4.2, 15.4.3, 15.4.4, 15.4.5, 15.4.6, 15.4.7, 15.4.8, 15.4.9, 15.4.10, 16.4.1, 16.4.2, 16.4.3, 16.4.4, 16.4.5, 16.4.6, 16.4.7, 16.4.8, 16.4.9, 16.4.10, 17.4.1, 17.4.2, 17.4.3, 17.4.4, 17.4.5, 17.4.6, 17.4.7, 17.4.8, 17.4.9, 17.4.10, 18.4.1, 18.4.2, 18.4.3, 18.4.4, 18.4.5, 18.4.6, 18.4.7, 18.4.8, 18.4.9, 18.4.10, 19.4.1, 19.4.2, 19.4.3, 19.4.4, 19.4.5, 19.4.6, 19.4.7, 19.4.8, 19.4.9, 19.4.10, 20.4.1, 20.4.2, 20.4.3, 20.4.4, 20.4.5, 20.4.6, 20.4.7, 20.4.8, 20.4.9, 20.4.10, 21.4.1, 21.4.2, 21.4.3, 21.4.4, 21.4.5, 21.4.6, 21.4.7, 21.4.8, 21.4.9, 21.4.10, 22.4.1, 22.4.2, 22.4.3, 22.4.4, 22.4.5, 22.4.6, 22.4.7, 22.4.8, 22.4.9, 22.4.10, 1.5.1, 1.5.2, 1.5.3, 1.5.4, 1.5.5, 1.5.6, 1.5.7, 1.5.8, 1.5.9, 1.5.10, 2.5.1, 2.5.2, 2.5.3, 2.5.4, 2.5.5, 2.5.6, 2.5.7, 2.5.8, 2.5.9, 2.5.10, 3.5.1, 3.5.2, 3.5.3, 3.5.4, 3.5.5, 3.5.6, 3.5.7, 3.5.8, 3.5.9, 3.5.10, 4.5.1, 4.5.2, 4.5.3, 4.5.4, 4.5.5, 4.5.6, 4.5.7, 4.5.8, 4.5.9, 4.5.10, 5.5.1, 5.5.2, 5.5.3, 5.5.4, 5.5.5, 5.5.6, 5.5.7, 5.5.8, 5.5.9, 5.5.10, 6.5.1, 6.5.2, 6.5.3, 6.5.4, 6.5.5, 6.5.6, 6.5.7, 6.5.8, 6.5.9, 6.5.10, 7.5.1, 7.5.2, 7.5.3, 7.5.4, 7.5.5, 7.5.6, 7.5.7, 7.5.8, 7.5.9, 7.5.10, 8.5.1, 8.5.2, 8.5.3, 8.5.4, 8.5.5, 8.5.6, 8.5.7, 8.5.8, 8.5.9, 8.5.10, 9.5.1, 9.5.2, 9.5.3, 9.5.4, 9.5.5, 9.5.6, 9.5.7, 9.5.8, 9.5.9, 9.5.10, 10.5.1, 10.5.2, 10.5.3, 10.5.4, 10.5.5, 10.5.6, 10.5.7, 10.5.8, 10.5.9, 10.5.10, 11.5.1, 11.5.2, 11.5.3, 11.5.4, 11.5.5, 11.5.6, 11.5.7, 11.5.8, 11.5.9, 11.5.10, 12.5.1, 12.5.2, 12.5.3, 12.5.4, 12.5.5, 12.5.6, 12.5.7, 12.5.8, 12.5.9, 12.5.10, 13.5.1, 13.5.2, 13.5.3, 13.5.4, 13.5.5, 13.5.6, 13.5.7, 13.5.8, 13.5.9, 13.5.10, 14.5.1, 14.5.2, 14.5.3, 14.5.4, 14.5.5, 14.5.6, 14.5.7, 14.5.8, 14.5.9, 14.5.10, 15.5.2, 15.5.3, 15.5.4, 15.5.5, 15.5.6, 15.5.7, 15.5.8, 15.5.9, 15.5.10, 16.5.1, 16.5.2, 16.5.3, 16.5.4, 16.5.5, 16.5.6, 16.5.7, 16.5.8, 16.5.9, 16.5.10, 17.5.1, 17.5.2, 17.5.3, 17.5.4, 17.5.5, 17.5.6, 17.5.7, 17.5.8, 17.5.9, 17.5.10, 18.5.1, 18.5.2, 18.5.3, 18.5.4, 18.5.5, 18.5.6, 18.5.7, 18.5.8, 18.5.9, 18.5.10, 19.5.1, 19.5.2, 19.5.3, 19.5.4, 19.5.5, 19.5.6, 19.5.7, 19.5.8, 19.5.9, 19.5.10, 20.5.1, 20.5.2, 20.5.3, 20.5.4, 20.5.5, 20.5.6, 20.5.7, 20.5.8, 20.5.9, 20.5.10, 21.5.1, 21.5.2, 21.5.3, 21.5.4, 21.5.5, 21.5.6, 21.5.7, 21.5.8, 21.5.9, 21.5.10, 22.5.1, 22.5.2, 22.5.3, 22.5.4, 22.5.5, 22.5.6, 22.5.7, 22.5.8, 22.5.9, 22.5.10, 1.6.1, 1.6.2, 1.6.3, 1.6.4, 1.6.5, 1.6.6, 1.6.7, 1.6.8, 1.6.9, 1.6.10, 2.6.1, 2.6.2, 2.6.3, 2.6.4, 2.6.5, 2.6.6, 2.6.7, 2.6.8, 2.6.9, 2.6.10, 3.6.1, 3.6.2, 3.6.3, 3.6.4, 3.6.6, 3.6.7, 3.6.8, 3.6.9, 3.6.10, 4.6.1, 4.6.2, 4.6.3, 4.6.4, 4.6.5, 4.6.6, 4.6.7, 4.6.8, 4.6.9, 4.6.10, 5.6.1, 5.6.2, 5.6.3, 5.6.4, 5.6.5, 5.6.6, 5.6.7, 5.6.8, 5.6.9, 5.6.10, 6.6.1, 6.6.2, 6.6.3, 6.6.4, 6.6.5, 6.6.6, 6.6.7, 6.6.8, 6.6.9, 6.6.10, 7.6.1, 7.6.2, 7.6.3, 7.6.4, 7.6.5, 7.6.6, 7.6.7, 7.6.8, 7.6.9, 7.6.10, 8.6.1, 8.6.2, 8.6.3, 8.6.4, 8.6.5, 8.6.6, 8.6.7, 8.6.8, 8.6.9, 8.6.10, 9.6.1, 9.6.2, 9.6.3, 9.6.4, 9.6.5, 9.6.6, 9.6.7, 9.6.8, 9.6.9, 9.6.10, 10.6.1, 10.6.2, 10.6.3, 10.6.4, 10.6.5, 10.6.6, 10.6.7, 10.6.8, 10.6.9, 10.6.10, 11.6.1, 11.6.2, 11.6.3, 11.6.4, 11.6.5, 11.6.6, 11.6.7, 11.6.8, 11.6.9, 11.6.10, 12.6.1, 12.6.2, 12.6.3, 12.6.4, 12.6.5, 12.6.6, 12.6.7, 12.6.8, 12.6.9, 12.6.10, 13.6.1, 13.6.2, 13.6.3, 13.6.4, 13.6.5, 13.6.6, 13.6.7, 13.6.8, 13.6.9, 13.6.10, 14.6.1, 14.6.2, 14.6.3, 14.6.4, 14.6.5, 14.6.6, 14.6.7, 14.6.8, 14.6.9, 14.6.10, 15.6.1, 15.6.2, 15.6.3, 15.6.4, 15.6.5, 15.6.6, 15.6.7, 15.6.8, 15.6.9, 15.6.10, 16.6.1, 16.6.2, 16.6.3, 16.6.4, 16.6.5, 16.6.6, 16.6.7, 16.6.8, 16.6.9, 16.6.10, 17.6.1, 17.6.2, 17.6.3, 17.6.4, 17.6.5, 17.6.6, 17.6.7, 17.6.8, 17.6.9, 17.6.10, 18.6.1, 18.6.2, 18.6.3, 18.6.4, 18.6.5, 18.6.6, 18.6.7, 18.6.8, 18.6.9, 18.6.10, 19.6.1, 19.6.2, 19.6.3, 19.6.4, 19.6.5, 19.6.6, 19.6.7, 19.6.8, 19.6.9, 19.6.10, 20.6.1, 20.6.2, 20.6.3, 20.6.4, 20.6.5, 20.6.6, 20.6.7, 20.6.8, 20.6.9, 20.6.10, 21.6.1, 21.6.2, 21.6.3, 21.6.4, 21.6.5, 21.6.6, 21.6.7, 21.6.8, 21.6.9, 21.6.10, 22.6.1, 22.6.2, 22.6.3, 22.6.4, 22.6.5, 22.6.6, 22.6.7, 22.6.8, 22.6.9, 22.6.10, 1.7.1, 1.7.2, 1.7.3, 1.7.4, 1.7.5, 1.7.6, 1.7.7, 1.7.8, 1.7.9, 1.7.10, 2.7.1, 2.7.2, 2.7.3, 2.7.4, 2.7.5, 2.7.6, 2.7.7, 2.7.8, 2.7.9, 2.7.10, 3.7.1, 3.7.2, 3.7.3, 3.7.4, 3.7.5, 3.7.6, 3.7.7, 3.7.8, 3.7.9, 3.7.10, 4.7.1, 4.7.2, 4.7.3, 4.7.4, 4.7.5, 4.7.6, 4.7.7, 4.7.8, 4.7.9, 4.7.10, 5.7.1, 5.7.2, 5.7.3, 5.7.4, 5.7.5, 5.7.6, 5.7.7, 5.7.8, 5.7.9, 5.7.10, 6.7.1, 6.7.2, 6.7.3, 6.7.4, 6.7.5, 6.7.6, 6.7.7, 6.7.8, 6.7.9, 6.7.10, 7.7.1, 7.7.2, 7.7.3, 7.7.4, 7.7.5, 7.7.6, 7.7.7, 7.7.8, 7.7.9, 7.7.10, 8.7.1, 8.7.2, 8.7.3, 8.7.4, 8.7.5, 8.7.6, 8.7.7, 8.7.8, 8.7.9, 8.7.10, 9.7.1, 9.7.2, 9.7.3, 9.7.4, 9.7.5, 9.7.6, 9.7.7, 9.7.8, 9.7.9, 9.7.10, 10.7.1, 10.7.2, 10.7.3, 10.7.4, 10.7.5, 10.7.6, 10.7.7, 10.7.8, 10.7.9, 10.7.10, 11.7.1, 11.7.2, 11.7.3, 11.7.4, 11.7.5, 11.7.6, 11.7.7, 11.7.8, 11.7.9, 11.7.10, 12.7.1, 12.7.2, 12.7.3, 12.7.4, 12.7.5, 12.7.6, 12.7.7, 12.7.8, 12.7.9, 12.7.10, 13.7.1, 13.7.2, 13.7.3, 13.7.4, 13.7.5, 13.7.6, 13.7.7, 13.7.8, 13.7.9, 13.7.10, 14.7.1, 14.7.2, 14.7.3, 14.7.4, 14.7.5, 14.7.6, 14.7.7, 14.7.8, 14.7.9, 14.7.10, 15.7.1, 15.7.2, 15.7.3, 15.7.4, 15.7.5, 15.7.6, 15.7.7, 15.7.8, 15.7.9, 15.7.10, 16.7.1, 16.7.2, 16.7.3, 16.7.4, 16.7.5, 16.7.6, 16.7.7, 16.7.8, 16.7.9, 16.7.10, 17.7.1, 17.7.2, 17.7.3, 17.7.4, 17.7.5, 17.7.6, 17.7.7, 17.7.8, 17.7.9, 17.7.10, 18.7.1, 18.7.2, 18.7.3, 18.7.4, 18.7.5, 18.7.6, 18.7.7, 18.7.8, 18.7.9, 18.7.10, 19.7.1, 19.7.2, 19.7.3, 19.7.4, 19.7.5, 19.7.6, 19.7.7, 19.7.8, 19.7.9, 19.7.10, 20.7.1, 20.7.2, 20.7.3, 20.7.4, 20.7.5, 20.7.6, 20.7.7, 20.7.8, 20.7.9, 20.7.10, 21.7.1, 21.7.2, 21.7.3, 21.7.4, 21.7.5, 21.7.6, 21.7.7, 21.7.8, 21.7.9, 21.7.10, 22.7.1, 22.7.2, 22.7.3, 22.7.4, 22.7.5, 22.7.6, 22.7.7, 22.7.8, 22.7.9, 22.7.10, 1.8.1, 1.8.2, 1.8.3, 1.8.4, 1.8.5, 1.8.6, 1.8.7, 1.8.8, 1.8.9, 1.8.10, 2.8.1, 2.8.2, 2.8.3, 2.8.4, 2.8.5, 2.8.6, 2.8.7, 2.8.8, 2.8.9, 2.8.10, 3.8.1, 3.8.2, 3.8.3, 3.8.4, 3.8.5, 3.8.6, 3.8.7, 3.8.8, 3.8.9, 3.8.10, 4.8.1, 4.8.2, 4.8.3, 4.8.4, 4.8.5, 4.8.6, 4.8.7, 4.8.8, 4.8.9, 4.8.10, 5.8.1, 5.8.2, 5.8.3, 5.8.4, 5.8.5, 5.8.6, 5.8.7, 5.8.8, 5.8.9, 5.8.10, 6.8.1, 6.8.2, 6.8.3, 6.8.4, 6.8.5, 6.8.6, 6.8.7, 6.8.8, 6.8.9, 6.8.10, 7.8.1, 7.8.2, 7.8.3, 7.8.4, 7.8.5, 7.8.6, 7.8.7, 7.8.8, 7.8.9, 7.8.10, 8.8.1, 8.8.2, 8.8.3, 8.8.4, 8.8.5, 8.8.6, 8.8.7, 8.8.8, 8.8.9, 8.8.10, 9.8.1, 9.8.2, 9.8.3, 9.8.4, 9.8.5, 9.8.6, 9.8.7, 9.8.8, 9.8.9, 9.8.10, 10.8.1, 10.8.2, 10.8.3, 10.8.4, 10.8.5, 10.8.6, 10.8.7, 10.8.8, 10.8.9, 10.8.10, 11.8.1, 11.8.2, 11.8.3, 11.8.4, 11.8.5, 11.8.6, 11.8.7, 11.8.8, 11.8.9, 11.8.10, 12.8.1, 12.8.2, 12.8.3, 12.8.4, 12.8.5, 12.8.6, 12.8.7, 12.8.8, 12.8.9, 12.8.10, 13.8.1, 13.8.2, 13.8.3, 13.8.4, 13.8.5, 13.8.6, 13.8.7, 13.8.8, 13.8.9, 13.8.10, 14.8.1, 14.8.2, 14.8.3, 14.8.4, 14.8.5, 14.8.6, 14.8.7, 14.8.8, 14.8.9, 14.8.10, 15.8.1, 15.8.2, 15.8.3, 15.8.4, 15.8.5, 15.8.6, 15.8.7, 15.8.8, 15.8.9, 15.8.10, 16.8.1, 16.8.2, 16.8.3, 16.8.4, 16.8.5, 16.8.6, 16.8.7, 16.8.8, 16.8.9, 16.8.10, 17.8.1, 17.8.2, 17.8.3, 17.8.4, 17.8.5, 17.8.6, 17.8.7, 17.8.8, 17.8.9, 17.8.10, 18.8.1, 18.8.2, 18.8.3, 18.8.4, 18.8.5, 18.8.6, 18.8.7, 18.8.8, 18.8.9, 18.8.10, 19.8.1, 19.8.2, 19.8.3, 19.8.4, 19.8.5, 19.8.6, 19.8.7, 19.8.8, 19.8.9, 19.8.10, 20.8.1, 20.8.2, 20.8.3, 20.8.4, 20.8.5, 20.8.6, 20.8.7, 20.8.8, 20.8.9, 20.8.10, 21.8.1, 21.8.2, 21.8.3, 21.8.4, 21.8.5, 21.8.6, 21.8.7, 21.8.8, 21.8.9, 21.8.10, 22.8.1, 22.8.2, 22.8.3, 22.8.4, 22.8.5, 22.8.6, 22.8.7, 22.8.8, 22.8.9 and 22.8.10.

Identification of Active Precursors. It is desirable to select the amino acid residue or sequence of the invention compounds having one or more peptide bonds, such as formula VII compounds, based on the substrate specificity of esterases and/or carboxypeptidases expected to be found within cells where precursor hydrolysis is desired. To the extent that the specificity of these enzymes is unknown, one will screen a plurality of nucleotide analogs or esters until the desired substrate specificity is found. This will be apparent from assay either of the generation of free phosphonate or of antimicrobial activity. One selects compounds that are (i) not hydrolyzed or hydrolyzed comparatively slowly in the upper gut, (ii) gut and cell permeable and (iii) hydrolyzed in the cell cytoplasm and/or systemic circulation. Screens with cells from particular tissues are used to identify precursors that are released in organs susceptible to a target viral or microbial infection, e.g. in the case of liver, precursor drugs capable of hydrolysis in the liver. Other infections, e.g. CMV or HIV, are treated with a precursor that is hydrolyzed at substantially the same rate and to substantially the same degree in all tissues, with no one tissue preferentially hydrolyzing the precursor nucleosides.

The assays used can be those known in the art including intestinal lumen stability, cell permeation, liver homogenate stability and plasma stability assays. These assays are used to determine the bioavailability characteristics of particular active precursors according to routinely used methods and as described herein.

The cell permeation assay using CaCo-2 intestinal cells described below is performed using commercially available apparatus (filter assembly/cluster plate) according to manufacturer's (Costar Corp) instructions. The assay measures transport of a compound added to a chamber ("donor half cell") that is connected to a second chamber ("receptor half cell") by a filter containing a monolayer of CaCo-2 cells. The rate of transport from the donor cell to the receptor half cell provides an estimate of the transport or permeation of the drug across intestinal leumen cells. A filter assembly/ cluster plate suitable for the cell permeation assay is the Snapwell™ assembly/cluster plate available commercially from Costar Corp. The Caco-2 cells typically form a monolayer in 20 to 30 days using the conditions described in the cell permeation assay.

The compounds of this invention most desirably have a permeability coefficient (P) of greater than about $3 \times 10^{-6}$ cm/sec according to the equation $P = V_o \cdot dC / A \cdot C \cdot dt$ where $V_o$ is the volume of the receiver chamber (receptor half cell), A is the exposed surface area of the filter, C is the initial nucleotide analog amidate concentration (dpm/mL in donor half cell) and dC/dt is the change in receiver chamber concentration over time of the nucleotide analog amidate or its hydrolysis product (dpm/mL/sec) in a cell permeation assay comprising:

prewetting the outside (receptor or serosal side) of a filter assembly having an exposed surface area of 1 cm² for 15 min. in sterile phosphate buffered saline;

prewetting the inside (donor or mucosal side) of the filter assembly for 15 min. in sterile phosphate buffered saline;

seeding the inside of the prewetted filter assembly with 63,000 Caco-2 cells in 0.5 mL DME (Dulbecco's modified Eagle's medium with 25 mM HEPES and supplemented with 10% FCS, 1% nonessential amino acids, 1% glutamine and optionally supplemented with 100 U/mL penicillin and 100 µg/mL streptomycin);

placing the filter assembly containing the Caco-2 cells in cluster plates having wells for receiving the filter assembly and adding 0.5 mL of DME to the inside of each well and 2 mL to the outside of each well;

incubating the cluster plates at 37° C. and changing the medium every other day until a monolayer of Caco-2 cells has grown on the filter assembly;

rinsing the inside of the filter assembly with 1–2 mL Krebs buffer (pH 7.4, 1.1 mM $MgCl_2$, 1.25 mM $CaCl_2$, 114 mM NaCl, 5 mM KCl, 25 mM $NaHCO_3$, 1.65 mM $Na_2HPO_4$, 0.30 mM $NaHPO_4$) at 37° C.;

inserting the rinsed filter assembly into a diffusion chamber prewarmed to 37° C. having a donor half cell and a receptor half cell for the filter assembly;

sealing the diffusion chamber containing the filter assembly;

placing the diffusion chamber containing the filter assembly into a heating block to maintain the temperature at 37° C.;

filling the donor half cell with mucosal buffer (Krebs buffer having radiolabeled phosphonate nucleoside amidate and mannitol at a total concentration of 40 mM) prewarmed to 37° C.;

filling the receptor half cell with serosal buffer (Krebs buffer containing 40 mM D-glucose) prewarmed to 37° C.;

aerating the donor and receptor half cells;

removing an aliquot of mucosal buffer and determining the radiolabeled nucleotide analog activity in the mucosal buffer;

removing 1 mL aliquots of serosal buffer at 30 minute intervals, replacing the sampled volume with prewarmed serosal buffer and determining the radioactivity in each 1 mL aliquot; and determining the permeability coefficient of the nucleotide analog amidate for movement from the donor half cell through the Caco-2 cells into the receptor half cell.

The liver homogenate assay described below is preferably performed using fresh or freshly thawed human liver tissue. A suitable homogenizer is a Kontes model #885510-0021 Potter-Elvehjem homogenizer and a suitable motor drive is a Kontes model #787900-0000.

The nucleotide analog prodrugs of this invention will be hydrolyzable to a corresponding phosphonate nucleotide analog in human liver homogenate as determined by an assay comprising:

rinsing human liver in ice cold buffer A (5.324 g/L $Na_2HPO_4$; 1.701 g/L $KH_2PO_4$; 0.750 g/L KCl adjusted to pH 7.4 with NaOH or HCl) three times;

mincing the rinsed tissue in buffer A at a ratio of 3 mL of buffer A per 1.0 g of tissue;

homogenizing the tissue at 4° C. using 15 strokes of a Potter-Elvehjem homogenizer operating at 1200 to 1500 rpm equipped with an overhead motor drive to obtain a homogenate;

filtering the homogenate through cheese cloth into a container on ice;

centrifuging the homogenate at 9000 G at 4° C. for 20 minutes to obtain an S9 fraction and a fatty layer;

removing the fatty layer and decanting the S9 fraction;

determining the protein concentration of the S9 fraction;

diluting the S9 fraction to a concentration of 20 mg protein per mL using buffer A and optionally storing the diluted S9 fraction at −70° C.;

adding 100 µL NADP (4.167 mg NADP in 10 mL buffer A), 100 µL glucose-6-phosphate (14.105 mg in 10 mL buffer A), 50 µL $MgCl_2$ (0.1M in $H_2O$), 10 µL nicotinamide (48.84 mg in 10 mL buffer A), 10 µL glucose-6-phosphate dehydrogenase (100 units/mL in buffer A), 250 µL diluted S9 fraction, 380 µL buffer A to obtain a reaction mixture;

preincubating the reaction mixture in a shaker bath at 37° C. and 100 oscillations/min. for 5 minutes;

adding 100 µL of a solution containing 10–100 µg/mL of nucleotide analog in dimethyl sulfoxide to the reaction mixture to obtain an active reaction;

maintaining the temperature at 37° C. and the shaker at 100 oscillations per minute to obtain nucleotide analog amidate and phosphonate hydrolysis product(s) of the nucleotide analog amidate;

withdrawing a 250 µL aliquot of the active reaction at selected times from about 1 minute to about 120 minutes after addition of nucleotide analog amidate to the reaction mixture;

adding the aliquot to 500 µL of 0.5% (w/w) trifluoroacetic acid in acetonitrile to obtain a quenched reaction;

centrifuging the quenched reaction for 5 minutes at room temperature to obtain a quenched supernatant; and determining the amount of the nucleotide analog amidate or its corresponding phosphonate hydrolysis product in the quenched supernatant.

Therapeutic Indications.

The hydrolysis products of the invention compounds have activity against viruses, malignant cells and/or parasitic protozoans. For example, 9-(3-hydroxy-2-phosphonylmethoxypropyl (HPMP) and (2-phosphonylmethoxy)ethyl (PME) analogs of purine (adenine (A), guanine (G), 2,6-diaminopurine (DAP), 2-monoaminopurine (MAP), hypoxanthine (Hx) and pyrimidine (cytosine (C), uracil (U), thymine (T) were evaluated for antiviral properties. (S)-HPMPA, (S)-cyclic HPMPA, (S)-HPMPC, (S)-HPMPG, (S)-HPMPDAP, PMEDAP, PMEG and PMEA were active against herpes simplex virus, type 1 and 2 (HSV-1 and -2). (S)-HPMPA and (S)-cyclic HPMPA were active against varicella zoster virus (VZV). (S)-HPMPC was active against human cytomegalovirus (HCMV). (S)-HPMPA and (S)-cyclic HPMPA were shown to be active against adenovirus and vaccinia virus. PMEA, PMEDAP, and PMEMAP are active against human immunodeficiency virus (HIV).

Acyclic nucleotide analogs having a common PME side chain covalently linked to a purine or pyrimidine base were prepared and tested for in vivo antiviral activity against retroviruses and herpes viruses. The adenine analog, PMEA, was active in vitro against HIV and Rauscher murine leukemia virus (R-MuLV), and was more potent in vivo than 3'-azido-3'-deoxythymidine (AZT) in the treatment of R-MuLV in mice. PMEA also had a significant antiviral effect in vivo against murine cytomegalovirus (MCMV), and in vitro activity against HCMV. The guanine analog, PMEG, was active in vitro against herpes viruses. In vivo, PMEG was >50-fold more potent than acyclovir against HSV 1 infection in mice.

(S)-HPMPA has potent and selective activity against a broad spectrum of DNA viruses, including HSV-1 and 2, VZV, thymidine kinase-deficient (TK−) mutants of herpes simplex virus, HCMV, phocid herpesvirus type 1 (seal herpesvirus, SeHV), simian herpesvirus type 1 (SHV-1), or pseudorabies virus or Aujeszky's disease virus), bovid herpesvirus type 1 (infectious bovine rhinotracheitis virus, BHV-1), equid herpesvirus type 1 (equine abortion virus, EHV-1), African swine fever (ASP) virus, vaccinia virus; and human adenoviruses, and retroviruses such as murine sarcoma virus (MSV). It is also reported that, in mice and rabbits in vivo, the compound is effective against both local and systemic infections with herpes simplex virus type 1, including herpetic keratitis caused by a TK− mutant which is resistant to the classical antiherpes drugs (DeClercq, E., et al, *Antiviral Res* (1987) 8:261–272; DeClercq, E., et al, *Nature* (1986) 323:464–467; Gil-Fernandez, C., et al, *Antiviral Res* (1987) Z:151–160; Baba, M., et al, *Antimicrob Agents Chemother* (1987) 31:337–339).

Phosphonylmethoxyalkylpurine analogs have also been evaluated for their antitumor activity in murine tumor models. HPMPA, PMEA, and PMEG were found to be active against intraperitoneal P388 leukemia. PMEG was also found to be active against B16 melanoma.

As indicated above, the compounds of the invention are useful for treatment of microbial infections, for treatment of tumors or for other indications described below. Microbial infections include infection by viruses, parasites, yeasts and fungi. Exemplary viral infections that may be treated include infections mediated by DNA or RNA viruses including herpesviruses (CMV, HSV 1, HSV 2, EBV, varicella zoster virus, bovid herpesvirus type 1, equid herpesvirus type 1), papillomaviruses (HPV types 1–55), flaviviruses (including African swine fever virus and Japanese encephalitis virus), togaviruses (including Venezuelan equine encephalomyelitis virus), influenza viruses (types A–C), retroviruses (HIV 1, HIV 2, HTLV I, HTLV II, SIV, HBV, FeLV, FIV, MoMSV), adenoviruses (types 1–8), poxviruses (vaccinia virus), enteroviruses (polio virus type 1–3, hepatitis A virus), gastroenteritis viruses (Norwalk viruses, rotaviruses), hantaviruses (Hantaan virus), papovaviruses, rhinoviruses, parainfluinza virus types 1–4, rabies virus, and the like.

Some of the phosphonate compounds (such as PMEA) have a broad spectrum of antimicrobial activity and are thus unusual antiviral or antiparasitic agents. The activity of individual nucleotide analogs and nucleotide analog amidates is determined by routine assay of antiviral (or other antimicrobial) activity using enzyme inhibition assays, tissue culture assays, animal model assays and/or other acceptable assays.

Nucleotide analogs (phosphonates such as HPMPC, PMEA, etc) are believed to exert their antimicrobial activity, at least in part, by a two step enzyme-mediated conversion to a diphosphate, followed by incorporation of the diphosphorylated nucleotide analog into nucleic acids. The incorporation of the diphosphates into nucleic acid is mediated by viral or other microbial DNA or RNA polymerases (bacterial, retroviral, etc). Thus, nucleotide analogs (when diphosphorylated) are useful as chain terminators for dideoxynucleotide-type DNA sequencing protocols, provided that the nucleotide analog lacks a free hydroxyl group suitable for polymerase mediated chain elongation. These compounds will not have a hydroxyl group at $R^{27}$ in compounds of formulas IV and VI or are acyclic. Nucleotide analogs of formula XV, $(HO)_2P(O)$—O—$P(O)(OH)$—O—$(HO)P(O)$—Z—B, can be prepared (Otvos, et al, *Nucl Acids Res* (1987) 15:1763–1777) and provided in a kit with other reagents (such as klenow polymerase or T4 polymerase, dNTPs, etc) needed for DNA sequencing. The invention nucleotide analogs and nucleotide analog amidates can also be (1) applied to tissue culture systems to eliminate or reduce viral spread or growth during the production of biopharmaceuticals or other products (such as proteins or vaccines), (2) used to eliminate or reduce viral spread or growth in clinical samples (such as blood), and (3) used to stop growth of tissue culture or bacterial cells (using toxic amounts of compound) without interfering with protein production.

Infections mediated by protozoan parasites can be treated using the compounds of the invention. Such infections can also be treated using the corresponding nucleotide analogs of the invention nucleotide analog amidates. The term protozoa is intended to include those members of the subphyla Sarcomastigophora and Sporozoa of the phylum Protozoa. More particularly, the term protozoa as used herein is intended to include those genera of parasitic protozoa which are important to man because they either cause disease in man or in his domestic animals. These genera are for the most part found classified in the superclass Mastighphora of the subphylum Sarcomastigophora and the class Telosporea of the subphylum Sporozoa in the classification according to Baker (1969). Illustrative genera of these parasitic protozoa include Histomonas, Pneumocystis, Trypanosoma, Giardia, Trichomonas, Eimeria, Isopora, Leishmania, Entamoeba, Toxoplasma and Plasmodium. Parasitic protozoans include *Plasmodium falciparum, Plasmodium berghei, Plasmodium malariae, Plasmodium vivax, Leishmania braziliensis, Leishmania donovani, Trypanosoma cruzi, Trypanosoma brucei, Trypanosoma rhodesiense, Pneumocystis carinii, Entamoeba histolytica, Trichomonas vaginalis* and the like (de Vries, E., et al, *Mol Biochem Parasitol* (1991) 47:43–50). Nucleoside analog amidates of the invention and/or their corresponding nucleotide analogs can also be used to treat yeast or fungal infections caused by *Candida glabrata, Candida tropicalis, Candida albicans,* and other Candida species Cryptococcus species including *Cryptococcus neoformans,* Blastomyces species including *Blastomyces dermatidis,* Torutopsis species including *Torulopsis glabrata,* Coccidioides species including *Coccidioides immitis,* Aspergillus species and the like.

Pharmaceutical formulations.

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). It will be appreciated that the preferred route may vary with for example the condition of the recipient.

While it is possible for the active ingredients to be administered alone it is preferably to present them as pharmaceutical formulations. The formulations, both for veterinary and for human use, of the present invention comprise at least one active ingredient, as above defined, together with one or more acceptable carriers therefor and optionally other therapeutic ingredients. The carrier(s) must be "acceptable"

in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are preferably applied as a topical ointment or cream containing the active ingredient (s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the present invention include Tween®60, Span®80, cetostearyl alcohol, benzyl alcohol, myristyl alcohol, glyceryl mono-stearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods. Controlled release formulations may be employed for the treatment or prophylaxis of various microbial infections particularly human bacterial, human parasitic protozoan or human viral infections caused by microbial species including Plasmodium, Pneumocystis, herpesviruses (CMV, HSV 1, HSV 2, VZV, and the like), retroviruses, adenoviruses and the like. The controlled release formulations can be used to treat HIV infections and related conditions such as tuberculosis, malaria, pneumocystis pneumonia, CMV retinitis, AIDS, AIDS-related complex (ARC) and progressive generalized lymphadeopathy (PGL), and AIDS-related neurological conditions such as multiple sclerosis, and tropical spastic paraparesis. Other human retroviral infections that may be treated with the controlled release formulations according to the invention include Human T-cell Lymphotropic virus (HTLV)-I and IV and HIV-2 infections.

The invention accordingly provides pharmaceutical formulations for use in the treatment or prophylaxis of the above-mentioned human conditions and microbial infections.

Therapeutic Administration.

For each of the above-indicated utilities and indications the amount required of an active ingredient (as above defined) will depend upon a number of factors including the severity of the condition to be treated and the identity of the recipient and will ultimately be at the discretion of the attendant physician or veterinarian. In general however, for each of these utilities and indications, a suitable, effective dose will be in the range 0.1 to 250 mg per kilogram bodyweight of recipient per dose (including active ingredient(s) in a range between 0.1 mg and 250 mg/Kg/dose in increments of 0.5 mg/Kg/dose such as 2.5 mg/Kg/dose, 3.0 mg/Kg/dose, 3.5 mg/Kg/dose, etc), preferably in the range 0.5 to 50 mg per kilogram body weight per dose and most preferably in the range 1 to 15 mg per kilogram body weight per dose; an optimum dose is about 3.0 mg per kilogram body weight per dose. (Unless otherwise indicated all weights of active ingredient are calculated as the parent compound of formula I: for salts thereof the figures would be increased proportionately). The desired dose is preferably presented as one dose or two sub-doses administered at appropriate intervals throughout a period of one to seven days. It is preferred to administer a dose once every 2, 3, 4, 5 or 6 days. The doses may be administered in unit dosage forms. The desired dose is may be presented as one, two, or three sub-doses administered at appropriate intervals throughout the one to seven day period. These sub-doses may be administered in unit dosage form, for example, containing 10 to 1000 mg, and or 100 to 500 mg of active ingredient per unit dosage form. The formulations should be desirably administered to achieve peak plasma concentrations of the active compound of from about 1 to about 100 µM, preferably about 2 to 50 µM, most preferably about 3 to about 30 µM.

The compounds of the invention may be employed in combination with other therapeutic agents for the treatment or prophylaxis of the infections or conditions indicated above. Examples of such further therapeutic agents include agents that are effective for the treatment or prophylaxis of viral, parasitic or bacterial infections or associated conditions or for treatment of tumors or related conditions include 3'-azido-3'-deoxythymidine (zidovudine, AZT), 2'-deoxy-3'-thiacytidine (3TC), 2',3'-dideoxy-2',3'-didehydroadenosine (D4A), 2',3'-dideoxy-2',3'-didehydrothymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chlorodeoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-arabinosyl)-5-iodocytidine (FIAC), tetrahydro-imidazo(4,5,1-jk)—(1,4)-benzodiazepin-2(1H)-thione (TIBO), 2'-nor-cyclicGMP, 6-methoxypurine arabinoside (ara-M), 6-methoxypurine arabinoside 2'-O-valerate, cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI), acyclic nucleosides such as acyclovir, penciclovir, famciclovir, ganciclovir, HPMPC, PMEA, PMEG, PMPA, PMPDAP, FPMPA, HPMPA, HPMPDAP, (2R, 5R)-9-[tetrahydro-5-(phosphonomethoxy)-2-furanyl]adenine, (2R, 5R)-1—[tetrahydro-5-(phosphonomethoxy)-2-furanyl]thymine, other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate), antibacterial agents including bactericidal fluoroquinolones (ciprofloxacin, pefloxacin and the like), aminoglycoside bactericidal antibiotics (streptomycin, gentamicin, amicacin and the like) β-lactamase inhibitors (cephalosporins, penicillins and the like), other antibacterials including tetracycline, isoniazid, rifampin, cefoperazone, claithromycin and azithromycin, antiparasite or antifungal agents including pentamidine (1,5-bis(4'-aminophenoxy)pentane), 9-deazainosine, sulfamethoxazole, sulfadiazine, quinapyramine, quinine, fluconazole, ketoconazole, itraconazole, Amphotericin B, 5-fluorocytosine, clotrimazole, hexadecylphosphocholine and nystatin, renal excretion inhibitors such as probenicid, nucleoside transport inhibitors such as dipyridamole, dilazep and nitrobenzylthioinosine, immunomodulators such as FK506, cyclosporin A, thymosin α-1, cytokines including TNF and TGF-β, interferons including IFN-α, IFN-β and IFN-γ, interleukins including interleukin I, II, III, IV, V, VI, VII, VIII, X, XII, XIII macrophage/granulocyte colony stimulating factors including GM-CSF, G-CSF, M-CSF, cytokine antagonists including anti-TNF antibodies, anti-interleukin antibodies, soluble interleukin receptors, protein kinase C inhibitors and the like.

Immunogens and Antibodies.

The compounds of this invention, or the biologically active substances produced from these compounds by hydrolysis in vivo, are used as immunogens to prepare antibodies capable of binding specifically to the compounds or their hydrolysis products. The immunogenic compositions therefore are useful as intermediates in the preparation of antibodies for use in diagnostic or quality control assays for the compounds or their hydrolysis products. The antibodies are useful for measuring the presence, absence or amounts of the compounds by any convenient homogenous or heterogenous procedure such as fluorescence polarization immunoassay, fluorescence immunoassay (using fluorescent labels such as fluorescein and the like), radioimmunoassay, enzyme immunoassay (using enzyme indicators such as alkaline phosphatase, horseradish peroxidase, glucose oxidase, urease and the like) and nephelometric inhibition assay by described methods (WO 92/22639, incorporated herein by reference). Such assays usually require a tracer (such as a fluorescent or radiolabeled labeled invention compound), an antibody and the sample to be analyzed containing the compound.

The hydrolysis products of interest are the phosphonates resulting from the hydrolysis of the amidate or ester bond(s) of the precursor compounds of this invention, for example HPMPC, 6-aza-HPMPC, cyclic HPMPC, PMEA, PMEG, PMPDAP, PMPA, D4TMPI, D4AMPI, cyclic HPMPA, FPMPA, PMEDAP, PMEMAP, 7-deaza-8-aza-FPMPA, 7-deaza-8-aza-HPMPA, cyclic 7-deaza-8-aza-HPMPA, 7-deaza-8-aza-PMPA, 8-aza-FPMPA, 8-aza-HPMPA, cyclic 8-aza-HPMPA, 8-aza-PMPA, PMPG, PMPMAP, 1-deaza-HPMPA, cyclic 1-deaza-HPMPA, 1-deaza-PMPA, 1-deaza-PMPG, 1-deaza-PMPMAP, 1-deaza-PMPDAP, 3-deaza-HPMPA, cyclic 3-deaza-HPMPA or 3-deaza-PMPA. Thus, the antibodies of this invention will be capable of binding to the precursors without binding to the hydrolysis products, will be capable of binding to the hydrolysis products without binding to the precursors, or will be capable of binding specifically to both. The antibodies will not cross-react with naturally-occurring nucleotides or nucleosides.

The immunogens of this invention contain the precursor or hydrolytic products in association with an immunogenic substance such as a protein or peptide. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the precursor or a compound having the structure of a precursor hydrolytic product is covalently conjugated to an immunogenic polypeptide or polysaccharide by the use of a polyfunctional (ordinarily bifunctional) cross-linking agent. Methods for the manufacture hapten immunogens are conventional per se, and any of the methods used heretofore for conjugating haptens to immunogenic polypeptides or the like are suitably employed here as well, taking into account the functional groups on the precursors or hydrolytic products which are available for cross-linking.

Typically the polypeptide is conjugated to a site on the base functionality of the compound or hydrolysis product rather than to a site on the alkyl or substituted-alkyl phosphonate moiety. In general, the site will be an amino group located on the purine or pyrimidine moiety of the nucleoside phosphonate, at the 5 position of pyrimidines (such as cytosine or uracil), at the 1 position of purines (such as adenosine or guanine) or, for compounds having a cyclic structure corresponding to a sugar or sugar analog and having a free hydroxyl group, through the hydroxyl group (usually at the 3' or 2' positions). Alternatively, the precursor compound is cross-linked through the phosphonate, typically by amidation or esterification of the phosphonate by the polypeptide itself or by a cross-linking functionality covalently bonded to the polypeptide. Thus, the groups $L^1$ or $L^2$ in structures $(L^1)(L^2)$—P(O)—Z—B can be immunogenic proteins (having more than 50 amino acid residues, usually less than 1000 residues) or peptides (about 5 to 50 amino acid residues).

The conjugates are prepared in conventional fashion. For example, N-hydroxysuccinimide, succinic anhydride or alkN=C=Nalk are useful in preparing the conjugates of this invention. The conjugates contain a precursor, its hydrolysis product, or both. Ordinarily, the conjugates will comprise the hydrolysis product, i.e., the biologically active drug. The conjugates are separated from starting materials and byproducts using chromatography or the like, and then are sterile filtered and vialed for storage.

Animals are typically immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with ⅕ to ¹⁄₁₀ the original amount of conjugate in Freund's complete adjuvant (or other suitable adjuvant) by subcutaneous injection at multiple sites. 7 to 14 days later animals are bled and the serum is assayed for the desired antibody titer. Animals are boosted until the titer plateaus. Preferably, the animal is boosted with the conjugate in which the precursor or product is linked to a different protein, through a different cross-linking agent or both. Optionally, aggregating agents such as alum are used to enhance the immune response.

After immunization, monoclonal antibodies are prepared by recovering immune lymphold cells (typically spleen cells or lymphocytes from lymph node tissue) from immunized animals and immortalizing the cells in conventional fashion, e.g., by fusion with myeloma cells or by Epstein-Barr virus transformation and screening for clones expressing the desired antibody. The hybridoma technique described originally be Kohler and Milstein, *Eur. J. Immunol.* (1976) 6:511 has been widely applied to produce hybrid cell lines that secrete high levels of monoclonal antibodies against many specific antigens.

It is possible to fuse cells of one species with another. However, it is preferably that the source of the immunized antibody producing cells and the myeloma be from the same species.

The hybrid cell lines are maintained in culture in vitro. The cell lines of this invention are selected or maintained in a hypoxanthine-aminopterin thymidine (HAT) medium. However, the established hybridoma cell line can be maintained on a variety of nutritionally adequate media. The secreted antibody is recovered from culture by conventional methods such as precipitation, ion exchange chromatography, affinity chromatography, or the like. The antibodies described herein are also recovered from hybridoma cell cultures by conventional methods for purification of IgG or IgM as the case may be that heretofore have been used to purify immunoglobulins from pooled plasma, e.g., ethanol or polyethylene glycol precipitation procedures. The purified antibodies are sterile filtered, and optionally are conjugated to a detectable marker such as an enzyme or spin label for use in diagnostic assays of test samples.

The antibodies of this invention are obtained from any animal species, but ordinarily are murine or rat. Once a monoclonal antibody having the desired specificity and affinity is obtained, other conventional modifications of the antibodies are within the scope of this invention. For example, the complementarity determining regions of an animal antibody, together with as much of the framework domain as is needed, are substituted into an antibody of another animal species or class to produce a cross-class or cross-species chimeric antibody. Fragments or other amino acid sequence variants of monoclonal antibodies also are encompassed within the meaning of antibody as that term is used herein, for example, Fab, Fab' or (Fab')2 fragments, single chain antibodies, bi or polyspecific antibodies, and the like.

The antibodies of this invention are from any suitable class or isotype, e.g. IgG, IgM, IgA, IgD or IgE. They may or may not participate in complement binding or ADCC.

Typically, hybridomas which are capable of binding to the immunogen are screened for the ability to bind to the hapten itself in typical test samples (plasma, serum and the like) with the requisite degree of affinity. The desired affinity will depend upon the use intended for the antibody, but should be adequate to function in a conventional competitive-type ELISA or radioimmunoassays, or in conventional EMIT immunoassays.

The antibodies of this invention are used in such assays together with a labeled from of the precursor or its hydrolyric product. Alternatively, the antibody is labeled. Suitable labels are well-known and include radioisotopes, enzymes, stable free radicals, fluorophors, chemiluminescent moieties and other detectable groups heretofore employed to prepare covalent conjugates for use in assays. Methods for linking the labels to ligand amino groups, or amino acid side chains or termini of polypeptides, are known and are suitable for use herein. Other suitable linking methods will be apparent to the ordinary artisan.

The antibodies and labeled ligands herein optionally are assembled into kits for use in therapeutic drug monitoring or evaluation, or for process quality control, and used in the conventional manner.

Bis amidate synthesis.

Synthesis of bis-phosphoroamidate nucleotide analogs of Formula Id,

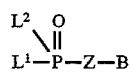

where $L^1$ and $L^2$ are the same and are an amino acid, dipeptide, tripeptide or oligopeptide (4 to 6 amino acid residues) are prepared by conversion of a nucleotide analog (such as PMEA, HPMPC, HPMPA, PMEG, FPMPA, PMPDAP, 9-[2,3-dideoxy-2,3-dihydro-4-phosphonomethoxy-β-D-erythrofuranosyl]adenine (D4AMPI; reg no. 132178-53-1), 1-[2,3-dideoxy-2,3-didehydro-4-phosphonomethoxyβ-D-erythrofuranosyl] thymine (D4TMPI; reg no. 132178-49-5) and the like) directly to the corresponding bis-phosphoroamidate compound. $L^1$ is a protein, an amino acid, dipeptide, tripeptide or oligopeptide (4 to 6 amino acid residues) which is esterified at free α-carboxyl group(s) by $R^4$. Suitable $R^4$ groups include methyl, ethyl, propyl, isopropyl, butyl, t-butyl, phenyl, benzyl, N-ethylmorpholino, pivaloyloxymethyl and the like. The amino acids can comprise an aliphatic or aromatic side group (such as ala, phe, pro, leu, ile, met, trp and the like) or a dipeptide comprising amino acids having aliphatic or aromatic side groups (such as gly-gly, ala-ala, gly-ala, ala-gly, phe-gly, gly-phe, ala-phe, phe-ala, leu-ala, ala-leu and the like), or is a tripeptide comprising amino acids having aliphatic or aromatic side groups or is an oligopeptide comprising amino acids having aliphatic or aromatic side groups.

The procedure is suitable for all of the nucleotide analogs described herein. The synthesis is accomplished by suspension of the nucleotide analog and approximately 2 equivalents of the $L^1$ species in a solvent such as dry pyridine or DMF (dimethylformamide) optionally containing a non-nucleophilic organic base such as triethylamine (about 3 to 10 equivalents). The dehydration step is accomplished by modification of a described reaction (Mukaiyama, T. et al, *J Am Chem Soc* (1972) 94:8528–8532) by adding a 1:1 mixture of triphenylphosphine (reg. no. 603-35-0; Aldrich) and 2,2'-dipyridyl disulfide (2 to 4 equivalents; reg. no. 2127-03-9; Aldrich) in pyridine to the nucleotide analog/ amino acid mixture and (a) stirring at room temperature for about 4 to 16 hours or (b) heating to 60° C. to 100° C. (including any temperature in one degree C increments between 60° and 100° C. such as 70°, 80° or 90° C.) for about 4 to 16 hours. The resulting reaction mixture is then concentrated and the final bis-amidate product is recovered and purified by conventional methods.

Synthesis of compounds of Formula Id having amino acids that contain amino, guanidino or carboxyl groups (such as lys, arg, his, asn, gln, lys-lys, arg-arg, lys-arg and the like) is accomplished by the same method, but using protected amine or carboxyl groups. After synthesis of the protected bis-amidate compound, the protecting groups are removed by conventional methods. Suitable protecting groups are well known and include acid labile groups such as p-tosyl, BOC (t-butoxycarbonyl) and FMOC (fluorene methoxycarbonyl) for protecting amine groups. Groups such as t-butyl, methyl, ethyl, benzyl and the like can be used to protect carboxyl groups. These groups can be removed under acid, base or hydrogenolysis conditions or can be removed with an esterase according to conventional methods.

Synthesis of compounds of Formula Id having amino acids such as tyr, cys, ser and thr is accomplished by optionally protecting hydroxyl or thiol groups using protecting groups know in the art. For example, the hydroxyl group of ser, thr or tyr can be protected using benzyl, ethyl and the like and the thiol group of cys can be protected using trityl, p-methylbenzyl and the like. The choice of a protecting group will depend on the stability of the bis-amidate toward conditions used to remove a particular protecting group. Appropriate protecting groups can be selected or determined by the skilled artisan using routine methods.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (see: Bai,J.P.F., *Pharm Res* (1992) 9:969–978, incorporated herein by reference). Transport competent peptides can thus be used to enhance bioavailability of bis amidate compounds. Di- or tripeptides having one or more amino acids in the D configuration are also compatible with peptide transport and can be utilized in bis amidate compounds. The use of amino acids in the D configuration can be used to reduce the susceptibility of a di- or tripeptide to hydrolysis by proteases common to the brush border such as aminopeptidase N (EC 3.4.11.2). In addition, di- or tripeptides with amino acid residues can selected on the basis of their relative resistance to hydrolysis by proteases found in the lumen of the intestine. For example, tripeptides or oligopeptides lacking asp and/or glu are poor substrates for aminopeptidase A (EC 3.4.11.7) and di- or tripeptides lacking amino acid residues on the N-terminal side of hydrophobic amino acids (leu, tyr, phe, val, trp) are poor substrates for endopepridase 24.11 (EC 3.4.24.11) while peptides lacking a pro residue at the penultimate position at a free carboxyl terminus are poor substrates for carboxypeptidase P (EC 3.4.17). Similar considerations can also be applied to the selection of peptides that are either relatively resistant or relatively susceptible to hydrolysis by cytosolic, renal, hepatic, serum or other peptidases.

Amidate-ester synthesis.

Synthesis of mixed amidate-ester nucleotide analog amidates of Formula Id where $L^1$ is an amino acid ester and $L^2$ is a group of the Formula OR, SR or $OR^{31}$ is accomplished by conversion of a nucleotide analog (such as PMEA, HPMPC, HPMPA, PMEG, FPMPA, PMPDAP, D4AMPI, D4TMPI and the like) di- or bis-ester to a corresponding mixed ester-phosphoroamidate compound.

Bis esters of the formula $(RO)_2P(O)$—Z—B are synthesized in a manner similar to that described in EP 481 214. Dialkyl phosphonate esters are synthesized via conversion of a dichloropholsphonate such as $(Cl)_2P(O)$—Z—B (Quast, H. et al, *Synthesis* (1974) 7:489–490; Quast, H. et al, *Synthesis* (1974) 7:490; Moedritzer, K. et al, *Synth Reac Inorg Met—Org Chem* (1974) 5:417–27; Moedritzer, K., *Chem Abs* 82:86340; Stowell, M.H.B., et al *Tet Lett* (1990) 31:3261–3262) to a corresponding dialkylester (or dialkylamide) by reaction with alcohols (or amines). Monoalkylesters (or mono alkylamides) are obtained by hydrolysis of the disubstituted phosphonate in base (NaOH, KOH and the like). Disubstituted diacyloxyalkyl phosphonates are obtained by reaction of the unsubstituted phosphonate with a substituted chloromethyl ester (R—C(O)—O—CH(R)—Cl). A corresponding monosubstituted acyloxyalkyl phosphonate is obtained by hydrolysis in acid or base.

For synthesis of Z substructures having a free hydroxyl group, such as $(RO)_2P(O)$—$CH_2$—O—$CH(CH_2OH)$—$CH_2$—, the hydroxyl is, in some cases, protected by a protecting group such as benzyl, acetyl, trityl, dimethoxytrityl and the like.

Bis esters having aryl, substituted aryl, alkyl-aryl or substituted alkyl-aryl (such as phenyl, alkoxyphenyl, benzyl, alkoxybenzyl) are also synthesized as described by reaction of $(OH)_2P(O)$—B—Z with thionyl chloride and a catalytic amount of DMF in a solvent such as acetonitrile. The resulting dichloridate, $P(O)(Cl)_2$—Z—B is then reacted with about 4, 5 or 6 equivalents of the sodium or potasium alkoxide or a sodium or potassium aryloxide obtained from reaction with sodium hydride or potassium hydride and the alcohol (such as phenol, benzyl alcohol and the like) in a solvent such as THF or acetonitrile at a reduced temperature (below about −70° C., preferably about −76° C. to −78° C.).

Exemplary esters are of the formula, $(R^{31}O)(R^{31}O)P(O)$—Z—B, $(RO)(R^{31}O)P(O)$—Z—B or $(RO)(RO)P(O)$—Z—B, wherein $R^{31}$ is independently 2,3-dihydro-6-hydroxyindene, sesamol, catechol monoester, $C_3$–$C_6$ aryl (including phenyl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 2-, 3- and 4-pyridinyl and 2-, 4- and 5-pyrimidinyl) substituted by 3 to 5 halogen atoms or 1 to 2 atoms or groups selected from halogen, $C_1$–$C_{12}$ alkoxy (including methoxy, ethoxy, 2,3-, 2,4-, 2,5-, 2,6-, 3,4- and 3,5-dimethoxy and 2,3-, 2,4-, 2,5-, 2,6-, 3,4- and 3,5-diethoxy substituted phenyl), cyano, nitro, OH, $C_1$–$C_{12}$ haloalkyl (1 to 6 halogen atoms), $C_1$–$C_{12}$ alkyl (including methyl and ethyl), $C_2$–$C_{12}$ alkenyl or $C_2$–$C_{12}$ alkynyl; or $R^{31}$ is $C_1$–$C_4$ alkylene-$C_3$–$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$–$C_{12}$ alkoxy (including methoxy and ethoxy), cyano, nitro, OH, $C_1$–$C_{12}$ haloalkyl (1 to 6 halogen atoms), $C_1$–$C_{12}$ alkyl (including methyl and ethyl), $C_2$–$C_{12}$ alkenyl or $C_2$–$C_{12}$ alkynyl. The compounds are used as intermediates in the synthesis of mixed amidate-ester nucleotide analog amidates, or in some cases, as prodrugs per se. Additional exemplary ester compounds have the formulas $(R^{31}O)_2P(O)$—$Z^1$—B or $(RO)(R^{31}O)P(O)$—$Z^1$—B, where $Z^1$ is defined to mean the substructure in the following representative structures; $(R^{31}O)_2$—P(O)—$CH_2$—O—$CH_2$—$CH_2$—B, $(R^{31}O)_2$—P(O)—$CH_2$—O—C#H($CH_2OH$)—$CH_2$—B, $(R^{31}O)_2$—P(O)—$CH_2$—O—C#H($CH_3$)—$CH_2$—B, $(R^{31}O)_2$—P(O)—$CH_2O$—C#H($CH_2F$)—$CH_2$—B, $(R^{31}O)_2$—P(O)—$CH_2$—O—C#H(CH=$CH_2$)—$CH_2$—B, $R^{31}O)_2$—P(O)—$CH_2$—O—C#H($CH_2N_3$)—$CH_2$—B,

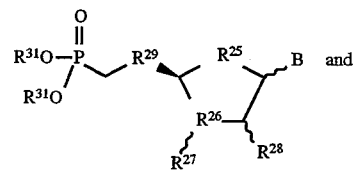

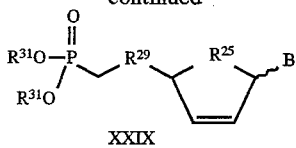

XXIX where C#, $R^{25}$–$R^{29}$, $R^{31}$ and B have the meanings previously defined with the proviso that PMEA bis(4-nitrobenzyl ester) and PMEA bis(4-trifluoromethyl ester) are excluded and for structure XXIX, $R^{29}$ and $R^{25}$ are both O. Additional ester and nucleotide compounds are of the formula

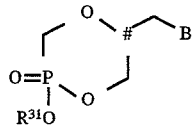

where the carbon atom designated # is in the R, S or RS configuration and $R^{31}$ and B are as previously defined. Nucleotides and esters of the formulas

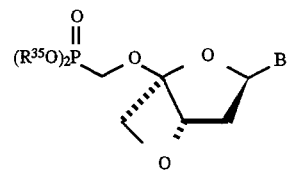

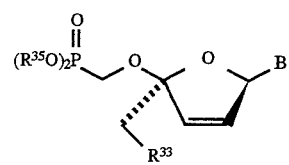

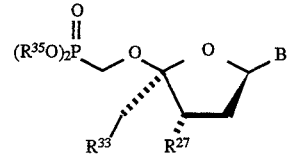

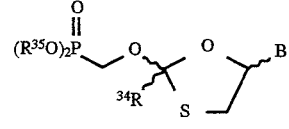

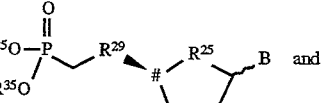 and

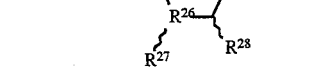

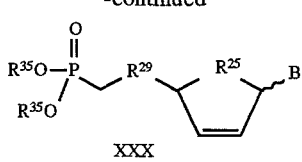

XXX wherein #, B, $R^{25}$, $R^{26}$ $R^{27}$, $R^{28}$, $R^{29}$, $R^{31}$, $R^{33}$ and $R^{34}$ are as defined, $R^{35}$ is defined as R or $R^{31}$ and for structure XXX, when $R^{29}$ is $CH_2$ or O and $R^{25}$ is $CH_2$ or O, $R^{35}$ is not H or $C_1$–$C_6$ alkyl, are new. Compounds having $R^{35}$ include species where both $R^{35}$ are both H and their pharmaceutically acceptable salts.

Exemplary $R^{31}$ include 2-, 3- and 4-alkoxyphenyl ($C_1$–$C_{12}$ alkyl including 2-, 3- and 4-methoxyphenyl and 2-, 3- and 4-ethoxyphenyl), 2-, 3- and 4-carboethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$–$C_{12}$ alkyl including 4-trifluoromethylphenyl), 2-, 3- and 4-cyanophenyl, and 2-, 3- and 4-nitrophenyl, 2-, 3- and 4-haloalkylbenzyl (1 to 5 halogen atoms, $C_1$–$C_{12}$ alkyl including 4-trifluoromethylbenzyl). The bis esters of formula $(OR^{31})(OR^{31})P(O)$—Z—B and $(OR)(OR^{31})P(O)$—Z—B are novel and are useful as intermediates in the synthesis of the mixed amidate-ester nucleotide analog amidates of the invention. These compounds can also be used directly as antimicrobial agents per se. Table 5 lists a group of exemplary bis esters of compounds having the structure $(OR^{31})_2P(O)$—Z—B.

TABLE 5

| $OR^{31}$* | —P(O)-Z-B** |
|---|---|
| 1 —O—$C_6H_4F$ | 1 —P(O)—$CH_2$—O—$CH_2$—$CH_2$—B |
| 2 —O—$C_6H_3F_2$ | 2 —P(O)—$CH_2$—O—C#H($CH_2$—$OR^4$)—$CH_2$—B |
| 3 —O—$C_6H_4$—$OCH_3$ | 3 —P(O)—$CH_2$—O—C#H($CH_3$)—$CH_2$—B |

TABLE 5-continued

| | | | |
|---|---|---|---|
| 4 | —O—C₆H₃—(OCH₃)₂ | 4 | —P(O)—CH₂—O—C*H(CH₂F)—CH₂—B |
| 5 | —O—C₆H₄—OC₂H₅ | 5 | CH=CH₂)—CH₂—B |
| 6 | —O—C₆H₃—(OC₂H₅)₂ | 6 | —P(O)—CH₂—O—C*H(CH₂N₃)—CH₂—B |
| 7 | —O—CH₂—C₆H₄F | 7 | ** |
| 8 | —O—C₆H₄—(C(O)—O—C₂H₅)₂ | 8 | ** |
| 9 | —O—C₆H₄—C(O)—O—C₂H₅ | | |
| 10 | —O—C₆H₃—(O—C(O)—CH₃)₂ | | |
| 11 | —O—C₆H₃—C(O)—O—C₃H₇ | | |
| 12 | —O—CH₂—C₆H₄—O—CO—CH₃ | | |
| 13 | —O—C₅H₄N | | |
| 14 | —O—C₆H₃—(OC₂H₅)(OH) | | |

B 1 adenin-9-yl
2 guanin-9-yl
3 cytosin-1-yl
4 2,6-diaminopurin-9-yl
5 2-aminopurin-9-yl
6 thymidin-1-yl
7 5-fluorocytosin-1-yl

*Monosubstituted phenyl and benzyl compounds (i.e., $R^{31}$ numbers 1,3,5, etc) include 2-, 3- and 4-substituted compounds and disubstituted phenyl compounds (i.e., $R^{31}$ numbers 2, 4, 6, etc) include 2,3-, 2,4-, 2,5-, 2,6-, 3,4- and 3,5-substituted compounds.
**The structure =P(O)— indicates that two bonds are occupied by $OR^{31}$; Z structure 7 is of formula IV where $R^{25}$ $R^{29}$ are O, $R^{26}$ is S, $R^{27}$ is absent and $R^{28}$ is H and includes the (+) and (−) enantiomers; structure 8 is of formula V where $R^{25}$ and $R^{29}$ are O.

Compounds listed in Table 5 are designated herein by numbers assigned to $(OR^{31})_2$ (where each $R^{31}$ is the same), Z and B according to the following convention, $R^{31}$.Z.B. Exemplary compounds include 1.1.1, 2.1.1, 3.1.1, 4.1.1, 5.1.1, 6.1.1, 7.1.1, 8.1.1, 9.1.1, 10.1.1, 11.1.1, 12.1.1, 13.1.1, 14.1.1, 1.2.1, 2.2.1, 3.2.1, 4.2.1, 5.2.1, 6.2.1, 7.2.1, 8.2.1, 9.2.1, 10.2.1, 11.2.1, 12.2.1, 13.2.1, 14.2.1, 1.3.1, 2.3.1, 3.3.1, 4.3.1, 5.3.1, 6.3.1, 7.3.1, 8.3.1, 9.3.1, 10.3.1, 11.3.1, 12.3.1, 13.3.1, 14.3.1, 1.4.1, 2.4.1, 3.4.1, 4.4.1, 5.4.1, 6.4.1, 7.4.1, 8.4.1, 9.4.1, 10.4.1, 11.4.1, 12.4.1, 13.4.1, 14.4.1, 1.5.1, 2.5.1, 3.5.1, 4.5.1, 5.5.1, 6.5.1, 7.5.1, 8.5.1, 9.5.1, 10.5.1, 11.5.1, 12.5.1, 13.5.1, 14.5.1, 1.6.1, 2.6.1, 3.6.1, 4.6.1, 5.6.1, 6.6.1, 7.6.1, 8.6.1, 9.6.1, 10.6.1, 11.6.1, 12.6.1, 13.6.1, 14.6.1, 1.7.1, 2.7.1, 3.7.1, 4.7.1, 5.7.1, 6.7.1, 7.7.1, 8.7.1, 9.7.1, 10.7.1, 11.7.1, 12.7.1, 13.7.1, 14.7.1, 1.8.1, 2.8.1, 3.8.1, 4.8.1, 5.8.1, 6.8.1, 7.8.1, 8.8.1, 9.8.1, 10.8.1, 11.8.1, 12.8.1, 13.8.1, 14.8.1, 1.1.2, 2.1.2, 3.1.2, 4.1.2, 5.1.2, 6.1.2, 7.1.2, 8.1.2, 9.1.2, 10.1.2, 11.1.2, 12.1.2, 13.1.2, 14.1.2, 1.2.2, 2.2.2, 3.2.2, 4.2.2, 5.2.2, 6.2.2, 7.2.2, 8.2.2, 9.2.2, 10.2.2, 11.2.2, 12.2.2, 13.2.2, 14.2.2, 1.3.2, 2.3.2, 3.3.2, 4.3.2, 5.3.2, 6.3.2, 7.3.2, 8.3.2, 9.3.2, 10.3.2, 11.3.2, 12.3.2, 13.3.2, 14.3.2, 1.4.2, 2.4.2, 3.4.2, 4.4.2, 5.4.2, 6.4.2, 7.4.2, 8.4.2, 9.4.2, 10.4.2, 11.4.2, 12.4.2, 13.4.2, 14.4.2, 1.5.2, 2.5.2, 3.5.2, 4.5.2, 5.5.2, 6.5.2, 7.5.2, 8.5.2, 9.5.2, 10.5.2, 11.5.2, 12.5.2, 13.5.2, 14.5.2, 1.6.2, 2.6.2, 3.6.2, 4.6.2, 5.6.2, 6.6.2, 7.6.2, 8.6.2, 9.6.2, 10.6.2, 11.6.2, 12.6.2, 13.6.2, 14.6.2, 1.7.2, 2.7.2, 3.7.2, 4.7.2, 5.7.2, 6.7.2, 7.7.2, 8.7.2, 9.7.2, 10.7.2, 11.7.2, 12.7.2, 13.7.2, 14.7.2, 1.8.2, 2.8.2, 3.8.2, 4.8.2, 5.8.2, 6.8.2, 7.8.2, 8.8.2, 9.8.2, 10.8.2, 11.8.2, 12.8.2, 13.8.2, 14.8.2, 1.1.3, 2.1.3, 3.1.3, 4.1.3, 5.1.3, 6.1.3, 7.1.3, 8.1.3, 9.1.3, 10.1.3, 11.1.3, 12.1.3, 13.1.3, 14.1.3, 1.2.3, 2.2.3, 3.2.3, 4.2.3, 5.2.3, 6.2.3, 7.2.3, 8.2.3, 9.2.3, 10.2.3, 11.2.3, 12.2.3, 13.2.3, 14.2.3, 1.3.3, 2.3.3, 3.3.3, 4.3.3, 5.3.3, 6.3.3, 7.3.3, 8.3.3, 9.3.3, 10.3.3, 11.3.3, 12.3.3, 13.3.3, 14.3.3, 1.4.3, 2.4.3, 3.4.3, 4.4.3, 5.4.3, 6.4.3, 7.4.3, 8.4.3, 9.4.3, 10.4.3, 11.4.3, 12.4.3, 13.4.3, 14.4.3, 1.5.3, 2.5.3, 3.5.3, 4.5.3, 5.5.3, 6.5.3, 7.5.3, 8.5.3, 9.5.3, 10.5.3, 11.5.3, 12.5.3, 13.5.3, 14.5.3, 1.6.3, 2.6.3, 3.6.3, 4.6.3, 5.6.3, 6.6.3, 7.6.3, 8.6.3, 9.6.3, 10.6.3, 11.6.3, 12.6.3, 13.6.3, 14.6.3, 1.7.3, 2.7.3, 3.7.3, 4.7.3, 5.7.3, 6.7.3, 7.7.3, 8.7.3, 9.7.3, 10.7.3, 11.7.3, 12.7.3, 13.7.3, 14.7.3, 1.8.3, 2.8.3, 3.8.3, 4.8.3, 5.8.3, 6.8.3, 7.8.3, 8.8.3, 9.8.3, 10.8.3, 11.8.3, 12.8.3, 13.8.3, 14.8.3, 1.1.4, 2.1.4, 3.1.4, 4.1.4, 5.1.4, 6.1.4, 7.1.4, 8.1.4, 9.1.4, 10.1.4, 11.1.4, 12.1.4, 13.1.4, 14.1.4, 1.2.4, 2.2.4, 3.2.4, 4.2.4, 5.2.4, 6.2.4, 7.2.4, 8.2.4, 9.2.4, 10.2.4, 11.2.4, 12.2.4, 13.2.4, 14.2.4, 1.3.4, 2.3.4, 3.3.4, 4.3.4, 5.3.4, 6.3.4, 7.3.4, 8.3.4, 9.3.4, 10.3.4, 11.3.4, 12.3.4, 13.3.4, 14.3.4, 1.4.4, 2.4.4, 3.4.4, 4.4.4, 5.4.4, 6.4.4, 7.4.4, 8.4.4, 9.4.4, 10.4.4, 11.4.4, 12.4.4, 13.4.4, 14.4.4, 1.5.4, 2.5.4, 3.5.4, 4.5.4, 5.5.4, 6.5.4, 7.5.4, 8.5.4, 9.5.4, 10.5.4, 11.5.4, 12.5.4, 13.5.4, 14.5.4, 1.6.4, 2.6.4, 3.6.4, 4.6.4, 5.6.4, 6.6.4, 7.6.4, 8.6.4, 9.6.4, 10.6.4, 11.6.4, 12.6.4, 13.6.4, 14.6.4, 1.7.4, 2.7.4, 3.7.4, 4.7.4, 5.7.4, 6.7.4, 7.7.4, 8.7.4, 9.7.4, 10.7.4, 11.7.4, 12.7.4, 13.7.4, 14.7.4, 1.8.4, 2.8.4, 3.8.4, 4.8.4, 5.8.4, 6.8.4, 7.8.4, 8.8.4, 9.8.4, 10.8.4, 11.8.4, 12.8.4, 13.8.4, 14.8.4, 1.1.5, 2.1.5, 3.1.5, 4.1.5, 5.1.5, 6.1.5, 7.1.5, 8.1.5, 9.1.5, 10.1.5, 11.1.5, 12.1.5, 13.1.5, 14.1.5, 1.2.5, 2.2.5, 3.2.5, 4.2.5, 5.2.5, 6.2.5, 7.2.5, 8.2.5, 9.2.5, 10.2.5, 11.2.5, 12.2.5, 13.2.5, 14.2.5, 1.3.5, 2.3.5, 3.3.5, 4.3.5, 5.3.5, 6.3.5, 7.3.5, 8.3.5, 9.3.5, 10.3.5, 11.3.5, 12.3.5, 13.3.5, 14.3.5, 1.4.5, 2.4.5, 3.4.5, 4.4.5, 5.4.5, 6.4.5, 7.4.5, 8.4.5, 9.4.5, 10.4.5, 11.4.5, 12.4.5, 13.4.5, 14.4.5, 1.5.5, 2.5.5, 3.5.5, 4.5.5, 5.5.5, 6.5.5, 7.5.5, 8.5.5, 9.5.5, 10.5.5, 11.5.5, 12.5.5, 13.5.5, 14.5.5, 1.6.5, 2.6.5, 3.6.5, 4.6.5, 5.6.5, 6.6.5, 7.6.5, 8.6.5, 9.6.5, 10.6.5, 11.6.5, 12.6.5, 13.6.5, 14.6.5, 1.7.5, 2.7.5, 3.7.5, 4.7.5, 5.7.5, 6.7.5, 7.7.5, 8.7.5, 9.7.5, 10.7.5, 11.7.5, 12.7.5, 13.7.5, 14.7.5, 1.8.5, 2.8.5, 3.8.5, 4.8.5, 5.8.5, 6.8.5, 7.8.5, 8.8.5, 9.8.5, 10.8.5, 11.8.5, 12.8.5, 13.8.5, 14.8.5, 1.1.6, 2.1.6, 3.1.6, 4.1.6, 5.1.6, 6.1.6, 7.1.6, 8.1.6, 9.1.6, 10.1.6, 11.1.6, 12.1.6, 13.1.6, 14.1.6, 1.2.6, 2.2.6, 3.2.6, 4.2.6, 5.2.6, 6.2.6, 7.2.6, 8.2.6, 9.2.6, 10.2.6, 11.2.6, 12.2.6, 13.2.6, 14.2.6, 1.3.6, 2.3.6, 3.3.6, 4.3.6, 5.3.6, 6.3.6, 7.3.6, 8.3.6, 9.3.6, 10.3.6, 11.3.6, 12.3.6, 13.3.6, 14.3.6, 1.4.6, 2.4.6, 3.4.6, 4.4.6, 5.4.6, 6.4.6, 7.4.6, 8.4.6, 9.4.6, 10.4.6, 11.4.6, 12.4.6, 13.4.6, 14.4.6, 1.5.6, 2.5.6, 3.5.6, 4.5.6, 5.5.6, 6.5.6, 7.5.6, 8.5.6, 9.5.6, 10.5.6, 11.5.6, 12.5.6, 13.5.6, 14.5.6, 1.6.6, 2.6.6, 3.6.6, 4.6.6, 5.6.6, 6.6.6, 7.6.6, 8.6.6, 9.6.6, 10.6.6, 11.6.6, 12.6.6, 13.6.6, 14.6.6, 1.7.6, 2.7.6, 3.7.6, 4.7.6, 5.7.6, 6.7.6, 7.7.6, 8.7.6, 9.7.6, 10.7.6, 11.7.6, 12.7.6, 13.7.6, 14.7.6, 1.8.6, 2.8.6, 3.8.6, 4.8.6, 5.8.6, 6.8.6, 7.8.6, 8.8.6, 9.8.6, 10.8.6, 11.8.6, 12.8.6, 13.8.6, 14.8.6, 1.1.7, 2.1.7, 3.1.7, 4.1.7, 5.1.7, 6.1.7, 7.1.7, 8.1.7, 9.1.7, 10.1.7, 11.1.7, 12.1.7, 13.1.7, 14.1.7, 1.2.7, 2.2.7, 3.2.7, 4.2.7, 5.2.7, 6.2.7, 7.2.7, 8.2.7, 9.2.7, 10.2.7, 11.2.7, 12.2.7, 13.2.7, 14.2.7, 1.3.7, 2.3.7, 3.3.7, 4.3.7, 5.3.7, 6.3.7, 7.3.7, 8.3.7, 9.3.7, 10.3.7, 11.3.7, 12.3.7, 13.3.7, 14.3.7, 1.4.7, 2.4.7, 3.4.7, 4.4.7, 5.4.7, 6.4.7, 7.4.7, 8.4.7, 9.4.7, 10.4.7, 11.4.7, 12.4.7, 13.4.7, 14.4.7, 1.5.7, 2.5.7, 3.5.7, 4.5.7, 5.5.7, 6.5.7, 7.5.7, 8.5.7, 9.5.7, 10.5.7, 11.5.7, 12.5.7, 13.5.7, 14.5.7, 1.6.7, 2.6.7, 3.6.7, 4.6.7, 5.6.7, 6.6.7, 7.6.7, 8.6.7, 9.6.7, 10.6.7, 11.6.7, 12.6.7, 13.6.7, 14.6.7, 1.7.7, 2.7.7, 3.7.7, 4.7.7, 5.7.7, 6.7.7, 7.7.7, 8.7.7, 9.7.7, 10.7.7, 11.7.7, 12.7.7, 13.7.7, 14.7.7, 1.8.7, 2.8.7, 3.8.7, 4.8.7, 5.8.7, 6.8.7, 7.8.7, 8.8.7, 9.8.7, 10.8.7, 11.8.7, 12.8.7, 13.8.7 and 14.8.7.

Exemplary bis esters include bis(pivaloyloxymethyl) PMEA (i.e. bis(pivaloyloxymethyl)-9-(2-phosphonylmethoxyethyl)adenine), bis(pivaloyloxymethyl) HPMPC, bis(pivaloyloxymethyl)D4AMPI, bis (pivaloyloxymethyl)D4TMPI, bis(N-ethylmorpholino) PMEA, bis(N-ethylmorpholino)HPMPC, bis(N-ethylmorpholino)PMPDAP, bis(N-ethylmorpholino) HPMPA, bis(N-ethylmorpholino)PMEG, bis(N-ethylmorpholino)D4AMPI, bis(N-ethylmorpholino) D4TMPI, bis(phenyl)PMEA, bis(phenyl)HPMPC, bis (phenyl)HPMPA, bis(phenyl)D4AMPI, bis(phenyl) D4TMPI, bis(t-butyl)PMEA, bis(t-butyl)D4AMPI, bis(t-butyl)D4TMPI, bis(t-butyl)HPMPC, bis(2-ethoxyphenyl) PMEA, bis(2-ethoxyphenyl)HPMPC,, bis(4-fluorophenyl) PMEA, bis(4-fluorophenyl)HPMPC, bis(3,5-dimethoxyphenyl)PMEA, bis(3,5-dimethoxyphenyl) HPMPC and the like.

$L^1$ is an amino acid which is, in general, esterified at free α-carboxyl group(s) by $R^4$, or is a dipeptide, tripeptide or oligopeptide which is optionally esterified at the free α-carboxyl group by $R^4$. $L^2$ is an ester or thioester group. Suitable $L^2$ esters (and the corresponding thioesters) include methyl ester, ethyl ester, propyl ester, isopropyl ester, butyl ester, t-butyl ester, phenyl ester, benzyl ester, N-ethylmorpholino ester (—O—CH$_2$—CH$_2$—N[(CH$_2$)$_2$(CH$_2$)$_2$]O), pivaloyloxymethyl ester (—O—CH$_2$—O—C(O)—C(CH$_3$)$_3$) and the like. The suitability of the presence or absence of any particular $L^2$ or $R^4$ group is determined by stability and/or bioavailability assays (e.g., stability assay in aqueous conditions such as low pH/intestinal lumen conditions or assay in the presence of cellular extracts containing esterases or by bioavailability assay using animal models) known in the art. These assays are routinely performed by the skilled artisan.

The bis ester is then converted to a monoester by chemical hydrolysis in base or acid according to the bis ester used. For example, treatment with NaOH (0.5 to 2N) or NH$_4$OH in a solvent such as THF (tetrahydrofuran), dioxane or an alcohol for 1 to 24 hours at 22° to 90° is suitable for most esters. The choice of solvent will depend on the characteristics of the bis ester used. The stability of the ester groups of phosphonate bis esters and phosphonate bis thioesters toward hydrolysis is unequal and provides a means for obtaining the monoester. Selection of hydrolysis conditions is determined by routine testing. Alkaline hydrolysis yields the phosphonate monoester and a corresponding alcohol or phenol. $L^1$ is then linked to the monoester or monothioester using reagents and conditions (i.e., a 1:1 mixture of triphenylphosphine (PPh$_3$) and 2,2'-dipyridyl disulfide in a suitable solvent such as pyridine or DMF) essentially as described for synthesis of bis amidates.

Nucleoside bis esters of formulas VI, VII and VIII compounds are shown in FIGS. 4–7. 3',4'-Unsaturated nucleosides that are used as a starting material was previously described (Zemlicka, et al *J Am Chem Soc* (1970) 92:4744–4745). 4'-Modified nucleosides have also been described (Yang, et al *Tet Lett* (1992) 33: 41–44; Yang, et al *Tet Lett* (1992) 33: 37–40; Prisbe, et al *Nucleosides and Nucleotides as Antitumor and Antiviral Agents* (1993) Plemun Press, New York, Chu, C. K. et al eds., p. 101–113). The phosphonate ester is condensed with the unsaturated nucleoside using an oxidizing agent such as MCPBA (m-chloroperoxybenzoic acid), IBr or N-iodosuccinimide (NIS). The choice of a particular oxidizing agent will be guided by considerations such as the type of base or sugar substituent that is present. For example, IBr may not be generally compatible with a substituent such as azide (at $R^{27}$ or $R^{33}$) or 1-propynyl (at B). In these cases, NIS or MCPBA is used. A further example is reduction of the 2',3'-double bond using H$_2$/Pd/C, which is generally not compatible with an alkynyl group that can be present at B. In this case, the alkynyl group would be added to an appropriate base (a purine such as 7-deaza-7-iodoadenine or 7-deaza-7-iodoguardne, etc or a pyrimidine such as 5-iodocytosine, 5-iodouracil, uracil, etc) that is later converted to the alkynyl derivative (7-deaza-7-(1-propynyl)adenine, 5-(1-propynyl) uracil, etc) using an alkyne such as propyne and palladium (08/050,698; PCT/US92/10115; Hobbs et al, *J Org Chem* (1989) 54:3420–3422). For FIGS. 3–7, $R^{33}$ is H, OH, TBSO, halogen, cyano, CH$_2$N$_3$, C$_1$–C$_4$ alkyl, C$_1$–C$_4$ alkoxy (including OCH$_3$), CH$_2$OH or azido; $R^{34}$ is H, OH halogen (fluorine is preferred), azide, O-alkyl (C$_1$–C$_6$ including O-methyl and O-ethyl), S-alkyl (C$_1$–C$_6$ including S-methyl and S-ethyl) and O-alkenyl (including O-allyl); R is as defined above, except that for the structure (RO)$_2$P(O)—CH$_2$—OH, R is not hydrogen, and R includes C$_1$–C$_{20}$ alkoxyacyl groups including methoxyacyl (pivaloyloxymethyl, adamantoyl oxymethyl and the like) and ethoxyacyl (pivaloyloxyethyl and the like) moieties; TBSO is t-butyldimethylsilyl ether. The phosphonates and monoesters shown in FIGS. 4–7 are converted to bis amidates or mixed amidate ester compounds using reagents and conditions (i.e., a 1:1 mixture of triphenylphosphine (PPh$_3$) and 2,2'-dipyridyl disulfide in a suitable solvent such as pyridine or DMF) essentially as described above.

Mixed bis amidate synthesis.

Synthesis of compounds of formula Id where $L^1$ and $L^2$ are both amino acids or where $L^1$ is an amino acid and $L^2$ is an amine (NH$_2$, NHR$^6$, N(R$^6$)$_2$) but are not both the same is accomplished by direct conversion as described above for bis amidates followed by separation of the final products. Another method to synthesize mixed bis amidates is amidation of an appropriate phosphonate monoester to give a compound of formula Id, followed by removal of the ester group under conditions that do not remove the first amide. Synthesis of phosphonate monoester compounds has been described (EP 481 214). This compound is then converted to a mixed bis amide by condensation with a second amino acid to yield the final product as described (i.e., using a 1:1 mixture of triphenylphosphine and 2,2'-dipyridyl disulfide). Mono amidate synthesis.

Synthesis of compounds of formula Ib where $L^1$ is an amino acid and $X^1$ is O (oxygen) is accomplished essentially as described for bis amidate synthesis using a cyclic nucleotide analog such as cHPMPC (cyclic HPMPC), cHPMPA, cHPMPDAP, cHPMPG and the like. Cyclic HPMP series compounds (cHPMPC, etc) are prepared by direct dehydration of the corresponding HPMP nucleotide analog using DCC (dicyclohexylcarbodiimide) or using 4-morpholino-N, N'-dicyclohexylcarboxamide as described (Ho, et al *Mol Pharmacol* (1992) 41:197–202). The cyclic phosphonate is condensed with an optionally protected amino acid ester in the presence of a 1:1 mixture of triphenylphosphine and 2,2'-dipyridyl disulfide in a suitable solvent such as pyridine or DMF.

Synthesis of formula Ib compounds where $X^1$ is S is accomplished as shown in FIG. 1. Conversion of the six-membered heterocycle to an amidate is accomplished in essentially the same manner as described (i.e., using triphenylphosphlne and 2,2'-dipyridyl disulfide).

Figure 3:
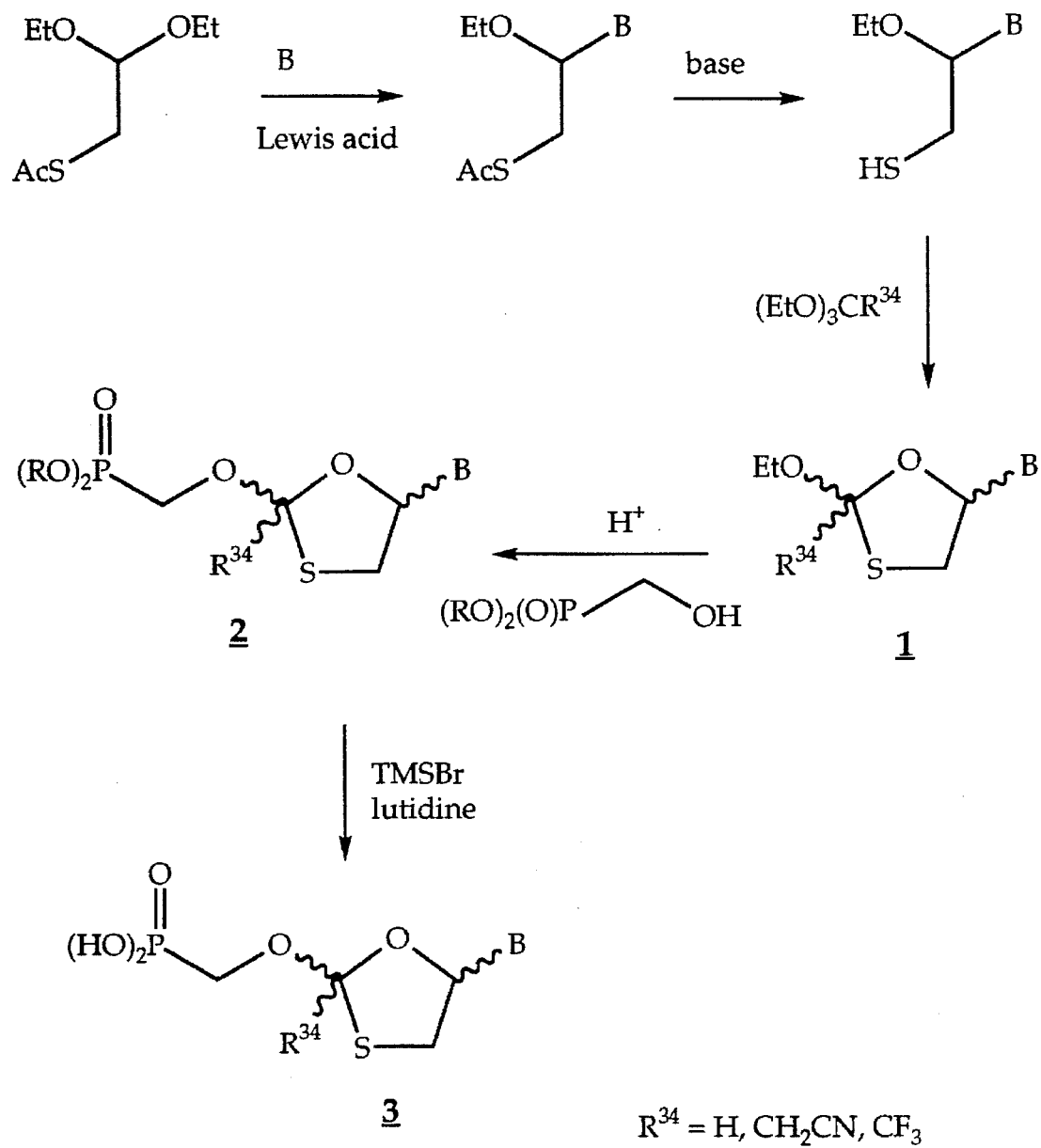
FIG. 3. Synthesis of formula IV compounds.
Figure 4:
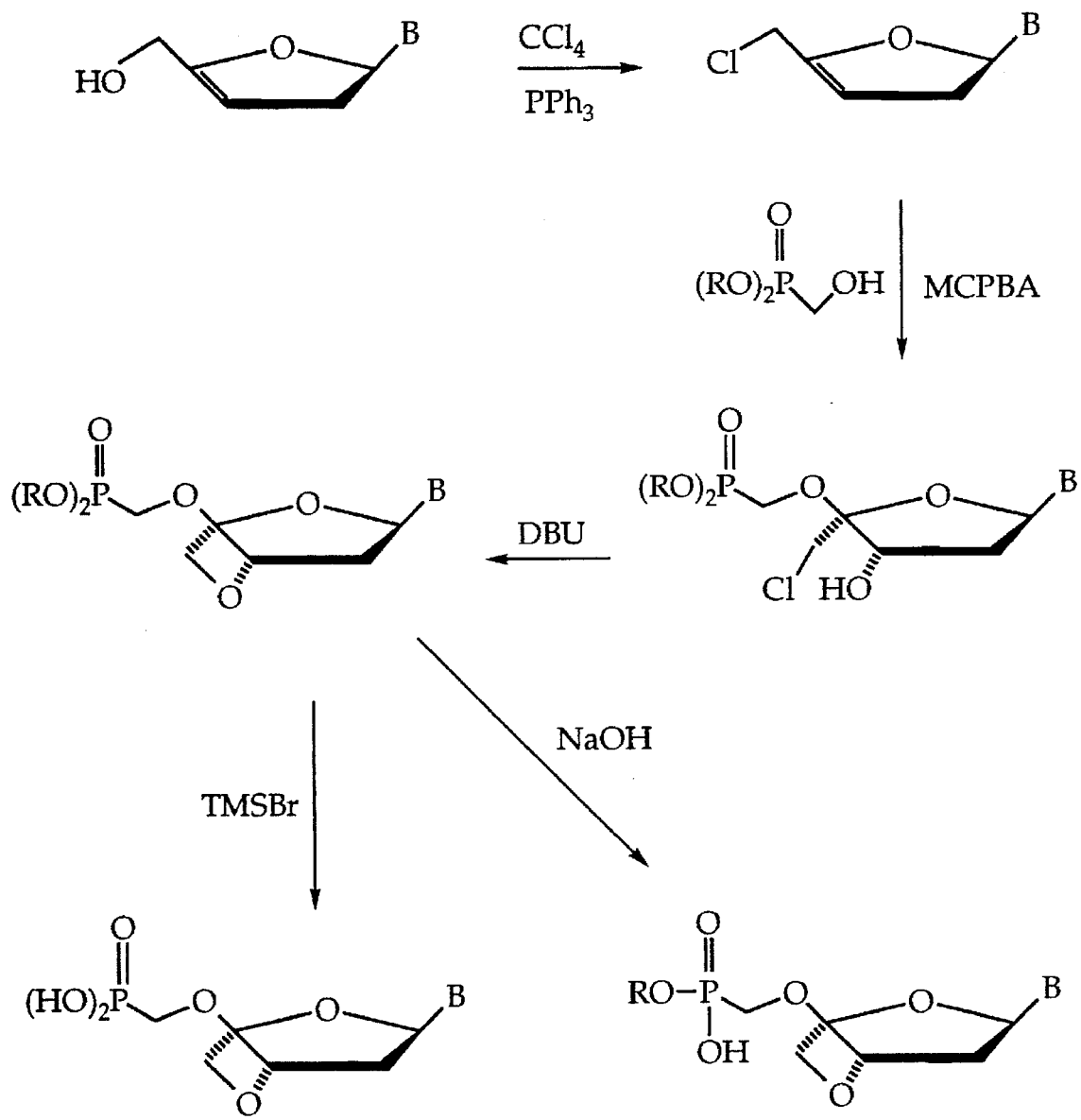
FIG. 4. Synthesis of formula VII compounds.
Figure 5:
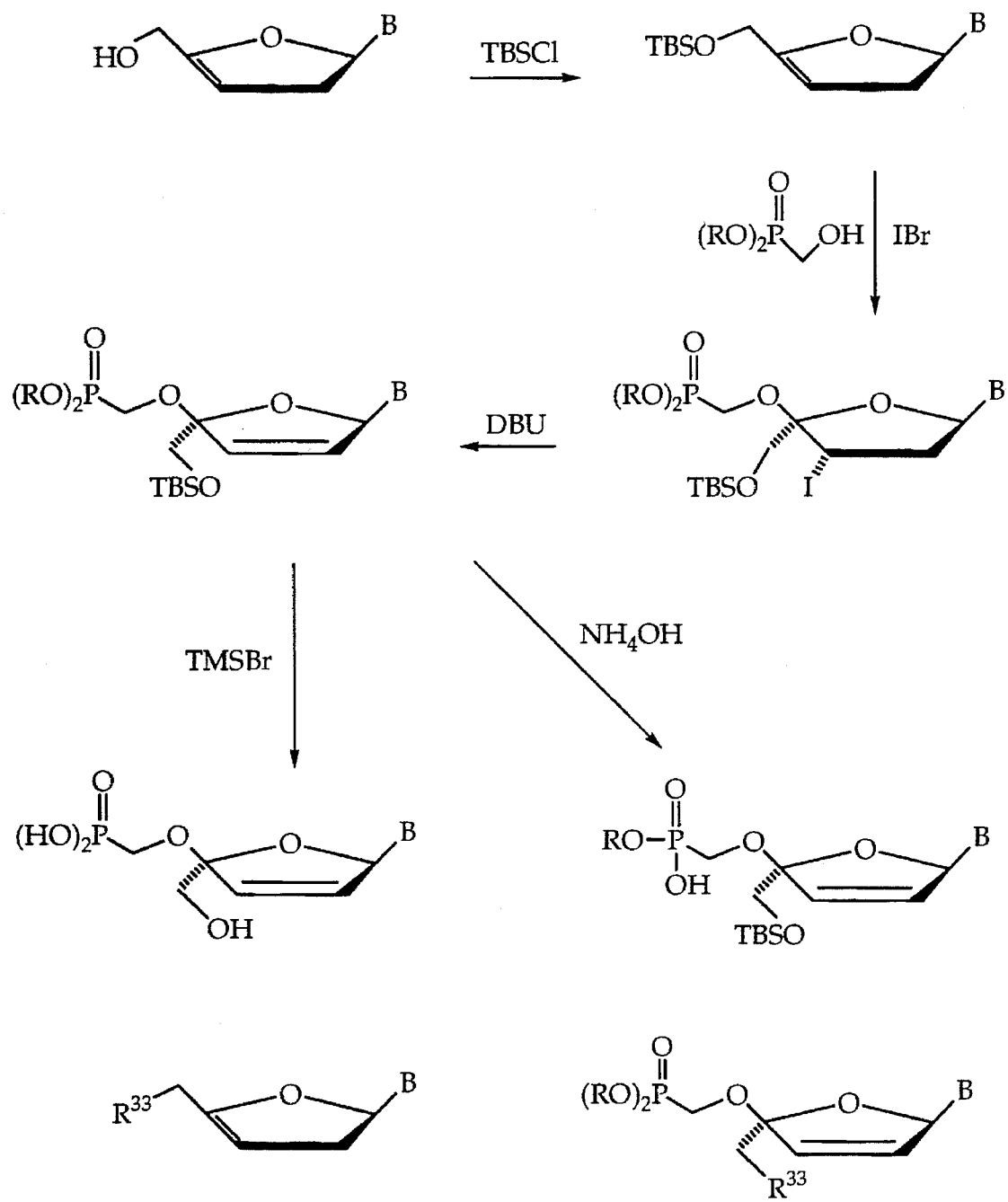
FIG. 5. Synthesis of formula VIII compounds.
Figure 6:
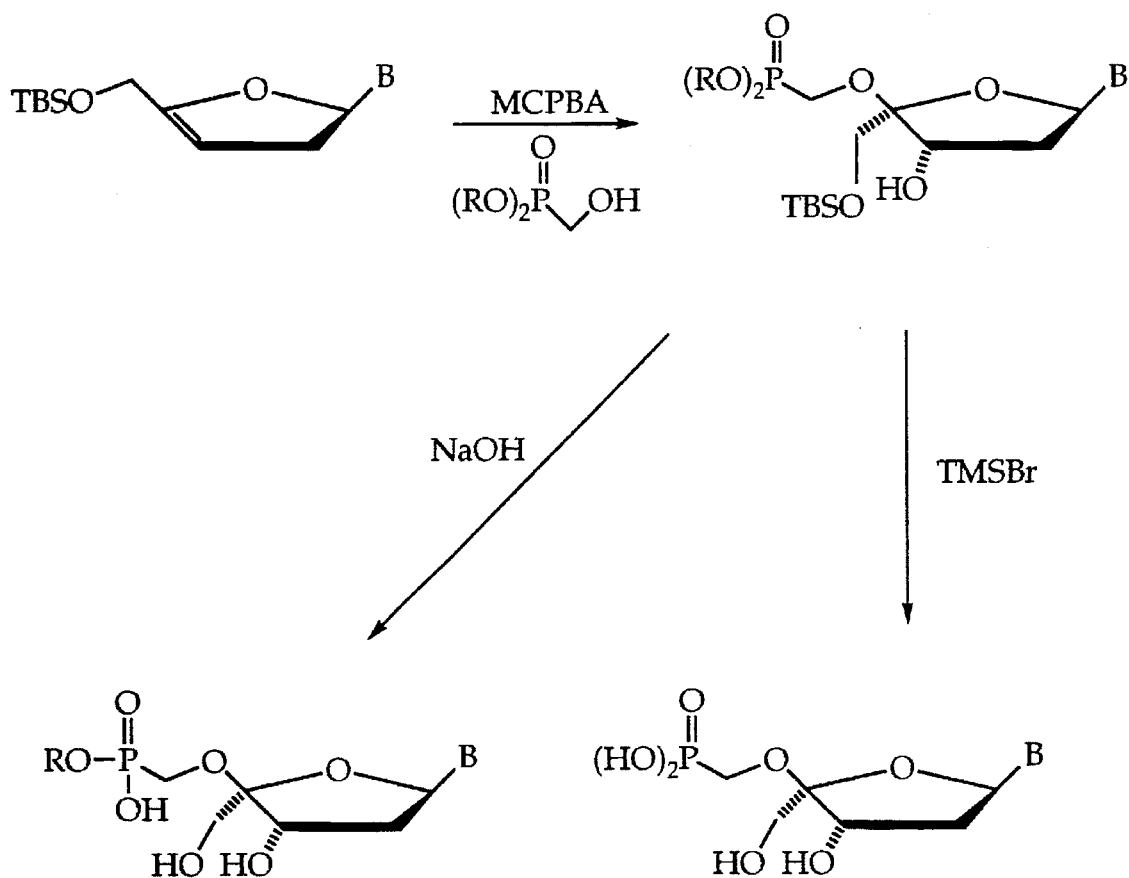
FIG. 6. Synthesis of formula VI compounds.
Figure 7:
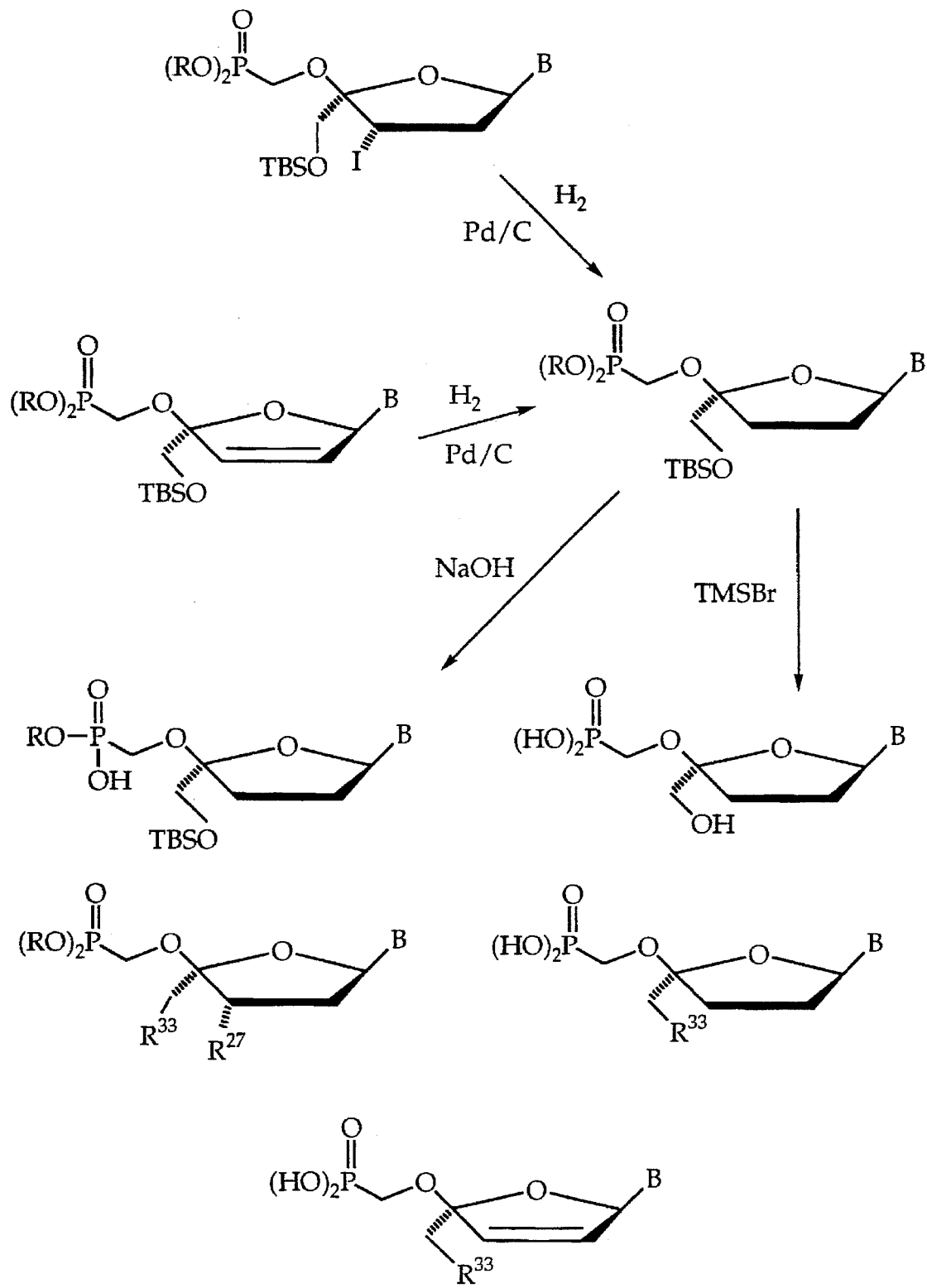
FIG. 7. Synthesis of formula VI compounds.

Synthesis of formula IV compounds where $R^{26}$ is S and $R^{25}$ and $R^{29}$ are O is accomplished as shown in FIG. 3. The starting material is synthesized by reaction of thiolacetic acid (Aldrich Cat. No. T3,080-5), bromoacetaldehyde diethyl acetal (Aldrich Cat. No. 12,398-6) and potassium tert-butoxide (Aldrich Cat. No. 15,667-1) in DMF. Synthesis of 1 where $R^{34}$ is H is accomplished using neat $(EtO)_3CH$. Synthesis of 1 where $R^{34}$ is $CH_2CN$ or $CF_3$ is accomplished using $(EtO)_3CH_2CN$ or $(EtO)_3CF_3$ in methylene chloride with a catalytic acid (such as p-toluenesulfonic add). Conversion of the thiaorthoester 1 to the phosphonate 2 is accomplished using an acid such as tosic acid or perchloric acid in catalytic amounts. The resulting bis ester is then converted to a bis amidate in essentially the same manner as described (i.e., using triphenylphosphine and 2,2'-dipyridyl disulfide). Mixed ester-amidate compounds are obtained by removing a single ester from the bis ester using base (NaOH, $NH_4OH$, etc) as described. The phosphonate 3 is obtained by treatment with a base such as TMSBr or TMSI in a solvent (such as methylene chloride, DMF or acetonitrile) in the presence of lutidine (where R is alkyl, aryl or substituted aryl, acyloxyalkyl such as isopropyl, phenyl, 2-ethoxyphenyl) or by treatment with $Pd/C/H_2$ (where R is alkaryl or substituted alkaryl such as benzyl and the like). $R^{34}$ in FIG. 3 is H, $CF_3$ or $CH_2CN$.

All citations are hereby expressly incorporated by reference. The following examples are illustrative and do not limit the scope of this invention.

Example 1: Synthesis of phosphonate amidate compounds.

The compounds of structural formula Id shown are in Table 6 (bis(glycyl benzyl ester)PMEA (compound Ex 4), bis(alanyl benzyl ester)PMEA (Ex 1), bis(phenylalanyl benzyl ester)PMEA (Ex 5), etc. Compounds Ex 1–Ex 12 were synthesized by the following procedure. PMEA (Z—B=—CH$_2$—O—CH$_2$—CH$_2$—B, where B is adenin-9-yl) (0.3 g; 1.1 mmol) and amino acid ester·HCl (2.2 mmol; Sigma) were suspended in dry pyridine (6 mL) containing triethylamine (0.3 mL; 22.2 mmol), followed by addition of freshly prepared triphenylphosphine (3.3 mmol) and 2,2'-dipyridyl disulfide (3.3 mmol) in pyridine (3 mL). The mixture was stirred at room temperature overnight, concentrated and partitioned between methylene chloride and water. The organic solution was dried over $MgSO_4$, concentrated and purified by flash column chromatography on silica gel.

Ex 14 was synthesized using freshly prepared triphenylphosphine (6.0 mmol) and 2,2'-dipyridyl disulfide (6.0 mmol) in pyridine (20 mL) at room temperature to which PMEA (2.0 mmol) was added. The suspension was stirred for 10 min. and ethyl sarcosine HCl (N-methylglycine HCl ethyl ester; 1.2 g, 8.0 mmol) was added. The suspension was warmed to 90° C. and stirred for 24 hours. Crude product was concentrated by rotary evaporation and purified by silica flash chromatography (mobile phase 1% methanol gradient to 20% methanol/80% methylene chloride).

Compound Ex 13 was synthesized in a similar manner using PMEA and phenylalanine N-ethylmorpholino ester.

TABLE 6

| Compound | $L^1$ |
|---|---|
| Ex 1 | —NH—CH(CH$_3$)—C(O)OCH$_2$C$_6$H$_5$ |
| Ex 2 | —NH—CH(CH$_2$C$_6$H$_5$)—C(O)OCH$_2$C$_6$H$_5$ |
| Ex 3 | —NH—CH(CH$_2$CH(CH$_3$)$_2$)—C(O)OCH$_2$C$_6$H$_5$ |
| Ex 4 | —NH—CH$_2$—C(O)OCH$_2$C$_6$H$_5$ |
| Ex 5 | —NH—CH(CH$_3$)—C(O)OC$_2$H$_5$ |
| Ex 6 | —NH—CH(CH$_2$CH(CH$_3$)$_2$)—C(O)OC$_2$H$_5$ |
| Ex 7 | —NH—CH$_2$—C(O)OC$_2$H$_5$ |
| Ex 8 | —NH—CH(CH$_2$C$_6$H$_5$)—C(O)OC(CH$_3$)$_3$ |
| Ex 9 | —NH—CH(CH$_2$CH(CH$_3$)$_2$)—C(O)OC(CH$_3$)$_3$ |
| Ex 10 | —NH—CH(CH$_3$)—C(O)OC(CH$_3$)$_3$ |
| Ex 11 | —NH—CH$_2$—C(O)OC(CH$_3$)$_3$ |
| Ex 12 | —NH—CH(CH$_2$C$_6$H$_5$)—C(O)OC$_2$H$_5$ |
| Ex 13 | —NH—CH(CH$_2$C$_6$H$_5$)C(O)O—(CH$_2$)$_2$—N[(CH$_2$)$_2$(CH$_2$)$_2$]O |
| Ex 14 | —N(CH$_3$)—CH$_2$—C(O)OC$_2$H$_5$ |

Example 2: Antiviral activity.

Compounds were individually tested for activity against HSV-1 and/or HSV-2. HSV-2 (strain 414-92) was tested using MA 104 cells in the following assay protocol. 96-Well plates were seeded with 1×10$^4$ MA 104 cells per well using 200 µL minimal essential medium (MEM) containing 10% calf serum per well, and incubated overnight at 37° C. The compounds were dissolved in MEM Earle's Salts without serum. The medium was removed by aspiration and 100 µL MEM Earle's Salts without serum was added to the wells. Serial 3-fold dilutions of the compounds were prepared by serial transfer of 50 µL of medium from wells containing compound to wells lacking compound. The plates were incubated 15 minutes at 37° C. followed by addition of 100 PFU/well of virus in MEM Earle's Salts with 2% fetal bovine serum. The plates were then incubated at 37° C. for three days until approximately 90% of the cells in virus infected control wells containing no compound were killed. Following incubation, medium was aspirated and the wells were washed with sterile PBS. 100 µL 0.5% crystal violet in 20% methanol was then added to the wells for 5 minutes, aspirated and the wells were washed two or three times with distilled water. 200 µL of 0.01N HCl was added to the wells and the absorbance of each well at 595 nm was determined. The results, shown in Table 6, were expressed as the IC$_{50}$, the concentration (µM) that inhibits cell killing mediated by HSV-2 by 50%. IC$_{50}$ values varied from 2 µM to >100 µM compared to an IC$_{50}$ for PMEA of 21 µM. Thus, some of the compounds were more active against HSV-1 than PMEA. The toxidty of the compounds were expressed as the CC$_{50}$, the concentration that kills 50% of uninfected cells.

The compounds were also tested for activity against the KOS strain of HSV-1 in VERO cells. The restfits, shown in Table 7, were expressed as the EC$_{50}$, the concentration (µM) that inhibits cell killing mediated by HSV-2 by 50%. EC$_{50}$ values varied from 2 µM to >200 µM compared to an EC$_{50}$ for PMEA of 138 µM. Thus, some of the compounds were more active against HSV-2 than PMEA.

TABLE 7

| | HSV-1 | HSV-2 | |
|---|---|---|---|
| compound | EC$_{50}$ | IC$_{50}$ | CC$_{50}$ |
| Ex 7 | >200 | >100 | >100 |
| Ex 5 | nt* | >100 | >100 |
| Ex 6 | 20 | 33 | >100 |
| Ex 12 | nt | 20 | 80 |
| Ex 11 | >200 | >100 | >100 |

TABLE 7-continued

| compound | HSV-1 EC$_{50}$ | HSV-2 IC$_{50}$ | HSV-2 CC$_{50}$ |
|---|---|---|---|
| Ex 10 | >200 | >100 | >100 |
| Ex 9 | 63 | 63 | >100 |
| Ex 8 | 3 | 9 | 20 |
| Ex 4 | nt | 60 | >100 |
| Ex 1 | nt | 20 | >100 |
| Ex 3 | nt | 2 | 30 |
| Ex 2 | nt | 4 | 20 |

*nt - not tested

Example 3: PMEA, monophenyl ester, mono N-ethylmorpholino-phenylalanyl phosphoroamidate.

Bis(phenyl)PMEA is selectively hydrolyzed to the monophenyl ester of PMEA using NaOH in THF. The reaction mixture is neutralized with acid (1N HCl), and the monophenyl ester is isolated by filtration. The anhydrous monophenyl PMEA and 2 equivalents of a freshly prepared 1:1 mixture of triphenylphosphine and 2,2'-dipyridyl disulfide in pyridine is condensed with 1 equivalent of phenylalanine N-ethyl-morpholino ester in triethylamine and pyridine to afford the title compound. The title compound is recovered by evaporation of the solvents under reduced pressure and purified by silica gel chromatography.

Example 4: Antiviral activity of PMEA esters.

PMEA and PMEA esters were tested for inhibition of cytopathic effects by HSV II in MA 104 cells as described except that CPE was determined after incubation with virus by addition of 100 µL XTT, 1 mg/mL in deficient DME containing 25 µM PMF followed by measuring absorbance. The esters tested were bis(POM)PMEA, bis(phenyl)PMEA, monophenylPMEA, bis(3-dimethylaminophenyl)PMEA, bis(3-methoxyphenyl)PMEA, bis(2-carboethoxyphenyl) PMEA, bis(adamantoyl oxymethyl)PMEA, bis(4-fluorophenyl)PMEA and bis(2-ethoxyphenyl)PMEA. All of the compounds tested were active, which indicated that the ester groups were removed, thereby allowing free PMEA to inhibit virus replication and/or cytopathic effects. The IC$_{50}$ and CC$_{50}$ of PMEA in the assay was 19.3 µM and 2000 µM respectively and the IC$_{50}$ and CC$_{50}$ of bis(POM)PMEA in the assay was 0.5 µM and >10 µM respectively. IC$_{50}$ values for the mono and bis esters ranged from 1.1 µM to 67.5 µM and the CC$_{50}$ values ranged from 70 µM to 500 µM.

Example 5: Oral bioavailability of nucleotide analog amidates and PMEA esters.

Nucleotide analog amidates and nucleotide analogs are tested for their bioavailabililty when administered to cynomologous (or rhesus) monkeys by oral, subcutaneous or intramuscular routes. Bioavailability is determined by measuring PMEA levels in plasma or urine at different times after administering the drug using radiolabeled ($^3$H, $^{14}$C, etc) compound or, for compounds having adenine, essentially as described (Naesens, et al, Clin Chem (1992) 38:480–485; Russell, et al, J Chromatogr (Netherlands) (1991) 572:321–326). Radiolabeled compounds are obtained commercially (Moravek Biochemicals, Brea, Calif.) or by standard procedures, such as catalytic hydrogen exchange for $^3$H labeling. Compounds such as bis(2-ethoxyphenyl)PMEA, bis(2-carboethoxyphenyl)PMEA, bis(O-benzylphenylalanyl)PMEA, bis(3,5-dimethoxyphenyl)PMEA, bis(4-fluorophenyl)PMEA, bis(adamantoyl oxymethyl)PMEA, bis(phenyl)PMEA, bis(3-methoxyphenyl)PMEA are tested for oral bioavailability by administering about 10–30 mg/Kg (usually 15 to 25 mg/Kg) containing about 20–50 µCi/Kg (usually about 40 µCi/Kg) of radiolabeled compound, followed by withdrawing blood samples at several times after administration (exemplary time points are 0.1, 0.25, 0.5, 1.0, 1.5, 2.0, 2.5, 3.0, 4, 6, 12, 18, 24, 36, 48, 72, 96 hours after administration), obtaining plasma and determining the amount of radiolabeled compound present per volume (about 0.1–1.0 mL) of serum. Oral bioavailability of the tested compounds is 2–80% (or any value between 2% and 80% in 1% increments), preferably 10–80% and more preferably 15 to 80%. The oral bioavailability of bis(POM)PMEA by this type of assay is typically about 25% in monkeys and PMEA is about 2–4% (Balzarini et al, Animal Models in AIDS (1990) p. 131–138, Schellekens, H. et al (ed), Elsevier Science Publications, Amsterdam) while nucleotide analog amidates and nucleotide analogs (including mono- and diesters) can have oral bioavailabilities of about 5%, 10%, 15%, 30%, 40%, 50%, 60% or 80%.

Total radioactivity in plasma is determined by mixing about 200 µL of plasma with a scintillation counting cocktail (such as 10 mL of Scinti-Safe plus LSC cocktail) and counting in a scintillation counter (usually for about 5–30 minutes). Detailed analysis of the radiochemical composition is accomplished using about 350 µL of plasma, denaturing proteins in the serum (using about 700 µL 0.1% trifluoroacetic acid in acetonitrile for example), drying the resulting sample under reduced pressure, suspending the sample in an appropriate buffer (for example using about 100 µL of 2% acetonitrile in 25 mM potassium phosphate buffer with 10 mM tetrabutyl ammonium hydrogen phosphate (TBAHP), pH 6.0 for HPLC analysis), centrifuging the sample and analyzing the supernatant for individual radiolabeled species by reverse phase HPLC on commercially available columns (The Separation Group, Hesperia, Calif.; Vydac C18, 5 µm, 250×4.6 mm column with an injection volume of about 50 µL and a flow rate of about 1.0 mL/min. at about 35° C. using buffer for 2 minutes followed by a linear gradient to about 65% acetonitrile in 25 mM potassium phosphate buffer with 10 mM TBAHP, pH 6.0 over 13 about minutes). Radiolabel detection is accomplished using means such as commercially available radioactive flow detection systems or scintillation counting systems (Packard, Meridian, Conn.).

Fluorescence detection of PMEA in plasma is accomplished by measuring fluorescence emission (420 nm, with excitation at about 236 nm) with a detector (model F2000, Spectra Physics, San Jose, Calif.) from the HPLC gradient essentially as described above (2 to 65% acetonitrile). Samples for analysis are prepared from plasma (200 µL) by protein precipitation with TFA (400 µL 0.1% in acetonitrile), drying and conversion of adenine to N6-ethenoadenine in 200 µL of reaction buffer (0.34% chloroacetaldehyde, 100 mM sodium acetate, pH 4.5) for 40 minutes at 95° C. followed by HPLC analysis using 50 µL.

Example 6: Bis(adamantoyl oxymethyl)PMEA ester.

DBU (1.53 g, 10 mmol) was added to a suspension of PMEA (1.365 g, 5 mmol) in DMF (25 mL). Adamantoyl oxymethyl chloride (5.72 g, 25 mmol) in DMF (25 mL) was added to the reaction mixture which was then stirred for four days at room temperature and the volatiles were removed under vacuum. The crude product obtained after removal of the solvent was loaded onto a silica gel column and washed with 3% MeOH/CH$_2$Cl$_2$ to remove nonpolar impurities. 1 g (30%) of bis(adamantoyl oxymethyl)PMEA ester was eluted in 8% MeOH/CH$_2$Cl$_2$. Adamantoyl oxymethyl chloride was obtained by conversion of 1-adamantanecarbonyl chloride (Aldrich No. 11,772-2) with (CH$_2$O)$_n$/ZnCl$_2$ and has been described (Bodor, et al J Med Chem (1980) 23:474–480).

Example 7: Bis(phenyl)PMEA and bis(2-ethoxyphenyl) PMEA esters.

PMEA (2.0 g, 7.3 mmol), acetonitrile (20 mL), thionyl chloride (20 mL) and N,N-dimethylformamide (2 drops) were added to a 250 mL single neck round bottom flask equipped with a magnetic stirrer, water cooled condenser and $N_2$ atmosphere. The flask was immersed in a 85° C. oil bath and the resulting suspension was stirred for two hours. The resulting solution was then concentrated to dryness and acetonitrile (50 mL) was added to redissolve the crude chloridate.

To a separate 250 mL single neck round bottom flask equipped with a mechanical stirrer, and $N_2$ atmosphere, phenol (3.25 g, 35 mmol), tetrahydrofuran (80 mL) and sodium hydride (1.4 g, 34 mmol, 60% (w/w) dispersion in mineral oil) was charged. After stirring for 30 minutes, the solution was cooled to −78° C. with a dry ice-acetone bath. The acetonitrile from the previous step was then added drop-wise at a rate that the internal temperature did not rise above −76° C. After the addition was complete, the resulting suspension was poured into saturated aqueous $NaHCO_3$ (100 mL) and extracted with methylene chloride (3×150 mL). The combined organic extracts were washed with $H_2O$ (100 mL), brine (100 mL) and dried with anhydrous $Na_2SO_4$. Concentration by rotary evaporation afforded a yellow solid. Purification by recrystallization (ethyl acetate/hexanes) afforded pure bis(phenyl)PMEA (1.64 g, 53%). Bis(2-ethoxyphenyl)PMEA was made similarly using 2-ethoxyphenol in place of phenol in 36% yield.

The claims shall be construed to exclude any subject matter that, at the date of the invention, would not have been patentable under applicable statutory and judicial authority.

What is claimed is:

1. A compound of the formula IIb

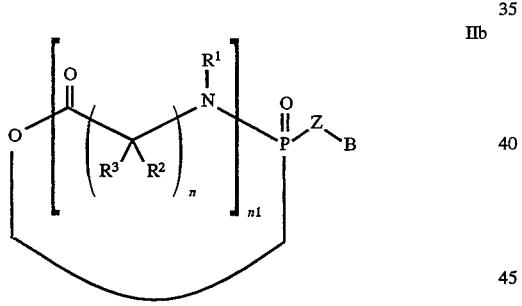

IIb wherein n is an integer having a value from 1 to 5 and if n>1, each —C($R^3$)($R^2$)— may be the same or different;

n1 is an integer;

$R^1$ is H or $C_1$–$C_9$ alkyl which is unsubstituted or substituted by substituents independently selected from the group consisting of OH, O, N, $COOR^4$ and halogen, $C_3$–$C_6$ aryl which is unsubstituted or substituted by substituents independently selected from the group consisting of OH, O, N, $COOR^4$ and halogen or $C_3$–$C_9$ aryl-alkyl which is unsubstituted or substituted by substituents independently selected from the group consisting of OH, O, N, $COOR^4$ and halogen;

$R^2$ is independently H or $C_1$–$C_9$ alkyl which is unsubstituted or substituted by substituents independently selected from the group consisting of OH, O, N, $COOR^4$ and halogen, $C_3$–$C_6$ aryl which is unsubstituted or substituted by substituents independently selected from the group consisting of OH, O, N, $COOR^4$ and halogen or $C_3$–$C_9$ aryl-alkyl which is unsubstituted or substituted by substituents independently selected from the group consisting of OH, O, N, $COOR^4$ and halogen;

$R^3$ is independently C(O)—$OR^4$, amino, $C_1$–$C_3$ alkylamino, $C_1$–$C_3$ alkyldiamino, $C_1$–$C_6$ alkenylamino, hydroxy, thiol, $C_1$–$C_3$ alkoxy, $C_1$–$C_3$ alkthiol, $(CH_2)_n$ $COOR^4$, alkoxyphenyl, $C_1$–$C_6$ alkyl, $C_2$–$C_6$ alkenyl, $C_6$–$C_{12}$ aryl which is substituted or unsubstituted with OH, halogen, SH, $NH_2$, phenyl, hydroxyphenyl or alkoxyphenyl;

$R^4$ is H provided that n1 is greater than 1, or is $C_3$–$C_9$ alkyl which is unsubstituted or substituted by substituents independently selected from the group consisting of OH, O, N and halogen, $C_3$–$C_6$ aryl which is unsubstituted or substituted by substituents independently selected from the group consisting of OH, O, N and halogen, $C_3$–$C_9$ aryl-alkyl which is unsubstituted or substituted by substituents independently selected from the group consisting of OH, O, N and halogen;

Z is —$CHR^7$—$R^{11}$—$(CH_2)_{m1}$—$C\#(R^8)((CH^2)_{m2}(R^9))$— $(CH_2)_{m3}$—$R^{10}$—$(CH_2)_{m4}$—, —O—$C_6H_4$—$CH_2$—, —$CHR^7$—O—$CHR^7$—O—$CHR^7$, —$CHR^7$— $(CHR^{13})_{m1}$—$CHR^{14}$—$R^{10}$—,

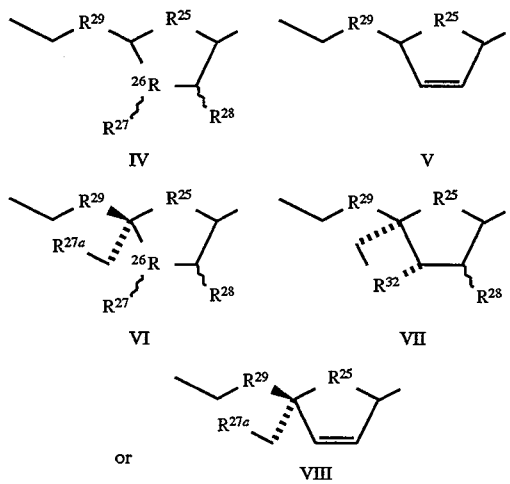

$R^7$ is H or $C_1$–$C_4$alkyl;

$R^8$ is H or $C_1$–$C_4$alkyl, $C_2$–$C_4$ alkenyl, azidomethyl or azidoethyl;

$R^9$ is halogen (F, Cl, Br or I), H or OH;

$R^{10}$ is O, $CH_2$ or a chemical bond;

$R^{11}$ is O, S, $CH_2$, CHF, $CF_2$;

O is —C($R^{12}$)$_2$—$CH_2$—, —C($R^{12}$)—O—, —$CR^{12}$=$CR^{12}$, or —C≡C—, wherein each $R^{12}$ is independently H, or halogen;

$R^{13}$ is H, halogen, OH, $CH_3$, $CH_2OH$, or $C_3$–$C_{12}$ acyloxymethyl;

$R^{14}$ is independently H, halogen, OH, $CH_3$, $CH_2OH$, $C_3$–$C_{12}$ acyloxymethyl, or $C_{2-C12}$ acyloxy;

$R^{25}$ is $CH_2$, CHF or O;

$R^{26}$ is CH or S, provided that when $R^{25}$ is CH, $R^{26}$ is not S;

$R^{27}$ is H, OH, halogen, $N_3$, $C_1$–$C_4$ alkoxy or when, $R^{26}$ is S, $R^{27}$ is absent;

$R^{27a}$ is H, OH, halogen, $N_3$, $C_1$–$C_4$ alkyl, $C_1$–$C_4$ alkoxy;

$R^{28}$ is H, OH, halogen, $N_3$, $C_1$–$C_4$ alkyl or $C_1$–$C_4$ alkoxy;

$R^{29}$ is O, S, $CH_2$, CHF, $CF_2$;

$R^{32}$ is O;

n2 is an integer having a value from 0 to 6;

m1 is an integer having a value from 0 to 4;

m2 is an integer having a value from 0 to 4;

m3 is an integer having a value from 0 to 4;

m4 is an integer having a value from 0 to 4;

the carbon atom designated C# is in the R, S or RS configuration; and

B is a base.

2. A compound of the formula Ib

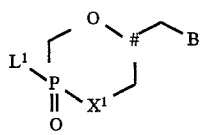

wherein $L^1$ is an amino acid or polypeptide residue bonded to the phosphorus atom of the compound by an amidate bond and any carboxyl group that is linked by less than about 5 atoms to the amidate N is esterified or amidated;

$X^1$ is O or S;

the carbon atom designated # is in the R, S or RS configuration; and

B is a base.

3. The compound of claim 2 of the formula IIa

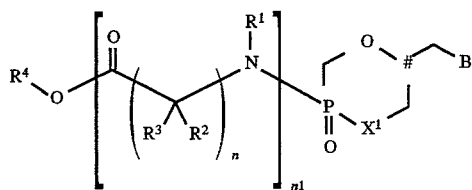

wherein n is an integer having a value from 1 to 5 and if n>1, each —$C(R^3)(R^2)$— may be the same or different;

n1 is an integer;

$R^1$ is H or $C_1$–$C_9$ alkyl which is unsubstituted or substituted by substituents independently selected from the group consisting of OH, O, N, $COOR^4$ and halogen, $C_3$–$C_6$ aryl which is unsubstituted or substituted by substituents independently selected from the group consisting of OH, O, N, $COOR^4$ and halogen or $C_1$–$C_9$ aryl-alkyl which is unsubstituted or substituted by substituents independently selected from the group consisting of OH, O, N, $COOR^4$ and halogen;

$R^2$ is independently H or $C_1$–$C_9$ alkyl which is unsubstituted or substituted by substituents independently selected from the group consisting of OH, O, N, $COOR^4$ and halogen, $C_3$–$C_6$ aryl which is unsubstituted or substituted by substituents independently selected from the group consisting of OH, O, N, $COOR^4$ and halogen or $C_3$–$C_9$ aryl-alkyl which is unsubstituted or substituted by substituents independently selected from the group consisting of OH, O, N, $COOR^4$ and halogen;

$R^3$ is independently C(O)—$OR^4$, amino, $C_1$–$C_3$ alkylamino, $C_1$–$C_3$ alkyldiamino, $C_1$–$C_6$ alkenylamino, hydroxy, thiol, $C_1$–$C_3$ alkoxy, $C_1$–$C_3$ alkthiol, $(CH_2)_n$ $COOR^4$, alkoxyphenyl, $C_1$–$C_6$ alkyl, $C_2$–$C_6$ alkenyl, $C_6$–$C_{12}$ aryl which is substituted or unsubstituted with OH, halogen, SH, $NH_2$, phenyl, hydroxyphenyl or alkoxyphenyl; and $R^4$ is H provided that n1 is greater than 1, or is $C_3$–$C_9$ alkyl which is unsubstituted or substituted by substituents independently selected from the group consisting of OH, O, N and halogen, $C_3$–$C_6$ aryl which is unsubstituted or substituted by substituents independently selected from the group consisting of OH, O, N and halogen, $C_3$–$C_9$ aryl-alkyl which is unsubstituted or substituted by substituents independently selected from the group consisting of OH, O, N and halogen.

4. The compound of claim 3 wherein n and n1 are 1;

$R^1$ is H, methyl, phenyl or benzyl;

$R^2$ is H;

$R^3$ is H, —$CH_3$, —$CH(CH_3)_2$, —$CH_2$—$CH(CH_3)_2$, —$CHCH_3$—$CH_2$—$CH_3$, —$CH_2$—$C_6H_5$, —$CH_2CH_2$—S—$CH_3$, —$CH_2OH$, —$CH(OH)$—$CH_3$, —$CH_2$—SH, —$CH_2$–$C_6H_4OH$, —$CH_2$—CO—$NH_2$, —$CH_2$—$CH_2$—CO—$NH_2$, —$CH_2$—COOH, —$CH_2$—$CH_2$—COOH, —$(CH_2)_4$—$NH_2$, —$(CH_2)_3$—NH—$C(NH_2)$—$NH_2$, 1-guanidinoprop-3-yl, benzyl, 4-hydroxybenzyl, imidazol4-yl, indol-3-yl, methoxyphenyl or ethoxyphenyl; and $R^4$ is methyl, ethyl, propyl, isopropyl, butyl, t-butyl, phenyl, benzyl, 1-pyridyl, 3-pyridyl, 1-pyrimidinyl, pivaloyloxymethyl, N-ethylmorpholino, N-2-propylmorpholino, methoxyethyl, 4-N-methylpiperidyl, 3-N-methylpiperidyl, 2-, 3-, and 4-N,N-dimethylaminophenyl and 2-, 3-, and 4-N,N-diethylaminophenyl or 1-ethylpiperazinyl.

5. The compound of claim 4 wherein B is cytosin-1-yl, 6-azacytosin-1-yl, adenin-9-yl, guanin-9-yl or 2,6-diaminopurin-9-yl, and $X^1$ is O.

6. A compound of the formula Id

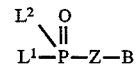

wherein $L^1$ and $L^2$ are independently an amino acid or polypeptide residue bonded to the phosphorus atom of the nucleotide analog amidate by an amidate bond, or an oxyester, thioester, a substituted or unsubstituted amine, or hydroxy, provided that one or both of $L^1$ and $L^2$ is an amino acid or polypeptide residue and any carboxyl group that is linked by less than about 5 atoms to the amidate N is esterified or amidated;

Z is —$CHR^7$—$R^{11}$—$(CH_2)_{m1}$—$C\#(R^8)((CH_2)_{m2}(R^9))$—$(CH_2)_{m3}$—$R^{10}$—$(CH_2)_{m4}$—, —O—$C_6H_4$—$CH_2$—, —$CHR^7$—O—$CHR^7$—O—$CHR^7$—$CHR^7$—$(CHR^{13})_{m1}$—$CHR^{14}R^{10}$—,

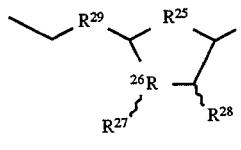 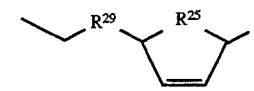

IV      V

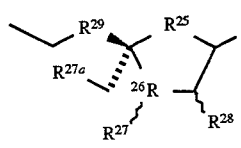 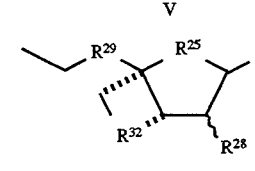

VI      VII

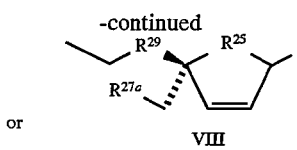

or VIII $R^7$ is H or $C_1$–$C_4$ alkyl;

$R^8$ is H or $C_1$–$C_4$ alkyl, $C_2$–$C_4$ alkenyl, azidomethyl or azidoethyl;

$R^9$ is halogen (F, Cl, Br or I), H or OH;

$R^{10}$ is O, $CH_2$ or a chemical bond;

$R^{11}$ is O, S, $CH_2$, CHF, $CF_2$;

O is —C($R^{12}$)$_2$—$CH_2$—, —C($R^{12}$)$_2$—O—, —$CR^{12}$=$CR^{12}$, or —C≡C—, wherein each $R^{12}$ is independently H, or halogen;

$R^{13}$ is H, halogen, OH, $CH_3$, $CH_2OH$, or $C_3$–$C_{12}$ acyloxymethyl;

$R^{14}$ is independently H, halogen, OH, $CH_3$, $CH_2OH$, $C_3$–$C_{12}$ acyloxymethyl, or $C_2$–$C_{12}$ acyloxy;

$R^{25}$ is $CH_2$, CHF or O;

$R^{26}$ is CH or S, provided that when $R^{25}$ is CH, $R^{26}$ is not S;

$R^{27}$ is H, OH, halogen, $N_3$, $C_1$–$C_4$ alkyl, $C_1$–$C_4$ alkoxy or when, $R^{26}$ is S, $R^{27}$ is absent;

$R^{27a}$ is H, OH, halogen, $N_3$, $C_1$–$C_4$ alkyl, $C_1$–$C_4$ alkoxy;

$R^{28}$ is H, OH, halogen, $N_3$, $C_1$–$C_4$ alkyl or $C_1$–$C_4$ alkoxy;

$R^{29}$ is O, S, $CH_2$, CHF, $CF_2$;

$R^{32}$ is O;

n2 is an integer having a value from 0 to 6;

m1 is an integer having a value from 0 to 4;

m2 is an integer having a value from 0 to 4;

m3 is an integer having a value from 0 to 4;

m4 is an integer having a value from 0 to 4;

the carbon atom designated C# is in the R, S or RS configuration; and

B is a base.

7. The compound of claim 6 wherein $L^1$ is of the formula III

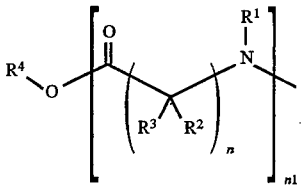

wherein $L^2$ is OR, SR or is the same as $L^1$ wherein, R is H, $C_3$–$C_{24}$ acyloxyalkyl, $C_6$–$C_{24}$ acyloxyarylalkyl, $C_3$–$C_{24}$ acyloxyalkoxyalkyl, $C_3$–$C_{24}$ acyloxyhaloalkyl, or $C_1$–$C_{20}$ alkyl which is unsubstituted or substituted by substituents independently selected from the group consisting of OH, O, N and halogen (F, Cl, Br, I), $C_3$–$C_{20}$ aryl which is unsubstituted or substituted by substituents independently selected from the group consisting of $C_1$–$C_6$ alkyl, $C_1$–$C_6$ alkoxy, $C_1$–$C_6$ haloalkyl (1 to 3 halogen atoms), cyano, nitro, OH, O, N and halogen, or $C_4$–$C_{20}$ aryl-alkyl which is unsubstituted or substituted in the aryl moiety by substituents independently selected from the group consisting of $C_1$–$C_6$ alkyl, $C_1$–$C_6$ alkoxy, $C_1$–$C_6$ haloalkyl (1 to 3 halogen atoms), cyano, nitro, OH, O, N and halogen.

8. The compound of claim 7 wherein n and n1 are 1;

R is N-ethylmorpholino, pivaloyloxymethyl, phenyl, benzyl, isopropyl, t-butyl, ethyl, isopropyl, butyl, adamantoyloxymethyl, 3-methoxyphenyl, 2-carboethoxyphenyl, 4-fluorophenyl, 2,4-difluorophenyl, 3,5-dimethoxyphenyl, 2,4-dichlorophenyl, 2-ethoxyphenyl, 3-dimethylaminophenyl, 4-trifluoromethylbenzyl, 2-ethylsalicyl, —O—$CH_2$—O—C(O)—$C_{10}H_{16}$, —$C_6H_4$—$CH_2$—N($CH_3$)$_2$, —$CH_2$—$CH_2$F, —$CH_2$—$CH_2$Cl, —$CH_2$—$CF_3$, —$CH_2$—$CCl_3$, $R^5$, $NHR^6$ or N($R^6$)$_2$ wherein, $R^5$ is $CH_2$C(O)N($R^6$)$_2$, $CH_2$C(O)O$R^6$, $CH_2$OC(O)$R^6$, CH($R^6$)OC(O)$R^6$, $CH_2$C($R^6$)$_2$$CH_2$OH, or $CH_2$O$R^6$, and $R^6$ is $C_1$–$C_{20}$ alkyl which is unsubstituted or substituted by substituents independently selected from the group consisting of OH, O, N and halogen (1 to 5 halogen atoms), $C_6$–$C_{20}$ aryl which is unsubstituted or substituted by substituents independently selected from the group consisting of OH, O, N and halogen (1 to 5 halogen atoms) or $C_7$–$C_{20}$ aryl-alkyl which is unsubstituted or substituted by substituents independently selected from the group consisting of OH, O, N and halogen (1 to 5 halogen atoms);

$R^1$ is H, methyl, ethyl, isopropyl, phenyl or benzyl;

$R^2$ is H;

$R^3$ is H, —$CH_3$, —CH($CH_3$)$_2$, —$CH_2$—CH($CH3_2$, —CHCH$_3$—$CH_2$—$CH_3$, —$CH_2$—$C_6H_5$, —$CH_2CH_2$—S—$CH_3$, —$CH_2OH$, —CH(OH)—$CH_3$, —$CH_2$—SH, —$CH_2$-$C_6H_4$OH, —$CH_2$—CO—$NH_2$, —$CH_2$—$CH_2$—CO—$NH_2$, —$CH_2$—COOH, —$CH_2$—$CH_2$—COOH, —($CH_2$)$_4$—$NH_2$, —($CH_2$)$_3$—NH—C($NH_2$)—$NH_2$, 1-guarddinoprop-3-yl, benzyl, 4-hydroxybenzyl, imidazol-4-yl, indol-3-yl, methoxyphenyl or ethoxyphenyl; and $R^4$ is methyl, ethyl, propyl, isopropyl, butyl, t-butyl, phenyl, benzyl, 1-pyridyl, 3-pyridyl, 1-pyrimidinyl, pivaloyloxymethyl, N-ethylmorpholino, N-2-propylmorpholino, methoxyethyl, 4-N-methylpiperidyl, 3-N-methylpiperidyl, 2-, 3-, and 4-N,N-dimethylaminophenyl and 2-, 3-, and 4-N,N-diethylaminophenyl or 1-ethylpiperazinyl.

9. The compound of claim 8 wherein Z is —$CHR^7$— $R^{11}$—($CH_2$)$_{m1}$—C($R^8$)(($CH_2$)$_{m2}$($R^9$))—($CH_2$)$_{m3}$—$R^{10}$—($CH_2$)$_{m4}$—,

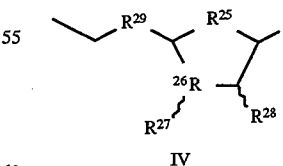 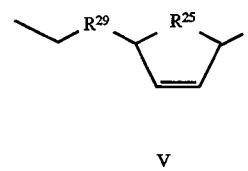

IV                V

10. The compound of claim 9 wherein

Z is —$CH_2$—O—$CH_2$—$CH_2$—, —$CH_2$—O—$CH_2$—CH($CH_2OH$)—, —$CH_2$—O—$CH_2$—CH($CH_2$F)—, —$CH_2$—O—$CH_2$—CH($CH_3$)—, —$CH_2$—O—$CH_2$—CH(CH=$CH_2$)- or —$CH_2$—O—$CH_2$—CH($CH_2N_3$)—, or is of formula IV or V

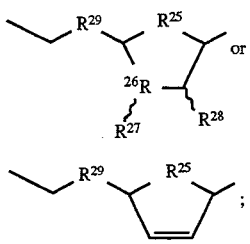

wherein $R^{25}$ and $R^{29}$ are O;
$R^{26}$ is CH;
$R^{27}$ and $R^{28}$ are H; and B is adenin-9-yl, 1-deazaadenin-9-yl, 3-deazaadenin-9-yl, 7-deaza-8-azaadenin-9-yl, 8-azaadenin-9-yl, guanin-9-yl, 2,6-diaminopurin-9-yl, 2-aminopurin-9-yl, thymin-1-yl, cytosin-1-yl, 5-fluorocytosin-1-yl, 6-azacytosin-1-yl, 5-methylcytosin-1-yl, 5-bromovinyluracil-1-yl, 5-fluorouracil-yl or 5-trifluoromethyluracil-1-yl.

11. A compound of claim 1, wherein the compound is labeled with a detectable moiety selected from the group of an enzyme, radioisotope, stable free radical, fluorophor, and a chemiluminescent group.

12. The compound of claim 7 wherein $L^2$ is the same as $L^1$.

13. The compound of claim 12 wherein

B is adenin-9-yl, guanin-9-yl, cytosin-1-yl, 2,6-diaminopurin-9-yl, 2-aminopurin-9-yl, 6-azacytosin-1-yl, 1-deazaadenin-9-yl, 3-deazaadenin-9-yl, 8-azaadenin-9-yl or 7-deaza-8-azaadenin-9-yl;

Z is —CH₂—O—CH₂—CH₂—, —CH₂—O—C#H(CH₂—OR⁴)—CH₂— or —CH₂—O—C#H(CH₃)—CH₂—;

L¹ is —NH—CH(CH(CH₃)₂)—C(O)—OR⁴, —NH—CH(CH₃)(CH₃)₂)—C(O)—OR⁴, —NH—CH(CH₂—C₆H₅)—C(O)—OR⁴, —NH—CH(CH₂—C₆H₄OH)—C(O)—OR⁴, —NH—CH(CH(OH)(CH₃))—C(O)—OR⁴, —NH—CH(CH₂CH₂CH₂NH₂)—CH₂—C(O)—OR⁴, —NH—CH(CH₂CH₂CH₂CH₂NH₂)—CH₂—C(O)—OR⁴, —NH—CH(CH₂CH₂C(O)OR⁴)—C(O)—OR⁴ or —NH—CH(CH₃)₂)—CH₂—C(O)—C)R₄; and R⁴ is hydrogen, methyl, ethyl, propyl, isopropyl, butyl, t-butyl, phenyl, benzyl, 1-pyridinyl, 3-pyridyl, 1-pyrimidinyl, pivaloyloxymethyl, N-ethylmorpholino, N-2-propylmorpholino, methoxyethyl, 4-hydroxy-N-methylpiperidinyl, 4-N-methylpiperidyl, 3-N-methylpiperidyl, 2-N,N-dimethylaminophenyl, 3-N,N-dimethylaminophenyl, 4-N,N-dimethylaminophenyl and 2-N,N-diethylaminophenyl, 3-N,N-diethylaminophenyl, 4-N,N-diethylaminophenyl, 1-ethylpiperazinyl, 3-hydroxy-N-methylpiperidinyl or 1-ethylpiperazinyl.

14. The compound of claim 1 wherein n1 is 1 or 2.

15. The compound of claim 3 wherein n1 is 1 or 2.

16. The compound of claim 15 wherein $X^1$ is oxygen.

17. The compound of claim 16 wherein $L^1$ is a naturally occurring amino acid.

18. The compound of claim 17 wherein $R^2$ is hydrogen and $R^3$ is a side chain of the naturally occurring amino acid.

19. The compound of claim 18 wherein $R^3$ is hydrogen, —CH₃, —CH(CH₃)₂, —CH₂—CH(CH₃)₂, —CHCH₃—CH₂—CH₃, —CH₂—C₆t-IS, —CH₂CH₂—S—CH₃, —CH₂OH, —CH(OH)—CH₃, —CH₂—SH, —CH₂—C₆H₄OH, —CH₂—CO—NH₂, —CH₂—CH₂—CO—NH₂, —CH₂—COOH, —CH₂—CH₂—COOH, —(CH₂)₄—NH₂ or —(CH₂)₃—NH—C(NH₂)—NH₂.

20. The compound claim 19 wherein B is cytosin-1-yl, 6-azacytosin-1-yl, adenin-9-yl, guanin-9-yl or 2,6-diaminopurin-9-yl.

21. The compound of claim 7 wherein n1 is 1 or 2.

22. The compound of claim 21 wherein $L^2$ and $L^1$ are a naturally occurring amino acid.

23. The compound of claim 22 wherein $L^1$ and $L^2$ are the same.

24. The compound of claim 23 wherein $R^2$ is hydrogen and $R^3$ is a side chain of the naturally occuring amino acid.

25. The compound of claim 24 wherein $R^3$ is hydrogen, —CH₃, —CH(CH₃)₂, —CH₂—CH(CH₃)₂, —CHCH₃—CH₂—CH₃, —CH₂—C₆H₅, —CH₂CH₂—S—CH₃, —CH₂OH, —CH(OH)—CH₃, —CH₂—SH, —CH₂—C₆H₄OH, —CH₂—CO—NH₂, —CH₂—CH₂—CO—NH₂, —CH₂—COOH, —CH₂—CH₂—COOH, —(CH₂)₄—NH₂ or —(CH₂)₃—NH—C(NH₂)—NH₂.

26. The compound claim 25 wherein Z is —CH₂—O—CH₂—CH₂—, —CH₂—O—CH₂—CH(CH₂OH)—, —CH₂—O—CH₂—CH(CH₃)—, or

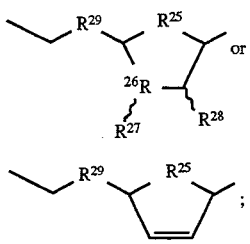

27. The compound claim 26 wherein Z is —CH₂—O—CH₂—CH₂—, —CH₂—O—CH₂—CH(CH₂OH)—, or —CH₂—O—CH₂—CH(CH₃)—.

28. The compound claim 27 wherein B is adenin-9-yl, 1-deazaadenin-9-yl, 3-deazaadenin-9-yl, 7-deaza-8-azaadenin-9-yl, 8-azaadenin-9-yl, guanin-9-yl, 2,6-diaminopurin-9-yl, 2-aminopurin-9-yl, thymin-1-yl, cytosin-1-yl, 5-fluorocytosin-1-yl, 6-azacytosin-1-yl, 5-methylcytosin-1-yl, 5-bromovinyluracil-1-yl, 5-fluorouracil-1-yl or 5-trifluoromethyluracil-1-yl.

29. The compound of claim 28 wherein B is adenin-9-yl, guanin-9-yl, or cytosin-1-yl.

* * * * *